(12) United States Patent
Mochizuki et al.

(10) Patent No.: US 8,088,796 B2
(45) Date of Patent: Jan. 3, 2012

(54) TRIAMINE DERIVATIVE

(75) Inventors: Akiyoshi Mochizuki, Edogawa-ku (JP);
Tsutomu Nagata, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 1124 days.

(21) Appl. No.: 11/909,802

(22) PCT Filed: Mar. 31, 2006

(86) PCT No.: PCT/JP2006/306930
§ 371 (c)(1),
(2), (4) Date: Oct. 5, 2007

(87) PCT Pub. No.: WO2006/106963
PCT Pub. Date: Oct. 12, 2006

(65) Prior Publication Data
US 2009/0239857 A1    Sep. 24, 2009

(30) Foreign Application Priority Data

Mar. 31, 2005    (JP) .................................. 2005-100335

(51) Int. Cl.
*A61K 31/444* (2006.01)
*C07D 419/04* (2006.01)
(52) U.S. Cl. .......................... 514/318; 546/193; 546/194
(58) Field of Classification Search .................. 546/193, 546/194; 514/318
See application file for complete search history.

(56) References Cited

FOREIGN PATENT DOCUMENTS

| JP | 2003-183286 | 7/2003 |
|---|---|---|
| WO | 03/000657 | 1/2003 |
| WO | 2004/058715 | 7/2004 |
| WO | WO 2004/082687 A1 | 9/2004 |

OTHER PUBLICATIONS

Vippagunta et al., "Crystalline Solids", Advanced Drug Delivery Reviews 48 (2001) 3-26.*
Guillory (in Brittain ed.), "Polymorphism, etc.," NY: Marcel Dekker, Inc., 1999, 1-2, 183-226.*
Jan J. Sixma, et al., "The Ideal Anti-Thrombotic Drug", Erratum, Thrombosis Research, vol. 68, No. 6, 1992, pp. 507-512.
Susan Elódi, et al., "Optimization of Conditions for the Catalytic Effect of the Factor IXa-Factor VIII Complex: Probable Role of the Complex in the Amplification of Blood Coagulation", Thrombosis Research, vol. 15, Pergamon Press Ltd., Mar. 22, 1979, pp. 617-629.
Lloyd Waxman, et al., "Tick Anticoagulant Peptide (TAP) Is a Novel Inhibitor of Blood Coagulation Factor Xa", Science, vol. 248, May 4, 1990, pp. 593-596.
Elka Nutt, et al., "The Amino Acid Sequence of Antistasin, A Potent Inhibitor of Factor Xa Reveals a Repeated Internal Structure", The Journal of Biological Chemistry, vol. 263, No. 21, Jul. 25, 1988, pp. 10162-10167.
Extended European Search Report issued Oct. 10, 2010 in PCT/JP2006306930.

* cited by examiner

*Primary Examiner* — Patricia Morris
(74) *Attorney, Agent, or Firm* — Oblon, Spivak, McClelland, Maier & Neustadt, L.L.P.

(57) ABSTRACT

An object of the present invention is to provide a novel compound which has a potent inhibitory effect on FXa and exhibits an excellent antithrombotic effect when orally administered. The present invention provides a compound represented by the following general formula (1):

$$\begin{array}{c} R^3 \\ | \\ N-R^4 \\ (CH_2)_m \quad (CH_2)_n \\ Q^1-Q^2-T^0-N(R^1) \quad N(R^2)-T^1-Q^4 \end{array} \quad (1)$$

wherein $R^1$ and $R^2$ each independently represent a hydrogen atom, a hydroxy group, an alkyl group or an alkoxy group; $Q^1$ represents a saturated or unsaturated bicyclic or tricyclic fused hydrocarbon group which may be substituted, a saturated or unsaturated bicyclic or tricyclic fused heterocyclic group which may be substituted, or the like; $Q^2$ represents a single bond, a straight-chained or branched alkylene group having 1 to 6 carbon atoms, a straight-chained or branched alkenylene group having 2 to 6 carbon atoms, or the like; $R^3$ and $R^4$ each represent an alkyl group, or the like; m and n each represent an integer from 0 to 3; $Q^4$ represents an aryl group; and $T^0$ and $T^1$ each represent a carbonyl group or the like, and a medicine containing the compound.

19 Claims, No Drawings

TRIAMINE DERIVATIVE

TECHNICAL FIELD

The present invention relates to a novel compound which inhibits activated blood coagulation factor X (hereinafter, abbreviated as "FXa") to exhibit a potent anticoagulant effect and can be orally administered, or a blood coagulation inhibitor or a prophylactic and/or therapeutic agent for thrombosis or embolism, which comprises the compound as an active ingredient.

BACKGROUND ART

In unstable angina, cerebral infarction, cerebral embolism, myocardial infarction, pulmonary infarction, pulmonary embolism, Buerger's disease, deep venous thrombosis, disseminated intravascular coagulation syndrome, thrombus formation after artificial valve replacement, reocclusion after angioplasty, thrombus formation during extracorporeal circulation and the like, enhancement of blood coagulability is one of crucial factors. Therefore, there is a demand for excellent anticoagulants which have excellent dose responsiveness, sustainability, reduced risk of hemorrhage and few side effects, and can immediately exhibit satisfactory effects even when orally administered (Non-Patent Document 1).

Among various studies of anticoagulants based on mechanisms of action, it is suggested that FXa inhibitors have a potential to be excellent anticoagulants. The blood coagulation system comprises a series of reactions in which a large amount of thrombin is produced through an amplification process with a multi-stage enzymatic reaction to form insoluble fibrin. In an endogenous system, after a multi-stage reaction following the activation of a contact factor, activated factor IX activates factor X on a phospholipid membrane in the presence of activated factor VIII and calcium ions. In an exogenous system, activated factor VII activates factor X in the presence of a tissue factor. In other words, activation of the factor X into FXa in the coagulation system is an essential reaction for the formation of thrombin. In both systems, the activated factor X (FXa) limitedly degrades prothrombin to produce thrombin. Since the produced thrombin activates the upstream coagulation factors, the generation of thrombin is further amplified. As described above, since the coagulation system upstream of FXa is divided into an endogenous system and an exogenous system, inhibiting the enzymes in the coagulation system upstream of FXa cannot sufficiently suppress production of FXa, and accordingly, thrombin is produced. Meanwhile, since the coagulation system involves self-amplification reactions, suppression of the coagulation system can be efficiently achieved by inhibiting FXa, which is upstream of thrombin, rather than by inhibiting the already produced thrombin (Non-Patent Document 2). Another excellent advantage of FXa inhibitors is that there is a large difference between the dose which is effective in a thrombosis model and the dose which prolongs bleeding time in an experimental hemorrhage model. From these experimental results, it is conceived that FXa inhibitors are anticoagulants with reduced risk of hemorrhage.

Various compounds have been reported as FXa inhibitors. However, it is known that antithrombin III and antithrombin III-dependent pentasaccharides generally cannot inhibit prothrombinase complexes which play a practical role in the thrombus formation in vivo (Non-Patent Documents 3 to 5), and furthermore, they do not exhibit effectiveness when orally administered. Tick anticoagulant peptide (TAP) (Non-Patent Document 3) and antistasin (AST) (Non-Patent Document 4), which are isolated from bloodsucking animals such as mites or leeches, also inhibit FXa and exhibit anti-thrombotic effects in venous thrombosis models as well as arterial thrombosis models. However, these compounds are high molecular weight peptides, and ineffective when orally administered. As such, low-molecular weight FXa inhibitors have been developed, which can be orally administrable and directly inhibit coagulation factors without depending anti-thrombin III.

[Non-Patent Document 1] Thrombosis Research, Vol. 68, pp. 507-512 (1992)
[Non-Patent Document 2] Thrombosis Research, Vol. 15, pp. 617-629 (1979)
[Non-Patent Document 3] Science, Vol. 248, pp. 593-596 (1990)
[Non-Patent Document 4] Journal of Biological Chemistry, Vol. 263, pp. 10162-10167 (1988)

DISCLOSURE OF THE INVENTION

Problem to be Solved by the Invention

Therefore, an object of the present invention is to provide a novel compound which has a potent FXa inhibiting effect and exhibits excellent absorbability upon oral administration.

Means for Solving the Problem

The inventors of the present invention conducted an investigation on the synthesis of a novel FXa inhibitor and the pharmacological effects thereof, and as a result, discovered a triamine derivative, a salt thereof, a solvate and an N-oxide of the derivative and the salt, which exhibit a potent FXa inhibiting effect and a potent anticoagulant effect. The inventors also found that these compounds are useful as a prophylactic and therapeutic agent for various diseases attributable to thrombosis and embolism since they exhibit excellent absorbability even upon oral administration, and thus strongly inhibiting FXa to exhibit a potent anticoagulant effect and anti-thrombotic effect. Thus, the inventors completed the present invention.

Therefore, the present invention provides a compound represented by general formula (1):

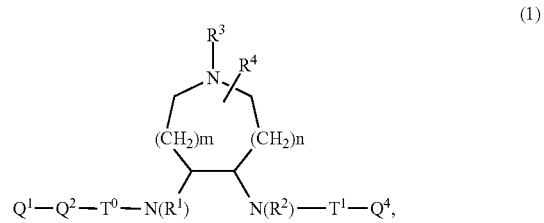

a salt thereof, a solvate of the compound or the salt, or an N-oxide of the compound or the salt, wherein $R^1$ and $R^2$ each independently represent a hydrogen atom, a hydroxy group, an alkyl group or an alkoxy group;

$Q^1$ represents a saturated or unsaturated 5- to 6-membered cyclic hydrocarbon group which may be substituted, a saturated or unsaturated 5- to 7-membered heterocyclic group which may be substituted, a saturated or unsaturated, bicyclic or tricyclic fused hydrocarbon group which may be substituted, or a saturated or unsaturated, bicyclic or tricyclic fused heterocyclic group which may be substituted;

$Q^2$ represents a single bond, a straight-chained or branched alkylene group having 1 to 6 carbon atoms, a straight-chained or branched alkenylene group having 2 to 6 carbon atoms, a straight-chained or branched alkynylene group having 2 to 6 carbon atoms, a divalent saturated or unsaturated, 5- to 6-membered cyclic hydrocarbon group which may be substituted, a divalent saturated or unsaturated, 5- to 7-membered heterocyclic group which may be substituted, a divalent saturated or unsaturated, bicyclic or tricyclic fused hydrocarbon group which may be substituted, or a divalent saturated or unsaturated, bicyclic or tricyclic fused heterocyclic group which may be substituted;

$R^3$ and $R^4$ are substituted at the carbon atom or nitrogen atom on the ring, and each independently represent a hydrogen atom, a hydroxy group, an alkyl group, an alkenyl group, an alkynyl group, a halogen atom, a halogenoalkyl group, a cyano group, a cyanoalkyl group, an amino group, an aminoalkyl group, an N-alkylaminoalkyl group, an N,N-dialkylaminoalkyl group, an acyl group, an acylalkyl group, an acylamino group which may be substituted, an alkoxyimino group, a hydroxyimino group, an acylaminoalkyl group, an alkoxy group, an alkoxyalkyl group, a hydroxyalkyl group, a carboxy group, a carboxyalkyl group, an alkoxycarbonyl group, an alkoxycarbonylalkyl group, an alkoxycarbonylalkylamino group, a carboxyalkylamino group, an alkoxycarbonylamino group, an alkoxycarbonylaminoalkyl group, a carbamoyl group, an N-alkylcarbamoyl group which may have a substituent on the alkyl group, an N,N-dialkylcarbamoyl group which may have a substituent on the alkyl group, an N-alkenylcarbamoyl group, an N-alkenylcarbamoylalkyl group, an N-alkenyl-N-alkylcarbamoyl group, an N-alkenyl-N-alkylcarbamoylalkyl group, an N-alkoxycarbamoyl group, an N-alkyl-N-alkoxycarbamoyl group, an N-alkoxycarbamoylalkyl group, an N-alkyl-N-alkoxycarbamoylalkyl group, a carbazoyl group which may be substituted with 1 to 3 alkyl groups, an alkylsulfonyl group which may be substituted with a halogen atom, an alkylsulfonylalkyl group, a 3- to 6-membered heterocyclic carbonyl group which may be substituted, a carbamoylalkyl group, an N-alkylcarbamoylalkyl group which may have a substituent on the alkyl group, an N,N-dialkylcarbamoylalkyl group which may have a substituent on the alkyl group, a carbamoyloxyalkyl group, an N-alkylcarbamoyloxyalkyl group, an N,N-dialkylcarbamoyloxyalkyl group, a 3- to 6-membered heterocyclic carbonylalkyl group which may be substituted, a 3- to 6-membered heterocyclic carbonyloxyalkyl group which may be substituted, an aryl group, an aralkyl group, a 3- to 6-membered heterocyclic group which may be substituted, a 3- to 6-membered heterocyclic alkyl group which may be substituted, an alkylsulfonylamino group, an arylsulfonylamino group, an alkylsulfonylaminoalkyl group, an arylsulfonylaminoalkyl group, an alkylsulfonylaminocarbonyl group, an arylsulfonylaminocarbonyl group, an alkylsulfonylaminocarbonylalkyl group, an arylsulfonylaminocarbonylalkyl group, an oxo group, a carbamoyloxy group, an aralkyloxy group, a carboxyalkyloxy group, an alkoxycarbonylalkyloxy group, an acyloxy group, an acyloxyalkyl group, an arylsulfonyl group, an alkoxycarbonylalkylsulfonyl group, a carboxyalkylsulfonyl group, an alkoxycarbonylacyl group, an alkoxyalkyloxycarbonyl group, a hydroxyacyl group, an alkoxyacyl group, a halogenoacyl group, a carboxyacyl group, an aminoacyl group, an acyloxyacyl group, an acyloxyalkylsulfonyl group, a hydroxyalkylsulfonyl group, an alkoxyalkylsulfonyl group, a 3- to 6-membered heterocyclic sulfonyl group which may be substituted, an N-alkylaminosulfonyl group, an N,N-dialkylaminosulfonyl group, a 3- to 6-membered heterocyclic oxy group which may be substituted, an N-alkylaminoacyl group, an N,N-dialkylaminoacyl group, an N,N-dialkylcarbamoylacyl group which may have a substituent on the alkyl group, an N,N-dialkylcarbamoylalkylsulfonyl group which may have a substituent on the alkyl group, an alkylsulfonylacyl group, an N-arylcarbamoyl group, an N-3- to 6-membered heterocyclic carbamoyl group, an N-alkyl-N-arylcarbamoyl group, an N-alkyl-N-3- to 6-membered heterocyclic carbamoyl group, an N-arylcarbamoylalkyl group, an N-3- to 6-membered heterocyclic carbamoylalkyl group, an N-alkyl-N-arylcarbamoylalkyl group, an N-alkyl-N-3- to 6-membered heterocyclic carbamoylalkyl group, an N-alkylaminooxalyl group, an N,N-dialkylaminooxalyl group, an aminocarbothioyl group, an N-alkylaminocarbothioyl group, an N,N-dialkylaminocarbothioyl group, an alkoxyalkyl(thiocarbonyl) group, an alkylthioalkyl group or an N-acyl-N-alkylaminoalkyl group, or $R^3$ and $R^4$ are joined together to represent an alkylene group having 1 to 5 carbon atoms, an alkenylene group having 2 to 5 carbon atoms, an alkylenedioxy group having 1 to 5 carbon atoms, or a carbonyldioxy group;

m and n each independently represent an integer from 0 to 3;

$Q^4$ represents an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic fused hydrocarbon group which may be substituted, or a saturated or unsaturated, bicyclic or tricyclic fused heterocyclic group which may be substituted;

$T^0$ represents a carbonyl group or a thiocarbonyl group; and $T^1$ represents a carbonyl group, a sulfonyl group, a —C(=O)—C(=O)—N(R')— group, a —C(=S)—C(=O)—N(R')— group, a —C(=O)—C(=S)—N(R')— group, a —C(=S)—C(=S)—N(R')— group (wherein R' represents a hydrogen atom, a hydroxy group, an alkyl group or an alkoxy group), a —C(=O)-$A^1$-N(R")— group (wherein $A^1$ represents a $C_{1-5}$ alkylene group which may be substituted; and R" represents a hydrogen atom, a hydroxy group, an alkyl group or an alkoxy group), a —C(=O)—NH— group, a —C(=S)—NH— group, a —C(=O)—NH—NH— group, a —C(=O)-$A^2$-C(=O)— group (wherein $A^2$ represents a single bond or an alkylene group having 1 to 5 carbon atoms), a —C(=O)-$A^3$-C(=O)—NH— group (wherein $A^3$ represents an alkylene group having 1 to 5 carbon atoms), a —C(=O)—C(=NOR$^a$)—N(R$^b$)— group, a —C(=S)—C(=NOR$^a$)—N(R$^b$)— group (wherein R$^a$ represents a hydrogen atom, an alkyl group or an alkanoyl group; and R$^b$ represents a hydrogen atom, a hydroxy group, an alkyl group or an alkoxy group), a —C(=O)—N=N— group, a —C(=S)—N=N— group, a —C(=NOR$^C$)—C(=O)—N(R$^d$)— group (wherein R$^C$ represents a hydrogen atom, an alkyl group, an alkanoyl group, an aryl group or an aralkyl group; and R$^d$ represents a hydrogen atom, a hydroxy group, an alkyl group or an alkoxy group), a —C(=N—N(R$^e$)(R$^f$)—C(=O)—N(R$^g$)— group (wherein R$^e$ and R$^f$ each independently represent a hydrogen atom, an alkyl group, an alkanoyl group or an alkyl(thiocarbonyl) group; and R$^g$ represents a hydrogen atom, a hydroxy group, an alkyl group or an alkoxy group), a —C(=O)—NH—C(=O)— group, a —C(=S)—NH—C(=O)— group, a —C(=O)—NH—C(=S)— group, a —C(=S)—NH—C(=S)— group, a —C(=O)—NH—SO$_2$— group, a —SO$_2$—NH— group, a —C(=NCN)—NH—C(=O)— group, a —C(=S)—C(=O)— group or a thiocarbonyl group.

Furthermore, the present invention provides a medicine containing the compound represented by general formula (1), the salt thereof, the solvate of the compound or the salt, or the N-oxide of the compound or the salt, and particularly provides an activated blood coagulation factor X inhibitor, an anticoagulant, a prophylactic and/or therapeutic agent for thrombosis or embolism, and a prophylactic and/or therapeutic agent for cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after artificial valve/joint replacement, thrombus formation and reocclusion after angioplasty, systemic inflammatory response syndrome (SIRS), multiple organ dysfunction syndrome (MODS), thrombus formation during extracorporeal circulation, or blood clotting upon blood drawing.

Also, the present invention provides an intermediate for producing compound (1) represented by the general formula (1).

The present invention provides the use of the compound represented by general formula (1), the salt thereof, the solvate of the compound or the salt, or the N-oxide of the compound or the salt, for the manufacture of a medicine.

Furthermore, the present invention provides a method of treating thrombosis or embolism, comprising administering an effective amount of the compound represented by general formula (1), the salt thereof, the solvate of the compound or the salt, or the N-oxide of the compound or the salt.

Effect of the Invention

The triamine derivative of the present invention exhibits a potent inhibitory effect on activated blood coagulation factor X, and exhibits excellent oral absorbability. Thus, the triamine derivative of the invention is useful as a medicine, an activated blood coagulation factor X inhibitor, an anticoagulant, a prophylactic and/or therapeutic agent for thrombosis or embolism, a prophylactic and/or therapeutic agent for thrombotic diseases, and a prophylactic and/or therapeutic agent for cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after artificial valve or joint replacement, thrombus formation and reocclusion after angioplasty, systemic inflammatory response syndrome (SIRS), multiple organ dysfunction syndrome (MODS), thrombus formation during extracorporeal circulation, or blood clotting upon blood drawing.

BEST MODE FOR CARRYING OUT THE INVENTION

Hereinafter, the substituents for the triamine derivative of the present invention represented by the general formula (1) will be described.

[Group $Q^4$]

The group $Q^4$ means an aryl group which may be substituted, an arylalkenyl group which may be substituted, an arylalkynyl group which may be substituted, a heteroaryl group which may be substituted, a heteroarylalkenyl group which may be substituted, a saturated or unsaturated, bicyclic or tricyclic fused hydrocarbon group which may be substituted, or a saturated or unsaturated, bicyclic or tricyclic fused heterocyclic group which may be substituted.

With regard to the group $Q^4$, the aryl group may include an aryl group having 6 to 14 carbon atoms such as a phenyl group, a naphthyl group, an anthryl group, and a phenanthryl group. The arylalkenyl group means a group constituted by an aryl group having 6 to 14 carbon atoms and an alkenylene group having 2 to 6 carbon atoms, and may include a styryl group. The arylalkynyl group means a group constituted by an aryl group having 6 to 14 carbon atoms and an alkynylene group having 2 to 6 carbon atoms, and may include a phenylethynyl group.

The heteroaryl group means an aromatic monovalent group having at least one heteroatom selected from an oxygen atom, a sulfur atom and a nitrogen atom, and may include a heteroaryl group having 5 or 6 atoms in total such as a pyridyl group, a pyridazinyl group, a pyrazinyl group, a furyl group, a thienyl group, a pyrrolyl group, a thiazolyl group, an oxazolyl group, a pyrimidinyl group and a tetrazolyl group. The heteroarylalkenyl group means a group constituted by the heteroaryl group described above and an alkenylene group having 2 to 6 carbon atoms, and may include a thienylethenyl group and a pyridylethenyl group.

The saturated or unsaturated, bicyclic or tricyclic fused hydrocarbon group represents a monovalent group derived from a saturated or unsaturated, bicyclic or tricyclic fused hydrocarbon, and the saturated or unsaturated, bicyclic or tricyclic fused hydrocarbon represents a bicyclic or tricyclic fused hydrocarbon formed by condensing 2 or 3 same or different types of saturated or unsaturated 5- to 6-membered cyclic hydrocarbons. The saturated or unsaturated 5- to 6-membered cyclic hydrocarbon in this case may include, for example, cyclopentane, cyclopentene, cyclohexane, cyclohexene, cyclohexadiene, benzene and the like. Specific examples of the saturated or unsaturated, bicyclic or tricyclic fused hydrocarbon group may include an indenyl group, an indanyl group, a tetrahydronaphthyl group, a naphthyl group and the like. In addition, the position at which the saturated or unsaturated, bicyclic or tricyclic fused hydrocarbon group is attached to $T^1$ in the general formula (1) is not particularly limited.

The saturated or unsaturated, bicyclic or tricyclic fused heterocyclic group represents a monovalent group derived from a saturated or unsaturated, bicyclic or tricyclic fused heterocyclic ring, and the saturated or unsaturated, bicyclic or tricyclic fused heterocyclic ring represents any of the following (1) to (3):

(1) A bicyclic or tricyclic fused heterocyclic ring formed by condensation of 2 or 3 same or different types of saturated or unsaturated 5- to 7-membered heterocyclic rings;

(2) A bicyclic or tricyclic fused heterocyclic ring formed by condensation of one saturated or unsaturated, 5- to 7-membered heterocyclic ring and 1 or 2 saturated or unsaturated, 5- to 6-membered cyclic hydrocarbons; and (3) A tricyclic fused heterocyclic ring formed by condensation of two saturated or unsaturated 5- to 7-membered heterocyclic rings and one saturated or unsaturated, 5- to 6-membered cyclic hydrocarbon.

The position at which the saturated or unsaturated, bicyclic or tricyclic fused heterocyclic group is attached to $T^1$ in the general formula (1) is not particularly limited.

The aforementioned saturated or unsaturated, 5- to 7-membered heterocyclic ring represents a heterocyclic ring having at least one heteroatom selected from an oxygen atom, a sulfur atom and a nitrogen atom, and may specifically include furan, pyrrole, thiophene, pyrazole, imidazole, oxazole, oxazolidine, thiazole, thiadiazole, furazan, pyrane, pyridine, pyrimidine, pyridazine, pyrrolidine, piperazine, piperidine, oxazine, oxadiazine, morpholine, thiazine, thiadiazine, thiomorpholine, tetrazole, triazole, triazine, thiadiazine, oxadiazine, azepine, diazepine, triazepine, thiazepine, oxazepine and the like. Furthermore, the saturated or unsaturated 5- to 6-membered cyclic hydrocarbon represents the same species as the saturated or unsaturated, 5- to 6-membered cyclic hydrocarbon exemplified for the saturated or unsaturated, bicyclic or tricyclic fused hydrocarbon group. Specific examples of the saturated or unsaturated, bicyclic or tricyclic fused heterocyclic group may include a benzofuryl group, an isobenzofuryl group, a benzothienyl group, an indolyl group, an indolinyl group, an isoindolyl group, an isoindolinyl group, an indazolyl group, a quinolyl group, a dihydroquinolyl group, a 4-oxodihydroquinolyl group (dihydroquinolin-4-one), a tetrahydroquinolyl group, an isoquinolyl group, a tetrahydroisoquinolyl group, a chromenyl group, a chromanyl group, an isochromanyl group, a 4H-4-oxobenzopyranyl group, a 3,4-dihydro-4H-4-oxobenzopyranyl group, a 4H-quinolidinyl group, a quinazolinyl group, a dihydroquinazolinyl group, a tetrahydroquinazolinyl group, a quinoxalinyl group, a tetrahydroquinoxalinyl group, a cinnolinyl group, a tetrahydrocinnolinyl group, an indolidinyl group, a tetrahydroindolidinyl group, a benzothiazolyl group, a tetrahydrobenzothiazolyl group, a benzoxazolyl group, a benzisothiazolyl group, a benzisoxazolyl group, a benzimidazolyl group, a naphthylidinyl group, a tetrahydronaphthylidinyl group, a thienopyridyl group, a tetrahydrothienopyridyl group, a thiazolopyridyl group, a tetrahydrothiazolopyridyl group, a thiazolopyridazinyl group, a tetrahydrothiazolopyridazinyl group, a pyrrolopyridyl group, a dihydropyrrolopyridyl group, a tetrahydropyrrolopyridyl group, a pyrrolopyrimidinyl group, a dihydropyrrolopyrimidinyl group, a pyridoquinazolinyl group, a dihydropyridoquinazolinyl group, a pyridopyrimidinyl group, a tetrahydropyridopyrimidinyl group, a pyranothiazolyl group, a dihydropyranothiazolyl group, a furopyridyl group, a tetrahydrofuropyridyl group, an oxazolopyridyl group, a tetrahydrooxazolopyridyl group, an oxazolopyridazinyl group, a tetrahydrooxazolopyridazinyl group, a pyrrolothiazolyl group, a dihydropyrrolothiazolyl group, a pyrrolooxazolyl group, a dihydropyrrolooxazolyl group, a thienopyrrolyl group, a thiazolopyrimidinyl group, a 4-oxotetrahydrocinnolinyl group, a 1,2,4-benzothiadiazinyl group, a 1,1-dioxy-2H-1,2,4-benzothiadiazinyl group, a 1,2,4-benzoxadiazinyl group, a cyclopentapyranyl group, a thienofuranyl group, a furopyranyl group, a pyridooxazinyl group, a pyrazolooxazolyl group, an imidazothiazolyl group, an imidazopyridyl group, a tetrahydroimidazopyridyl group, a pyrazinopyridazinyl group, a benzisoquinolyl group, a furocinnolyl group, a pyrazolothiazolopyridazinyl group, a tetrahydropyrazolothiazolopyridazinyl group, a hexahydrothiazolopyridazinopyridazinyl group, an imidazotriazinyl group, an oxazolopyridyl group, a benzoxepinyl group, a benzazepinyl group, a tetrahydrobenzazepinyl group, a benzodiazepinyl group, a benzotriazepinyl group, a thienoazepinyl group, a tetrahydrothienoazepinyl group, a thienodiazepinyl group, a thienotriazepinyl group, a thiazoloazepinyl group, a tetrahydrothiazoloazepinyl group, a 4,5,6,7-tetrahydro-5,6-tetramethylenethiazolopyridazinyl group, a 5,6-trimethylene-4,5,6,7-tetrahydrothiazolopyridazinyl group and the like.

There is no particular limitation on the type of condensation of the fused heterocyclic group. For example, the naphthyridinyl group may be any of 1,5-, 1,6-, 1,7-, 1,8-, 2,6- and 2,7-naphthyridinyl groups; the thienopyridyl group may be any of a thieno[2,3-b]pyridyl group, a thieno[2,3-c]pyridyl group, a thieno[3,2-b]pyridyl group, a thieno[3,2-c]pyridyl group, a thieno[3,4-b]pyridyl group and a thieno[3,4-c]pyridyl group; the thienopyrrolyl group may be any of a thieno[2,3-b]pyrrolyl group and a thieno[2,3-b]pyrrolyl group; the thiazolopyridyl group may be any of a thiazolo[4,5-b]pyridyl group, a thiazolo[4,5-c]pyridyl group, a thiazolo[5,4-b]pyridyl group, a thiazolo[5,4-c]pyridyl group, a thiazolo[3,4-a]pyridyl group and a thiazolo[3,2-a]pyridyl group; the thiazolopyridazinyl group may be any of a thiazolo[4,5-c]pyridazinyl group, a thiazolo[4,5-d]pyridazinyl group, a thiazolo[5,4-c]pyridazinyl group and a thiazolo[3,2-b]pyridazinyl group; the pyrrolopyridyl group may be any of a pyrrolo[2,3-b]pyridyl group, a pyrrolo[2,3-c]pyridyl group, a pyrrolo[3,2-b]pyridyl group, a pyrrolo[3,2-c]pyridyl group, a pyrrolo[3,4-b]pyridyl group and a pyrrolo[3,4-c]pyridyl group; the pyridopyrimidinyl group may be any of a pyrido[2,3-d]pyrimidinyl group, a pyrido[3,2-d]pyrimidinyl group, a pyrido[3,4-d]pyrimidinyl group, a pyrido[4,3-d]pyrimidinyl group, a pyrido[1,2-c]pyrimidinyl group and a pyrido[1,2-a]pyrimidinyl group; the pyranothiazolyl group may be any of a pyrano[2,3-d]thiazolyl group, a pyrano[4,3-d]thiazolyl group, a pyrano[3,4-d]thiazolyl group and a pyrano[3,2-d]thiazolyl group; the furopyridyl group may be any of a furo[2,3-b]pyridyl group, a furo[2,3-c]pyridyl group, a furo[3,2-b]pyridyl group, a furo[3,2-c]pyridyl group, a furo[3,4-b]pyridyl group and a furo[3,4-c]pyridyl group; the oxazolopyridyl group may be any of an oxazolo[4,5-b]pyridyl group, an oxazolo[4,5-c]pyridyl group, an oxazolo[5,4-b]pyridyl group, an oxazolo[5,4-c]pyridyl group, an oxazolo[3,4-a]pyridyl group and an oxazolo[3,2-a]pyridyl group; the oxazolopyridazinyl group may be any of an oxazolo[4,5-c]pyridazinyl group, an oxazolo[4,5-d]pyridazinyl group, an oxazolo[5,4-c]pyridazinyl group and an oxazolo[3,4-b]pyridazinyl group; the pyrrolothiazolyl group may be any of a pyrrolo[2,1-b]thiazolyl group, a pyrrolo[1,2-c]thiazolyl group, a pyrrolo[2,3-d]thiazolyl group, a pyrrolo[3,2-d]thiazolyl group and a pyrrolo[3,4-d]thiazolyl group; the pyrrolooxazolyl group may be any of a pyrrolo[2,1-b]oxazolyl group, a pyrrolo[1,2-c]oxazolyl group, a pyrrolo[2,3-d]oxazolyl group, a pyrrolo[3,2-d]oxazolyl group and a pyrrolo[3,4-d]oxazolyl group; the benzazepinyl group may be any of a 1H-1-benzazepinyl group, a 1H-2-benzazepinyl group and a 1H-3-benzazepinyl group, or may be a dihydro-oxo derivative type benzazepinyl group such as a 4,5-dihydro-1-oxo-1H-2-benzazepinyl group; the benzodiazepinyl group may be any of a 1H-1,3-benzodiazepinyl group, a 1H-1,4-benzodiazepinyl group and a 1H-1,5-benzodiazepinyl group, or may be a dihydro-oxo derivative type benzodiazepinyl group such as a 4,5-dihydro-4-oxo-1H-1,3-benzodiazepinyl group; the benzotriazepinyl group may be any of a 1H-1,3,4-benzotriazepinyl group and a 1H-1,3,5-benzotriazepinyl group, or may be a dihydro-oxo derivative type benzotriazepinyl group such as a 4,5-dihydro-5-oxo-1H-1,3,4-benzotriazepinyl group; the thienoazepinyl group may be any of a thieno[2,3-b]azepinyl group, a thieno[2,3-c]azepinyl group, a thieno[2,3-d]azepinyl group, a thieno[3,2-c]azepinyl group and a thieno[3,2-b]azepinyl group, or may be a dihydro-oxo derivative type thienoazepinyl group such as a 5,6,7,8-tetrahydro-4-oxo-4H-thieno[3,2-c]azepinyl group; the thienodiazepinyl group or the thienotriazepinyl group may also be of any fused form, or may be a group of dihydro-oxo derivative type; the benzothiazepinyl group may be any of a 1H-1-benzothiazepinyl group, a 1H-2-benzothiazepinyl group and a 1H-3-benzothiazepinyl group, or may be a dihydro-oxo derivative type benzothiazepinyl group such as a 4,5-dihydro-1-oxo-1H-2-benzothiazepinyl group; and the benzoxazepinyl group may be any of a 1H-1-benzoxazepinyl group, a 1H-2-benzoxazepinyl group and a 1H-3-benzoxazepinyl group, or may be a dihydro-oxo derivative type benzoxazepinyl group such as a 4,5-dihydro-1-oxo-1H-2-benzoxazepinyl group. Fused forms other than those described above are also allowed.

The aforementioned aryl group, heteroaryl group, arylalkenyl group, heteroarylalkenyl group, saturated or unsaturated, bicyclic or tricyclic fused hydrocarbon group and saturated or unsaturated, bicyclic or tricyclic fused heterocyclic group may respectively have 1 to 3 substituents, and examples of the substituents may include a hydroxy group, a halogen atom such as a fluorine atom, a chlorine atom, a bromine atom or an iodine atom, a halogenoalkyl group having 1 to 6 carbon atoms and substituted with 1 to 3 halogen atoms, an amino group, a cyano group, an aminoalkyl group, a nitro group, a hydroxyalkyl group (for example, a hydroxymethyl group, a 2-hydroxyethyl group, etc.), an alkoxyalkyl group (for example, a methoxymethyl group, a 2-methoxyethyl group, etc.), a carboxy group, a carboxyalkyl group (for example, a carboxymethyl group, a 2-carboxyethyl group, etc.), an alkoxycarbonylalkyl group (for example, a methoxycarbonylmethyl group, an ethoxycarbonylmethyl group, etc.), an acyl group (for example, an alkanoyl group such as a formyl group, an acetyl group or a propionyl group), an amidino group, a hydroxyamidino group (an amino(hydroxyimino)methyl group), a straight-chained, branched or cyclic alkyl group having 1 to 6 carbon atoms (for example, a methyl group, an ethyl group, etc.), a straight-chained, branched or cyclic alkoxy group having 1 to 6 carbon atoms (for example, a methoxy group, an ethoxy group, etc.), an amidino group substituted with a straight-chained, branched or cyclic alkyl group having 1 to 6 carbon atoms (for example, an imino(methylamino)methyl group, etc.), an amidino group substituted with a straight-chained, branched or cyclic alkoxy group having 1 to 6 carbon atoms (for example, an amino(methoxyimino)methyl group, etc.), an amidino group substituted with a straight-chained, branched or cyclic alkoxycarbonyl group having 2 to 7 carbon atoms (for example, an amino(methoxycarbonylimino)methyl group, an amino(ethoxycarbonylimino)methyl group, etc.), a straight-chained, branched or cyclic alkenyl group having 2 to 6 carbon atoms (for example, a vinyl group, an allyl group, etc.) a straight-chained or branched alkynyl group having 2 to 6 carbon atoms (for example, an ethynyl group, a propynyl group, etc.), a straight-chained, branched or cyclic alkoxycarbonyl group having 2 to 6 carbon atoms (for example, a methoxycarbonyl group, an ethoxycarbonyl group, etc.), a carbamoyl group, a mono- or dialkylcarbamoyl group substituted on the nitrogen atom with a straight-chained, branched or cyclic alkyl group having 1 to 6 carbon atoms (for example, a methylcarbamoyl group, an ethylcarbamoyl group, a dimethylcarbamoyl group, an ethylmethylcarbamoyl group, etc.), a mono- or dialkylamino group substituted with a straight-chained, branched or cyclic alkyl group having 1 to 6 carbon atoms (for example, an ethylamino group, a dimethylamino group, a methylethylamino group), and a 5- to 6-membered nitrogen-containing heterocyclic group (for example, a pyrrolidinyl group, a piperidinyl group, a piperazinyl group, a morpholinyl group, etc.).

The group $Q^4$ is, among the above-mentioned groups, preferably the following 12 groups (a) to (l). Namely, the followings are exemplified as preferred groups.

(a)

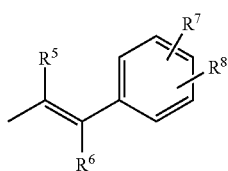

wherein $R^5$ and $R^6$ each independently represent a hydrogen atom, a cyano group, a halogen atom, an alkyl group, a hydroxyalkyl group, an alkoxy group, an alkoxyalkyl group, a carboxy group, a carboxyalkyl group, an acyl group, an alkoxycarbonyl group, an alkoxycarbonylalkyl group, or a phenyl group which may be substituted with a cyano group, a hydroxy group, a halogen atom, an alkyl group or an alkoxy group; and $R^7$ and $R^8$ each independently represent a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group;

(b)

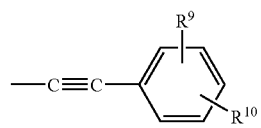

wherein $R^9$ and $R^{10}$ each independently represent a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group;

(c)

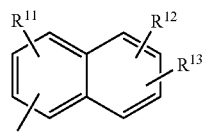

wherein $R^{11}$, $R^{12}$ and $R^{13}$ each independently represent a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group;

(d)

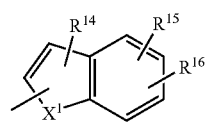

wherein $X^1$ represents $CH_2$, CH, NH, NOH, N, O or S; and $R^{14}$, $R^{15}$ and $R^{16}$ each independently represent a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group;

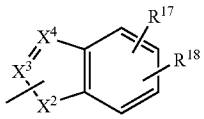 (e)

wherein $X^2$ represents NH, N, O or S; $X^3$ represents N, C or CH; $X^4$ represents N, C or CH; and $R^{17}$ and $R^{18}$ each independently represents a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group, provided that the cases where $X^3$ and $X^4$ represent interchangeably C and CH, and where both represent C or CH are excluded;

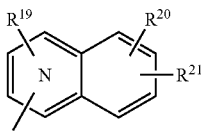 (f)

wherein N indicates that 1 or 2 carbon atoms of the ring substituted with $R^{19}$ have been replaced with a nitrogen atom; and $R^{19}$, $R^{20}$ and $R^{21}$ each independently represent a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group;

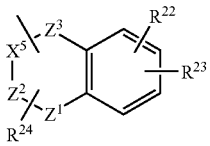 (g)

wherein $X^5$ represents $CH_2$, CH, N or NH; $Z^1$ represents N, NH or O; $Z^2$ represents $CH_2$, CH, C or N; $Z^3$ represents $CH_2$, CH, S, $SO_2$ or C=O; $X^5$-$Z^2$ indicates that $X^5$ and $Z^2$ are bound to each other through a single bond or a double bond; $R^{22}$ and $R^{23}$ each independently represent a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group; and $R^{24}$ represents a hydrogen atom or an alkyl group;

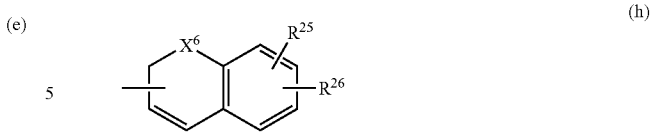 (h)

wherein $X^6$ represents O or S; and $R^{25}$ and $R^{26}$ each independently represent a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group;

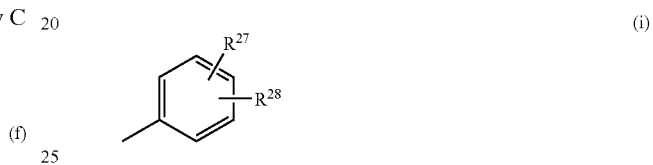 (i)

wherein $R^{27}$ and $R^{28}$ each independently represent a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group;

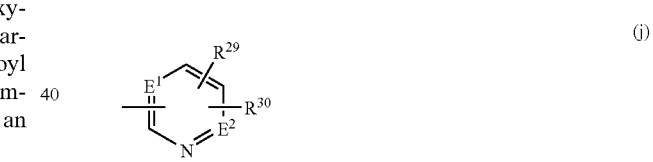 (j)

wherein $E^1$ and $E^2$ each independently represent N or CH; and $R^{29}$ and $R^{30}$ each independently represent a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group;

 (k)

wherein $Y^1$ represents CH or N; $Y^2$ represents —N($R^{33}$)— (wherein $R^{33}$ represents a hydrogen atom or an alkyl group having 1 to 6 carbon atoms), O or S; and $R^{31}$ and $R^{32}$ each independently represents a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group;

and the following group

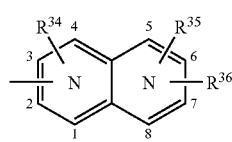

(l)

wherein numbers 1 to 8 indicate positions, each N indicates that any one of carbon atoms at position 1 to 4 and any one of carbon atoms at position 5 to 8 have been respectively replaced with a nitrogen atom; and $R^{34}$, $R^{35}$ and $R^{36}$ each independently represent a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group.

Hereinafter, the above groups will be further described.

The halogen atom described for $R^5$ to $R^{36}$ in the above groups represents a fluorine atom, a chlorine atom, a bromine atom or an iodine atom; the alkyl group represents a straight-chained, branched or cyclic alkyl group having 1 to 6 carbon atoms; the alkenyl group represents a straight-chained, branched or cyclic alkenyl group having 2 to 6 carbon atoms; the alkynyl group represents a straight-chained or branched alkynyl group having 2 to 6 carbon atoms; the hydroxyalkyl group represents a $C_1$-$C_6$ alkyl group as described above, which has been substituted with a hydroxy group; the alkoxy group represents a straight-chained, branched or cyclic alkoxy group having 1 to 6 carbon atoms; the alkoxyalkyl group represents a $C_1$-$C_6$ alkyl group as described above, which has been substituted with one of the $C_1$-$C_6$ alkoxy group described above; the carboxyalkyl group represents a $C_1$-$C_6$ alkyl group as described above, which has been substituted with a carboxy group; the acyl group represents an alkanoyl group having 1 to 6 carbon atoms (including formyl), an aroyl group such as a benzoyl group or a naphthoyl group, or an arylalkanoyl group in which the above-described $C_1$-$C_6$ alkanoyl group is substituted with the above-described $C_6$-$C_{14}$ aryl group; the N-alkylcarbamoyl group represents a carbamoyl group having the above-described $C_1$-$C_6$ alkyl group substituted on the nitrogen atom; the N,N-dialkylcarbamoyl group represents a carbamoyl group having two of the above-described $C_1$-$C_6$ alkyl groups substituted on the nitrogen atom; the alkoxycarbonyl group represents a group consisting of the above-described $C_1$-$C_6$ alkoxy group and a carbonyl group; the alkoxycarbonylalkyl group represents the $C_1$-$C_6$ alkyl group as described above, which has been substituted with the $C_1$-$C_6$ alkoxycarbonyl group, a halogenoalkyl group represents the $C_1$-$C_6$ alkyl group as described above, which has been substituted with 1 to 3 halogen atoms. In the above description, the position of substitution is not particularly limited.

With regard to the following group:

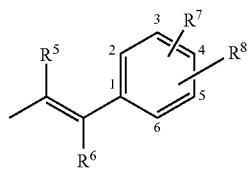

(a)

wherein $R^5$, $R^6$, $R^7$ and $R^8$ have the same meanings as defined above; numbers 1 to 6 indicate positions, $R^5$ and $R^6$ are preferably each independently a hydrogen atom, a cyano group, a halogen atom, an alkyl group, an alkenyl group, an alkynyl group or a halogenoalkyl group. $R^5$ and $R^6$ are each more preferably a hydrogen atom, a halogen atom or an alkyl group; in this case, the halogen atom is preferably a fluorine atom, and the alkyl group is preferably a methyl group. Furthermore, $R^7$ and $R^8$ are preferably such that one of them is a hydrogen atom, and the other is a hydrogen atom, a cyano group, a halogen atom, an alkyl group, an alkenyl group, an alkynyl group or a halogenoalkyl group, and it is particularly preferable when the other is a hydrogen atom, a halogen atom, an alkyl group or an alkynyl group. In this case, the halogen atom is preferably a fluorine atom, a chlorine atom and a bromine atom, the alkyl group is preferably a methyl group, and the alkynyl group is particularly preferably an ethynyl group. As specific groups represented by the above formula, a chlorostyryl group, a fluorostyryl group, a bromostyryl group, a methylstyryl group, an ethynylstyryl group and the like may be mentioned as preferred examples, and the position on these groups at which the halogen atom, alkyl group or alkynyl group is substituted is not particularly limited, but the 4-position in the above formula is particularly preferred. Specifically, a 4-chlorostyryl group, a 4-fluorostyryl group, a 4-bromostyryl group, a 4-methylstyryl group, a 4-ethynylstyryl group, a α-fluoro-4-chlorostyryl group, a α-fluoro-4-fluorostyryl group, a α-fluoro-4-bromostyryl group and the like may be mentioned as preferred groups.

In the following group:

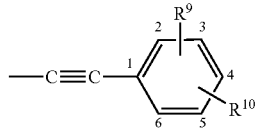

(b)

wherein $R^9$ and $R^{10}$ have the same meanings as defined above; and numbers 1 to 6 indicate positions, $R^9$ and $R^{10}$ are preferably each independently a hydrogen atom, a halogen atom, an alkyl group or an alkynyl group. Furthermore, it is preferable when $R^9$ is a hydrogen atom, and $R^{10}$ is a hydrogen atom, a halogen atom, an alkyl group or an alkynyl group. In this case, the halogen atom is preferably a fluorine atom, a chlorine atom or a bromine atom, the alkyl group is preferably a methyl group, and the alkynyl group is particularly preferably an ethynyl group. As specific groups represented by the above formula, a chlorophenylethynyl group, a fluorophenylethynyl group, a bromophenylethynyl group, a methylphenylethynyl group, an ethynylphenylethynyl group and the like may be mentioned as preferred examples, and the position in the above formula at which the halogen atom, alkyl group or alkynyl group is substituted is not particularly limited, but the 4-position in the above formula is particularly preferred. Specifically, a 4-chlorophenylethynyl group, a 4-fluorophenylethynyl group, a 4-bromophenylethynyl group, a 4-methylphenylethynyl group, a 4-ethynylphenylethynyl group and the like may be mentioned as preferred groups.

In the following group:

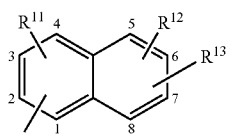

(c)

wherein $R^{11}$, $R^{12}$ and $R^{13}$ have the same meanings as defined above; and numbers 1 to 8 indicate positions, $R^{11}$, $R^{12}$ and $R^{13}$ are preferably each independently a hydrogen atom, a cyano group, a halogen atom, an alkyl group, an alkenyl group, an alkynyl group or a halogenoalkyl group. $R^{11}$ is preferably a hydrogen atom, an alkyl group, a halogen atom or a hydroxy group, and particularly preferably a hydrogen atom. $R^{12}$ and $R^{13}$ are preferably such that one of them is a hydrogen atom, and the other is a hydrogen atom, a cyano group, a halogen atom, an alkyl group, an alkenyl group, an alkynyl group or a halogenoalkyl group, and it is particularly preferable that the other is a hydrogen atom, a halogen atom, an alkyl group or an alkynyl group. In this case, the halogen atom is preferably a fluorine atom, a chlorine atom or a bromine atom, the alkyl group is preferably a methyl group, and the alkynyl group is preferably an ethynyl group. The naphthyl group in the above is preferably a 2-naphthyl group, rather than a 1-naphthyl group, and in the case of being a 2-naphthyl group, the position at which the halogen atom, alkyl group or alkynyl group is substituted is not particularly limited, but the 6-position or 7-position in the above formula is preferred, with the 6-position being most preferred. Furthermore, it is more preferable that the naphthyl group is substituted with a chlorine atom, a fluorine atom, a bromine atom, an alkynyl group or the like, and particularly preferably with a chlorine atom, a fluorine atom, a bromine atom, an alkynyl group or the like. Specifically, a 6-chloro-2-naphthyl group, a 6-fluoro-2-naphthyl group, a 6-bromo-2-naphthyl group, a 6-ethynyl-2-naphthyl group, a 7-chloro-2-naphthyl group, a 7-fluoro-2-naphthyl group, a 7-bromo-2-naphthyl group, a 7-ethynyl-2-naphthyl group and the like may be mentioned as preferred examples.

In the following group:

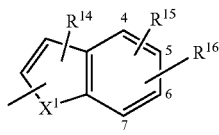

(d)

wherein $X^1$, $R^{14}$, $R^{15}$ and $R^{16}$ have the same meanings as defined above; and numbers 4 to 7 indicate positions, $X^1$ is preferably NH, NOH, N, O or S, and more preferably NH, O or S. $R^{14}$ is preferably a hydrogen atom, a halogen atom, an acyl group, an N-alkylcarbamoyl group, an N,N-dialkylcarbamoyl group or an alkyl group, and $R^{15}$ and $R^{16}$ are preferably each independently a hydrogen atom, a cyano group, a halogen atom, an alkyl group, an alkenyl group, an alkynyl group or a halogenoalkyl group. $R^{15}$ and $R^{16}$ are preferably such that one of them is a hydrogen atom or a halogen atom, preferably a fluorine atom or a chlorine atom, and the other is a hydrogen atom, a cyano group, a halogen atom, an alkyl group, an alkenyl group, an alkynyl group or a halogenoalkyl group, and it is particularly preferable that the other is a hydrogen atom, a halogen atom, an alkyl group or an alkynyl group. In this case, the halogen atom is preferably a fluorine atom, a chlorine atom or a bromine atom, the alkyl group is preferably a methyl group, and the alkynyl group is preferably an ethynyl group. The position at which the halogen atom, alkyl group or alkynyl group is substituted is not particularly limited, but the 4-position, 5-position or 6-position in the above formula is preferred.

As specific groups represented by the above formula, preferred examples may include a 5-chloroindolyl group, a 5-fluoroindolyl group, a 5-bromoindolyl group, a 5-ethynylindolyl group, a 5-methylindolyl group, a 5-chloro-4-fluoroindolyl group, a 5-chloro-3-fluoroindolyl group, a 5-fluoro-3-chloroindolyl group, a 5-ethynyl-3-fluoroindolyl group, a 5-chloro-3-(N,N-dimethylcarbamoyl)indolyl group, a 5-fluoro-3-(N,N-dimethylcarbamoyl)indolyl group, a 5-chloro-3-formylimidolyl group, a 5-fluoro-3-formylindolyl group, a 6-chloroindolyl group, a 6-fluoroindolyl group, a 6-bromoindolyl group, a 6-ethynylindolyl group, a 6-methylindolyl group, a 5-chlorobenzothienyl group, a 5-fluorobenzothienyl group, a 5-bromobenzothienyl group, a 5-ethynylbenzothienyl group, a 5-methylbenzothienyl group, a 5-chloro-4-fluorobenzothienyl group, a 6-chlorobenzothienyl group, a 6-fluorobenzothienyl group, a 6-bromobenzothienyl group, a 6-ethynylbenzothienyl group, a 6-methylbenzothienyl group, a 5-chlorobenzofuryl group, a 5-fluorobenzofuryl group, a 5-bromobenzofuryl group, a 5-ethynylbenzofuryl group, a 5-methylbenzofuryl group, a 5-chloro-4-fluorobenzofuryl group, a 6-chlorobenzofuryl group, a 6-fluorobenzofuryl group, a 6-bromobenzofuryl group, a 6-ethynylbenzofuryl group, a 6-methylbenzofuryl group or the like.

The position at which these substituents are attached to $T^1$ is not particularly limited, but preferred examples may include the 2-position or 3-position in the above formula (d) is preferred. Specifically, a 5-chloroindol-2-yl group, a 5-fluoroindol-2-yl group, a 5-bromoindol-2-yl group, a 5-ethynylindol-2-yl group, a 5-methylindol-2-yl group, a 5-chloro-4-fluoroindol-2-yl group, a 5-chloro-3-fluoroindol-2-yl group, a 3-bromo-5-chloroindol-2-yl group, a 3-chloro-5-fluoroindol-2-yl group, a 3-bromo-5-fluoroindol-2-yl group, a 5-bromo-3-chloroindol-2-yl group, a 5-bromo-3-fluoroindol-2-yl group, a 5-chloro-3-formylindol-2-yl group, a 5-fluoro-3-formylindol-2-yl group, a 5-bromo-3-formylindol-2-yl group, a 5-ethynyl-3-formylindol-2-yl group, a 5-chloro-3-(N,N-dimethylcarbamoyl)indol-2-yl group, a 5-fluoro-3-(N,N-dimethylcarbamoyl)indol-2-yl group, a 5-bromo-3-(N,N-dimethylcarbamoyl)indol-2-yl group, a 5-ethynyl-3-(N,N-dimethylcarbamoyl)indol-2-yl group, a 6-chloroindol-2-yl group, a 6-fluoroindol-2-yl group, a 6-bromoindol-2-yl group, a 6-ethynylindol-2-yl group, a 6-methylindol-2-yl group, a 5-chloroindol-3-yl group, a 5-fluoroindol-3-yl group, a 5-bromoindol-3-yl group, a 5-ethynylindol-3-yl group, a 5-methylindol-3-yl group, a 5-chloro-4-fluoroindol-3-yl group, a 6-chloroindol-3-yl group, a 6-fluoroindol-3-yl group, a 6-bromoindol-3-yl group, a 6-ethynylindol-3-yl group, a 6-methylindol-3-yl group, a 5-chlorobenzothiophen-2-yl group, a 5-fluorobenzothiophen-2-yl group, a 5-bromobenzothiophen-2-yl group, a 5-ethynylbenzothiophen-2-yl group, a 5-methylbenzothiophen-2-yl group, a 5-chloro-4-fluorobenzothiophen-2-yl group, a 6-chlorobenzothiophen-2-yl group, a 6-fluorobenzothiophen-2-yl group, a 6-bromobenzothiophen-2-yl group, a 6-ethynylbenzothiophen-2-yl group, a 6-methylbenzothiophen-2-yl group, a 5-chlorobenzothiophen-3-yl group, a 5-fluorobenzothiophen-3-yl group, a 5-bromobenzothiophen-3-yl group, a 5-ethynylbenzothiophen-3-yl group, a 5-methylbenzothiophen-3-yl group, a 5-chloro-4-fluorobenzothiophen-3-yl group, a 6-chlorobenzothiophen-3-yl group, a 6-fluorobenzothiophen-3-yl group, a 6-bromobenzothiophen-3-yl group, a 6-ethynylbenzothiophen-3-yl group, a 6-methylbenzothiophen-3-yl group, a 5-chlorobenzofuran-2-yl group, a 5-fluorobenzofuran-2-yl group, a 5-bromobenzofuran-2-yl group, a 5-ethynylbenzofuran-2-yl group, a 5-methylbenzofuran-2-yl group, a 5-chloro-4-fluorobenzofuran-2-yl group, a 6-chlorobenzofuran-2-yl group, a 6-fluorobenzofuran-2-yl group, a 6-bromobenzofuran-2-yl group, a 6-ethynylbenzofuran-2-yl group, a 6-methylbenzofuran-2-yl group, a 5-chlorobenzofuran-3-yl group, a 5-fluorobenzofuran-3-yl group, a 5-bromobenzofuran-3-yl group, a 5-ethynylbenzofuran-3-yl group, a 5-methylbenzofuran-3-yl group, a 5-chloro-4-fluorobenzofuran-3-yl group, a 6-chlorobenzofuran-3-yl group, a 6-fluorobenzofuran-3-yl group, a 6-bromobenzofuran-3-yl group, a 6-ethynylbenzofuran-3-yl group, a 6-methylbenzofuran-3-yl group or the like; and particularly preferred is a 5-chloroindol-2-yl group, a 5-fluoroindol-2-yl group, a 5-bromoindol-2-yl group, a 5-ethynylindol-2-yl group, a 5-methylindol-2-yl group, a 5-chloro-4-fluoroindol-2-yl group, a 6-chloroindol-2-yl group, a 6-fluoroindol-2-yl group, a 6-bromoindol-2-yl group, a 6-ethynylindol-2-yl group, a 6-methylindol-2-yl group, a 5-chloro-3-fluoroindol-2-yl group, a 3-bromo-5-chloroindol-2-yl group, a 3-chloro-5-fluoroindol-2-yl group, a 3-bromo-5-fluoroindol-2-yl group, a 5-bromo-3-chloroindol-2-yl group, a 5-bromo-3-fluoroindol-2-yl group, a 5-chloro-3-formylindol-2-yl group, a 5-fluoro-3-formylindol-2-yl group, a 5-bromo-3-formylindol-2-yl group, a 5-ethynyl-3-formylindol-2-yl group, a 5-chloro-3-(N,N-dimethylcarbamoyl)indol-2-yl group, a 5-fluoro-3-(N,N-dimethylcarbamoyl)indol-2-yl group, a 5-bromo-3-(N,N-dimethylcarbamoyl)indol-2-yl group, a 5-ethynyl-3-(N,N-dimethylcarbamoyl)indol-2-yl group, a 5-chlorobenzothiophen-2-yl group, a 5-fluorobenzothiophen-2-yl group, a 5-bromobenzothiophen-2-yl group, a 5-ethynylbenzothiophen-2-yl group, a 5-methylbenzothiophen-2-yl group, a 5-chloro-4-fluorobenzothiophen-2-yl group, a 6-chlorobenzothiophen-2-yl group, a 6-fluorobenzothiophen-2-yl group, a 6-bromobenzothiophen-2-yl group, a 6-ethynylbenzothiophen-2-yl group, a 6-methylbenzothiophen-2-yl group, a 5-chlorobenzofuran-2-yl group, a 5-fluorobenzofuran-2-yl group, a 5-bromobenzofuran-2-yl group, a 5-ethynylbenzofuran-2-yl group, a 5-methylbenzofuran-2-yl group, a 5-chloro-4-fluorobenzofuran-2-yl group, a 6-chlorobenzofuran-2-yl group, a 6-fluorobenzofuran-2-yl group, a 6-bromobenzofuran-2-yl group, a 6-ethynylbenzofuran-2-yl group, or a 6-methylbenzofuran-2-yl group.

In the following group:

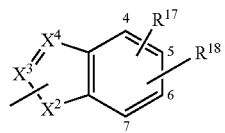

(e)

wherein $X^2$, $X^3$, $X^4$, $R^{17}$ and $R^{18}$ have the same meanings as defined above; and numbers 4 to 7 indicate positions, $X^2$ is preferably NH, O or S; and $X^3$ and $X^4$ are preferably such that any one of them is CH or C, and it is particularly preferable that one of them is C. $R^{17}$ and $R^{18}$ are preferably each independently a hydrogen atom, a cyano group, a halogen atom, an alkyl group, an alkenyl group, an alkynyl group or a halogenoalkyl group. $R^{17}$ and $R^{18}$ are preferably such that one of them is a hydrogen atom, and the other is a hydrogen atom, a cyano group, a halogen atom, an alkyl group, an alkenyl group, an alkynyl group or a halogenoalkyl group, and it is particularly preferable that the other is a hydrogen atom, a halogen atom, an alkyl group or an alkynyl group. In this case, the halogen atom is preferably a fluorine atom, a chlorine atom or a bromine atom, the alkyl group is preferably a methyl group, and the alkynyl group is preferably an ethynyl group. The position at which the halogen atom, alkyl group or alkynyl group is substituted is not particularly limited, but the 5-position or 6-position in the above formula is preferred.

As specific groups represented by the above formula, preferred examples may include a 5-chloroindazolyl group, a 5-fluoroindazolyl group, a 5-bromoindazolyl group, a 5-ethynylindazolyl group, a 6-chloroindazolyl group, a 6-fluoroindazolyl group, a 6-bromoindazolyl group, a 6-ethynylindazolyl group, a 5-chlorobenzimidazolyl group, a 5-fluorobenzimidazolyl group, a 5-bromobenzimidazolyl group, a 5-ethynylbenzimidazolyl group, a 6-chlorobenzimidazolyl group, a 6-fluorobenzimidazolyl group, a 6-bromobenzimidazolyl group, a 6-ethynylbenzimidazolyl group, a 5-chlorobenzothiazolyl group, a 5-fluorobenzothiazolyl group, a 5-bromobenzothiazolyl group, a 5-ethynylbenzothiazolyl group, a 6-chlorobenzothiazolyl group, a 6-fluorobenzothiazolyl group, a 6-bromobenzothiazolyl group, a 6-ethynylbenzothiazolyl group, a 5-chlorobenzoxazolyl group, a 5-fluorobenzoxazolyl group, a 5-bromobenzoxazolyl group, a 5-ethynylbenzoxazolyl group, a 6-chlorobenzoxazolyl group, a 6-fluorobenzoxazolyl group, a 6-bromobenzoxazolyl group, a 6-ethynylbenzoxazolyl group, a 5-chlorobenzisothiazolyl group, a 5-fluorobenzisothiazolyl group, a 5-bromobenzisothiazolyl group, a 5-ethynylbenzisothiazolyl group, a 6-chlorobenzisothiazolyl group, a 6-fluorobenzisothiazolyl group, a 6-bromobenzisothiazolyl group, a 6-ethynylbenzisothiazolyl group, a 5-chlorobenzisoxazolyl group, a 5-fluorobenzisoxazolyl group, a 5-bromobenzisoxazolyl group, a 5-ethynylbenzisoxazolyl group, a 6-chlorobenzisoxazolyl group, a 6-fluorobenzisoxazolyl group, a 6-bromobenzisoxazolyl group, a 6-ethynylbenzisoxazolyl group or the like.

The position at which these substituents are attached to $T^1$ is not particularly limited, but more preferred is a 5-chloroindazol-3-yl group, a 5-fluoroindazol-3-yl group, a 5-bromoindazol-3-yl group, a 5-ethynylindazol-3-yl group, a 6-chloroindazol-3-yl group, a 6-fluoroindazol-3-yl group, a 6-bromoindazol-3-yl group, a 6-ethynylindazol-3-yl group, a 5-chlorobenzimidazol-2-yl group, a 5-fluorobenzimidazol-2-yl group, a 5-bromobenzimidazol-2-yl group, a 5-ethynylbenzimidazol-2-yl group, a 6-chlorobenzimidazol-2-yl group, a 6-fluorobenzimidazol-2-yl group, a 6-bromobenzimidazol-2-yl group, a 6-ethynylbenzimidazol-2-yl group, a 5-chlorobenzothiazol-2-yl group, a 5-fluorobenzothiazol-2-yl group, a 5-bromobenzothiazol-2-yl group, a 5-ethynylbenzothiazol-2-yl group, a 6-chlorobenzothiazol-2-yl group, a 6-fluorobenzothiazol-2-yl group, a 6-bromobenzothiazol-2-yl group, a 6-ethynylbenzothiazol-2-yl group, a 5-chlorobenzoxazol-2-yl group, a 5-fluorobenzoxazol-2-yl group, a 5-bromobenzoxazol-2-yl group, a 5-ethynylbenzoxazol-2-yl group, a 6-chlorobenzoxazol-2-yl group, a 6-fluorobenzoxazol-2-yl group, a 6-bromobenzoxazol-2-yl group, a 6-ethynylbenzoxazol-2-yl group, a 5-chlorobenzisothiazol-3-yl group, a 5-fluorobenzisothiazol-3-yl group, a 5-bromobenzisothiazol-3-yl group, a 5-ethynylbenzisothiazol-3-yl group, a 6-chlorobenzisothiazol-3-yl group, a 6-fluorobenzisothiazol-3-yl group, a 6-bromobenzisothiazol-3-yl group, a 6-ethynylbenzisothiazol-3-yl group, a 5-chlorobenzisoxazol-3-yl group, a 5-fluorobenzisoxazol-3-yl group, a 5-bromobenzisoxazol-3-yl group, a 5-ethynylbenzisoxazol-3-yl group, a 6-chlorobenzisoxazol-3-yl group, a 6-fluorobenzisoxazol-3-yl group, a 6-bromobenzisoxazol-3-yl group, or a 6-ethynylbenzisoxazol-3-yl group; and particularly preferred is a 5-chlorobenzimidazol-2-yl group, a 5-fluorobenzimidazol-2-yl group, a 5-bromobenzimidazol-2-yl group, a 5-ethynylbenzimidazol-2-yl group, a 6-chlorobenzimidazol-2-yl group, a 6-fluorobenzimidazol-2-yl group, a 6-bromobenzimidazol-2-yl group, a 6-ethynylbenzimidazol-2-yl group, a 5-chlorobenzothiazol-2-yl group, a 5-fluorobenzothiazol-2-yl group, a 5-bromobenzothiazol-2-yl group, a 5-ethynylbenzothiazol-2-yl group, a 6-chlorobenzothiazol-2-yl group, a 6-fluorobenzothiazol-2-yl group, a 6-bromobenzothiazol-2-yl group, a 6-ethynylbenzothiazol-2-yl group, a 5-chlorobenzoxazol-2-yl group, a 5-fluorobenzoxazol-2-yl group, a 5-bromobenzoxazol-2-yl group, a 5-ethynylbenzoxazol-2-yl group, a 6-chlorobenzoxazol-2-yl group, a 6-fluorobenzoxazol-2-yl group, a 6-bromobenzoxazol-2-yl group, or a 6-ethynylbenzoxazol-2-yl group, with a 5-chlorobenzimidazol-2-yl group, a 5-fluorobenzimidazol-2-yl group, a 5-bromobenzimidazol-2-yl group or a 5-ethynylbenzimidazol-2-yl group being even more preferred among them.

In the following group:

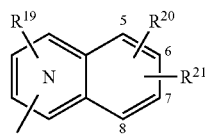

(f)

wherein N indicates that one or two carbon atoms of the ring substituted with $R^{19}$ have been replaced with a nitrogen atom; $R^{19}$, $R^{20}$ and $R^{21}$ have the same meanings as defined above; and numbers 5 to 8 indicate positions, $R^{19}$, $R^{20}$ and $R^{21}$ are preferably each independently a hydrogen atom, a cyano group, a halogen atom, an alkyl group, an alkenyl group, an alkynyl group or a halogenoalkyl group. $R^{19}$ is particularly preferably a hydrogen atom, and $R^{20}$ and $R^{21}$ are preferably such that one of them is a hydrogen atom, and the other is a hydrogen atom, a cyano group, a halogen atom, an alkyl group, an alkenyl group, an alkynyl group or a halogenoalkyl group, and inter alia, it is particularly preferable that the other is a hydrogen atom, a halogen atom, an alkyl group or an alkynyl group. In this case, the halogen atom is preferably a fluorine atom, a chlorine atom or a bromine atom, the alkyl group is preferably a methyl group, and the alkynyl group is preferably an ethynyl group. The position at which the halogen atom, alkyl group or alkynyl group is substituted is not particularly limited, but the 6-position or 7-position in the above formula is preferred.

As specific groups represented by the above formula, included is a quinolinyl group, an isoquinolinyl group and a cinnolinyl group, and preferred is a 6-chloroquinolinyl group, a 6-fluoroquinolinyl group, a 6-bromoquinolinyl group, a 6-ethynylquinolinyl group, a 6-chloroisoquinolinyl group, a 6-fluoroisoquinolinyl group, a 6-bromoisoquinolinyl group, a 6-ethynylisoquinolinyl group, a 7-chloroisoquinolinyl group, a 7-fluoroisoquinolinyl group, a 7-bromoisoquinolinyl group, a 7-ethynylisoquinolinyl group, a 7-chlorocinnolinyl group, a 7-fluorocinnolinyl group, a 7-bromocinnolinyl group, a 7-ethynylcinnolinyl group and the like. Particularly preferred is a 6-chloroquinolin-2-yl group, a 6-fluoroquinolin-2-yl group, a 6-bromoquinolin-2-yl group, a 6-ethynylquinolin-2-yl group, a 6-chloroquinolin-3-yl group, a 6-fluoroquinolin-3-yl group, a 6-bromoquinolin-3-yl group, a 6-ethynylquinolin-3-yl group, a 7-chloroquinolin-2-yl group, a 7-fluoroquinolin-2-yl group, a 7-bromoquinolin-2-yl group, a 7-ethynylquinolin-2-yl group, a 7-chloroquinolin-3-yl group, a 7-fluoroquinolin-3-yl group, a 7-bromoquinolin-3-yl group, a 7-ethynylquinolin-3-yl group, a 6-chloroisoquinolin-3-yl group, a 6-fluoroisoquinolin-3-yl group, a 6-bromoisoquinolin-3-yl group, a 6-ethynylisoquinolin-3-yl group, a 7-chloroisoquinolin-3-yl group, a 7-fluoroisoquinolin-3-yl group, a 7-bromoisoquinolin-3-yl group, a 7-ethynylisoquinolin-3-yl group, a 7-chlorocinnolin-3-yl group, a 7-fluorocinnolin-3-yl group, a 7-bromocinnolin-3-yl group, a 7-ethynylcinnolin-3-yl group and the like. Among them, even more preferred is a 6-chloroquinolin-2-yl group, a 6-fluoroquinolin-2-yl group, a 6-bromoquinolin-2-yl group, a 6-ethynylquinolin-2-yl group, a 7-chloroquinolin-3-yl group, a 7-fluoroquinolin-3-yl group, a 7-bromoquinolin-3-yl group, a 7-ethynylquinolin-3-yl group, a 7-chloroisoquinolin-3-yl group, a 7-fluoroisoquinolin-3-yl group, a 7-bromoisoquinolin-3-yl group, a 7-ethynylisoquinolin-3-yl group, a 7-chlorocinnolin-3-yl group, a 7-fluorocinnolin-3-yl group, a 7-bromocinnolin-3-yl group, and a 7-ethynylcinnolin-3-yl group.

In the following group:

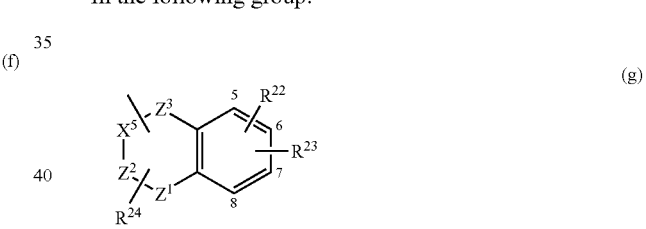

(g)

wherein numbers 5 to 8 indicate positions; $X^5$ represents $CH_2$, CH, N or NH; $Z^1$ represents N, NH or O; $Z^2$ represents $CH_2$, CH, C or N; $Z^3$ represents $CH_2$, CH, S, $SO_2$ or C=O; $X^5$-$Z^2$ indicates that $X^5$ and $Z^2$ are bound to each other through a single bond or a double bond; and $R^{22}$, $R^{23}$ and $R^{24H}$ ave the same meanings as defined above, $R^{22}$ and $R^{23}$ are preferably each independently a hydrogen atom, a cyano group, a halogen atom, an alkyl group, an alkenyl group, an alkynyl group or a halogenoalkyl group. $R^{22}$ and $R^{23}$ are preferably such that one of them is a hydrogen atom, and the other is a hydrogen atom, a cyano group, a halogen atom, an alkyl group, an alkenyl group, an alkynyl group or a halogenoalkyl group, and inter alia, it is particularly preferable that the other is a hydrogen atom, a halogen atom, an alkyl group or an alkynyl group. In this case, the halogen atom is preferably a fluorine atom, a chlorine atom or a bromine atom, the alkyl group is preferably a methyl group, and the alkynyl group is preferably an ethynyl group. The position at which the halogen atom, alkyl group or alkynyl group is substituted is not particularly limited, but the 6-position or 7-position in the above formula is preferred. $R^{24}$ is preferably a hydrogen atom or an alkyl group, with the alkyl group being preferably a methyl group. $R^{24}$ is particularly preferably a hydrogen atom.

As specific groups represented by the above formula, included is a 4-oxodihydroquinolinyl group, a tetrahydroquinolinyl group, a 4-oxodihydroquinazolin-2-yl group, a 4-oxotetrahydrocinnolinyl group, a 4-oxobenzopyranyl group, a 4-oxobenzothiadiazinyl group, a 1,1-dioxy-4-oxobenzothiadiazinyl group, a benzoxadiazinyl group and the like. As more specific groups, included is a 6-chloro-4-oxodihydroquinolinyl group, a 6-fluoro-4-oxodihydroquinolinyl group, a 6-bromo-4-oxodihydroquinolinyl group, a 6-ethynyl-4-oxodihydroquinolinyl group, a 7-chloro-4-oxodihydroquinolinyl group, a 7-fluoro-4-oxodihydroquinolinyl group, a 7-bromo-4-oxodihydroquinolinyl group, a 7-ethynyl-4-oxodihydroquinolinyl group, a 6-chloro-4-oxo-1,4-dihydroquinazolinyl group, a 6-fluoro-4-oxo-1,4-dihydroquinazolinyl group, a 6-bromo-4-oxo-1,4-dihydroquinazolinyl group, a 6-ethynyl 4-oxo-1,4-dihydroquinazolinyl group, a 7-chloro-4-oxo-1,4-dihydroquinazolinyl group, a 7-fluoro-4-oxo-1,4-dihydroquinazolinyl group, a 7-bromo-4-oxo-1,4-dihydroquinazolinyl group, a 7-ethynyl-4-oxo-1,4-dihydroquinazolinyl group, a 6-chloro-1,2,3,4-tetrahydroquinolinyl group, a 6-fluoro-1,2,3,4-tetrahydroquinolinyl group, a 6-bromo-1,2,3,4-tetrahydroquinolinyl group, a 6-ethynyl-1,2,3,4-tetrahydroquinolinyl group, a 7-chloro-1,2,3,4-tetrahydroquinolinyl group, a 7-fluoro-1,2,3,4-tetrahydroquinolinyl group, a 7-bromo-1,2,3,4-tetrahydroquinolinyl group, a 7-ethynyl-1,2,3,4-tetrahydroquinolinyl group, a 6-chloro-1,2,3,4-tetrahydro-4-oxocinnolinyl group, a 6-fluoro-1,2,3,4-tetrahydro-4-oxocinnolinyl group, a 6-bromo-1,2,3,4-tetrahydro-4-oxocinnolinyl group, a 6-ethynyl-1,2,3,4-tetrahydro-4-oxocinnolinyl group, a 7-chloro-1,2,3,4-tetrahydro-4-oxocinnolinyl group, a 7-fluoro-1,2,3,4-tetrahydro-4-oxocinnolinyl group, a 7-bromo-1,2,3,4-tetrahydro-4-oxocinnolinyl group, a 7-ethynyl-1,2,3,4-tetrahydro-4-oxocinnolinyl group, a 6-chloro-4H-4-oxobenzopyranyl group, a 6-fluoro-4H-4-oxobenzopyranyl group, a 6-bromo-4H-4-oxobenzopyranyl group, a 6-ethynyl-4H-4-oxobenzopyranyl group, a 7-chloro-4H-4-oxobenzopyranyl group, a 7-fluoro-4H-4-oxobenzopyranyl group, a 7-bromo-4H-4-oxobenzopyranyl group, a 7-ethynyl-4H-4-oxobenzopyranyl group, a 6-chloro-1,1-dioxy-2H-1,2,4-benzothiadiazinyl group, a 6-fluoro-1,1-dioxy-2H-1,2,4-benzothiadiazinyl group, a 6-bromo-1,1-dioxy-2H-1,2,4-benzothiadiazinyl group, a 6-ethynyl-1,1-dioxy-2H-1,2,4-benzothiadiazinyl group, a 7-chloro-1,1-dioxy-2H-1,2,4-benzothiadiazinyl group, a 7-fluoro-1,1-dioxy-2H-1,2,4-benzothiadiazinyl group, a 7-bromo-1,1-dioxy-2H-1,2,4-benzothiadiazinyl group, a 7-ethynyl-1,1-dioxy-2H-1,2,4-benzothiadiazinyl group, a 6-chloro-2H-1,2,4-benzoxadiazinyl group, a 6-fluoro-2H-1,2,4-benzoxadiazinyl group, a 6-bromo-2H-1,2,4-benzoxadiazinyl group, a 6-ethynyl-2H-1,2,4-benzoxadiazinyl group, a 7-chloro-2H-1,2,4-benzoxadiazinyl group, a 7-fluoro-2H-1,2,4-benzoxadiazinyl group, a 7-bromo-2H-1,2,4-benzoxadiazinyl group, a 7-ethynyl-2H-1,2,4-benzoxadiazinyl group and the like.

Particularly preferred is a 6-chloro-4-oxo-1,4-dihydroquinolin-2-yl group, a 6-fluoro-4-oxo-1,4-dihydroquinolin-2-yl group, a 6-bromo-4-oxo-1,4-dihydroquinolin-2-yl group, a 6-ethynyl-4-oxo-1,4-dihydroquinolin-2-yl group, a 7-chloro-4-oxo-1,4-dihydroquinolin-2-yl group, a 7-fluoro-4-oxo-1,4-dihydroquinolin-2-yl group, a 7-bromo-4-oxo-1,4-dihydroquinolin-2-yl group, a 7-ethynyl-4-oxo-1,4-dihydroquinolin-2-yl group, a 6-chloro-4-oxo-1,4-dihydroquinazolin-2-yl group, a 6-fluoro-4-oxo-1,4-dihydroquinazolin-2-yl group, a 6-bromo-4-oxo-1,4-dihydroquinazolin-2-yl group, a 6-ethynyl-4-oxo-1,4-dihydroquinazolin-2-yl group, a 7-chloro-4-oxo-1,4-dihydroquinazolin-2-yl group, a 7-fluoro-4-oxo-1,4-dihydroquinazolin-2-yl group, a 7-bromo-4-oxo-1,4-dihydroquinazolin-2-yl group, a 7-ethynyl-4-oxo-1,4-dihydroquinazolin-2-yl group, a 6-chloro-1,2,3,4-tetrahydroquinolin-2-yl group, a 6-fluoro-1,2,3,4-tetrahydroquinolin-2-yl group, a 6-bromo-1,2,3,4-tetrahydroquinolin-2-yl group, a 6-ethynyl-1,2,3,4-tetrahydroquinolin-2-yl group, a 6-chloro-1,2,3,4-tetrahydro-4-oxocinnolin-2-yl group, a 6-fluoro-1,2,3,4-tetrahydro-4-oxocinnolin-2-yl group, a 6-bromo-1,2,3,4-tetrahydro-4-oxocinnolin-2-yl group, a 6-ethynyl-1,2,3,4-tetrahydro-4-oxocinnolin-2-yl group, a 7-chloro-1,2,3,4-tetrahydro-4-oxocinnolin-2-yl group, a 7-fluoro-1,2,3,4-tetrahydro-4-oxocinnolin-2-yl group, a 7-bromo-1,2,3,4-tetrahydro-4-oxocinnolin-2-yl group, a 7-ethynyl-1,2,3,4-tetrahydro-4-oxocinnolin-2-yl group, a 6-chloro-4H-4-oxobenzopyran-2-yl group, a 6-fluoro-4H-4-oxobenzopyran-2-yl group, a 6-bromo-4H-4-oxobenzopyran-2-yl group, a 6-ethynyl-4H-4-oxobenzopyran-2-yl group, a 7-chloro-4H-4-oxobenzopyran-2-yl group, a 7-fluoro-4H-4-oxobenzopyran-2-yl group, a 7-bromo-4H-4-oxobenzopyran-2-yl group, a 7-ethynyl-4H-4-oxobenzopyran-2-yl group, a 6-chloro-1,1-dioxy-2H-1,2,4-benzothiadiazin-3-yl group, a 6-fluoro-1,1-dioxy-2H-1,2,4-benzothiadiazin-3-yl group, a 6-bromo-1,1-dioxy-2H-1,2,4-benzothiadiazin-3-yl group, a 6-ethynyl-1,1-dioxy-2H-1,2,4-benzothiadiazin-3-yl group, a 7-chloro-1,1-dioxy-2H-1,2,4-benzothiadiazin-3-yl group, a 7-fluoro-1,1-dioxy-2H-1,2,4-benzothiadiazin-3-yl group, a 7-bromo-1,1-dioxy-2H-1,2,4-benzothiadiazin-3-yl group, a 7-ethynyl-1,1-dioxy-2H-1,2,4-benzothiadiazin-3-yl group, a 6-chloro-2H-1,2,4-benzoxadiazin-3-yl group, a 6-fluoro-2H-1,2,4-benzoxadiazin-3-yl group, a 6-bromo-2H-1,2,4-benzoxadiazin-3-yl group, a 6-ethynyl-2H-1,2,4-benzoxadiazin-3-yl group, a 7-chloro-2H-1,2,4-benzoxadiazin-3-yl group, a 7-fluoro-2H-1,2,4-benzoxadiazin-3-yl group, a 7-bromo-2H-1,2,4-benzoxadiazin-3-yl group, a 7-ethynyl-2H-1,2,4-benzoxadiazin-3-yl group and the like.

Among them, even more preferred is a 6-chloro-4-oxo-1,4-dihydroquinolin-2-yl group, a 6-fluoro-4-oxo-1,4-dihydroquinolin-2-yl group, a 6-bromo-4-oxo-1,4-dihydroquinolin-2-yl group, a 6-ethynyl-4-oxo-1,4-dihydroquinolin-2-yl group, a 6-chloro-4-oxo-1,4-dihydroquinazolin-2-yl group, a 6-fluoro-4-oxo-1,4-dihydroquinazolin-2-yl group, a 6-bromo-4-oxo-1,4-dihydroquinazolin-2-yl group, and a 6-ethynyl-4-oxo-1,4-dihydroquinazolin-2-yl group.

In the following group:

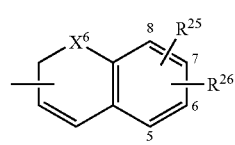

(h)

wherein $X^6$ represents O or S; $R^{25}$ and $R^{26}$ have the same meanings as defined above; and numbers 5 to 8 indicate positions, $X^6$ is preferably O, and $R^{25}$ and $R^{26}$ are preferably each independently a hydrogen atom, a cyano group, a halogen atom, an alkyl group, an alkenyl group, an alkynyl group or a halogenoalkyl group. $R^{25}$ and $R^{26}$ are preferably such that one of them is a hydrogen atom, and the other is a hydrogen atom, a cyano group, a halogen atom, an alkyl group, an alkenyl group, an alkynyl group or a halogenoalkyl group, and inter alia, it is particularly preferable that the other is a hydrogen atom, a halogen atom, an alkyl group or an alkynyl group. In this case, the halogen atom is preferably a fluorine atom, a chlorine atom or a bromine atom, the alkyl group is preferably a methyl group, and the alkynyl group is preferably an ethynyl group. The position at which the halogen atom, alkyl group or alkynyl group is substituted is not particularly limited, but the 6-position or 7-position in the above formula is preferred.

As specific groups, a 6-chloro-2H-chromen-3-yl group, a 6-fluoro-2H-chromen-3-yl group, a 6-bromo-2H-chromen-3-yl group, a 6-ethynyl-2H-chromen-3-yl group, a 7-chloro-2H-chromen-3-yl group, a 7-fluoro-2H-chromen-3-yl group, a 7-bromo-2H-chromen-3-yl group, and a 7-ethynyl-2H-chromen-3-yl group may be included. A 7-chloro-2H-chromen-3-yl group, a 7-fluoro-2H-chromen-3-yl group, a 7-bromo-2H-chromen-3-yl group, and a 7-ethynyl-2H-chromen-3-yl group are particularly preferred.

In the following group:

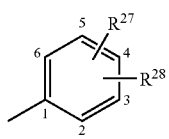

(i)

wherein $R^{27}$ and $R^{28}$ have the same meanings as defined above; and numbers 1 to 6 indicate positions, $R^{27}$ and $R^{28}$ are preferably such that one of them is a hydrogen atom or a halogen atom, and the other is a hydrogen atom, a cyano group, a nitro group, an amino group, a halogen atom, an alkyl group, an alkenyl group, an alkynyl group, a halogenoalkyl group or a N,N-dialkylcarbamoyl group, and inter alia, it is particularly preferable that the other is a hydrogen atom, a halogen atom, an alkyl group or an alkynyl group. In this case, the halogen atom is preferably a fluorine atom, a chlorine atom or a bromine atom, the alkyl group is preferably a methyl group, and the alkynyl group is particularly preferably an ethynyl group. As specific groups represented by the above formula, a phenyl group, a chlorophenyl group, a fluorophenyl group, a bromophenyl group, a methylphenyl group, an ethynylphenyl group, a chlorofluorophenyl group, and the like may be mentioned as preferred examples. The position on these groups at which the halogen atom, alkyl group or alkynyl group is substituted is not particularly limited, but in the case of substituting with one substituent, the 3-position and 4-position in the above formula are particularly preferred, and in the case of substituting with two substituents, a combination of the 4-position and the 2-position or 3-position is particularly preferred.

Specifically, preferred examples may include a phenyl group, a 4-chlorophenyl group, a 4-fluorophenyl group, a 4-bromophenyl group, a 4-methylphenyl group, a 4-ethynylphenyl group, a 3-chlorophenyl group, a 3-fluorophenyl group, a 3-bromophenyl group, a 3-ethynylphenyl group, a 3-chloro-4-fluorophenyl group, a 4-chloro-3-fluorophenyl group, a 4-chloro-2-fluorophenyl group, a 2-chloro-4-fluorophenyl group, a 4-bromo-2-fluorophenyl group, a 2-bromo-4-fluorophenyl group, a 2,4-dichlorophenyl group, a 2,4-difluorophenyl group, a 2,4-dibromophenyl group, a 4-chloro-3-methylphenyl group, a 4-fluoro-3-methylphenyl group, a 4-bromo-3-methylphenyl group, a 4-chloro-2-methylphenyl group, a 4-fluoro-2-methylphenyl group, a 4-bromo-2-methylphenyl group, a 3,4-dichlorophenyl group, a 3,4-difluorophenyl group, and a 3,4-dibromophenyl group.

In the following group:

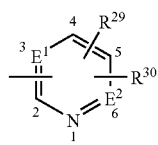

(j)

wherein $E^1$, $E^2$, $R^{29}$ and $R^{30}$ have the same meanings as defined above; and numbers 1 to 6 indicate positions, $R^{29}$ and $R^{30}$ are preferably such that one of them is a hydrogen atom or a halogen atom, and the other is a hydrogen atom, a cyano group, a halogen atom, an alkyl group, an alkenyl group, an alkynyl group or a halogenoalkyl group, and inter alia, it is particularly preferable that the other is a hydrogen atom, a halogen atom, an alkyl group or an alkynyl group. In this case, the halogen atom is preferably a fluorine atom, a chlorine atom or a bromine atom, the alkyl group is a methyl group, and the alkynyl group is particularly preferably an ethynyl group. As specific groups represented by the above formula, a pyridyl group, a pyrimidyl group, a pyridazinyl group and the like may be included. The position at which the halogen atom, alkyl group or alkynyl group is substituted in the formula is not particularly limited, but if the attachment to the group $T^1$ is at the 2-position of the above formula, the 4-position and 5-position in the above formula are particularly preferred.

Specifically, preferred examples may include a 2-pyridyl group, a 3-pyridyl group, a 4-pyridyl group, a 4-chloro-2-pyridyl group, a 4-fluoro-2-pyridyl group, a 4-bromo-2-pyridyl group, a 4-methyl-2-pyridyl group, a 4-ethynyl-2-pyridyl group, a 4-chloro-3-pyridyl group, a 4-fluoro-3-pyridyl group, a 4-bromo-3-pyridyl group, a 4-methyl-3-pyridyl group, a 4-ethynyl-3-pyridyl group, a 5-chloro-2-pyridyl group, a 5-fluoro-2-pyridyl group, a 5-bromo-2-pyridyl group, a 5-methyl-2-pyridyl group, a 5-ethynyl-2-pyridyl group, a 4-chloro-5-fluoro-2-pyridyl group, a 5-chloro-4-fluoro-2-pyridyl group, a 5-chloro-3-pyridyl group, a 5-fluoro-3-pyridyl group, a 5-bromo-3-pyridyl group, a 5-methyl-3-pyridyl group, a 5-ethynyl-3-pyridyl group, a 5-chloro-2-pyrimidyl group, a 5-fluoro-2-pyrimidyl group, a 5-bromo-2-pyrimidyl group, a 5-ethynyl-2-pyrimidyl group, a 4-chloro-3-pyridazinyl group, a 4-fluoro-3-pyridazinyl group, a 4-bromo-3-pyridazinyl group, a 4-ethynyl-3-pyridazinyl group, a 6-chloro-3-pyridazinyl group, a 6-fluoro-3-pyridazinyl group, a 6-bromo-3-pyridazinyl group, a 6-ethynyl-3-pyridazinyl group and the like. In particular, preferred examples is a 2-pyridyl group, a 3-pyridyl group, a 4-pyridyl group, a 4-chloro-2-pyridyl group, a 4-fluoro-2-pyridyl group, a 4-bromo-2-pyridyl group, a 4-methyl-2-pyridyl group, a 4-ethynyl-2-pyridyl group, a 4-chloro-3-pyridyl group, a 4-fluoro-3-pyridyl group, a 4-bromo-3-pyridyl group, a 4-methyl-3-pyridyl group, a 4-ethynyl-3-pyridyl group, a 5-chloro-2-pyridyl group, a 5-fluoro-2-pyridyl group, a 5-bromo-2-pyridyl group, a 5-methyl-2-pyridyl group, a 5-ethynyl-2-pyridyl group, a 4-chloro-5-fluoro-2-pyridyl group, a 5-chloro-4-fluoro-2-pyridyl group, a 5-chloro-3-pyridyl group, a 5-fluoro-3-pyridyl group, a 5-bromo-3-pyridyl group, a 5-methyl-3-pyridyl group, a 5-ethynyl-3-pyridyl group, a 6-chloro-3-pyridazinyl group, a 6-fluoro-3-pyridazinyl group, a 6-bromo-3-pyridazinyl group, a 6-ethynyl-3-pyridazinyl group, a 4-chloro-3-pyridazinyl group, a 4-fluoro-3-pyridazinyl group, a 4-bromo-3-pyridazinyl group, and a 4-ethynyl-3-pyridazinyl group. Among them, more preferred is a 2-pyridyl group, a 3-pyridyl group, a 4-pyridyl group, a 5-chloro-2-pyridyl group, a 5-fluoro-2-pyridyl group, a 5-bromo-2-pyridyl group, a 5-methyl-2-pyridyl group, a 5-ethynyl-2-pyridyl group, a 5-chloro-4-fluoro-2-pyridyl group, a 4-chloro-5-fluoro-2-pyridyl group, a 4-chloro-3-pyridazinyl group, a 4-fluoro-3-pyridazinyl group, a 4-bromo-3-pyridazinyl group, and a 4-ethynyl-3-pyridazinyl group.

Furthermore, in the following group:

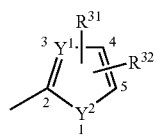

wherein $Y^1$, $Y^2$, $R^{31}$ and $R^{32}$ have the same meanings as defined above; and numbers 1 to 5 indicate positions, $R^{31}$ and $R^{32}$ are preferably such that one of them is a hydrogen atom or a halogen atom, and the other is a hydrogen atom, a cyano group, a halogen atom, an alkyl group, an alkenyl group, an alkynyl group or a halogenoalkyl group, and inter alia, it is particularly preferable that the other is a hydrogen atom, a halogen atom, an alkyl group or an alkynyl group. In this case, the halogen atom is preferably a fluorine atom, a chlorine atom or a bromine atom, the alkyl group is preferably a methyl group, and the alkynyl group is particularly preferably an ethynyl group. As specific groups represented by the above formula, a thienyl group, a pyrrolyl group, a furyl group, an oxazolyl group, a thiazolyl group and the like may be included, and the position at which the halogen atom, alkyl group or alkynyl group is substituted in the formula is not particularly limited, but the 4-position and 5-position in the above formula are particularly preferred. Specifically included is a 4-chloro-2-thienyl group, a 4-fluoro-2-thienyl group, a 4-bromo-2-thienyl group, a 4-methyl-2-thienyl group, a 4-ethynyl-2-thienyl group, a 4-chloro-2-pyrrolyl group, a 4-fluoro-2-pyrrolyl group, a 4-bromo-2-pyrrolyl group, a 4-methyl-2-pyrrolyl group, a 4-ethynyl-2-pyrrolyl group, a 4-chloro-2-furyl group, a 4-fluoro-2-furyl group, a 4-bromo-2-furyl group, a 4-methyl-2-furyl group, a 4-ethynyl-2-furyl group, a 5-chloro-2-thienyl group, a 5-fluoro-2-thienyl group, a 5-bromo-2-thienyl group, a 5-methyl-2-thienyl group, 5-ethynyl-2-thienyl group, a 5-chloro-2-thiazolyl group, a 5-fluoro-2-thiazolyl group, a 5-bromo-2-thiazolyl group, a 5-methyl-2-thiazolyl group, a 5-ethynyl-2-thiazolyl group, a 5-chloro-2-oxazolyl group, a 5-fluoro-2-oxazolyl group, a 5-bromo-2-oxazolyl group, a 5-methyl-2-oxazolyl group, a 5-ethynyl-2-oxazolyl group, and the like. In particular, a 5-chloro-2-thienyl group, a 5-fluoro-2-thienyl group, a 5-bromo-2-thienyl group, a 5-methyl-2-thienyl group, a 5-ethynyl-2-thienyl group, a 5-chloro-2-thiazolyl a group, a 5-fluoro-2-thiazolyl group, a 5-bromo-2-thiazolyl group, a 5-methyl-2-thiazolyl group, and a 5-ethynyl-2-thiazolyl group are preferred.

Furthermore, in the following group:

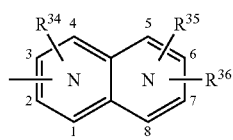

wherein numbers 1 to 8 indicate positions; each N indicates that any one of the carbon atoms of 1 to 4 and any one of the carbon atoms 5 to 8 have been respectively replaced with a nitrogen atom; and $R^{34}$ to $R^{36}$ have the same meanings as defined above, the position of each of the nitrogen atoms may be any position. $R^{34}$ is preferably a hydrogen atom or a halogen atom, $R^{35}$ and $R^{36}$ are preferably such that one of them is a hydrogen atom or a halogen atom, and the other is a hydrogen atom, a cyano group, a halogen atom, an alkyl group, an alkenyl group, an alkynyl group or a halogenoalkyl group, and inter alia, it is particularly preferable that the other is a hydrogen atom, a halogen atom, an alkyl group or an alkynyl group. The halogen atom is preferably a fluorine atom, a chlorine atom or a bromine atom, the alkyl group is preferably a methyl group, and the alkynyl group is particularly preferably an ethynyl group.

The position at which the halogen atom, alkyl group or alkynyl group is substituted is not to be particularly limited, but as specific groups represented by the above formula, included is a 6-chloro-1,5-naphthyridin-2-yl group, a 6-fluoro-1,5-naphthyridin-2-yl group, a 6-bromo-1,5-naphthyridin-2-yl group, a 6-ethynyl-1,5-naphthyridin-2-yl group, a 7-chloro-1,5-naphthyridin-2-yl group, a 7-fluoro-1,5-naphthyridin-2-yl group, a 7-bromo-1,5-naphthyridin-2-yl group, a 7-ethynyl-1,5-naphthyridin-2-yl group, a 6-chloro-1,5-naphthyridin-3-yl group, a 6-fluoro-1,5-naphthyridin-3-yl group, a 6-bromo-1,5-naphthyridin-3-yl group, a 6-ethynyl-1,5-naphthyridin-3-yl group, a 7-chloro-1,5-naphthyridin-3-yl group, a 7-fluoro-1,5-naphthyridin-3-yl group, a 7-bromo-1,5-naphthyridin-3-yl group, a 7-ethynyl-1,5-naphthyridin-3-yl group, a 6-chloro-1,7-naphthyridin-2-yl group, a 6-fluoro-1,7-naphthyridin-2-yl group, a 6-bromo-1,7-naphthyridin-2-yl group, a 6-ethynyl-1,7-naphthyridin-2-yl group, a 6-chloro-1,7-naphthyridin-3-yl group, a 6-fluoro-1,7-naphthyridin-3-yl group, a 6-bromo-1,7-naphthyridin-3-yl group, a 6-ethynyl-1,7-naphthyridin-3-yl group, a 6-chloro-1,8-naphthyridin-2-yl group, a 6-fluoro-1,8-naphthyridin-2-yl group, a 6-bromo-1,8-naphthyridin-2-yl group, a 6-ethynyl-1,8-naphthyridin-2-yl group, a 7-chloro-1,8-naphthyridin-2-yl group, a 7-fluoro-1,8-naphthyridin-2-yl group, a 7-bromo-1,8-naphthyridin-2-yl group, a 7-ethynyl-1,8-naphthyridin-2-yl group, a 6-chloro-1,8-naphthyridin-3-yl group, a 6-fluoro-1,8-naphthyridin-3-yl group, a 6-bromo-1,8-naphthyridin-3-yl group, a 6-ethynyl-1,8-naphthyridin-3-yl group, a 7-chloro-1,8-naphthyridin-3-yl group, a 7-fluoro-1,8-naphthyridin-3-yl group, a 7-bromo-1,8-naphthyridin-3-yl group, a 7-ethynyl-1,8-naphthyridin-3-yl group, a 6-chloro-2,5-naphthyridin-3-yl group, a 6-fluoro-2,5-naphthyridin-3-yl group, a 6-bromo-2,5-naphthyridin-3-yl group, a 6-ethynyl-2,5-naphthyridin-3-yl group, a 7-chloro-2,5-naphthyridin-3-yl group, a 7-fluoro-2,5-naphthyridin-3-yl group, a 7-bromo-2,5-naphthyridin-3-yl group, a 7-ethynyl-2,5-naphthyridin-3-yl group, a 7-chloro-2,6-naphthyridin-3-yl group, a 7-fluoro-2,6-naphthyridin-3-yl group, a 7-bromo-2,6-naphthyridin-3-yl group, a 7-ethynyl-2,8-naphthyridin-3-yl group, a 6-chloro-2,8-naphthyridin-3-yl group, a 6-fluoro-2,8-naphthyridin-3-yl group, a 6-bromo-2,8-naphthyridin-3-yl group, a 6-ethynyl-2,8-naphthyridin-3-yl group, a 7-chloro-2,8-naphthyridin-3-yl group, a 7-fluoro-2,8-naphthyridin-3-yl group, a 7-bromo-2,8-naphthyridin-3-yl group, a 7-ethynyl-2,8-naphthyridin-3-yl group.

Particularly preferred examples thereof include a 7-chloro-2,5-naphthyridin-3-yl group, a 7-fluoro-2,5-naphthyridin-3-yl group, a 7-bromo-2,5-naphthyridin-3-yl group, a 7-ethynyl-2,5-naphthyridin-3-yl group, and the like.

In addition to the 12 groups (a) to (l) described above, a thienopyrrolyl group which may be substituted is also preferred. The thienopyrrolyl group may be substituted with 1 to 3 substituents, and preferred examples of the substituents include a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group and an alkoxycarbonylalkyl group. Among them, preferred examples may include a cyano group, a halogen atom, an alkyl group, an alkenyl group, an alkynyl group and a halogenoalkyl group are preferred. Specifically, a 2-chlorothieno[2,3-b]pyrrol-5-yl group, a 2-fluorothieno[2,3-b]pyrrol-5-yl group, a 2-bromothieno[2,3-b]pyrrol-5-yl group and a 2-ethynylthieno[2,3-b]pyrrol-5-yl group.

[Group $Q^1$]

According to the present invention, $Q^1$ means a saturated or unsaturated, 5- to 6-membered cyclic hydrocarbon group which may be substituted, a saturated or unsaturated, 5- to 7-membered heterocyclic group which may be substituted, a saturated or unsaturated, bicyclic or tricyclic fused hydrocarbon group which may be substituted, or a saturated or unsaturated, bicyclic or tricyclic fused heterocyclic group which may be substituted.

The saturated or unsaturated, 5- to 6-membered cyclic hydrocarbon group may include a cyclopentyl group, a cyclopentenyl group, a cyclohexyl group, a cyclohexenyl group, a phenyl group, and the like, and a cyclopentyl group, a cyclohexyl group and a phenyl group are preferred, with a phenyl group being more preferred.

The saturated or unsaturated, 5- to 7-membered heterocyclic group represents a monovalent group derived from a heterocyclic ring having at least one heteroatom selected from an oxygen atom, a sulfur atom and a nitrogen atom, and examples thereof may include a furyl group, a pyrrolyl group, a thienyl group, a pyrazolyl group, an imidazolyl group, a pyrazolinyl group, an oxazolyl group, an oxazolinyl group, a thiazolyl group, a thiazolinyl group, a thiadiazolyl group, a furazanyl group, a pyranyl group, a pyridyl group, a pyrimidyl group, a pyridazinyl group, a pyrrolidinyl group, a piperazinyl group, a piperidinyl group, an oxazinyl group, an oxadiazinyl group, a morpholinyl group, a thiazinyl group, a thiadiazinyl group, a thiomorpholinyl group, a tetrazolyl group, a triazolyl group, a triazinyl group, an azepinyl group, a diazepinyl group and a triazepinyl group. Among these, preferred is a thienyl group, a pyrazolyl group, an imidazolyl group, an oxazolyl group, a thiazolyl group, a thiadiazolyl group, a furazanyl group, a pyridyl group, a pyrimidyl group, a pyridazinyl group, a pyrrolidinyl group, a piperazinyl group, a piperidinyl group, a morpholinyl group, a thiadiazinyl group and a triazolyl group. A thienyl group, a thiazolyl group, a pyrazolyl group, an imidazolyl group, a pyridyl group, a pyrimidyl group, a pyridazinyl group, a pyrrolidinyl group, a piperazinyl group, a piperidinyl group and a morpholinyl group are more preferred. Among these heterocyclic groups, a nitrogen-containing heterocyclic group may also be converted to an N-oxide.

The saturated or unsaturated, bicyclic or tricyclic fused hydrocarbon group means the same group as the saturated or unsaturated, bicyclic or tricyclic fused hydrocarbon group described in the definition of $Q^4$ in the general formula (1). Specific examples thereof include an indenyl group, an indanyl group, a naphthyl group, a tetrahydronaphthyl group, an anthryl group, a phenanthryl group and the like, and an indenyl group, an indanyl group, a naphthyl group and a tetrahydronaphthyl group are preferred.

The saturated or unsaturated, bicyclic or tricyclic fused heterocyclic group means the same group as the saturated or unsaturated, bicyclic or tricyclic fused heterocyclic group described in the definition of $Q^4$ in the general formula (1). Specific examples thereof include a benzofuryl group, an isobenzofuryl group, a benzothienyl group, an indolyl group, an indolinyl group, an isoindolyl group, an isoindolinyl group, an indazolyl group, a quinolyl group, a dihydroquinolyl group, a 4-oxo-dihydroquinolyl group (dihydroquinolin-4-one), a tetrahydroquinolyl group, an isoquinolyl group, a tetrahydroisoquinolyl group, a chromenyl group, a chromanyl group, an isochromanyl group, a 4H-4-oxobenzopyranyl group, a 3,4-dihydro-4H-4-oxobenzopyranyl group, a 4H-quinolidinyl group, a quinazolinyl group, a dihydroquinazolinyl group, a tetrahydroquinazolinyl group, a quinoxalinyl group, a tetrahydroquinoxalinyl group, a cinnolinyl group, a tetrahydrocinnolinyl group, an indolidinyl group, a tetrahydroindolidinyl group, a benzothiazolyl group, a tetrahydrobenzothiazolyl group, a benzoxazolyl group, a benzisothiazolyl group, a benzisooxazolyl group, a benzimidazolyl group, a naphthylidinyl group, a tetrahydronaphthylidinyl group, a thienopyridyl group, a tetrahydrothienopyridyl group, a thiazolopyridyl group, a tetrahydrothiazolopyridyl group, a thiazolopyridazinyl group, a tetrahydrothiazolopyridazinyl group, a pyrrolopyridyl group, a dihydropyrrolopyridyl group, a tetrahydropyrrolopyridyl group, a pyrrolopyrimidinyl group, a dihydropyrrolopyrimidinyl group, a pyridoquinazolinyl group, a dihydropyridoquinazolinyl group, a pyridopyrimidinyl group, a tetrahydropyridopyrimidinyl group, a pyranothiazolyl group, a dihydropyranothiazolyl group, a furopyridyl group, a tetrahydrofuropyridyl group, an oxazolopyridyl group, a tetrahydrooxazolopyridyl group, an oxazolopyridazinyl group, a tetrahydrooxazolopyridazinyl group, a pyrrolothiazolyl group, a dihydropyrrolothiazolyl group, a pyrrolooxazolyl group, a dihydropyrrolooxazolyl group, a thienopyrrolyl group, a thiazolopyrimidinyl group, a dihydrothiazolopyrimidinyl group, a 4-oxotetrahydrocinnolinyl group, a 1,2,4-benzothiadiazinyl group, a 1,1-dioxy-2H-1,2,4-benzothiadiazinyl group, a 1,2,4-benzoxadiazinyl group, a cyclopentapyranyl group, a thienofuranyl group, a furopyranyl group, a pyridoxazinyl group, a pyrazolooxazolyl group, an imidazothiazolyl group, an imidazopyridyl group, a tetrahydroimidazopyridyl group, a pyrazinopyridazinyl group, a benzisoquinolyl group, a furocinnolyl group, a pyrazolothiazolopyridazinyl group, a tetrahydropyrazolothiazolopyridazinyl group, a hexahydrothiazolopyridazinopyridazinyl group, an imidazotriazinyl group, an oxazolopyridyl group, a benzoxepinyl group, a benzazepinyl group, a tetrahydrobenzazepinyl group, a benzodiazepinyl group, a benzotriazepinyl group, a thienoazepinyl group, a tetrahydrothienoazepinyl group, a thienodiazepinyl group, a thienotriazepinyl group, a thiazoloazepinyl group, a tetrahydrothiazoloazepinyl group, a 4,5,6,7-tetrahydro-5,6-tetramethylenethiazolopyridazinyl group, a 5,6-trimethylene-4, 5,6,7-tetrahydrothiazolopyridazinyl group, and the like. Among these, preferred is a benzothiazolyl group, a tetrahydrobenzothiazolyl group, a thienopyridyl group, a naphthylidinyl group, a tetrahydronaphthylidinyl group, a tetrahydrothienopyridyl group, a thienopyrrolyl group, a thiazolopyridyl group, a tetrahydrothiazolopyridyl group, a thiazolopyridazinyl group, a tetrahydrothiazolopyridazinyl group, a pyrrolopyrimidinyl group, a dihydropyrrolopyrimidinyl group, a pyranothiazolyl group, a dihydropyranothiazolyl group, a furopyridyl group, a tetrahydrofuropyridyl group, an oxazolopyridyl group, a tetrahydrooxazolopyridyl group, a pyrrolopyridyl group, a dihydropyrrolopyridyl group, a tetrahydropyrrolopyridyl group, an oxazolopyridazinyl group, a tetrahydrooxazolopyridazinyl group, a pyrrolothiazolyl group, a dihydropyrrolothiazolyl group, a pyrrolooxazolyl group, a dihydropyrrolooxazolyl group, a thiazolopyrimidinyl group, a dihydrothiazolopyrimidinyl group, a benzazepinyl group, a tetrahydrobenzazepinyl group, a thiazoloazepinyl group, a tetrahydrothiazoloazepinyl group, a thienoazepinyl group, a tetrahydrothienoazepinyl group, a 4,5,6,7-tetrahydro-5,6-tetramethylenethiazolopyridazinyl group and a 5,6-trimethylene 4,5,6,7-tetrahydrothiazolopyridazinyl group. Particularly preferred is a tetrahydrobenzothiazolyl group, a tetrahydronaphthylidinyl group, a tetrahydrothienopyridyl group, a tetrahydrothiazolopyridyl group, a tetrahydrothiazolopyridazinyl group, a dihydropyrrolopyrimidinyl group, a dihydropyranothiazolyl group, a tetrahydrooxazolopyridyl group, a pyrrolopyridyl group, a dihydropyrrolothiazolyl group, a 4,5,6,7-tetrahydro-5,6-tetramethylenethiazolopyridazinyl group and a 5,6-trimethylene-4,5,6,7-tetrahydrothiazolopyridazinyl group.

There is no particular limitation on the type of condensation of the fused heterocyclic group. For example, thienopyridine may be any of thieno[2,3-b]pyridine, thieno[2,3-c]pyridine, thieno[3,2-b]pyridine, thieno[3,2-c]pyridine, thieno[3,4-b]pyridine and thieno[3,4-c]pyridine, and thieno[2,3-c]pyridine and thieno[3,2-c]pyridine are preferred. The thienopyrrolyl group may be any of thieno[2,3-b]pyrrolyl and thieno[3,2-b]pyrrolyl groups. Thiazolopyridine may be any of thiazolo[4,5-b]pyridine, thiazolo[4,5-c]pyridine, thiazolo[5,4-b]pyridine, thiazolo[5,4-c]pyridine, thiazolo[3,4-a]pyridine and thiazolo[3,2-a]pyridine, and thiazolo[4,5-c]pyridine and thiazolo[5,4-c]pyridine are preferred. Thiazolopyridazine may be any of thiazolo[4,5-c]pyridazine, thiazolo[4,5-d]pyridazine, thiazolo[5,4-c]pyridazine, thiazolo[3,2-b]pyridazine, and thiazolo[4,5-d]pyridazine is preferred. Pyrrolopyridine may be any of pyrrolo[2,3-b]pyridine, pyrrolo[2,3-c]pyridine, pyrrolo[3,2-b]pyridine, pyrrolo[3,2-c]pyridine, pyrrolo[3,4-b]pyridine and pyrrolo[3,4-c]pyridine, and pyrrolo[2,3-c]pyridine and pyrrolo[3,2-c]pyridine are preferred. Pyrrolopyrimidine may be any of pyrrolo[3,4-d]pyrimidine, pyrrolo[3,2-d]pyrimidine and pyrrolo[2,3-d]pyrimidine, and pyrrolo[3,4-d]pyrimidine is preferred. Pyridopyrimidine may be any of pyrido[2,3-d]pyrimidine, pyrido[3,2-d]pyrimidine, pyrido[3,4-d]pyrimidine, pyrido[4,3-d]pyrimidine, pyrido[1,2-c]pyrimidine and pyrido[1,2-a]pyrimidine, and pyrido[3,4-d]pyrimidine and pyrido[4,3-d]pyrimidine are preferred. Pyranothiazole may be any of pyrano[2,3-d]thiazole, pyrano[4,3-d]thiazole, pyrano[3,4-d]thiazole and pyrano[3,2-d]thiazole, and pyrano[4,3-d]thiazole and pyrano[3,4-d]thiazole are preferred. Furopyridine may be any of furo[2,3-b]pyridine, furo[2,3-c]pyridine, furo[3,2-b]pyridine, furo[3,2-c]pyridine, furo[3,4-b]pyridine and furo[3,4-c]pyridine, and furo[2,3-c]pyridine and furo[3,2-c]pyridine are preferred. Oxazolopyridine may be any of oxazolo[4,5-b]pyridine, oxazolo[4,5-c]pyridine, oxazolo[5,4-b]pyridine, oxazolo[5,4-c]pyridine, oxazolo[3,4-a]pyridine and oxazolo[3,2-a]pyridine, and oxazolo[4,5-c]pyridine and oxazolo[5,4-c]pyridine are preferred. Oxazolopyridazine may be any of oxazolo[4,5-c]pyridazine, oxazolo[4,5-d]pyridazine, oxazolo[5,4-c]pyridazine and oxazolo[3,4-b]pyridazine, and oxazolo[4,5-d]pyridazine is preferred. Pyrrolothiazole may be any of pyrrolo[2,1-b]thiazole, pyrrolo[1,2-c]thiazole, pyrrolo[2,3-d]thiazole, pyrrolo[3,2-d]thiazole and pyrrolo[3,4-d]thiazole, and pyrrolo[3,4-d]thiazole is preferred. Pyrrolooxazole may be any of pyrrolo[2,1-b]oxazole, pyrrolo[1,2-c]oxazole, pyrrolo[2,3-d]oxazole, pyrrolo[3,2-d]oxazole and pyrrolo[3,4-d]oxazole, and pyrrolo[3,4-d]oxazole is preferred. Benzazepine may be any of 1H-1-benzazepine, 1H-2-benzazepine and 1H-3-benzazepine, and 1H-3-benzazepine is preferred. Thiazolo[4,5-c]azepine may be any of 4H-thiazolo[4,5-c]azepine, 4H-thiazolo[4,5-d]azepine and 4H-thiazolo[5,4-c]azepine, and 4H-thiazolo[4,5-d]azepine is preferred. Thieno[2,3-c]azepine may be any of 4H-thieno[2,3-d]azepine and 4H-thieno[3,2-c]azepine, and 4H-thieno[2,3-d]azepine is preferred.

Furthermore, among these heterocyclic groups, a nitrogen-containing heterocyclic group may be converted to an N-oxide. In addition, the position at which the above-described substituents are attached to $Q^2$ is not particularly limited.

The saturated or unsaturated, 5- to 6-membered cyclic hydrocarbon group, the saturated or unsaturated, 5- to 7-membered heterocyclic group, the saturated or unsaturated, bicyclic or tricyclic fused hydrocarbon group, or the saturated or unsaturated, bicyclic or tricyclic fused heterocyclic group may be substituted with 1 to 3 substituents. Examples of the substituents include a hydroxy group, a halogen atom such as a fluorine atom, a chlorine atom, a bromine atom or an iodine atom, a halogenoalkyl group substituted with 1 to 3 halogen atoms, an amino group, a cyano group, an amidino group, a hydroxyamidino group, a straight-chained, branched or cyclic alkyl group having 1 to 6 carbon atoms (hereinafter referred to as $C_1$-$C_6$ alkyl group, which means those of straight-chained, branched or cyclic form; for example a straight-chained or branched $C_1$-$C_6$ alkyl group such as a methyl group, an ethyl group, an isopropyl group or a tert-butyl group, and a $C_3$-$C_6$ cycloalkyl group such as a cyclopropyl group, a cyclobutyl group, a cyclopentyl group or a 1-methylcyclopropyl group), a $C_3$-$C_6$ cycloalkyl-$C_1$-$C_6$ alkyl group (for example, a cyclopropylmethyl group, etc.), a hydroxy—$C_1$-$C_6$ alkyl group (for example, a hydroxyethyl group, a 1,1-dimethyl-2-hydroxyethyl group, etc.), a $C_1$-$C_6$ alkoxy group (for example, a methoxy group, an ethoxy group, etc.), a $C_1$-$C_6$ alkoxy-$C_1$-$C_6$ alkyl group, a carboxy group, a $C_2$-$C_6$ carboxyalkyl group (for example, a carboxymethyl group, etc.), a $C_2$-$C_6$ alkoxycarbonyl-$C_1$-$C_6$ alkyl group (for example, a methoxycarbonylmethyl group, a tert-butoxycarbonylmethyl group, etc.), an amidino group substituted with a $C_2$-$C_6$ alkoxycarbonyl group, a $C_2$-$C_6$ alkenyl group (for example, a vinyl group, an allyl group, etc.), a $C_2$-$C_6$ alkynyl group (for example, an ethynyl group, a propynyl group, etc.), a $C_2$-$C_6$ alkoxycarbonyl group (for example, a methoxycarbonyl group, an ethoxycarbonyl group, a tert-butoxycarbonyl group, etc.), an amino-$C_1$-$C_6$ alkyl group (for example, an aminomethyl group, an aminoethyl group, etc.), a $C_1$-$C_6$ alkylamino-$C_1$-$C_6$ alkyl group (for example, an N-methylaminomethyl group, an N-ethylaminomethyl group, etc.), a di($C_1$-$C_6$ alkyl)amino-$C_1$-$C_6$ alkyl group (for example, an N,N-dimethylaminomethyl group, an N,N-diethylaminomethyl group, an N-ethyl-N-methylaminomethyl group, etc.), a $C_2$-$C_6$ alkoxycarbonylamino-$C_1$-$C_6$ alkyl group (for example, a methoxycarbonylaminoethyl group, a tert-butoxycarbonylaminoethyl group, etc.), a $C_1$-$C_6$ alkanoyl group (for example, a formyl group, an acetyl group, a methylpropionyl group, a cyclopentanecarbonyl group, etc.), a $C_1$-$C_6$ alkanoylamino-$C_1$-$C_6$ alkyl group (for example, an acetylaminomethyl group, etc.), a $C_1$-$C_6$ alkylsulfonyl group (for example, a methanesulfonyl group, etc.), a $C_1$-$C_6$ alkylsulfonylamino-$C_1$-$C_6$ alkyl group (for example, a methanesulfonylaminomethyl group, etc.), a carbamoyl group, a $C_1$-$C_6$ alkylcarbamoyl group (for example, a methylcarbamoyl group, an ethylcarbamoyl group, an isopropylcarbamoyl group, a tert-butylcarbamoyl group, etc.), an N,N-di($C_1$-$C_6$ alkyl) carbamoyl group (for example, a dimethylcarbamoyl group, a diethylcarbamoyl group, a methylethylcarbamoyl group, etc.), a $C_1$-$C_6$ alkylamino group (for example, an N-methylamino group, an N-ethylamino group, etc.), a di($C_1$-$C_6$ alkyl)amino group (for example, an N,N-dimethylamino group, an N,N-diethylamino group, an N-ethyl-N-methylamino group, etc.), an aminosulfonyl group, an arylsulfonyl group (for example, a phenylsulfonyl group, etc.), an arylcarbonyl group which may be substituted with a halogen atom or the like (a benzoyl group, a 4-fluoro-benzoyl group, etc.), a $C_2$-$C_6$ alkoxycarbonyl($C_1$-$C_6$ alkyl)amino-$C_1$-$C_6$ alkyl group (for example, a methoxycarbonyl(methyl)aminomethyl group, a tert-butoxycarbonyl(methyl)aminomethyl group, etc.), a $C_1$-$C_6$ alkylsulfonyl-$C_1$-$C_6$ alkyl group (for example, a methylsulfonylmethyl group, etc.), a 5- to 6-membered heterocyclic group containing one, or two same or different nitrogen, oxygen or sulfur atoms (for example, a pyrrolidinyl group, a piperidinyl group, a piperazinyl group, a morpholinyl group, a pyridyl group, a pyrimidinyl group, a tetrahydropyranyl group, etc.), the above-mentioned 5- to 6-membered heterocyclic group-$C_1$-$C_4$ alkyl group (for example, a morpholinylmethyl group, etc.), the above-mentioned 5- to 6-membered heterocyclic group-carbonyl group (for example, a pyrrolidinylcarbonyl group, etc.), the above-mentioned 5- to 6-membered heterocyclic group-amino-$C_1$-$C_4$ alkyl group (for example, an N-(oxazol-2-yl)aminomethyl group, etc.), the above-mentioned 5- to 6-membered heterocyclic group-amino group (for example, a pyridylamino group, etc.), the above-mentioned 5- to 6-membered heterocyclic group-oxy group (for example, a 4-pyridinyloxy group, a (1-methyliminopiperidin-4-yl)oxy group, etc.), a 3- to 6-membered heterocyclic group-carbonyl-$C_1$-$C_4$ alkyl group (for example, a 4,4-dioxothiomorpholin-1-yl)carbonylmethyl group, etc.), the above-mentioned 5- to 6-membered heterocyclic group-($C_1$-$C_6$ alkyl)amino-$C_1$-$C_4$ alkyl group (for example, an N-(4,5-dihydro-1,3-oxazol-2-yl)-N-methylaminomethyl group, etc.) and an oxo group.

Specific examples of $Q^1$ include a 5- to 6-membered cyclic hydrocarbon group such as a 2-aminosulfonylphenyl group; a bicyclic heterocyclic group such as a 5-methyl-4,5,6,7-tetrahydrothiazolo[5,4-c]pyridin-2-yl group, a 4,5,6,7-tetrahydrothiazolo[5,4-c]pyridin-2-yl group, a 5-cyclopropyl-4,5,6,7-tetrahydrothiazolo[5,4-c]pyridin-2-yl group, a 5-carboxymethyl-4,5,6,7-tetrahydrothiazolo[5,4-c]pyridin-2-yl group, a 5-butyl-4,5,6,7-tetrahydrothiazolo[5,4-c]pyridin-2-yl group, a 5-(4-pyridyl)-4,5,6,7-tetrahydrothiazolo[5,4-c]pyridin-2-yl group, a 5-methyl-4,5,6,7-tetrahydrothiazolo[4,5-c]pyridin-2-yl group, a 6-methyl-4,5,6,7-tetrahydrothieno[2,3-c]pyridin-2-yl group, a 5-methyl-4,5,6,7-tetrahydrooxazolo[5,4-c]pyridin-2-yl group, a 5-methyl-4,6-dihydro-5H-pyrrolo[3,4-d]thiazol-2-yl group, a 5,7-dihydro-6-methylpyrrolo[3,4-d]pyrimidin-2-yl group, a 5,6-dimethyl-4,5,6,7-tetrahydrothiazolo[4,5-d]pyridazin-2-yl group, a 5,6-dimethyl-4,5,6,7-tetrahydrooxazolo[4,5-d]pyridazin-2-yl group, a 5-dimethylamino-4,5,6,7-tetrahydrobenzo[d]thiazol-2-yl group, a 5-(4-pyridyl)-4,5,6,7-tetrahydrothiazolo[5,4-c]pyridin-2-yl group, or a 6,7-dihydro-4H-pyrano[4,3-d]thiazol-2-yl group; a pyridyl group such as a 4-pyridyl group or a 2-pyridyl group; a dihydroxazolyl group such as a 4,5-dihydroxazol-2-yl group; or a 5- to 6-membered heterocyclic type group such as a 4-[N-(4,5-dihydroxazol-2-yl)-N-methylaminomethyl] thiophen-2-yl group, a 4-[N-(4,5-dihydroxazol-2-yl)-N-methylaminomethyl]-3-chlorothiophen-2-yl group, a 5-(N-methylaminomethyl)thiazol-2-yl group, a 5-(N-methylaminomethyl)thiophen-2-yl group, a 5-(N,N-dimethylaminomethyl)thiazol-2-yl group, a 5-(N,N-dimethylaminomethyl)thiophen-2-yl group or a 5-(N,N-dimethylaminomethyl)pyridin-2-yl group. However, these examples are not intended to limit $Q^1$ in any way.

[Group $Q^2$]

The group $Q^2$ means a single bond, a straight-chained or branched alkylene group having 1 to 6 carbon atoms, a straight-chained or branched alkenylene group having 2 to 6 carbon atoms, a straight-chained or branched alkynylene group having 2 to 6 carbon atoms, a divalent saturated or unsaturated, 5- to 6-membered cyclic hydrocarbon group which may be substituted, a divalent saturated or unsaturated, 5- to 7-membered heterocyclic group which may be substituted, a divalent saturated or unsaturated, bicyclic or tricyclic fused hydrocarbon group which may be substituted, or a divalent saturated or unsaturated, bicyclic or tricyclic fused heterocyclic group which may be substituted.

With regard to the group $Q^2$, the straight-chained or branched alkylene group having 1 to 6 carbon atoms may include a methylene group, an ethylene group, a trimethylene group, a propylene group, a tetramethylene group, a pentamethylene group, a hexamethylene group, and the like.

The straight-chained or branched alkenylene group having 2 to 6 carbon atoms may include a vinylene group, a propenylene group, a butenylene group, a pentenylene group, and the like. In addition, the position of double bond is not particularly limited.

The straight-chained or branched alkynylene group having 2 to 6 carbon atoms may include an ethynylene group, a propynylene group, a butynylene group, a pentynylene group, a hexynylene group, and the like. In addition, the position of triple bond is not particularly limited.

The divalent saturated or unsaturated, 5- to 6-membered cyclic hydrocarbon group means a divalent group derived from the saturated or unsaturated, 5- to 6-membered cyclic hydrocarbon described in the definition of $Q^4$ in the general formula (1), and specific examples thereof include a cyclohexylene group, a cyclohexenylene group, a phenylene group, and the like, with a cyclohexylene group and a phenylene group being preferred.

The divalent saturated or unsaturated, 5- to 7-membered heterocyclic group means a divalent group derived from the saturated or unsaturated, 5- to 7-membered heterocyclic ring described in the definition of $Q^4$ in the general formula (1), and specific examples thereof include divalent groups derived from furan, pyrrole, thiophene, pyrazole, imidazole, oxazole, oxazolidine, thiazole, thiadiazole, furazan, pyrane, pyridine, pyrimidine, pyridazine, pyrrolidine, piperazine, piperidine, oxazine, oxadiazine, morpholine, thiazine, thiadiazine, thiomorpholine, tetrazole, triazole, triazine, azepine, diazepine, triazepine and the like. Among them, divalent groups derived from pyrazole, imidazole, oxazole, thiazole, thiadiazole, furazan, pyridine, pyrimidine, pyridazine, pyrrolidine, piperazine, piperidine, triazole, triazine, azepine, diazepine and triazepine may be mentioned as preferred examples.

The divalent saturated or unsaturated, bicyclic or tricyclic fused hydrocarbon group means a divalent group derived from the saturated or unsaturated, bicyclic or tricyclic fused hydrocarbon described in the definition of $Q^4$ in the general formula (1), and specific examples thereof include divalent groups derived from indene, indane, naphthalene, tetrahydronaphthalene, anthracene, phenanthrene, and the like. Divalent groups derived from indane and naphthalene may be mentioned as preferred examples.

The divalent saturated or unsaturated, bicyclic or tricyclic fused heterocyclic group means a divalent group derived from the saturated or unsaturated, bicyclic or tricyclic fused heterocyclic ring described in the definition of $Q^4$ in the general formula (1). Specific examples thereof include divalent groups derived from benzofuran, benzothiophene, indole, isoindole, indazole, quinoline, tetrahydroquinoline, isoquinoline, tetrahydroisoquinoline, quinazoline, dihydroquinazoline, tetrahydroquinazoline, quinoxaline, tetrahydroquinoxaline, cinnoline, tetrahydrocinnoline, indolizine, tetrahydroindolizine, benzothiazole, tetrahydrobenzothiazole, naphthyridine, tetrahydronaphthyridine, thienopyridine, tetrahydrothienopyridine, thiazolopyridine, tetrahydrothiazolopyridine, thiazolopyridazine, tetrahydrothiazolopyridazine, pyrrolopyridine, dihydropyrrolopyridine, tetrahydropyrrolopyridine, pyrrolopyrimidine, dihydropyrrolopyrimidine, dihydropyridoquinazoline, pyranothiazole, dihydropyranothiazole, furopyridine, tetrahydrofuropyridine, oxazolopyridine, tetrahydroxazolopyridine, oxazolopyridazine, tetrahydroxazolopyridazine, pyrrolothiazole, dihydropyrrolothiazole, pyrrolooxazole, dihydropyrrolooxazole, benzazepine, and the like. Divalent groups derived from benzofuran, benzothiophene, indole, indazole, quinoline, isoquinoline, tetrahydroisoquinoline, benzothiazole, naphthyridine, thienopyridine, thiazolopyridine, tetrahydrothiazolopyridine, thiazolopyridazine, pyrrolopyridine, tetrahydropyrrolopyridine, pyridopyrimidine, pyranothiazole, dihydropyranothiazole, furopyridine, oxazolopyridine, oxazolopyridazine, pyrrolothiazole, dihydropyrrolothiazole, pyrrolooxazole and dihydropyrrolooxazole may be mentioned as preferred examples.

There is no particular limitation on the type of condensation for the above-described fused heterocyclic type group. For example, naphthyridine may be any of 1,5-, 1,6-, 1,7-, 1,8-, 2,6- and 2,7-naphthyridines; thienopyridine may be any of thieno[2,3-b]pyridine, thieno[2,3-c]pyridine, thieno[3,2-b]pyridine, thieno[3,2-c]pyridine, thieno[3,4-b]pyridine and thieno[3,4-c]pyridine; thiazolopyridine may be any of thiazolo[4,5-b]pyridine, thiazolo[4,5-c]pyridine, thiazolo[5,4-b]pyridine, thiazolo[5,4-c]pyridine, thiazolo[3,4-a]pyridine and thiazolo[3,2-a]pyridine; thiazolopyridazine may be any of thiazolo[4,5-c]pyridazine, thiazolo[4,5-d]pyridazine, thiazolo[5,4-c]pyridazine and thiazolo[3,2-b]pyridazine; pyrrolopyridine may be any of pyrrolo[2,3-b]pyridine, pyrrolo[2,3-c]pyridine, pyrrolo[3,2-b]pyridine, pyrrolo[3,2-c]pyridine, pyrrolo[3,4-b]pyridine and pyrrolo[3,4-c]pyridine; pyrrolopyrimidine may be any of pyrrolo[3,4-d]pyrimidine, pyrrolo[3,2-d]pyrimidine and pyrrolo[2,3-d]pyrimidine; pyridopyrimidine may be any of pyrido[2,3-d]pyrimidine, pyrido[3,2-d]pyrimidine and pyrido[3,4-d]pyrimidine; pyranothiazole may be any of pyrano[2,3-d]thiazole, pyrano[4,3-d]thiazole, pyrano[3,4-d]thiazole and pyrano[3,2-d]thiazole; furopyridine may be any of furo[2,3-b]pyridine, furo[2,3-c]pyridine, furo[3,2-b]pyridine, furo[3,2-c]pyridine, furo[3,4-b]pyridine and furo[3,4-c]pyridine; oxazolopyridine may be any of oxazolo[4,5-b]pyridine, oxazolo[4,5-c]pyridine, oxazolo[5,4-b]pyridine, oxazolo[5,4-c]pyridine, oxazolo[3,4-a]pyridine and oxazolo[3,2-a]pyridine; oxazolopyridazine may be any of oxazolo[4,5-c]pyridazine, oxazolo[4,5-d]pyridazine, oxazolo[5,4-c]pyridazine and oxazolo[3,4-b]pyridazine; pyrrolothiazole may be any of pyrrolo[2,1-b]thiazole, pyrrolo[1, 2-c]thiazole, pyrrolo[3,2-d]thiazole and pyrrolo[3,4-d]thiazole; and pyrrolooxazole may be any of pyrrolo[2,1-b]oxazole, pyrrolo[1,2-c]oxazole, pyrrolo[2,3-d]oxazole, pyrrolo[3,2-d]oxazole and pyrrolo[3,4-d]oxazole. Fused forms other than those described above are also allowed.

The divalent saturated or unsaturated, 5- to 6-membered cyclic hydrocarbon group, the divalent saturated or unsaturated, 5- to 7-membered heterocyclic group, the divalent saturated or unsaturated, bicyclic or tricyclic fused hydrocarbon group, and the divalent saturated or unsaturated, bicyclic or tricyclic fused heterocyclic group may be respectively substituted with 1 to 3 substituents. Examples of the substituents include a hydroxy group, a halogen atom such as a fluorine atom, a chlorine atom, a bromine atom or an iodine atom, a halogenoalkyl group substituted with 1 to 3 halogen atoms, an amino group, a cyano group, an aminoalkyl group, an amidino group, a hydroxyamidino group, a straight-chained, branched or cyclic alkyl group having 1 to 6 carbon atoms (for example, a methyl group, an ethyl group, etc.), a straight-chained, branched or cyclic alkoxy group having 1 to 6 carbon atoms (for example, a methoxy group, an ethoxy group, etc.), an amidino group substituted with a straight-chained, branched or cyclic alkoxycarbonyl group having 2 to 7 carbon atoms (for example, a methoxycarbonylamidino group, an ethoxycarbonylamidino group, etc.), a straight-chained, branched or cyclic alkenyl group having 2 to 6 carbon atoms (for example, a vinyl group, an allyl group, etc.), a straight-chained or branched alkynyl group having 2 to 6 carbon atoms (for example, an ethynyl group, a propynyl group, etc.), a straight-chained, branched or cyclic alkoxycarbonyl group having 2 to 6 carbon atoms (for example, a methoxycarbonyl group, an ethoxycarbonyl group, etc.), and a carbamoyl group.

Among the groups for $Q^2$ described above, a single bond, a divalent saturated or unsaturated, 5- to 6-membered cyclic hydrocarbon group which may be substituted, a divalent saturated or unsaturated, 5- to 7-membered heterocyclic group which may be substituted, and a divalent saturated or unsaturated, bicyclic or tricyclic fused heterocyclic group which may be substituted are preferred. Among them, a single bond, a divalent saturated or unsaturated, 5- to 6-membered cyclic hydrocarbon group, and a divalent saturated or unsaturated, 5- to 7-membered heterocyclic group are more preferred.

Moreover, when the group $Q^1$ is a saturated or unsaturated, bicyclic or tricyclic fused hydrocarbon group which may be substituted or a saturated or unsaturated, bicyclic or tricyclic fused heterocyclic group which may be substituted, the group $Q^2$ is preferably a single bond. Here, with regard to the combination described above, the case where $Q^2$ is a single bond implies that the general formula (1):

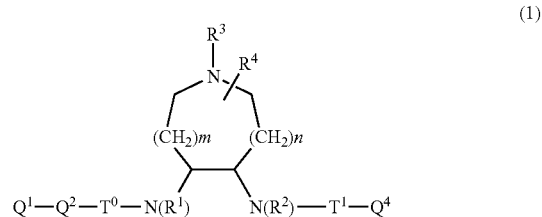

(1)

wherein $R^1$, $R^2$, $R^3$, $R^4$, $Q^1$, $Q^2$, $Q^4$, m, n, $T^0$ and $T^1$ have the same meanings as defined above, is of the following general formula (1'):

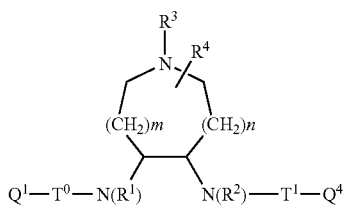

wherein $Q^1$ represents the above-mentioned bicyclic or tricyclic fused hydrocarbon group, or bicyclic or tricyclic fused heterocyclic group; and $R^1$, $R^2$, $R^3$, $R^4$, $Q^4$, m, n, $T^0$ and $T^1$ have the same meanings as defined above.

Even more preferably, the group $Q^1$ is a thienopyridyl group which may be substituted, a tetrahydrothienopyridyl group which may be substituted, a naphthylidinyl group which may be substituted, a tetrahydronaphthylidinyl group which may be substituted, a thiazolopyridyl group which may be substituted, a tetrahydrothiazolopyridyl group which may be substituted, a thiazolopyridazinyl group which may be substituted, a tetrahydrothiazolopyridazinyl group which may be substituted, a pyranothiazolyl group which may be substituted, a dihydropyranothiazolyl group which may be substituted, a furopyridyl group which may be substituted, a tetrahydrofuropyridyl group which may be substituted, an oxazolopyridyl group which may be substituted, a tetrahydroxazolopyridyl group which may be substituted, a pyrrolopyridyl group which may be substituted, a dihydropyrrolopyridyl group which may be substituted, a tetrahydropyrrolopyridyl group which may be substituted, a pyrrolopyrimidinyl group which may be substituted, a dihydropyrrolopyrimidinyl group which may be substituted, a oxazolopyridazinyl group which may be substituted, a tetrahydroxazolopyridazinyl group which may be substituted, a pyrrolothiazolyl group which may be substituted, a dihydropyrrolothiazolyl group which may be substituted, a pyrroloooxazolyl group which may be substituted, a dihydropyrroloooxazolyl group which may be substituted, a benzothiazolyl group which may be substituted, a tetrahydrobenzothiazolyl group which may be substituted, a thiazolopyrimidinyl group which may be substituted, a dihydrothiazolopyrimidinyl group which may be substituted, a benzazepinyl group which may be substituted, a tetrahydrobenzazepinyl group which may be substituted, a thiazoloazepinyl group which may be substituted, a tetrahydrothiazoloazepinyl group which may be substituted, a thienoazepinyl group which may be substituted, a tetrahydrothienoazepinyl group which may be substituted, a 4,5,6,7-tetrahydro-5,6-tetramethylenethiazolopyridazinyl group which may be substituted, or a 5,6-trimethylene-4,5,6,7-tetrahydrothiazolopyridazinyl group which may be substituted, while the group $Q^2$ is a single bond.

Furthermore, when the group $Q^1$ is a saturated or unsaturated 5- to 6-membered cyclic hydrocarbon group which may be substituted or a substituted saturated or unsaturated 5- to 7-membered heterocyclic group, the group $Q^2$ is preferably a divalent saturated or unsaturated, 5- to 6-membered cyclic hydrocarbon group which may be substituted, or a divalent saturated or unsaturated, 5- to 7-membered heterocyclic group which may be substituted. As the group $Q^1$-$Q^2$-, preferred examples is a 4-(4-pyridyl)phenyl group, a 4-(2-pyridyl)phenyl group, a 5-(4-pyridyl)thiazolyl group, a 1-(4-pyridyl)piperidyl group, a 4-(4-pyridyl)piperidyl group, a 4-hydroxy-1-(4-pyridyl)piperidin-4-yl group, a biphenyl group, a 4-(2-aminosulfonylphenyl)phenyl group, a 4-(2-amidinophenyl)phenyl group, a 4-(2-methylsulfonylphenyl)phenyl group, a 4-(2-aminomethylphenyl)phenyl group, a 4-(2-carbamoylphenyl)phenyl group, a 4-(2-imidazolyl)phenyl group, a 4-(1-methyl-2-imidazolyl)phenyl group, a 4-(2,3,4,5-tetrahydropyrimidin-2-yl)phenyl group, a 4-(1-methyl-2,3,4,5-tetrahydropyrimidin-2-yl)phenyl group, a 4-(5-tetrazolyl)phenyl group, a 1-(4-pyridyl)piperidin-4-yl group, a 3-(4-piperidyl)isoxazolin-5-yl group, a 3-(4-amidinophenyl)isoxazolin-5-yl group, a 3-(4-piperidyl)isoxazolidin-5-yl group, a 3-(4-amidinophenyl)isoxazolidin-5-yl group, a 2-(4-piperidyl)-1,3,4-thiadiazol-5-yl group, a 2-(4-aminophenyl)-1,3,4-oxadiazol-5-yl group, a 4-(4-piperidyl)piperidin-1-yl group, a 4-(4-piperidyl)piperazin-1-yl group, a 4-(4-piperazinyl)piperazin-1-yl group, a 1-(4-pyrimidinyl)piperidin-1-yl group, a 1-(2-methylpyrimidin-4-yl)piperidin-4-yl group, a 1-(4-pyrimidinyl)pyrrolidin-3-yl group, a 1-(4-methylpyrimidin-6-yl)piperazin-4-yl group, a 1-(2-methylpyrimidin-4-yl)pyrrolidin-4-yl group, a 1-(6-chloropyrimidin-4-yl)piperidin-4-yl group, a 5-(4-chlorophenyl)thiophen-2-yl group, a 2-(4-chlorophenyl)thiazol-4-yl group, a 3-(4-chlorophenyl)-1H-pyrrol-2-yl group, a 4-(4-pyrimidinyl)phenyl group, a 4-(4-imidazolyl)phenyl group, a 5-(pyridin-4-yl)pyrimidin-2-yl group, a 2'-[(dimethylamino)methyl][1,1'-biphenyl]-4-yl group, a 4-[2-(hydroxymethyl)pyridin-4-yl]phenyl group, a 4-[2-(aminomethyl)pyridin-4-yl]phenyl group, a 2'-(aminosulfonyl)[1,1'-biphenyl]-4-yl group, a 4-(3-oxomorpholin-4-yl)phenyl group, a 4-(3-oxomorpholin-4-yl)phenyl group, and the like.

A detailed description will be given for the following group:

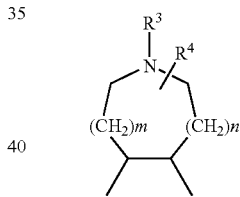

wherein $R^3$ and $R^4$ are substituted at a carbon atom or a nitrogen atom on the ring, and each independently represent a hydrogen atom, a hydroxy group, an alkyl group, an alkenyl group, an alkynyl group, a halogen atom, a halogenoalkyl group, a cyano group, a cyanoalkyl group, an amino group, an aminoalkyl group, an N-alkylaminoalkyl group, an N,N-dialkylaminoalkyl group, an acyl group, an acylalkyl group, an acylamino group which may be substituted, an alkoxyimino group, a hydroxyimino group, an acylaminoalkyl group, an alkoxy group, an alkoxyalkyl group, a hydroxyalkyl group, a carboxy group, a carboxyalkyl group, an alkoxycarbonyl group, an alkoxycarbonylalkyl group, an alkoxycarbonylalkylamino group, a carboxyalkylamino group, an alkoxycarbonylamino group, an alkoxycarbonylaminoalkyl group, a carbamoyl group, an N-alkylcarbamoyl group which may have a substituent on the alkyl group, an N,N-dialkylcarbamoyl group which may have a substituent on the alkyl group, an N-alkenylcarbamoyl group, an N-alkenylcarbamoylalkyl group, an N-alkenyl-N-alkylcarbamoyl group, an N-alkenyl-N-alkylcarbamoylalkyl group, an N-alkoxycarbamoyl group, an N-alkyl-N-alkoxycarbamoyl group, an N-alkoxycarbamoylalkyl group, an N-alkyl-N-alkoxycarbamoylalkyl group, a carbazoyl group which may be substituted with 1 to 3 alkyl groups, an alkylsulfonyl group which may be substituted with a halogen atom, an alkylsulfonylalkyl group, a 3- to 6-membered heterocyclic carbonyl group which may be substituted, a carbamoylalkyl group, an N-alkylcarbamoylalkyl group which may have a substituent on the alkyl group, an N,N-dialkylcarbamoylalkyl group which may have a substituent on the alkyl group, a carbamoyloxyalkyl group, an N-alkylcarbamoyloxyalkyl group, an N,N-dialkylcarbamoyloxyalkyl group, a 3- to 6-membered heterocyclic carbonylalkyl group which may be substituted, a 3- to 6-membered heterocyclic carbonyloxyalkyl group which may be substituted, an aryl group, an aralkyl group, a 3- to 6-membered heterocyclic group which may be substituted, a 3- to 6-membered heterocyclic alkyl group which may be substituted, an alkylsulfonylamino group, an arylsulfonylamino group, an alkylsulfonylaminoalkyl group, an arylsulfonylaminoalkyl group, an alkylsulfonylaminocarbonyl group, an arylsulfonylaminocarbonyl group, an alkylsulfonylaminocarbonylalkyl group, an arylsulfonylaminocarbonylalkyl group, an oxo group, a carbamoyloxy group, an aralkyloxy group, a carboxyalkyloxy group, an alkoxycarbonylalkyloxy group, an acyloxy group, an acyloxyalkyl group, an arylsulfonyl group, an alkoxycarbonylalkylsulfonyl group, a carboxyalkylsulfonyl group, an alkoxycarbonylacyl group, an alkoxyalkyloxycarbonyl group, a hydroxyacyl group, an alkoxyacyl group, a halogenoacyl group, a carboxyacyl group, an aminoacyl group, an acyloxyacyl group, an acyloxyalkylsulfonyl group, a hydroxyalkylsulfonyl group, an alkoxyalkylsulfonyl group, a 3- to 6-membered heterocyclic sulfonyl group which may be substituted, an N-alkylaminosulfonyl group, an N,N-dialkylaminosulfonyl group, a 3- to 6-membered heterocyclic oxy group which may be substituted, an N-alkylaminoacyl group, an N,N-dialkylaminoacyl group, an N,N-dialkylcarbamoylacyl group which may have a substituent on the alkyl group, an N,N-dialkylcarbamoylalkylsulfonyl group which may have a substituent on the alkyl group, an alkylsulfonylacyl group, an N-arylcarbamoyl group, an N-3- to 6-membered heterocyclic carbamoyl group, an N-alkyl-N-arylcarbamoyl group, an N-alkyl-N-3- to 6-membered heterocyclic carbamoyl group, an N-arylcarbamoylalkyl group, an N-3- to 6-membered heterocyclic carbamoylalkyl group, an N-alkyl-N-arylcarbamoylalkyl group, an N-alkyl-N-3- to 6-membered heterocyclic carbamoylalkyl group, an N-alkylaminooxalyl group, an N,N-dialkylaminooxalyl group, an aminocarbothioyl group, an N-alkylaminocarbothioyl group, an N,N-dialkylaminocarbothioyl group, an alkoxyalkyl(thiocarbonyl) group, an alkylthioalkyl group or an N-acyl-N-alkylaminoalkyl group, or alternatively, $R^3$ and $R^4$ are joined together to represent an alkylene group having 1 to 5 carbon atoms, an alkenylene group having 2 to 5 carbon atoms, an alkylenedioxy group having 1 to 5 carbon atoms, or a carbonyldioxy group; and m and n each represent an integer from 0 to 3.

Each of m and n are more preferably 0 or 1. Furthermore, it is particularly preferable if m is 0 and n is 1.

The substituents $R^3$ and $R^4$ described above will be explained in detail. The halogen atom means a fluorine atom, a chlorine atom, a bromine atom, or an iodine atom. The alkyl group include a straight-chained, branched or cyclic $C_1$-$C_6$ alkyl group (for example, a methyl group, a cyclopropyl group, an isobutyl group, etc.); and the halogenoalkyl group include an alkyl group as described above, which has been substituted with 1 to 3 halogen atoms (for example, a chloromethyl group, a 1-bromoethyl group, a trifluoromethyl group, etc.). The cyanoalkyl group includes a $C_1$-$C_6$ alkyl group as described above, which has been substituted with one cyano group (for example, a cyanomethyl group, a 1-cyanoethyl group, etc.). The alkenyl group include a straight-chained or branched group having 2 to 6 carbon atoms and one double bond (for example, a vinyl group, an allyl group, etc.). The alkynyl group include a straight-chained or branched group having 2 to 6 carbon atoms and one triple bond (for example, an ethynyl group, a propynyl group, etc.). The acyl group include a $C_1$-$C_6$ alkanoyl group (for example, a formyl group, an acetyl group, an isobutyryl group, etc.); a $C_7$-$C_{15}$ aroyl group such as a benzoyl group or a naphthoyl group; and an arylalkanoyl group in which a $C_1$-$C_6$ alkanoyl group is substituted with one $C_6$-$C_{14}$ aryl group (for example, a phenylacetyl group, etc.). The acylalkyl group includes a $C_1$-$C_6$ alkyl group as described above, which has been substituted with one acyl group (for example, an acetylmethyl group, etc.). The alkoxy group includes a straight-chained, branched or cyclic $C_1$-$C_6$ alkoxy group (for example, a methoxy group, a cyclopropoxy group, an isopropoxy group, etc.). The alkoxyalkyl group include a $C_1$-$C_6$ alkyl group as described above, which has been substituted with one $C_1$-$C_6$ alkoxy group as described above (for example, a methoxymethyl group, an ethoxymethyl group, etc.). The hydroxyalkyl group includes a $C_1$-$C_6$ alkyl group as described above, which has been substituted with one hydroxy group (for example, a hydroxymethyl group, a 1-hydroxyethyl group, etc.). The carboxyalkyl group includes a $C_1$-$C_6$ alkyl group as described above, which has been substituted with one carboxy group (for example, a carboxymethyl group, a 1-carboxyethyl group, etc.). The alkoxycarbonyl group includes a group composed of the $C_1$-$C_6$ alkoxy group described above and a carbonyl group (for example, a methoxycarbonyl group, an ethoxycarbonyl group, etc.). The alkoxycarbonylalkyl group includes a $C_1$-$C_6$ alkyl group as described above, which has been substituted with one alkoxycarbonyl group (for example, a methoxycarbonylethyl group, an ethoxycarbonylethyl group, an isopropoxycarbonyl group, etc.). The carbamoylalkyl group includes a $C_1$-$C_6$ alkyl group as described above, which has been substituted with a carbamoyl group (for example, a carbamoylmethyl group, a carbamoylethyl group).

The 3- to 6-membered heterocyclic group which may be substituted means a saturated or unsaturated, 3- to 6-membered heterocyclic group which may contain 1 to 3 heteroatoms (a nitrogen atom, an oxygen atom, a sulfur atom, etc.), the heterocyclic group may be substituted with a hydroxy group, a halogen atom, an amino group, a $C_1$-$C_6$ alkyl group, an oxo group, a halogenoalkyl group, or the like. The 3- to 6-membered heterocyclic group include a pyrrolyl group, a thienyl group, a pyrazolyl group, an imidazolyl group, a pyrazolinyl group, an oxazolyl group, an oxazolinyl group, an oxadiazolyl group, an oxazolidinyl group, a thiazolyl group, a thiazolinyl group, a thiadiazolyl group, a furazanyl group, a pyranyl group, a pyridyl group, a pyrimidyl group, a pyridazinyl group, a pyrrolidinyl group, a piperazinyl group, a piperidinyl group, an oxazinyl group, an oxadiazinyl group, a morpholinyl group, a thiazinyl group, a thiadiazinyl group, a thiatriazinyl group, a thiomorpholinyl group, a tetrazolyl group, a triazolyl group, a thiatriazolyl group and a triazinyl group. Specifically, a thiazolyl group, a 4,5-dihydrothiazolyl group, an oxazolyl group, a 4,5-dihydrooxazolyl group, a 5-methyloxazolyl group, an imidazolyl group, a pyrrolidinyl group, a 3-hydroxypyrrolidinyl group, a piperidyl group, a piperazinyl group, a morpholinyl group, a thiomorpholinyl group, a 1,1-dioxothiomorpholinyl group, a tetrahydropyranyl group, a pyridyl group, a 1,2,4-oxadiazolyl group, a 3-methyl-1,2,4-oxadiazolyl group, a 5-methyl-1,2,4-oxadiazolyl group, a 1,3,4-oxadiazolyl group, a 5-methyl-1,3,4-oxadiazolyl group, a 5-(trifluoromethyl)-1,3,4-oxadiazolyl group, a 1,3-oxazolyl group, a 1,3,4-thiadiazolyl group, a 5-methyl-1, 3,4-thiadiazolyl group, a 1,2,3,4-thiatriazolyl group, a 1,3-oxazolidinyl group, and the like may be mentioned.

The 3- to 6-membered heterocyclic alkyl group which may be substituted may include an alkyl group substituted with a 3- to 6-membered heterocyclic group as described above, which may be substituted (for example, a thiazolylmethyl group, a 4,5-dihydrothiazolylmethyl group, a morpholinylmethyl group, a 1,1-dioxothiomorpholinylmethyl group, etc.). The aryl group includes those having 6 to 14 carbon atoms, such as a phenyl group or a naphthyl group, and the aryl group may be substituted with 1 to 3 groups selected from a $C_1$-$C_6$ alkyl group as described above, a $C_1$-$C_6$ alkanoyl group as described above, a hydroxy group, a nitro group, a cyano group, a halogen atom, a $C_2$-$C_6$ alkenyl group as described above, a $C_2$-$C_6$ alkynyl group as described above, a $C_1$-$C_6$ halogenoalkyl group as described above, a $C_1$-$C_6$ alkoxy group as described above, a carboxy group, a carbamoyl group, a $C_1$-$C_6$ alkoxycarbonyl group as described above, and the like. The aralkyl group includes a $C_1$-$C_6$ alkyl group as described above, which has been substituted with one $C_6$-$C_{14}$ aryl group as described above (for example, a benzyl group, a phenethyl group, etc.). With regard to the above description, the position of substitution is not particularly limited.

The acylamino group which may be substituted includes, in addition to an amino group as described above, which has been substituted with the $C_1$-$C_6$ acyl group (for example, a formylamino group, an acetylamino group, etc.), an acyl group substituted with one or more of a halogen atom, a hydroxy group, a $C_1$-$C_6$ alkoxy group, an amino group, an N—$C_1$-$C_6$ alkylamino group, an N,N-di-$C_1$-$C_6$ alkylamino group, a carboxy group, a $C_2$-$C_6$ alkoxycarbonyl group and the like (for example, a 2-methoxyacetylamino group, a 3-aminopropionylamino group, etc.). The acylaminoalkyl group includes a $C_1$-$C_6$ alkyl group as described above, which has been substituted with the $C_1$-$C_6$ acylamino group (for example, a formylaminomethyl group, an acetylaminomethyl group, etc.). The aminoalkyl group includes the $C_1$-$C_6$ alkyl group substituted with one amino group (for example, an aminomethyl group, a 1-aminoethyl group, etc.). The N-alkylaminoalkyl group includes an amino-$C_1$-$C_6$ alkyl group substituted on the nitrogen atom with one $C_1$-$C_6$ alkyl group (for example, an N-methylaminomethyl group, an N-methylaminoethyl group, etc.). The N,N-dialkylaminoalkyl group includes an amino-$C_1$-$C_6$ alkyl group substituted on the nitrogen atom with two $C_1$-$C_6$ alkyl groups (for example, an N,N-dimethylaminomethyl group, an N-ethyl-N-methylaminoethyl group, etc.). The N-alkenylcarbamoyl group includes a carbamoyl group substituted with a straight-chained or branched $C_2$-$C_6$ alkenyl group (for example, an allylcarbamoyl group, etc.). The N-alkenylcarbamoylalkyl group includes a $C_1$-$C_6$ alkyl group substituted with the N—$C_2$-$C_6$ alkenylcarbamoyl group as described above (for example, an allylcarbamoylethyl group, etc.). The N-alkenyl-N-alkylcarbamoyl group includes the N—$C_2$-$C_6$ alkenylcarbamoyl group substituted on the nitrogen atom with a straight-chained or branched $C_1$-$C_6$ alkyl group (for example, an N-allyl-N-methylcarbamoyl group, etc.). The N-alkenyl-N-alkylcarbamoylalkyl group includes the N—$C_2$-$C_6$ alkenylcarbamoylalkyl group substituted on the nitrogen atom with a straight-chained or branched $C_1$-$C_6$ alkyl group (for example, an N-allyl-N-methylcarbamoylmethyl group, etc.). The N-alkoxycarbamoyl group includes a carbamoyl group substituted with a straight-chained or branched $C_1$-$C_6$ alkoxy group (for example, a methoxycarbamoyl group, etc.). The N-alkoxycarbamoylalkyl group includes a straight-chained or branched $C_1$-$C_6$ alkyl group substituted with the N—$C_1$-$C_6$ alkoxycarbamoyl group as described above (for example, a methoxycarbamoylmethyl group, etc.). The N-alkyl-N-alkoxycarbamoyl group includes a carbamoyl group substituted with a straight-chained or branched $C_1$-$C_6$ alkoxy group and a $C_1$-$C_6$ alkyl group (for example, an N-ethyl-N-methoxycarbamoyl group, etc.). The N-alkyl-N-alkoxycarbamoylalkyl group includes a straight-chained or branched $C_1$-$C_6$ alkyl group substituted with an N—$C_1$-$C_6$ alkyl-N—$C_1$-$C_6$ alkoxycarbamoyl group (for example, an N-ethyl-N-methoxycarbamoylmethyl group, etc.). The carbazoyl group which may be substituted with 1 to 3 alkyl groups includes a carbazoyl group, as well as a carbazoyl group substituted with 1 to 3 straight-chained or branched $C_1$-$C_6$ alkyl groups (for example, a 1-methylcarbazoyl group, a 1,2-dimethylcarbazoyl group, etc.). The alkylsulfonyl group which may be substituted with a halogen atom includes a group composed of a straight-chained, branched or cyclic $C_1$-$C_6$ alkyl group which may be substituted with 1 to 3 halogen atoms, and a sulfonyl group (for example, a methanesulfonyl group, a trifluoromethanesulfonyl group, etc.). The alkylsulfonylalkyl group includes a straight-chained or branched $C_1$-$C_6$ alkyl group substituted with the $C_1$-$C_6$ alkylsulfonyl group as described above (for example, a methanesulfonylmethyl group, etc.). The alkoxyimino group includes a $C_1$-$C_6$ alkoxyimino group (for example, a methoxyimino group, an ethoxyimino group, etc.).

The alkoxycarbonylalkylamino group includes an amino group substituted with one $C_1$-$C_6$ alkoxycarbonylalkyl group as described above (for example, a methoxycarbonylmethylamino group, an ethoxycarbonylpropylamino group, etc.). The carboxyalkylamino group includes an amino group substituted with one carboxy-$C_1$-$C_6$ alkyl group as described above (for example, a carboxymethylamino group, a carboxyethylamino group, etc.). The alkoxycarbonylamino group includes an amino group substituted with one $C_1$-$C_6$ alkoxycarbonyl group as described above (for example, a methoxycarbonylamino group, a tert-butoxycarbonylamino group, etc.). The alkoxycarbonylaminoalkyl group includes the alkyl group as described above which has been substituted with one $C_1$-$C_6$ alkoxycarbonylamino group as described above (for example, a methoxycarbonylaminomethyl group, a tert-butoxycarbonylaminoethyl group, etc.). The N-alkylcarbamoyl group which may have a substituent on the alkyl group, represents a carbamoyl group substituted with a straight-chained, branched or cyclic $C_1$-$C_6$ alkyl group which may be substituted with a hydroxy group, an amino group, an N—$C_1$-$C_6$ alkylamino group, an amidino group, a halogen atom, a carboxy group, a cyano group, a carbamoyl group, a $C_1$-$C_6$ alkoxy group, a $C_1$-$C_6$ alkanoyl group, a $C_1$-$C_6$ alkanoylamino group, a $C_1$-$C_6$ alkylsulfonylamino group or the like, including, for example, an N-methylcarbamoyl group, an N-ethylcarbamoyl group, an N-isopropylcarbamoyl group, an N-cyclopropylcarbamoyl group, an N-(2-hydroxyethyl)carbamoyl group, an N-(2-fluoroethyl)carbamoyl group, an N-(2-cyanoethyl)carbamoyl group, an N-(2-methoxyethyl)carbamoyl group, an N-carboxymethylcarbamoyl group, an N-(2-aminoethyl) carbamoyl group, an N-(2-amidinoethyl)carbamoyl group, and the like. The N,N-dialkylcarbamoyl group which may have a substituent on the alkyl group, represents a carbamoyl group substituted with two straight-chained, branched or cyclic $C_1$-$C_6$ alkyl groups which may be substituted with a hydroxy group, an amino group, an N—$C_1$-$C_6$, alkylamino group, an amidino group, a halogen atom, a carboxy group, a cyano group, a carbamoyl group, a $C_1$-$C_6$ alkoxy group, a $C_1$-$C_6$ alkanoyl group, a $C_1$-$C_6$ alkanoylamino group, a $C_1$-$C_6$ alkylsulfonylamino group or the like, including, for example, an N,N-dimethylcarbamoyl group, an N,N-diethylcarbamoyl group, an N-ethyl-N-methylcarbamoyl group, an N-isopropyl-N-methylcarbamoyl group, an N-(2-hydroxyethyl)-N-methylcarbamoyl group, an N,N-bis(2-hydroxyethyl)carbamoyl group, an N,N-bis(2-fluoroethyl)carbamoyl group, an N-(2-cyanoethyl)-N-methylcarbamoyl group, an N-(2-methoxy ethyl)-N-methylcarbamoyl group, an N-carboxymethyl-N-methylcarbamoyl group, an N,N-bis(2-aminoethyl)carbamoyl group, and the like. The N-alkylcarbamoylalkyl group which may have a substituent on the alkyl group, includes a straight-chained or branched $C_1$-$C_6$ alkyl group substituted with the N-alkylcarbamoyl group which may have a substituent on the alkyl group (for example, an N-methylcarbamoylmethyl group, an N-(2-hydroxyethyl)carbamoylmethyl group, etc.). The N,N-dialkylcarbamoylalkyl group which may have a substituent on the alkyl group, includes a straight-chained or branched $C_1$-$C_6$ alkyl group substituted with the N,N-dialkylcarbamoyl group which may have a substituent on the $C_1$-$C_6$ alkyl group (for example, an N,N-dimethylcarbamoylmethyl group, an N-(2-hydroxyethyl)-N-methylcarbamoylmethyl group, etc.). The 3- to 6-membered heterocyclic carbonyl group which may be substituted, includes a group composed of a 3- to 6-membered heterocyclic group which may be substituted the substituent as described above and a carbonyl group (for example, an aziridinylcarbonyl group, an azetidinylcarbonyl group, a 3-hydroxyazetidinylcarbonyl group, a 3-methoxyazetidinylcarbonyl group, a pyrrolidinylcarbonyl group, a 3-hydroxypyrrolidinylcarbonyl group, a 3-fluoropyrrolidinylcarbonyl group, a piperidylcarbonyl group, a piperazinylcarbonyl group, a morpholinylcarbonyl group, a thiomorpholinylcarbonyl group, a 1,1-dioxothiomorpholinylcarbonyl group, a tetrahydropyranylcarbonyl group, a pyridylcarbonyl group, a furoyl group, a thiophencarbonyl group, etc.). The 3- to 6-membered heterocyclic carbonylalkyl group which may be substituted, includes the $C_1$-$C_6$ alkyl group as described above, which has been substituted with one 3- to 6-membered heterocyclic carbonyl group which may be substituted the substituent as described above (for example, an azetidinylcarbonylmethyl group, a pyrrolidinylcarbonylethyl group, etc.).

The 3- to 6-membered heterocyclic carbonyloxyalkyl group which may be substituted, includes the $C_1$-$C_6$ alkyl group as described above, which has been substituted with one 3- to 6-membered heterocyclic carbonyloxy group composed of the 3- to 6-membered heterocyclic carbonyl group which may be substituted and an oxygen atom (for example, a piperidinylcarbonyloxyethyl group, a morpholinylcarbonyloxymethyl group, etc.). The carbamoyloxyalkyl group includes the $C_1$-$C_6$ alkyl group as described above, which has been substituted with one carbamoyloxy group composed of a carbamoyl group and an oxygen atom (for example, a carbamoyloxymethyl group, a carbamoyloxyethyl group, etc.). The N-alkylcarbamoyloxyalkyl group includes the $C_1$-$C_6$ alkyl group as described above, which has been substituted with one N-alkylcarbamoyloxy group composed of the N-alkylcarbamoyl group which may have a substituent on the $C_1$-$C_6$ alkyl group and an oxygen atom (for example, an N-methylcarbamoyloxymethyl group, an N-methylcarbamoyloxyethyl group, etc.). The N,N-dialkylcarbamoyloxyalkyl group includes the $C_1$-$C_6$ alkyl group as described above, which has been substituted with one N,N-dialkylcarbamoyloxy group composed of the N,N-dialkylcarbamoyl group which may have a substituent on the $C_1$-$C_6$ alkyl group, and an oxygen atom (for example, an N,N-dimethylcarbamoyloxymethyl group, an N-ethyl-N-methylcarbamoyloxyethyl group, etc.). The alkylsulfonylamino group includes an amino group substituted with one alkylsulfonyl group having the $C_1$-$C_6$ alkyl group as described above (for example, a methylsulfonylamino group, an isopropylsulfonylamino group, etc.). The arylsulfonylamino group includes an amino group substituted with one arylsulfonyl group having the aryl group as described above (for example, phenylsulfonylamino group, naphthylsulfonylamino group, etc.). The alkylsulfonylaminoalkyl group includes the $C_1$-$C_6$ alkyl group as described above, which has been substituted with one $C_1$-$C_6$ alkylsulfonylamino group as described above (for example, a methylsulfonylaminomethyl group, a methylsulfonylaminoethyl group, etc.). The arylsulfonylaminoalkyl group includes the $C_1$-$C_6$ alkyl group as described above, which has been substituted with one arylsulfonylamino group as described above (for example, a phenylsulfonylaminomethyl group, a naphthylsulfonylaminoethyl group, etc.). The alkylsulfonylaminocarbonyl group includes a group composed of the $C_1$-$C_6$ alkylsulfonylamino group as described above and a carbonyl group (for example, a methylsulfonylaminocarbonyl group, an isopropylsulfonylaminocarbonyl group, etc.). The arylsulfonylaminocarbonyl group includes a group composed of the arylsulfonylamino group as described above and a carbonyl group (for example, a phenylsulfonylaminocarbonyl group, a naphthylsulfonylaminocarbonyl group, etc.). The alkylsulfonylaminocarbonylalkyl group includes the $C_1$-$C_6$ alkyl group substituted with the $C_1$-$C_6$ alkylsulfonylaminocarbonyl group (for example, a methylsulfonylaminocarbonylmethyl group, an isopropylsulfonylaminocarbonylmethyl group, etc.).

The arylsulfonylaminocarbonylalkyl group includes the $C_1$-$C_6$ alkyl group as described above, which has been substituted with the arylsulfonylaminocarbonyl group as described above (for example, a phenylsulfonylaminocarbonylmethyl group, a naphthylsulfonylaminocarbonylmethyl group, etc.). The alkoxycarbonylalkyloxy group includes the $C_1$-$C_6$ alkoxy group as described above, which has been substituted with the alkoxycarbonyl group as described above (for example, a methoxycarbonylmethyloxy group, etc.). The acyloxy group means a group composed of an acyl group as described above and an oxygen atom (for example, a formyloxy group, an acetyloxy group, etc.). The acyloxyalkyl group includes the $C_1$-$C_6$ alkyl group as described above, which has been substituted with the acyloxy group as described above (for example, a formyloxymethyl group, an acetyloxymethyl group, etc.). The aralkyloxy group includes the $C_1$-$C_6$ alkoxy group as described above, which has been substituted with the aryl group as described above (for example, a benzyloxy group, a naphthylmethoxy group, etc.). The carboxyalkyloxy group includes the alkoxy group as described above, which has been substituted with a carboxy group (for example, a carboxymethoxy group, a carboxyethoxy group, etc.).

The arylsulfonyl group includes a $C_6$-$C_{14}$ arylsulfonyl group (for example, a phenylsulfonyl group, a naphthylsulfonyl group etc.). The alkoxycarbonylalkylsulfonyl group includes a group composed of the $C_1$-$C_6$ alkoxycarbonylalkyl group as described above and a sulfonyl group (for example, a methoxycarbonylethylsulfonyl group, an ethoxycarbonylethylsulfonyl group, etc.). The carboxyalkylsulfonyl group includes a group composed of the carboxyalkyl group as described above and a sulfonyl group (for example, a carboxymethylsulfonyl group, a carboxyethylsulfonyl group, etc.). The alkoxycarbonylacyl group includes a group composed of the alkoxycarbonylalkyl group as described above and a carbonyl group (for example, a methoxycarbonylmethylcarbonyl group, an ethoxycarbonylmethylcarbonyl group, etc.). The alkoxyalkyloxycarbonyl group includes the alkoxycarbonyl group as described above, which has been substituted with one $C_1$-$C_6$ alkoxy group as described above (for example, a methoxymethyloxycarbonyl group, a methoxyethyloxycarbonyl group, etc.). The hydroxyacyl group includes the acyl group (including $C_1$-$C_6$ alkanoyl and aroyl) as described above, which has been substituted with one hydroxy group (for example, a glycoloyl group, a lactoyl group, a benzyloyl group, etc.). The alkoxyacyl group includes the acyl group as described above, which has been substituted with one $C_1$-$C_6$ alkoxy group as described above (for example, a methoxyacetyl group, an ethoxyacetyl group, etc.). The halogenoacyl group includes a group composed of the halogenoalkyl group as described above and a carbonyl group (for example, a chloromethylcarbonyl group, a trifluoromethylcarbonyl group, etc.). The carboxyacyl group includes the acyl group as described above, which has been substituted with one carboxy group (for example, a carboxyacetyl group, a 2-carboxypropionyl group, etc.). The aminoacyl group includes the acyl group as described above (including $C_1$-$C_6$alkanoyl and aroyl), which has been substituted with one amino group (for example, an aminomethylcarbonyl group, a 1-aminoethylcarbonyl group, etc.). The acyloxyacyl group includes a group composed of the acyloxyalkyl group as described above and a carbonyl group (for example, a formyloxymethylcarbonyl group, an acetyloxymethylcarbonyl group, etc.).

The acyloxyalkylsulfonyl group includes a group composed of the acyloxyalkyl group as described above and a sulfonyl group (for example, a formyloxymethylsulfonyl group, an acetyloxymethylsulfonyl group, etc.). The hydroxyalkylsulfonyl group includes a group composed of the $C_1$-$C_6$ hydroxyalkyl group as described above and a sulfonyl group (for example, a hydroxymethylsulfonyl group, a 1-hydroxyethylsulfonyl group, etc.). The alkoxyalkylsulfonyl group includes a group composed of the $C_1$-$C_6$ alkoxyalkyl group as described above and a sulfonyl group (for example, a methoxymethylsulfonyl group, an ethoxyethylsulfonyl group, etc.). The N-alkylaminosulfonyl group includes a group composed of then N—$C_1$-$C_6$ alkylamino group as described above and a sulfonyl group (for example, an N-methylaminosulfonyl group, etc.). The N,N-dialkylaminosulfonyl group includes a group composed of the N,N-di($C_1$-$C_6$ alkyl)amino group as described above and a sulfonyl group (for example, an N,N-dimethylaminosulfonyl group, etc.). The 3- to 6-membered heterocyclic sulfonyl group which may be substituted, includes a group composed of a 3- to 6-membered heterocyclic ring which may be substituted as described above and a sulfonyl group (for example, an aziridinylsulfonyl group, an azetidinylsulfonyl group, a pyrrolidinylsulfonyl group, a piperidinylsulfonyl group, a piperazinylsulfonyl group, a morpholinylsulfonyl group, a tetrahydropyranylsulfonyl group, etc.). The 3- to 6-membered heterocyclic oxy group which may be substituted, includes a group composed of the 3- to 6-membered heterocyclic ring which may be substituted as described above and an oxygen atom (for example, a tetrahydrofuranyloxy group, etc.). The N-alkylaminoacyl group includes the aminoacyl group as described above, which has been substituted on the nitrogen atom with one $C_1$-$C_6$ alkyl group as described above (for example, an N-methylaminoacetyl group, an N-ethylaminoacetyl group, etc.) The N,N-dialkylaminoacyl group includes the aminoacyl group as described above, which has been substituted on the nitrogen atom with two $C_1$-$C_6$ alkyl groups as described above (for example, an N,N-dimethylaminoacetyl group, an N-ethyl-N-methylaminoacetyl group, etc.). The N,N-dialkylcarbamoylacyl group which may have a substituent on the alkyl group, includes the acyl group as described above, which has been substituted on the $C_1$-$C_6$ alkyl group with the N,N-dialkylcarbamoyl group which may have a substituent on the $C_1$-$C_6$ alkyl group (for example, an N,N-dimethylcarbamoylacetyl group, an N,N-diethylcarbamoylacetyl group, an N-ethyl-N-methylcarbamoylacetyl group, etc.). The N,N-dialkylcarbamoylalkylsulfonyl group which may have a substituent on the alkyl group, includes a group composed of the N,N-dialkylcarbamoyl group which may have a substituent on the $C_1$-$C_6$ alkyl group as described above and a sulfonyl group (for example, an N,N-dimethylcarbamoylmethylsulfonyl group, an N-(2-hydroxyethyl)-N-methylcarbamoylmethylsulfonyl group, etc.). The alkylsulfonylacyl group includes an acyl group substituted with one alkylsulfonyl group having the $C_1$-$C_6$ alkyl group as described above (for example, a methylsulfonylacetyl group, an isopropylsulfonylacetyl group, etc.).

The N-arylcarbamoyl group includes a carbamoyl group substituted with the aryl group as described above (for example, a phenylcarbamoyl group, a naphthylcarbamoyl group, etc.). The N-3- to 6-membered heterocyclic carbamoyl group includes a carbamoyl group substituted with the 3- to 6-membered heterocyclic group which may be substituted as described above (for example, a pyridylcarbamoyl group, a thienylcarbamoyl group, etc.). The N-alkyl-N-arylcarbamoyl group includes the N-arylcarbamoyl group as described above, which has been substituted on the nitrogen atom with a straight-chained or branched $C_1$-$C_6$ alkyl group (for example, an N-methyl-N-phenylcarbamoyl group, etc.). The N-alkyl-N-3- to 6-membered heterocyclic carbamoyl group includes the N-3- to 6-membered heterocyclic carbamoyl group as described above, which has been substituted on the nitrogen atom with a straight-chained or branched $C_1$-$C_6$ alkyl group (for example, an N-methyl-N-thienylcarbamoyl group, etc.). The N-arylcarbamoylalkyl group includes a straight-chained or branched $C_1$-$C_6$ alkyl group substituted with the N-arylcarbamoyl group as described above (for example, a phenylcarbamoylmethyl group, etc.). The N-3- to 6-membered heterocyclic carbamoylalkyl group includes a straight-chained or branched $C_1$-$C_6$ alkyl group substituted with the N-3- to 6-membered heterocyclic carbamoyl group as described above (for example, a pyridylcarbamoylmethyl group, etc.). The N-alkyl-N-arylcarbamoylalkyl group includes the N-arylcarbamoylalkyl group as described above, which has been substituted on the nitrogen atom with a straight-chained or branched $C_1$-$C_6$ alkyl group (for example, an N-methyl-N-phenylcarbamoylmethyl group, etc.). The N-alkyl-N-3- to 6-membered heterocyclic carbamoylalkyl group includes the N-3- to 6-membered heterocyclic carbamoylalkyl group as described above, which has been substituted on the nitrogen atom with a straight-chained or branched $C_1$-$C_6$ alkyl group (for example, an N-methyl-N-thienylcarbamoylmethyl group, etc.). The N-alkylaminooxalyl group includes a $C_1$-$C_6$ alkylaminooxalyl group substituted on the nitrogen atom of the aminooxalyl group with a straight-chained or branched $C_1$-$C_6$ alkyl group (for example, an N-methylaminooxalyl group, etc.). The N,N-dialkylaminooxalyl group includes an N,N-di($C_1$-$C_6$ alkyl)aminooxalyl group substituted on the nitrogen atom of the aminooxalyl group with a straight-chained or branched $C_1$-$C_6$ alkyl group (for example, an N,N-dimethylaminooxalyl group, an N-ethyl-N-methylaminooxalyl group, etc.).

The aminocarbothioyl group is a group represented by —C(=S)—NH$_2$, while the N-alkylaminocarbothioyl group represents an aminothiocarbonyl group substituted with one alkyl group as described above, and including, for example, a (methylamino)carbothioyl group, an (ethylamino)carbothioyl group and the like. The N,N-dialkylaminocarbothioyl group represents an aminothiocarbonyl group substituted with two alkyl groups as described above, and including, for example, a (dimethylamino)carbothioyl group, a (diethylamino)carbothioyl group, an (ethylmethylamino)carbothioyl group, and the like. The alkylthioalkyl group includes a straight-chained, branched or cyclic $C_1$-$C_6$ alkyl group substituted with a straight-chained, branched or cyclic $C_1$-$C_6$ alkylthio group (for example, a methylthiomethyl group, a 1-methylthioethyl group, etc.). The N-acyl-N-alkylaminoalkyl group includes an amino-$C_1$-$C_6$ alkyl group substituted on the nitrogen atom with a $C_1$-$C_6$ alkyl group and an acyl group (for example, an N-acetyl-N-methylaminomethyl group, etc.). The alkoxyalkyl(thiocarbonyl) group represents a group composed of the alkoxyalkyl group as described above and a thiocarbonyl group, and including, for example, a 2-ethoxyethanethioyl group, and the like.

The alkylene group means a straight-chained or branched alkylene group having 1 to 5 carbon atoms, and including, for example, a methylene group, an ethylene group, a propylene group and the like. The alkenylene group is an alkenylene group having 2 to 5 carbon atoms and one double bond, and including, for example, a vinylene group, a propenylene group and the like. The alkylenedioxy group includes those having 1 to 5 carbon atoms, such as a methylenedioxy group, an ethylenedioxy group or a propylenedioxy group. The carbonyldioxy group is a group represented by —O—C(=O)—O—. With regard to the above description, the position of substitution is not particularly limited.

Among the substituents represented by $R^3$ and $R^4$, preferred is a hydrogen atom, an alkyl group, an alkenyl group, an alkynyl group, a halogenoalkyl group, an aminoalkyl group, an N-alkylaminoalkyl group, an N,N-dialkylaminoalkyl group, an acyl group, an acylalkyl group, an acylaminoalkyl group, an alkoxy group, an alkoxyalkyl group, a hydroxyalkyl group, a carboxy group, a carboxyalkyl group, an alkoxycarbonyl group, an alkoxycarbonylalkyl group, an alkoxycarbonylamino group, an alkoxycarbonylaminoalkyl group, a carbamoyl group, an N-alkylcarbamoyl group which may have a substituent on the alkyl group, an N,N-dialkylcarbamoyl group which may have a substituent on the alkyl group, an N-alkenylcarbamoyl group, an N-alkenylcarbamoylalkyl group, an N-alkenyl-N-alkylcarbamoyl group, an N-alkenyl-N-alkylcarbamoylalkyl group, an N-alkoxycarbamoyl group, an N-alkyl-N-alkoxycarbamoyl group, an N-alkoxycarbamoylalkyl group, an N-alkyl-N-alkoxycarbamoylalkyl group, a carbazoyl group which may be substituted with 1 to 3 alkyl groups, an alkylsulfonyl group which may be substituted with a halogen atom, an alkylsulfonylalkyl group, a 3- to 6-membered heterocyclic carbonyl group which may be substituted, a 3- to 6-membered heterocyclic carbonyloxyalkyl group which may be substituted, a 3- to 6-membered heterocyclic group which may be substituted, a carbamoylalkyl group, a carbamoyloxyalkyl group, an N-alkylcarbamoyloxyalkyl group, an N,N-dialkylcarbamoyloxyalkyl group, an N-alkylcarbamoylalkyl group which may have a substituent on the alkyl group, an N,N-dialkylcarbamoylalkyl group which may have a substituent on the alkyl group, an alkylsulfonylaminoalkyl group, an oxo group, an acyloxyalkyl group, an arylsulfonyl group, an alkoxycarbonylalkylsulfonyl group, a carboxyalkylsulfonyl group, an alkoxycarbonylacyl group, a carboxyacyl group, an alkoxyalkyloxycarbonyl group, a halogenoacyl group, an N,N-dialkylaminoacyl group, an acyloxyacyl group, a hydroxyacyl group, an alkoxyacyl group, an alkoxyalkylsulfonyl group, an N,N-dialkylcarbamoylacyl group, an N,N-dialkylcarbamoylalkylsulfonyl group, an alkylsulfonylacyl group, an N-alkylaminosulfonyl group, an N,N-dialkylaminosulfonyl group, an N-alkylaminooxalyl group, an N,N-dialkylaminooxalyl group, an aminocarbothioyl group, an N-alkylaminocarbothioyl group, an N,N-dialkylaminocarbothioyl group, and an alkoxyalkyl(thiocarbonyl) group. Alternatively, an alkylene group, an alkenylene group, an alkyleneoxy group, a carbonyldioxy group and the like formed from $R^3$ and $R^4$ which are jointed together are preferable.

It is preferable for $R^3$ and $R^4$ that $R^4$ is a hydrogen atom or an oxo group, and $R^3$ is a substituent listed in the above as a preferred group. In this case, a more preferred group for $R^3$ includes a hydrogen atom, an alkyl group, an alkenyl group, an N-alkylaminoalkyl group, an N,N-dialkylaminoalkyl group, an acyl group, an acylaminoalkyl group, an alkoxyalkyl group, a hydroxyalkyl group, an alkoxycarbonyl group, an alkoxycarbonylalkyl group, a carbamoyl group, an N-alkylcarbamoyl group which may have a substituent on the alkyl group, an N,N-dialkylcarbamoyl group which may have a substituent on the alkyl group, an N-alkenylcarbamoyl group, an N-alkenylcarbamoylalkyl group, an N-alkenyl-N-alkylcarbamoyl group, an N-alkenyl-N-alkylcarbamoylalkyl group, an N-alkoxycarbamoyl group, an N-alkyl-N-alkoxycarbamoyl group, an N-alkoxycarbamoylalkyl group, an N-alkyl-N-alkoxycarbamoylalkyl group, a carbazoyl group which may be substituted with 1 to 3 alkyl groups, an alkylsulfonyl group which may be substituted with a halogen atom, an alkylsulfonylalkyl group, a 3- to 6-membered heterocyclic carbonyl group which may be substituted, a 3- to 6-membered heterocyclic carbonyloxyalkyl group which may be substituted, a 3- to 6-membered heterocyclic group which may be substituted, a carbamoylalkyl group, an N,N-dialkylcarbamoyloxyalkyl group, an N-alkylcarbamoylalkyl group which may have a substituent on the alkyl group, an N,N-dialkylcarbamoylalkyl group which may have a substituent on the alkyl group, an alkylsulfonylamino group, an alkylsulfonylaminoalkyl group, an acyloxy group, an arylsulfonyl group, an alkoxycarbonylalkylsulfonyl group, a carboxyalkylsulfonyl group, an alkoxycarbonylacyl group, a carboxyacyl group, an alkoxyalkyloxycarbonyl group, a halogenoacyl group, an N,N-dialkylaminoacyl group, an acyloxyacyl group, a hydroxyacyl group, an alkoxyacyl group, an alkoxyalkylsulfonyl group, an N,N-dialkylcarbamoylacyl group, an N,N-dialkylcarbamoylalkylsulfonyl group, an alkylsulfonylacyl group, an N-alkylaminosulfonyl group, an N,N-dialkylaminosulfonyl group, an N-alkylaminooxalyl group, an N,N-dialkylaminooxalyl group, an aminocarbothioyl group, an N-alkylaminocarbothioyl group, an N,N-dialkylaminocarbothioyl group, an alkoxyalkyl(thiocarbonyl) group and the like.

Moreover, among these groups, a particularly preferred group for $R^3$ may include a hydrogen atom, an alkyl group, an alkenyl group, an acyl group, an alkoxycarbonyl group, an N-alkylcarbamoyl group which may be substituted, an N,N-dialkylcarbamoyl group which may be substituted, alkylsulfonyl group which may be substituted with a halogen atom, a 3- to 6-membered heterocyclic group which may be substituted, an N-alkylaminosulfonyl group, an N,N-dialkylaminosulfonyl group, an N-alkylaminooxalyl group, an N,N-dialkylaminooxalyl group and the like.

Examples of specific preferred substituents for $R^3$ and $R^4$ may include a hydrogen atom, a methyl group, an ethyl group, an isopropyl group, an N,N-dimethylaminomethyl group, an N,N-dimethylaminoethyl group, an N,N-diethylaminomethyl group, an acetylaminomethyl group, an acetylaminoethyl group, a methoxymethyl group, a methoxyethyl group, a hydroxymethyl group, a 2-hydroxyethyl group, a 1-hydroxy-1-methylethyl group, a methoxycarbonyl group, an ethoxycarbonyl group, an isopropoxycarbonyl group, a methoxycarbonylamino group, an ethoxycarbonylamino group, an N-allylcarbamoyl group, an N-allylcarbamoylmethyl group, an N-allyl-N-methylcarbamoyl group, an N-allyl-N-methylcarbamoylmethyl group, an N-methoxy-N-methylcarbamoyl group, an N,N-dimethylcarbazoyl group, an N,N,N'-trimethylcarbazoyl group, a methanesulfonyl group, a trifluoromethanesulfonyl group, a phenylsulfonyl group, a methanesulfonylmethyl group, an ethanesulfonylmethyl group, an N-methylcarbamoyl group, an N-ethylcarbamoyl group, an N-propylcarbamoyl group, an N-isopropylcarbamoyl group, an N-tert-butylcarbamoyl group, an N-cyclopropylcarbamoyl group, an N-cyclopropylmethylcarbamoyl group, an N-(1-ethoxycarbonylcyclopropyl)carbamoyl group, an N-(2-hydroxyethyl)carbamoyl group, an N-(2-fluoroethyl)carbamoyl group, an N-(2-methoxyethyl)carbamoyl group, an N-(carboxymethyl)carbamoyl group, an N-(2-aminoethyl)carbamoyl group, an N-(2-amidinoethyl)carbamoyl group, an N,N-dimethylcarbamoyl group, an N,N-diethylcarbamoyl group, an N-ethyl-N-methylcarbamoyl group, an N-isopropyl-N-methylcarbamoyl group, an N-methyl-N-propylcarbamoyl group, an N-(2-hydroxyethyl)-N-methylcarbamoyl group, an N-(2-fluoroethyl)-N-methylcarbamoyl group, an N,N-bis(2-hydroxyethyl)carbamoyl group, an N,N-bis(2-fluoroethyl)carbamoyl group, an N-(2-methoxyethyl)-N-methylcarbamoyl group, an N-carboxymethyl-N-methylcarbamoyl group, an N,N-bis(2-aminoethyl)carbamoyl group, an azetidinylcarbonyl group, a 3-methoxyazetidinocarbonyl group, a 3-hydroxyazetidinocarbonyl group, a pyrrolidinylcarbonyl group, a 3-hydroxypyrrolidinocarbonyl group, a 3-fluoropyrrolidinocarbonyl group, a 3,4-dimethoxypyrrolidinocarbonyl group, a piperidinylcarbonyl group, a piperazinylcarbonyl group, a morpholinylcarbonyl group, a (tetrahydropyran-4-yl)carbonyl group, a benzoyl group, a pyridylcarbonyl group, a thiazolyl group, a 4,5-dihydrothiazolyl group, an oxazolyl group, a 4,5-dihydrooxazolyl group, a 5-methyloxazolyl group, an imidazolyl group, a pyrrolidinyl group, a 3-hydroxypyrrolidinyl group, a piperidyl group, a piperazinyl group, a morpholinyl group, a thiomorpholinyl group, a 1,1-dioxothiomorpholinyl group, a tetrahydropyranyl group, a pyridyl group, a 1,2,4-oxadiazolyl group, a 3-methyl-1,2,4-oxadiazolyl group, a 5-methyl-1,2,4-oxadiazolyl group, a 1,3,4-oxadiazolyl group, a 5-methyl-1,3,4-oxadiazolyl group, a 5-(trifluoromethyl)-1,3,4-oxadiazolyl group, a 1,3-oxazolyl group, a 1,3,4-thiadiazolyl group, a 5-methyl-1,3,4-thiadiazolyl group, a 1,2,3,4-thiatriazolyl group, a 1,3-oxazolidinyl group, an N-methylcarbamoylmethyl group, an N-methylcarbamoylethyl group, an N-ethylcarbamoylmethyl group, an N-(2-fluoroethyl)carbamoylmethyl group, an N-(2-methoxyethyl)carbamoylmethyl group, an N,N-dimethylcarbamoylmethyl group, an N,N-dimethylcarbamoylethyl group, an N-(2-fluoroethyl)-N-methylcarbamoylmethyl group, an N-(2-methoxyethyl)-N-methylcarbamoylmethyl group, an N,N-dimethylcarbamoyloxymethyl group, a 2-(N-ethyl-N-methylcarbamoyloxy)ethyl group, a methylsulfonylamino group, an ethylsulfonylamino group, a methylsulfonylaminomethyl group, a methylsulfonylaminoethyl group, a formyl group, an acetyl group, a propionyl group, an isobutyryl group, a 2-methoxyethoxycarbonyl group, a trifluoroacetyl group, an N,N-dimethylaminoacetyl group, an N-ethyl-N-methylaminoacetyl group, a hydroxyacetyl group, a 1,1-dimethyl-2-hydroxyethylcarbonyl group, a methoxyacetyl group, a 1,1-dimethyl-2-methoxyethylcarbonyl group, a dimethylaminosulfonyl group, a diethylaminosulfonyl group, a dimethylaminooxalyl group, an aminocarbothioyl group, a (dimethylamino)carbothioyl group, a 2-methoxyethanethioyl group, and the like.

As described above, it is preferable for $R^3$ and $R^4$ that $R^4$ is a hydrogen atom or an oxo group, and $R^3$ is a specific substituent described above. It is preferable if $R^4$ is a hydrogen atom, and $R^3$ is an alkanoyl group having 1 to 6 carbon atoms, particularly preferably a formyl group. However, $R^3$ and $R^4$ are not to be limited in any way to these specific substituents.

[Group $T^0$]

The group $T^0$ represents a carbonyl group or a thiocarbonyl group, but a carbonyl group is more preferred.

[Group $T^1$]

The group $T^1$ represents a carbonyl group, a sulfonyl group, a group —C(=O)—C(=O)—N(R')—, a group —C(=S)—C(=O)—N(R')—, a group —C(=O)—C(=S)—N(R')—, a group —C(=S)—C(=S)—N(R')— (wherein R' represents a hydrogen atom, a hydroxy group, an alkyl group or an alkoxy group), a group —C(=O)-$A^1$-N(R")— (wherein $A^1$ represents an alkylene group having 1 to 5 carbon atoms, which may be substituted; and R" represents a hydrogen atom, a hydroxy group, an alkyl group or an alkoxy group), a group —C(=O)—NH—, a group —C(=S)—NH—, a group —C(=O)—NH—NH—, a group —C(=O)-$A^2$-C(=O)— (wherein $A^2$ represents a single bond or an alkylene group having 1 to 5 carbon atoms), a group —C(=O)-$A^3$-C(=O)—NH— (wherein $A^3$ represents an alkylene group having 1 to 5 carbon atoms), a group —C(=O)—C(=NOR$^a$)—N(R$^b$)—, a group —C(=S)—C(=NOR$^a$)—N(R$^b$) (wherein R$^a$ represents a hydrogen atom, an alkyl group or an alkanoyl group; and R$^b$ represents a hydrogen atom, a hydroxy group, an alkyl group or an alkoxy group), a group —C(=O)—N=N—, a group —C(=S)—N=N—, a group —C(=NOR$^c$)—C(=O)—N(R$^d$)— (wherein R$^c$ represents a hydrogen atom, an alkyl group, an alkanoyl group, an aryl group or an aralkyl group; and R$^d$ represents a hydrogen atom, a hydroxy group, an alkyl group or an alkoxy group), a group —C(=N—N(R$^e$)(R$^f$)—C(=O)—N(R$^g$)— (wherein R$^e$ and R$^f$ each independently represent a hydrogen atom, an alkyl group, an alkanoyl group, an alkyl(thiocarbonyl) group; R$^g$ represents a hydrogen atom, a hydroxy group, an alkyl group or an alkoxy group), a group —C(=O)—NH—C(=O)—, a group —C(=S)—NH—C(=O)—, a group —C(=O)—NH—C(=S)—, a group —C(=S)—NH—C(=S)—, a group —C(=O)—NH—SO$_2$—, a group —SO$_2$—NH—, a group —C(=NCN)—NH—C(=O)—, a group —C(=S)—C(=O)— or a thiocarbonyl group.

Among the groups described above, the alkylene group having 1 to 5 carbon atoms for $A^1$, $A^2$ and $A^3$ means a straight-chained, branched or cyclic alkylene group having 1 to 5 carbon atoms, and including, for example, a methylene group, an ethylene group, a propylene group, a cyclopropylene group, a 1,3-cyclopentylene group and the like. With regard to R', R", $R^a$, $R^b$, $R^c$, $R^d$, $R^e$, $R^f$ and $R^g$, the alkyl group means a straight-chained, branched or cyclic alkyl group having 1 to 6 carbon atoms, and including, for example, a methyl group, an ethyl group and the like. The alkoxy group means a straight-chained, branched or cyclic alkoxy group having 1 to 6 carbon atoms, and including, for example, a methoxy group, an ethoxy group and the like.

With regard to $R^a$, $R^c$, $R^e$ and $R^f$, the alkanoyl group means a group composed of a straight-chained, branched or cyclic alkyl group having 1 to 6 carbon atoms and a carbonyl group, and including, for example, an acetyl group, a propionyl group and the like.

With regard to $R^c$, the aryl group means an aryl group having 6 to 14 carbon atoms, and including, for example, a phenyl group, a naphthyl group and the like. The aralkyl group means a straight-chained, branched or cyclic alkyl group having 1 to 6 carbon atoms, which has been substituted with an aryl group having 6 to 14 carbon atoms, and including, for example, a benzyl group, a phenethyl group and the like.

As the group $T^1$, a carbonyl group, a group —C(=O)—C(=O)—N(R')—, a group —C(=S)—C(=O)—N(R')—, a group —C(=O)—C(=S)—N(R')—, a group —C(=S)—C(=S)—N(R')— and a group —C(=O)—CH$_2$—N(R")— are preferred, and particularly a carbonyl group, a group —C(=O)—C(=O)—N(R')—, a group —C(=S)—C(=O)—N(R')—, a group —C(=O)—C(=S)—N(R')— and a group —C(=S)—C(=S)—N(R')— are preferred.

[Group $R^1$ and Group $R^2$]

$R^1$ and $R^2$ each independently represent a hydrogen atom, a hydroxy group, an alkyl group or an alkoxy group, and are each preferably a hydrogen atom or an alkyl group, and more preferably a hydrogen atom.

With regard to $R^1$ and $R^2$, the alkyl group means a straight-chained, branched or cyclic alkyl group having 1 to 6 carbon atoms, and including, for example, a methyl group, an ethyl group and the like. The alkoxy group means a straight-chained, branched or cyclic alkoxy group having 1 to 6 carbon atoms, and including, for example, a methoxy group, an ethoxy group and the like. With regard to $R^1$ and $R^2$, it is preferable that the groups are each independently a hydrogen atom or an alkyl group, and it is more preferable that both of them are a hydrogen atom.

According to the present invention, preferred combinations of the groups are as follows. A compound in which $Q^1$ is a saturated or unsaturated, bicyclic or tricyclic heterocyclic group which may be substituted, $Q^2$ is a single bond, $T^0$ is a carbonyl group, m is 0, n is 1, $R^1$ and $R^2$ are each a hydrogen atom, $T^1$ is a carbonyl group, a group —C(=O)—C(=O)—N(R')—, a group —C(=S)—C(=O)—N(R')—, a group —C(=O)—C(=S)—N(R')— or a group —C(=S)—C(=S)—N(R')—, and $Q^4$ is a group represented by group (a), (d), (f), (i), (j) or (k), is preferred. Furthermore, a compound in which $Q^1$ is a saturated or unsaturated, bicyclic or tricyclic heterocyclic group which may be substituted, $Q^2$ is a single bond, $T^0$ is a carbonyl group, m is 0, n is 1, $R^1$ and $R^2$ are each a hydrogen atom, $T^1$ is a carbonyl group, $Q^4$ is a group represented by group (a), (d) or (f), and a compound in which $Q^1$ is a saturated or unsaturated, bicyclic or tricyclic heterocyclic group which may be substituted, $Q^2$ is a single bond, $T^0$ is a carbonyl group, m is 0, n is 1, $R^1$ and $R^2$ are each a hydrogen atom, $T^1$ is a group —C(=O)—C(=O)—N(R')—, a group —C(=S)—C(=O)—N(R')—, a group —C(=O)—C(=S)—N(R')—, or group —C(=S)—C(=S)—N(R')—, $Q^4$ is a group represented by group (i), (j) or (k), are more preferred. Among the combination described above, the case in which $R^3$ is a formyl group, and $R^4$ is a hydrogen atom is still more preferred.

The compound represented by general formula (1) of the present invention may exist as a mixture of stereoisomers, or optical isomers attributed to the presence of asymmetrical carbon atoms. These stereoisomers, optical isomers and mixtures thereof are all included in the present invention.

The salt of the compound represented by general formula (1) of the present invention is not particularly limited, as long as the salt is a pharmaceutically acceptable salt, and specific examples thereof include mineral acid salts such as hydrochlorides, hydrobromides, hydroiodides, phosphates, nitrates and sulfates; benzoates; organic sulfonic acid salts such as methanesulfonates, 2-hydroxyethanesulfonates and p-toluenesulfonates; and organic carboxylates such as acetates, propanoates, oxalates, malonates, succinates, glutarates, adipates, tartrates, maleates, malates and mandelates. Furthermore, when the compound represented by general formula (1) has an acidic group, the salt may be a salt of an alkali metal ion or an alkaline earth metal ion. The solvate is not particularly limited, as long as it is a pharmaceutically acceptable solvate, and specific examples thereof include hydrates, ethanolates and the like. Also, in case there is a nitrogen atom in the general formula (1), the compound may exist in the form of N-oxide.

As the compound of the present invention, the compounds, salts thereof and the like presented in the following Examples, and the following compounds, salts thereof and the like are particularly preferred.

Hereinafter, the method of producing the triamine derivative (1) of the present invention will be described.

[Production Method 1]

The compound represented by general formula (1), a salt thereof, a solvate of the compound or the salt, or an N-oxide of the compound or the salt can be produced by, for example, the following method:

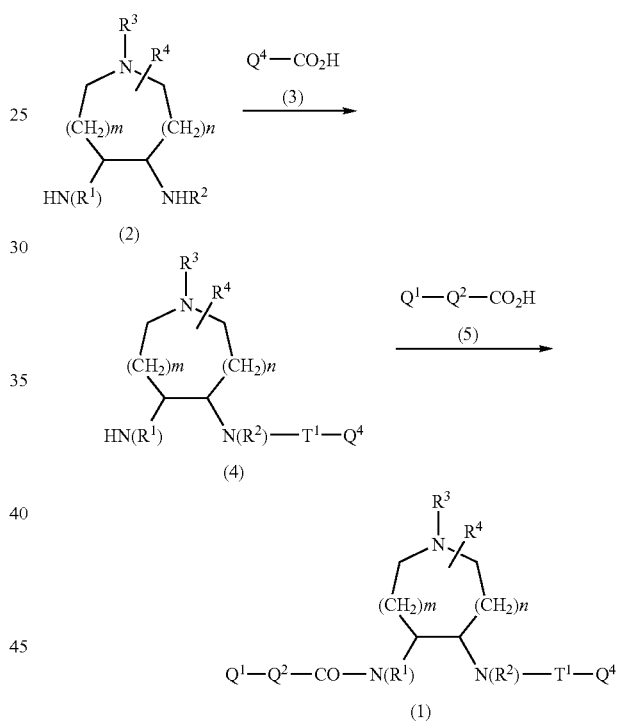

wherein $Q^1$, $Q^2$, $Q^4$, $R^1$, $R^2$, $R^3$, $R^4$, m and n have the same meanings as defined above; and $T^1$ represents a carbonyl group.

The compound (1) of the present invention can be produced by derivatizing a carboxylic acid (3) into a mixed acid anhydride, an acid halide or an activated ester, reacting the derivative with a triamine (2) to produce a compound (4), and reacting the resulting compound (4) with a carboxylic acid (5) under the same conditions.

With respect to the reactions in the respective processes described above, reaction reagents or conditions that are conventionally used in peptide synthesis may be applied correspondingly. The mixed acid anhydride can be produced by, for example, reacting a chloroformic acid ester such as ethyl chloroformate or isobutyl chloroformate with a carboxylic acid (3) in the presence of a base. The acid halide can be produced by treating the carboxylic acid (3) with an acid halide such as thionyl chloride or oxalyl chloride. There are various activated esters, but such an activated ester can be produced by, for example, reacting a phenol such as p-nitrophenol, N-hydroxybenzotriazole or N-hydroxysuccinimide, with the carboxylic acid (3), using a condensing agent such as N, N'-dicyclohexylcarbodiimide or 1-ethyl-3-(3-dimethylaminoipropyl)carbodiimide hydrochloride. Also, the activated ester can also be produced through a reaction between the carboxylic acid (3) and pentafluorophenyl trifluoroacetate or the like, a reaction between the carboxylic acid (3) and 1-benzotriazolyloxytripyrrolidinophosphonium hexafluorophosphite, a reaction between the carboxylic acid (3) and diethyl cyanophosphonate (Shioiri method), a reaction between the carboxylic acid (3) and triphenylphosphine with 2,2'-dipyridyldisulfide (Mukaiyama method), or the like. When the mixed acid anhydride, acid halide or activated ester of the carboxylic acid (3) thus obtained is reacted with a triamine (2) in the presence of an appropriate base in an inert solvent at −78° C. to 150° C., the compound (4) can be produced. Then, the compound (1) of the present invention can be produced by reacting the obtained compound (4) with the mixed acid anhydride, acid halide or activated ester of the carboxylic acid (5) under the same conditions. The reagents or reaction conditions used in the reaction between the compound (4) and the carboxylic acid (5) are the same as the reagents or reaction conditions for the reaction between the triamine (2) and the carboxylic acid (3).

Specific examples of the base used in the respective processes described above may include carbonates, alkali metal alkoxides, alkali metal hydroxides or hydrides of alkali metals or alkaline earth metals, such as sodium carbonate, potassium carbonate, sodium ethoxide, potassium butoxide, sodium hydroxide, potassium hydroxide, sodium hydride and potassium hydride; organic metal bases exemplified by an alkyllithium such as n-butyllithium, or dialkylaminolithium such as lithium diisopropylamide; organic metal bases of bis(silyl)amine, such as lithium bis(trimethylsilyl)amide; or organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent used in this reaction include halogenated-alkyl solvents such as dichloromethane, chloroform and carbon tetrachloride; ether solvents such as tetrahydrofuran, 1,2-dimethoxyethane and dioxane; aromatic solvents such as benzene and toluene; and amide solvents such as N,N-dimethylformamide, N,N-dimethylacetamide and N-methylpyrrolidin-2-one. In addition to these solvents, sulfoxide solvents such as dimethyl sulfoxide and sulfolane, ketone solvents such as acetone and methyl ethyl ketone, or the like may also be used in some cases.

[Production Method 2]

The compound (1) of the present invention can also be produced by the following method:

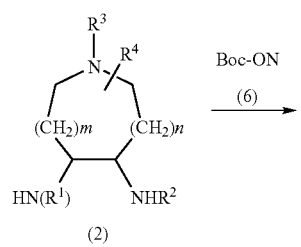

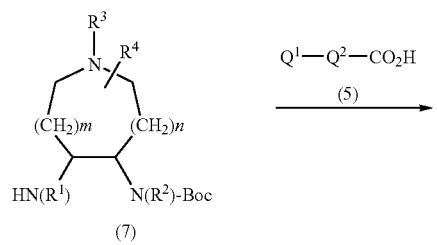

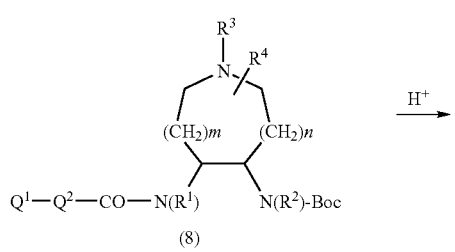

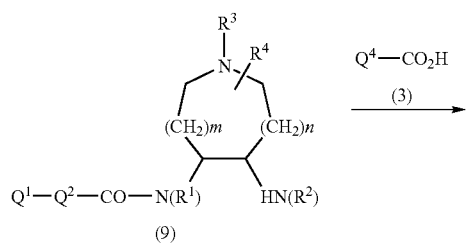

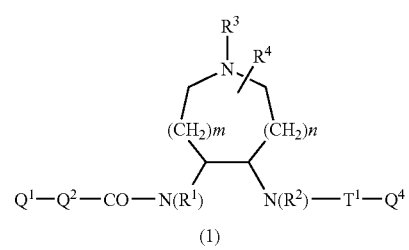

wherein $Q^1$, $Q^2$, $Q^4$, $R^1$, $R^2$, $R^3$, $R^4$, m and n have the same meanings as defined above; $T^1$ represents a carbonyl group; Boc represents a tert-butoxycarbonyl group; Boc-ON represents 2-(tert-butoxycarbonyloxyimino)-2-phenylacetonitrile.

As described above, the compound (1) of the present invention can be produced by treating a triamine (2) with Boc-ON (6) to produce a compound (7) in which one of the two amino groups is protected with a tert-butoxycarbonyl group, reacting the resulting compound (7) with a carboxylic acid (5) to produce a compound (8), subsequently treating the compound (8) with an acid to obtain a compound (9), and then reacting the compound (9) with the carboxylic acid (3). The compound (7) can be produced by a reaction in a solvent such as dichloromethane in the presence of triethylamine at −10°

C. to 40° C. The compound (8) can be produced by reacting the compound (7) with the mixed acid anhydride, acid halide or activated ester of the carboxylic acid (5) using the reagents or reaction conditions described in the Production Method 1. The obtained compound (8) can be treated with trifluoroacetic acid or the like at −20° C. to 70° C. to produce an amine (9). In the reaction between the resulting amine (9) and the carboxylic acid (4), the same reagents or conditions as those described in the Production Method 1 may be used.

However, the tert-butoxycarbonyl group of the compound (7) can be replaced by other protective groups for amino group. In this case, the reagent (6) is also replaced by other reagents, and it is necessary to use reaction conditions and the like in correspondence to the replacement. As the other protective groups for amino group, an alkanoyl group such as an acetyl group; an alkoxycarbonyl group such as a methoxycarbonyl group or an ethoxycarbonyl group; an arylmethoxycarbonyl group such as a benzyloxycarbonyl group, a para-methoxybenzyloxycarbonyl group or a para (or ortho)-nitrobenzyloxycarbonyl group; an arylmethyl group such as a benzyl group or a triphenylmethyl group; an aroyl group such as a benzoyl group, and an arylsulfonyl group such as a 2,4-dinitrobenzenesulfonyl group or an o-nitrobenzenesulfonyl group may be mentioned. These protective groups may be selected according to the nature and the like of the compound having amino group to be protected. Upon cleaving such a protective group, reagents or conditions may be selected in accordance with the protective group.

[Production Method 3]

The compound (1) of the present invention can be produced by reacting a triamine (2) with a sulfonic acid halide (10), and then condensing the product with a carboxylic acid (5).

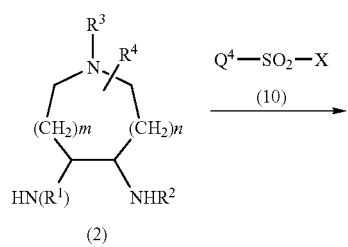

(2)

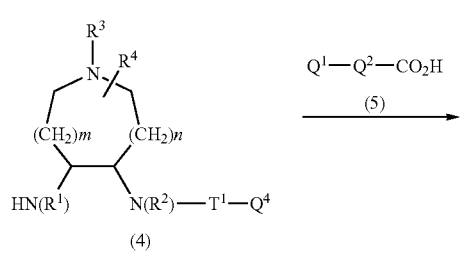

(4)

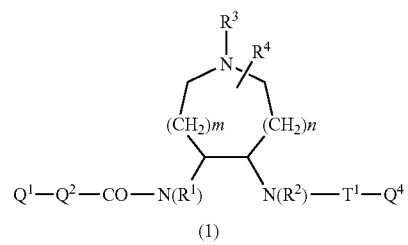

(1)

wherein $Q^1$, $Q^2$, $Q^4$, $R^1$, $R^2$, $R^3$, $R^4$, m and n have the same meanings as defined above; $T^1$ represents a sulfonyl group; and X represents a halogen atom.

A compound (4) can be produced by reacting the triamine (2) with the sulfonic acid halide (10) in an inert solvent in the presence of a base such as triethylamine at 10° C. to 30° C. The inert solvent or base may be appropriately selected from those mentioned in the Production Method 1, and used. The compound (1) of the present invention can be produced by condensing the resulting compound (4) with the carboxylic acid (5) using the reagents or conditions described in the Production Method 1. The sulfonic acid halide (10) can be synthesized by a known method (WO 96/10022, WO 00/09480) or a method equivalent thereto, in the presence of an appropriate base.

[Production Method 4]

The compound (1) of the present invention can also be produced by the following method.

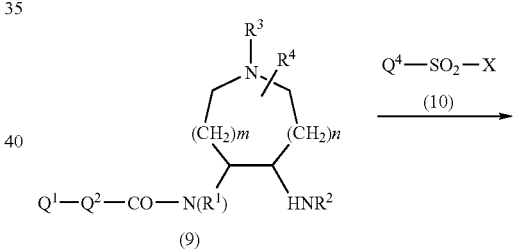

(9)

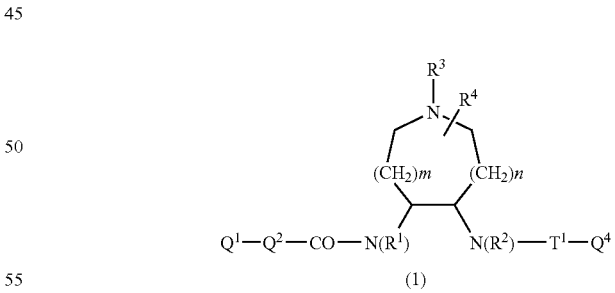

(1)

wherein $Q^1$, $Q^2$, $Q^4$, $R^1$, $R^2$, $R^3$, $R^4$, m, n and X have the same meanings as defined above.

Specifically, the compound (1) can be produced by reacting an amine (9) with a sulfonic acid halide (10) in an inert solvent in the presence of a base at −10° C. to 30° C. The inert solvent or base may be appropriately selected from those mentioned in the Production Method 1, and used.

[Production Method 5]

The compound (1) of the present invention can also be produced by the following method.

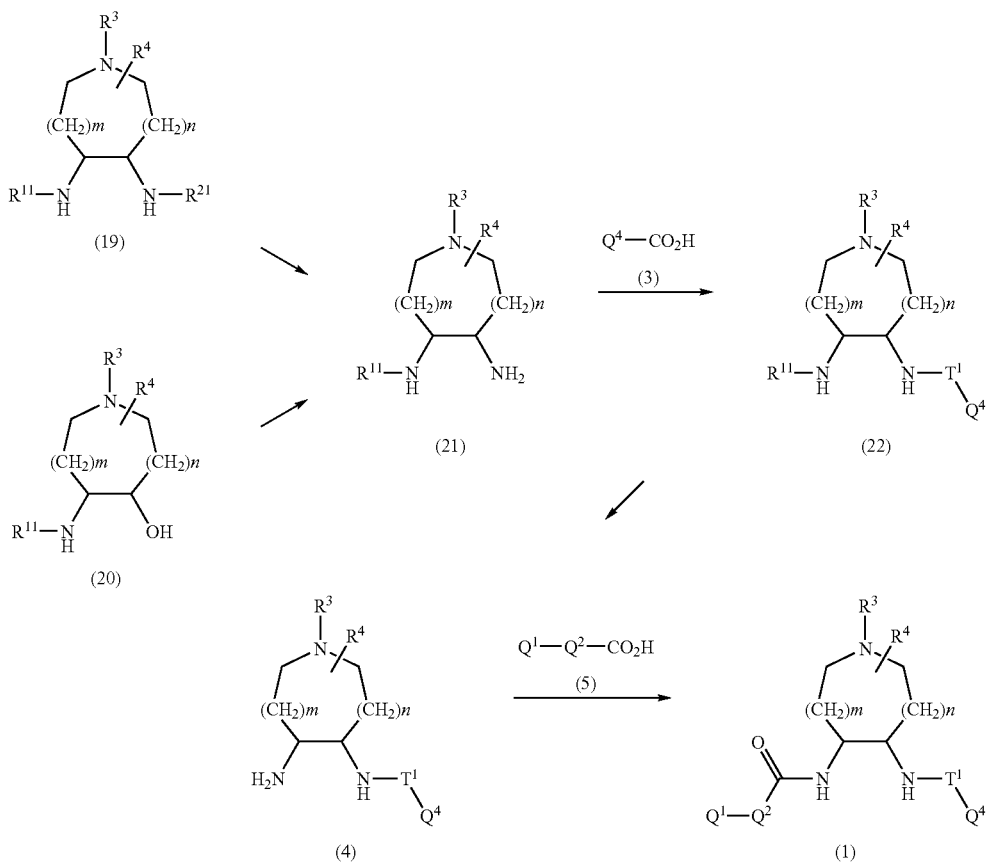

wherein $Q^1$, $Q^2$, $Q^4$, $R^3$, $R^4$, m and n have the same meanings as defined above; $T^1$ represents a carbonyl group; and $R^{11}$ and $R^{21}$ each represent a protective group for amino group.

A compound (21) can be produced by removing the protective group $R^{21}$ of a compound (19) obtained by protecting the amino group of the compound (2). Here, the protective groups for amino group represented by $R^{11}$ and $R^{21}$ are usually not particularly limited as long as they are groups used in the protection of amino group, and as a representative example, protective groups for amino group, such as the tert-butoxycarbonyl group, described in the Production Method 2 may be mentioned, but in this case, $R^{11}$ and $R^{21}$ need to be protective groups which can be removing by different methods or conditions. For example, a combination of a tert-butoxycarbonyl group for $R^{11}$ and a benzyloxycarbonyl group for $R^{21}$, or the like may be mentioned as a representative combination. These protective groups may be selected according to the nature and the like of the compound having amino group to be protected, and upon removal of these protective groups, reagents or conditions may be selected in accordance with the protective group.

Furthermore, the compound (21) can also be produced by converting the hydroxy group of an aminoalcohol derivative (20) to an amino group. As preparation examples of the aminoalcohol derivative (20), for example, conversion from methionine to 3-hydroxy-4-aminothiopyrane 1,1-dioxide (Tetrahedron Lett., Vol. 37, p. 7457 (1996)), and the like are known.

As the method of converting the hydroxy group of the aminoalcohol derivative (20) to an amino group, there may be mentioned a method of reacting the aminoalcohol derivative (20) with methanesulfonyl chloride, p-toluenesulfonyl chloride, trifluoromethanesulfonic anhydride or the like, subsequently reacting the reaction product with ammonia, a primary arylalkylamine such as benzylamine, p-methoxybenzylamine or 2,4-dimethoxybenzylamine, a secondary arylalkylamine such as dibenzylamine, or a hydroxylamine such as N-benzylhydroxylamine or N,O-dibenzylhydroxylamine, and removing the benzyl group as necessary, to produce a triamine (21). Also, when the aminoalcohol derivative (20) is reacted with phthalimide or succinimide through a reaction of treating the aminoalcohol derivative (20) with triphenylphosphine and ethyl azodicarboxylate (Mukaiyama method), and then the reaction product is treated with hydrazine or N-methylhydrazine, the aminoalcohol derivative can be derivatized to the triamine (21).

The compound (1) of the present invention can be produced by reacting the obtained triamine (21) with the carboxylic acid (3) to produce a compound (22), subsequently removing the protective group $R^{11}$ to obtain the compound (4), and then reacting the compound (4) with the carboxylic acid (5). In the reaction between the compound (21) and carboxylic acid (3) and the reaction between the compound (4) and carboxylic acid (5), the same reagents or reaction conditions as those used in the Production Method 1 may be used.

Likewise, in the reaction between the compound (21) and carboxylic acid (3), if the carboxylic acid (3) is replaced by the sulfonic acid halide (10), a compound (1c) having a sulfonyl group for $T^1$ can be produced.

[Production Method 6]

A representative method of producing the production intermediate (2) described in the Production Method 1 will be described.

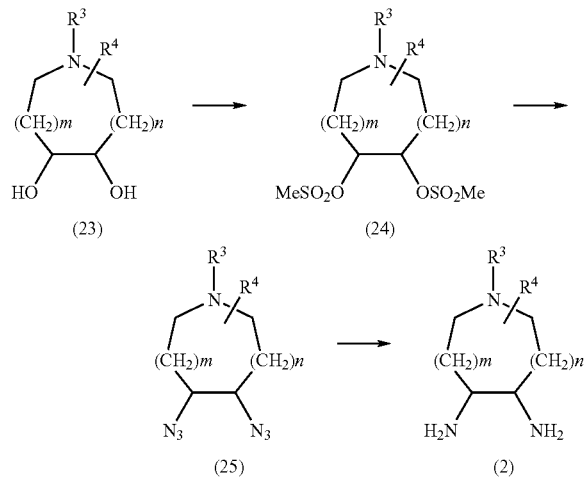

wherein $R^3$, $R^4$, m and n have the same meanings as defined above.

As a preparation example for a diol derivative (23), for example, conversion from 1,2,3,6-tetrahydropyridine to 1-benzyloxycarbonyl-3,4-cis-dihydroxypyrrolidine (JP-A-7-138264), conversion from L-tartaric acid to (R, R)-tetrahydrofurandiol or (R,R)—N-benzylpyrrolidinediol (Tetrahedron: Asymmetry, Vol. 8, p. 1861 (1997)), and the like are known. By using these known methods or modifying the methods to optionally perform removal of protective group or conversion of functional group, the diol derivative (23) can be produced.

The compound (24) can be produced by reacting the diol derivative (23) with methanesulfonyl chloride in the presence of a base in an inert solvent at a temperature under cooling to room temperature. The inert solvent may be appropriately selected from those mentioned in the Production Method 1, and used, and particularly halogenated-alkyl solvents such as dichloromethane and chloroform, and ether solvents such as tetrahydrofuran and 1,4-dioxane are preferred. As the base, organic bases such as pyridine, 2,6-lutidine, 4-dimethylaminopyridine, triethylamine, N-methylmorpholine, diisopropylethylamine and diazabicyclo[5.4.0]undec-7-ene (DBU) are preferred.

An azide derivative (25) can be produced by reacting the compound (24) with sodium azide in an appropriate solvent at a temperature under cooling to a temperature under heating. As the solvent, amide solvents such as N,N-dimethylformamide and N-methylpyrrolidin-2-one, alcohol solvents such as methanol and ethanol, ether solvents such as tetrahydrofuran and 1,4-dioxane, aromatic solvents such as benzene and toluene, halogenated-alkyl solvents such as dichloromethane and chloroform, dimethylsulfoxide, acetone, and the like are suitable. The above-described commonly used solvents may also be used as a mixture with water.

As the method of converting the azide derivative (25) to the compound (2), there may be mentioned a number of methods, including a method of hydrogenating the azide derivative using a palladium catalyst, a Raney nickel catalyst or a platinum catalyst; a reaction using a reducing agent such as lithium aluminum hydride, sodium borohydride; a reaction using zinc in the presence of nickel chloride or cobalt chloride; a reaction using triphenylphosphine; and the like, and the reagents or conditions may be selected according to the nature and the like of the compound, and used. The hydrogen pressure can be increased to above the atmospheric pressure. As the solvent, alcohol solvents such as methanol and ethanol, ether solvents such as tetrahydrofuran and 1,4-dioxane, amide solvents such as N,N-dimethylformamide and N-methylpyrrolidin-2-one, ester solvents such as ethyl acetate, acetic acid, hydrochloric acid, water, or mixed solvent thereof are suitable. The triamine (2) produced by the method described above can be derivatized to the compound (1) of the present invention according to the above-described Production Method 1, 2 or 3.

If the diol derivative (23) is trans-3,4-dihydroxytetrahydrofuran or trans-1-substituted-3,4-dihydroxypyrrolidine, there exist optically active isomers. These optically active diol derivatives (23) can be derivatized to optically active triamine (2), which can be further derivatized to an optically active compound (1) of the present invention according to the Production Method 1, 2 or 3.

[Production Method 7]

Representative production methods with regard to optically active compounds (30), (31) and (32), which are included in the compound (19) described in the Production Method 5, will be described. The conformation of the asymmetric carbon shown in the following production procedure is given as an example.

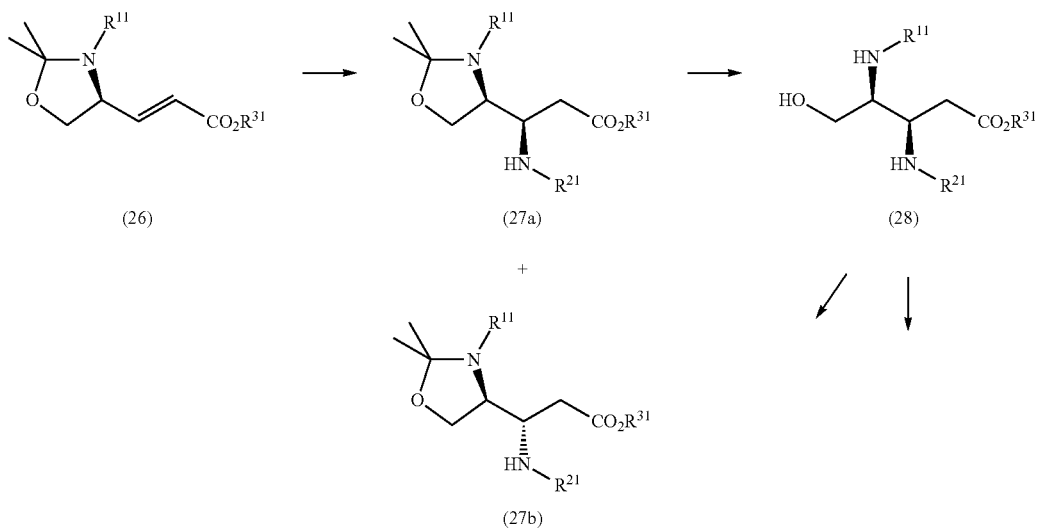

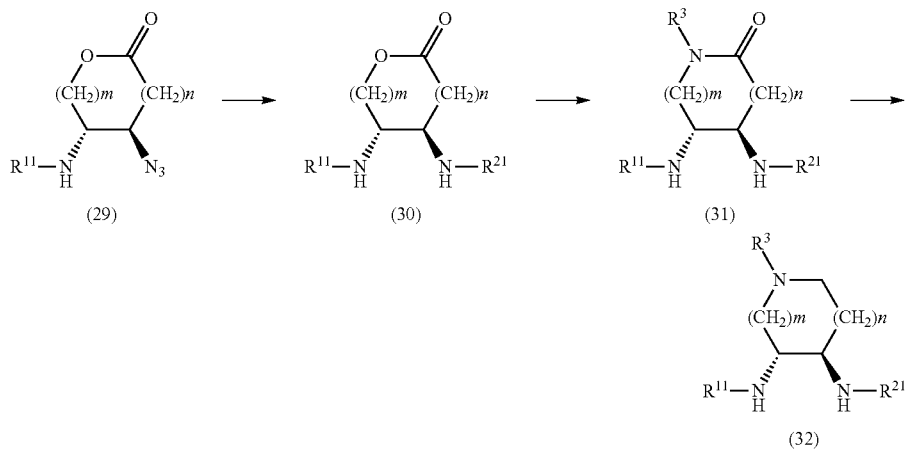

wherein m, n, $R^3$, $R^{11}$ and $R^{21}$ have the same meanings as defined above; and $R^{31}$ represents a protective group for carboxy group.

An optically active α,β-unsaturated ester derivative (26) can be produced by the methods described in the document (J. Org. Chem., Vol. 61, p. 581 (1996); J. Org. Chem., Vol. 57, p. 6279 (1992); etc.), or by the methods adapting thereof. The optically active α,β-unsaturated ester derivative (26) and an amine can be reacted in an appropriate solvent at a temperature under cooling to a temperature under heating, to produce diastereomers (27a) and (27b). The amine may be appropriately selected from those described in the above Production Method 5, and used. As the solvent, an organic solvent which does not react with substrates, products or reagents, particularly alcohol solvents such as methanol and ethanol, and ether solvents such as tetrahydrofuran, 1,2-dimethoxyethane and 1,4-dioxane are preferred. Furthermore, the diastereomers (27a) and (27b) can also be produced by adapting the method described in the document (J. Org. Chem., Vol. 63, p. 7263 (1998)) to react the α,β-unsaturated ester derivative (26) with an organic metal base such as lithium N-benzyl(trimethylsilyl)amide. Once these diastereomers are separated, for example, the diastereomer (27a) can be used in the subsequent reaction.

When the compound (27a) is treated with an acid in an appropriate solvent at a temperature under cooling to a temperature under heating, a compound (28) is produced. The acid that can be used includes hydrochloric acid, sulfuric acid or a Lewis acid such as boron trifluoride, trifluoroacetic acid, p-toluenesulfonic acid, and the like. The solvent used in the reaction includes water, an alcohol solvent such as methanol or ethanol, and the like. The above-described solvents may also be used as a mixture with water. Also, in the present reaction, the protective group for amino group $R^{11}$ and/or $R^{21}$ may be cleaved. In this case, it may be necessary to react the compound with an appropriate protective reagent for amino group, according to necessity.

When the compound (28) is treated with an acid in a solvent at a temperature under cooling to a temperature under heating, an optically active compound (30) can be produced.

The acid that can be used may be appropriately selected from the acids described above, and particularly Lewis acids such as boron trifluoride, and p-toluenesulfonic acid and the like are preferred. Examples of the solvent that can be used in the reaction include ether solvents such as 1,4-dioxane and tetrahydrofuran, and aromatic solvents such as benzene and toluene. Furthermore, the compound (30) can also be produced from an azide derivative (29). As a preparation example for an optically azide derivative (29), for example, conversion from L-aspartic acid to (R,R)-(3S,4S)-3-amino-4-azido-5-oxotetrahydrofuran (Can. J. Chem., Vol. 71, p. 1407 (1993)), and the like are known. By using these known methods or adapting the methods to perform removal of protective group or conversion of functional group as necessary, the optically active azide derivative (29) can be produced. The compound (30) can be produced by reducing the azide of the azide derivative (29) to an amino group, and then reacting the amino group with an appropriate protective reagent for amino group. In the reduction of azide, the same reagents or reaction conditions as those described for the method of converting the azide derivative (25) to the compound (2) of the Production Method 6 may be used.

A compound (31) can be produced by converting the hydroxy group moiety of the compound (28) to an amino group, and then treating the amino group with a base. The method of converting the hydroxy group of the compound (28) to an amino group can be performed, for example, according to the Production Method 6 described above. Alternatively, the compound (31) can be produced by treating the alcohol derivative (28) with an oxidizing agent, and then reductively aminating the resulting aldehyde derivative. As the oxidizing agent that can be used in the reaction, specifically, pyridinium chlorochromate (PCC), pyridinium dichromate (PDC), sulfur trioxide-pyridine complexes, and the like are preferred. The amine includes ammonia, a primary alkylamine such as methylamine or ethylamine, and a primary arylalkylamine such as benzylamine, p-methoxybenzylamine or 2,4-dimethoxybenzylamine. As the method for reduction, a method of hydrogenating using a palladium catalyst, a Raney nickel catalyst or a platinum catalyst; a method using a reducing agent such as sodium borohydride, sodium triacetoxyborohydride or sodium cyanoborohydride, and other methods are available. The reagents or conditions may be selected according to the nature and the like of the compound. Also, the base that can be used in the above process may be appropriately selected from the bases described in the Production Method 1. The compound (31) can be produced using the compound (30) and an amine, according to methods described in the document (Tetrahedron Lett., Vol. 41, p. 1141 (2000); Heterocycles, Vol. 53, p. 173 (2000)), or by adapting the methods. The amine that can be used includes ammonia; a primary alkylamine such as methylamine or ethylamine; a primary arylalkylamine such as benzylamine or p-methoxybenzylamine; aniline, and the like.

A compound (32) can be produced by treating the compound (31) with a reducing agent in a solvent at a temperature under cooling to a temperature under heating. The reducing agent includes borane-tetrahydrofuran complexes, borane-methyl sulfide complexes, and reducing agents such as lithium aluminum hydride, and the reagents or conditions may be selected in accordance with the nature and the like of the compound. As the solvent, an organic solvent which does not react with substrates, products or reagents, particularly ether solvents such as tetrahydrofuran and 1,4-dioxane, are preferred.

The compounds (30), (31) and (32) produced by the above-described methods can be derivatized to the optically active isomer (1) of the compound of the present invention according to the Production Method 5 described above.

The above production processes are illustrated for one of optically active isomers, but optically active isomers having different configurations can also be produced by similar processes by using starting materials having different configurations.

[Production Method 8]

The compound (1) in which $T^1$ is a group —CO—CO—N(R')— (wherein R' has the same meaning as defined above), can be produced through the following procedure.

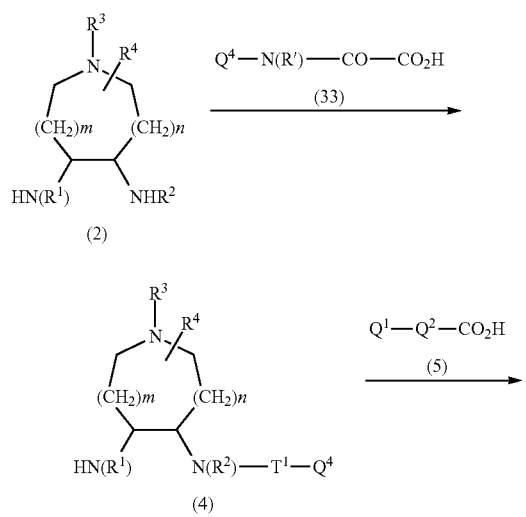

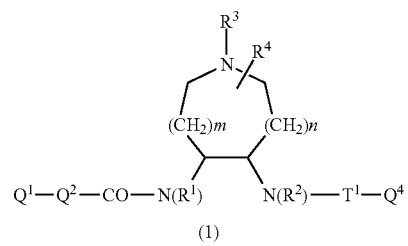

wherein $Q^1$, $Q^2$, $Q^4$, $R^1$, $R^2$, $R^3$, $R^4$, m, n and R' have the same meanings as defined above; and $T^1$ represents —CO—CO—N(R')— (wherein R' has the same meaning as defined above).

Thus, the compound (1) of the present invention can be produced by derivatizing a carboxylic acid (33) to an acid halide or an activated ester, reacting the product with the triamine (2) to produce the compound (4), and reacting the resulting compound (4) with the carboxylic acid (5) under the same conditions. With regard to the reactions of the respective processes, reaction reagents or conditions that are conventionally used in peptide synthesis may be employed. The acid halide can be produced by treating the carboxylic acid (33) with an acid halide such as thionyl chloride or oxalyl chloride. There are various activated esters, but for example, an activated ester can be produced by reacting a phenol such as p-nitrophenol, N-hydroxybenzotriazole or N-hydroxysuccinimide with the carboxylic acid (33), using a condensing agent such as N,N'-dicyclohexylcarbodiimide or 1-ethyl-3-(3-dimethylaminopropyl)carbodiimide-hydrochloride. The activated esters can also be produced through a reaction between the carboxylic acid (33) and pentafluorophenyl trifluoroacetate, a reaction between the carboxylic acid (33) and 1-benzotriazolyloxytripyrrolidinophosphonium hexafluorophosphite, a reaction between the carboxylic acid (33) and diethyl cyanophosphate (Shioiri method), a reaction between the carboxylic acid (33) and triphenylphosphine and 2,2'-dipyridyldisulfide (Mukaiyama method), or the like. The compound (4) can be produced by reacting a mixed acid anhydride, acid halide or activated ester of the carboxylic acid (33) thus obtained, with the triamine (2) in the presence of an appropriate base in an inert solvent at −78° C. to 150° C. The compound (1) of the present invention can be produced by reacting the obtained compound (4) with a mixed acid anhydride, acid halide or activated ester of the carboxylic acid (5) under the same conditions. The reagents or reaction conditions for the reaction between the compound (4) and the carboxylic acid (5) are the same as the reagents or reaction conditions for the reaction between the triamine (2) and the carboxylic acid (33). The base or solvent used in the respective processes described above may be appropriately selected from those described in the Production Method 1.

[Production Method 9]

A compound (1) in which $T^1$ is a group —CO—CO—N(R')— (wherein R' has the same meaning as defined above), can be produced by the following procedure.

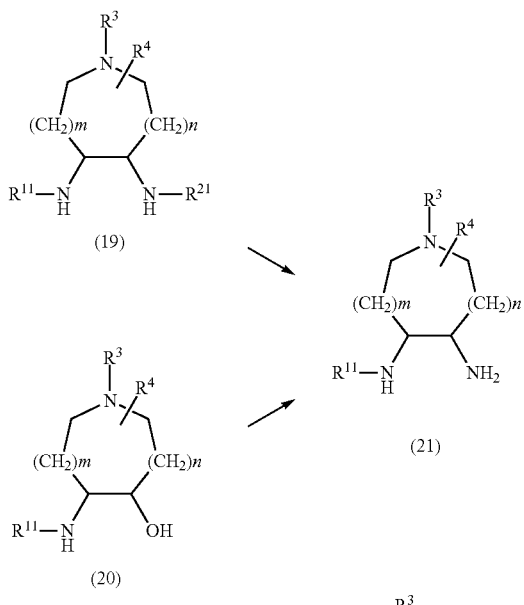
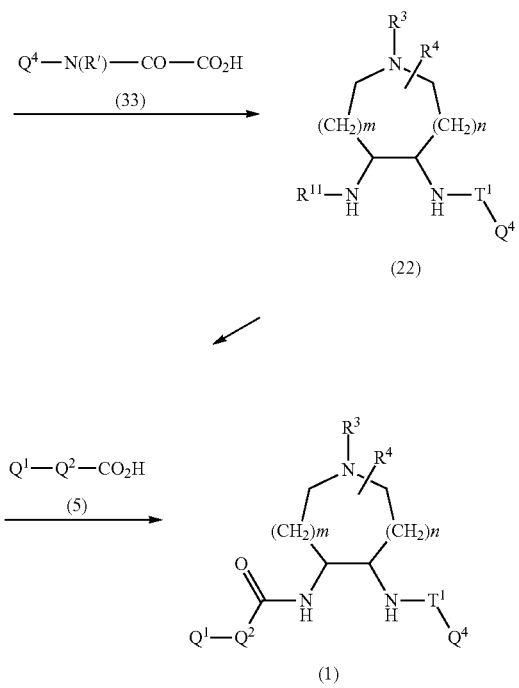

wherein $Q^1$, $Q^2$, $Q^4$, $R^3$, $R^4$, m and n have the same meaning as defined above; $T^1$ represents a group —CO—CO—N(R')— (wherein R' has the same meaning as defined above); and $R^{11}$ and $R^{21}$ each represent a protective group for amino group.

A compound (21) can be produced by removing the protective group $R^{21}$ of a compound (19) which is obtained by protecting the amino group of the compound (2). Here, the protective groups for amino group represented by $R^{11}$ and $R^{21}$ are usually not particularly limited as long as they are groups used in the protection of amino group, and as a representative example may include protective groups for amino group, described in the Production Method 2, but in this case, $R^{11}$ and $R^{21}$ need to be protective groups which can be removed by different methods or conditions. For example, a combination of a tert-butoxycarbonyl group for $R^{11}$ and a benzyloxycarbonyl group for $R^{21}$, or the like may be mentioned as a representative combination. These protective groups may be selected according to the nature and the like of the compound having amino group to be protected, and upon removal of these protective groups, reagents or conditions may be selected in accordance with the protective group.

Furthermore, the compound (21) can also be produced by converting the hydroxy group of an aminoalcohol derivative (20) to an amino group. As preparation examples of the aminoalcohol derivative (20), for example, conversion from methionine to 3-hydroxy-4-aminothiopyrane-1,1-dioxide (Tetrahedron Lett., Vol. 37, p. 7457 (1996)), and the like are known.

As the method of converting the hydroxy group of the aminoalcohol derivative (20) to an amino group, there may be mentioned a method of reacting the aminoalcohol derivative (20) with methanesulfonyl chloride, p-toluenesulfonyl chloride, trifluoromethanesulfonic anhydride or the like, subsequently reacting the reaction product with ammonia, a primary arylalkylamine such as benzylamine, p-methoxybenzylamine or 2,4-dimethoxybenzylamine, a secondary arylalkylamine such as dibenzylamine, or a hydroxylamine such as N-benzylhydroxylamine or N,O-dibenzylhydroxylamine, and optionally removing a benzyl group to produce the triamine (21). Also, when the aminoalcohol derivative (20) is reacted with phthalimide or succinimide through a reaction of treating the aminoalcohol derivative (20) with triphenylphosphine and ethyl azodicarboxylate (Mukaiyama method), and then the reaction product is treated with hydrazine or N-methylhydrazine, the aminoalcohol derivative can be derivatized to the triamine (21).

The compound (1) of the present invention can be produced by reacting the obtained triamine (21) with a carboxylic acid (33) to produce a compound (22), subsequently removing the protective group $R^{11}$ to obtain the compound (4), and then reacting the compound (4) with the carboxylic acid (5). In the reaction between the compound (21) and carboxylic acid (33) and the reaction between the compound (4) and carboxylic acid (5), the same reagents or reaction conditions as those used in the Production Method 1 may be used.

[Production Method 10]

A compound (1) in which $T^1$ is a group —CO-$A^1$-N(R")— (wherein R" represents a hydrogen atom, a hydroxy group, an alkyl group or an alkoxy group; $A^1$ represents an alkylene group having 1 to 5 carbon atoms which may be substituted), can be produced by reacting the compound (9) described in the Production Method 2 with $Q^4$-N(R'')-$A^1$-$CO_2$H (42) in an inert solvent using a condensing agent at −50 to 50° C. The condensing agent may include N,N'-dicyclohexylcarbodiimide, 1-ethyl-3-(3-dimethylaminopropyl)carbodiimide hydrochloride and the like. The inert solvent may include a halogenated-alkyl solvent such as dichloromethane, chloroform or carbon tetrachloride; an ether solvent such as tetrahydrofuran, 1,2-dimethoxyethane or dioxane; an aromatic solvent such as benzene or toluene; an amide solvent such as N,N-dimethylformamide; and the like.

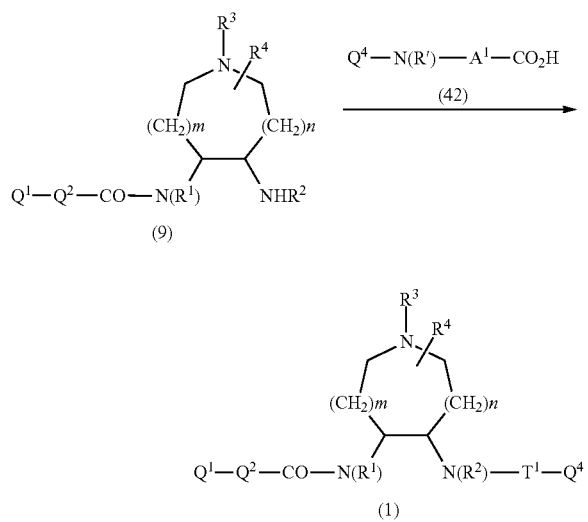

wherein $Q^1$, $Q^2$, $Q^4$, $R^1$, $R^2$, $R^3$, $R^4$, m, n and R'' have the same meanings as defined above; $T^1$ represents a group —CO-$A^1$-N(R'')— (wherein R'' represents a hydrogen atom, a hydroxy group, an alkyl group or an alkoxy group; and $A^1$ represents an alkylene group having 1 to 5 carbon atoms which may be substituted.

The compound (42) described in the above-described production method can be produced by, for example, reacting an arylamine such as 4-chloroaniline with an ester of bromoalkanoic acid in a solvent such as acetonitrile or N,N-dimethylformamide in the presence of a base such as potassium carbonate at 40 to 120° C., and then hydrolyzing the ester using an alkali such as lithium hydroxide, potassium hydroxide or sodium hydroxide. The compound (42) in the form of potassium salt or the like may be directly used in the reaction.

[Production Method 11]

A compound (1) in which $T^1$ is a group —C(=O)—NH— or a group —C(=S)—NH— can be produced by reacting the compound (9) described in the Production Method 2 with an isocyanate ($Q^4$-N=C=O) or an isothiocyanate ($Q^4$-N=C=S) in an inert solvent at −20 to 50° C. The inert solvent may include those described in the Production Method 10. With regard to the isocyanate or isothiocyanate used in this method, if commercially available ones cannot be used, the compound may be produced by a method generally used in the production of isocyanate or isothiocyanate.

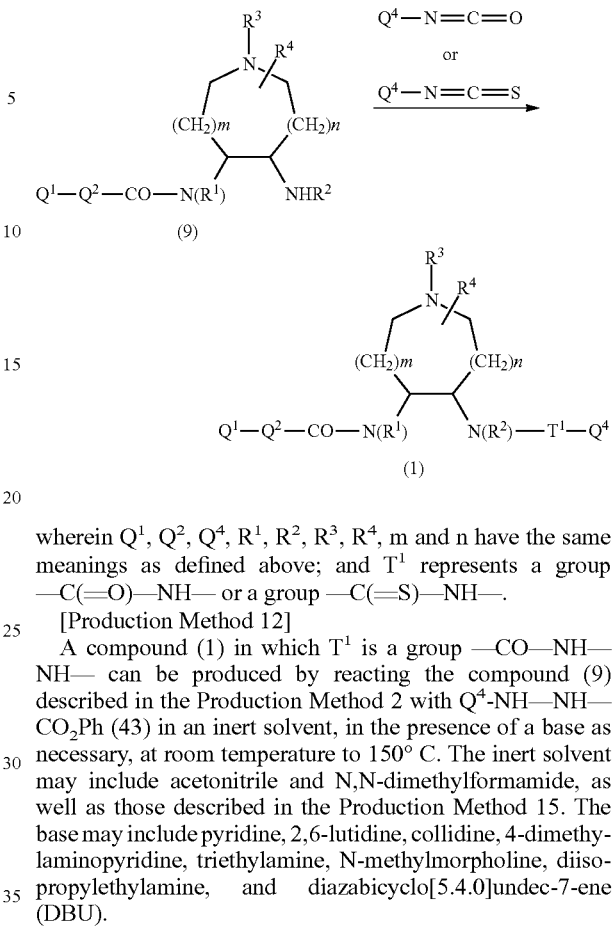

wherein $Q^1$, $Q^2$, $Q^4$, $R^1$, $R^2$, $R^3$, $R^4$, m and n have the same meanings as defined above; and $T^1$ represents a group —C(=O)—NH— or a group —C(=S)—NH—.

[Production Method 12]

A compound (1) in which $T^1$ is a group —CO—NH—NH— can be produced by reacting the compound (9) described in the Production Method 2 with $Q^4$-NH—NH—$CO_2$Ph (43) in an inert solvent, in the presence of a base as necessary, at room temperature to 150° C. The inert solvent may include acetonitrile and N,N-dimethylformamide, as well as those described in the Production Method 15. The base may include pyridine, 2,6-lutidine, collidine, 4-dimethylaminopyridine, triethylamine, N-methylmorpholine, diisopropylethylamine, and diazabicyclo[5.4.0]undec-7-ene (DBU).

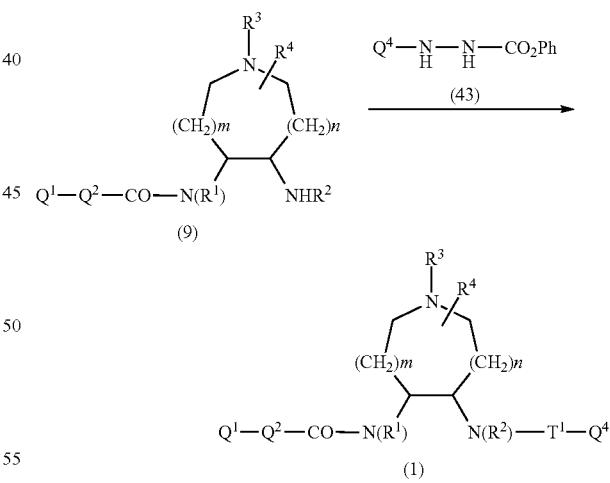

wherein $Q^1$, $Q^2$, $Q^3$, $Q^4$, m, n, $R^1$ and $R^2$ have the same meaning as defined above; $T^1$ represents a group —CO—NH—NH—; and Ph represents a phenyl group.

The compound (43) described in the above-described production method can be produced by, for example, reacting an arylhydrazine such as 4-chlorophenylhydrazine with diphenyl carbonate in a solvent such as acetonitrile, N,N-dimethylformamide, dichloromethane, chloroform, tetrahydrofuran, 1,2-dimethoxyethane, dioxane, benzene, toluene or the like, at room temperature to 120° C.

[Production Method 13]

A compound (1) in which $T^1$ is a group —CO-$A^2$-CO— (wherein $A^2$ represents a single bond or an alkylene group having 1 to carbon atoms) can be produced by reacting the compound (9) described in the Production Method 2 with $Q^4$-CO-$A^2$-CO$_2$H (44) in an inert solvent using a condensing agent at −50 to 50° C. The condensing agent may include N,N'-dicyclohexylcarbodiimide, 1-ethyl-3-(3-dimethylaminopropyl)carbodiimide.hydrochloride, or the like. The solvent may include the solvents described in the Production Method 10.

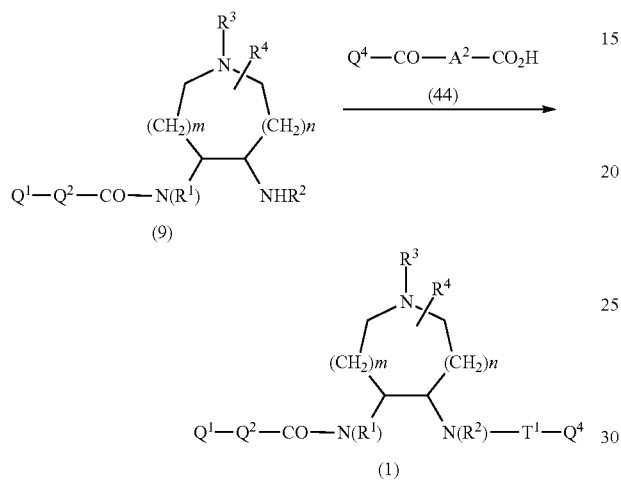

wherein $Q^1$, $Q^2$, $Q^4$, $R^1$, $R^2$, $R^3$, $R^4$, m and n have the same meanings as defined above; and $T^1$ represents a group —CO-$A^2$-CO— (wherein $A^2$ represents a single bond or an alkylene group having 1 to carbon atoms.

The compound (44) described in the above-described production method can be produced, in the case where $A^2$ is a single bond, for example, by hydrolyzing a compound (for example, $Q^4$-CO—CO$_2$Et) produced by a Friedel-Craft reaction between an aromatic hydrocarbon such as chlorobenzene or an aromatic heterocycle such as thiophene, with a chlorooxoacetic acid ester (for example, ClCO—CO$_2$Et), using an alkali such as lithium hydroxide, potassium hydroxide or sodium hydroxide.

Furthermore, in the case where $A^2$ is a methylene group, the compound (44) can be produced by, for example, hydrolyzing a ketoester derivative (for example, $Q^4$-CO—CH$_2$—CO$_2$Et), which is obtained by reacting an arylcarbonyl chloride such as 4-chlorobenzoic acid chloride, or a heteroarylcarbonyl chloride such as thiophenecarbonyl chloride, with potassium malonic acid monoester monocarboxylate in the presence of magnesium chloride and triethylamine, using an alkali such as lithium hydroxide, potassium hydroxide or sodium hydroxide. The ketoester derivative may be used in the reaction with compound (9) in the form of a carboxylic acid which is obtained by hydrolysis after conversion of its carbonyl group into ethylene ketal. Also, when $A^2$ is an alkylene group having at least 2 carbon atoms, the compound (44) can be produced by, for example, hydrolyzing a ketoester derivative (for example, $Q^4$-CO-$A^2$-CO$_2$Et) which is obtained by a Friedel-Crafts reaction of an aromatic hydrocarbon such as benzene or an aromatic heterocyclic compound such as thiophene with an alkylenedicarboxylic acid monoester monochloride, using an alkali such as lithium hydroxide, potassium hydroxide or sodium hydroxide.

[Production Method 14]

A compound (1) in which $T^1$ is a group —CO-$A^3$-CO—NH— (wherein $A^3$ represents an alkylene group having 1 to 5 carbon atoms), can be produced by reacting the compound (9) described in the Production Method 2 with $Q^4$-NH—CO-$A^3$-CO$_2$H (45) in an inert solvent using a condensing agent at −50 to 50° C. The condensing agent may include N,N'-dicyclohexylcarbodiimide, 1-ethyl-3-(3-dimethylaminopropyl)carbodiimide-hydrochloride, and the like. The inert solvent includes a halogenated-alkyl solvent such as dichloromethane, chloroform or carbon tetrachloride; an ether solvent such as tetrahydrofuran, 1,2-dimethoxyethane or dioxane; an aromatic solvent such as benzene or toluene; an amide solvent such as N,N-dimethylformamide; and the like.

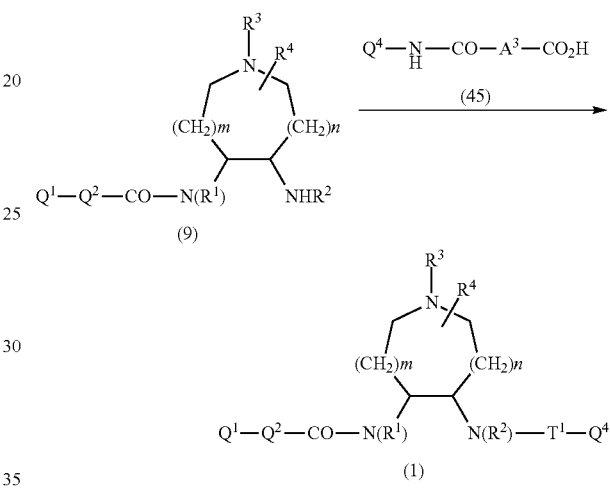

wherein $Q^1$, $Q^2$, $Q^4$, $R^1$, $R^2$, $R^3$, $R^4$, m and n have the same meanings as defined above; and $T^1$ represents a group —CO-$A^3$-CO— (wherein $A^3$ represents an alkylene group having 1 to 5 carbon atoms).

The compound (45) can be produced by hydrolyzing a compound (for example, $Q^4$-NH—CO-$A^3$-CO$_2$Et) produced by reacting an arylamine such as 4-chloroaniline or a heteroarylamine such as aminopyridine, which corresponds to $Q^4$-NH$_2$, with potassium alkylenedicarboxylic acid monoester monocarboxylate at −50 to 50° C. in an inert solvent using a condensing agent, with an alkali such as lithium hydroxide, potassium hydroxide or sodium hydroxide.

[Production Method 15]

A compound (1) in which $T^1$ is a group —CS—CO—N(R')— (wherein R' has the same meaning as defined above) can be produced by the following procedure.

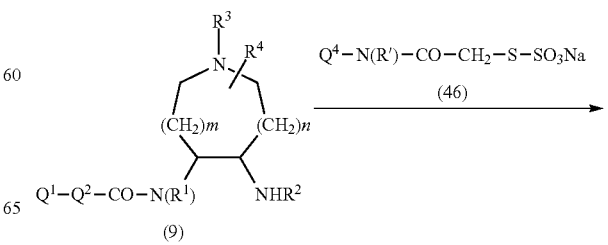

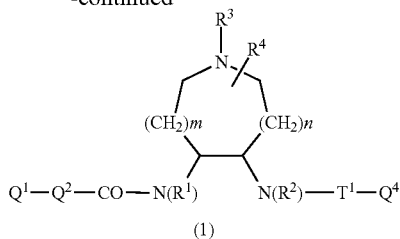

(1)

wherein $Q^1$, $Q^2$, $Q^4$, $R^1$, $R^2$, $R^3$, $R^4$, R', m and n have the same meanings as defined above; and $T^1$ represents a group —CS—CO—N(R')— (wherein R' has the same meaning as defined above).

Specifically the compound (1) of the present invention can be produced by dissolving or suspending sodium thiosulfate (46) and the compound (9) in a solvent, followed by heating. The reaction temperature is preferably 80 to 200° C., and particularly preferably more or less 150° C. The solvent used in this reaction may include water; an alcohol such as methanol or ethanol; a basic solvent such as pyridine or N-methylmorpholine; a halogenated-alkyl solvent such as dichloromethane or chloroform; an ether solvent such as tetrahydrofuran, 1,2-dimethoxyethane or dioxane; an amide solvent such as N,N-dimethylformamide; and the like. These solvents may be suitably mixed for use. Examples of mixed solvents include a mixed solvent of methanol and dichloromethane. Also, in this reaction, the solvent is not necessarily to be refluxed. For example, in the case of using a mixed solvent of methanol and dichloromethane, the reaction solution (or the reaction mixture) is heated at an external temperature of 150° C. to distill off the solvent, and then the residue is continuously heated at the same temperature.

[Production Method 16]

A compound (1) in which $T^1$ is a group —CO—CS—N(R')— (wherein R' has the same meaning as defined above) can be produced by the following procedure.

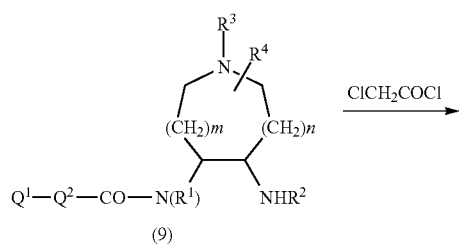

(9)

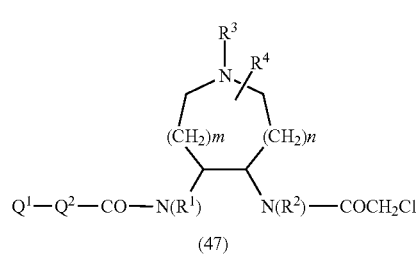

(47)

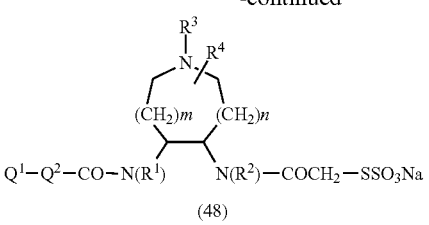

(48)

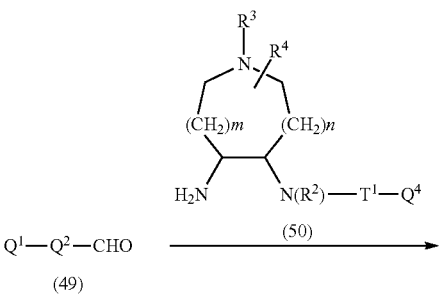

(1)

wherein $Q^1$, $Q^2$, $Q^4$, $R^1$, $R^2$, $R^3$, $R^4$, R', m and n have the same meanings as defined above; and $T^1$ represents a group —CO—CS—N(R')— (wherein R' has the same meaning as defined above).

Specifically a sodium thiosulfate derivative (48) can be produced by reacting the compound (9) with chloroacetic acid chloride in the presence of a base to obtain a compound (47), and then heating the compound (47) together with sodium thiosulfate in a solvent. The compound (1) of the present invention can be produced by heating the derivative (48) thus obtained, together with an amine, namely, HN(R')-$Q^4$.

For the conditions, solvents or the like for producing the compound (47) from the compound (9), those commonly used in the reaction of an amine with an acid chloride may be employed. In order to produce the compound (48) from the compound (47), the compound (47) may be heated to reflux, together with sodium thiosulfate for about 1 hour in a solvent such as ethanol. In the case where the compound (47) is a salt such as hydrochloride or the like, the reaction may be performed in the presence of a base such as sodium hydrogencarbonate. The production conditions for the compound (48) are not limited to those described herein, and the temperature, the type of the solvent and the type of the base may be appropriately modified. The conditions for the reaction between the compound (48) and HN(R')-$Q^4$ are the same as those described in the Production Method 20.

[Production Method 17]

A compound (1) in which $T^0$ is a thiocarbonyl group (—CS— group) can be produced by the following procedure.

$Q^1$—$Q^2$—CHO (49)

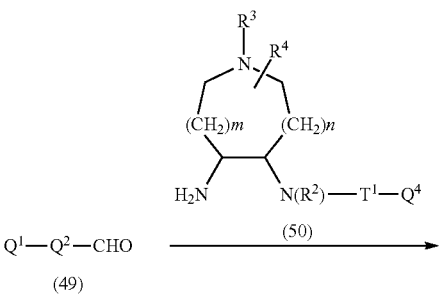

-continued

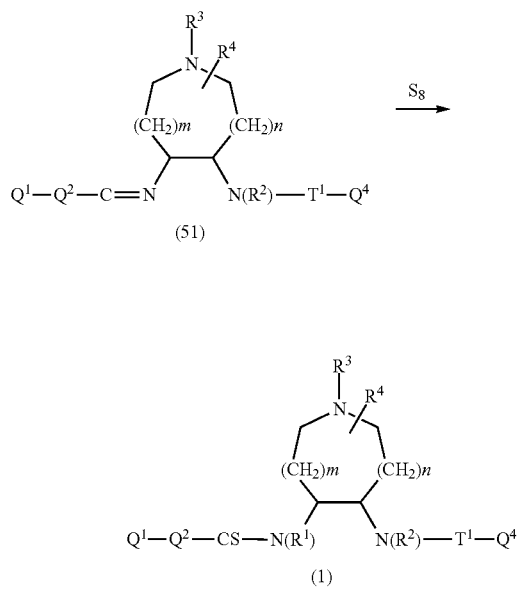

wherein $Q^1$, $Q^2$, $Q^4$, $R^2$, $R^3$, $R^4$, m and n have the same meanings as defined above; $T^1$ represents a group —$SO_2$—, a group —CO—, a group —CO—NH—, a group —CS—NH—, a group —CO—NH—NH—, a group —CO—CO—N(R')— (wherein R' has the same meaning as defined above), a group —CO—CS—N(R')— (wherein R' has the same meaning as defined above), a group —CS—CO—N(R')— (wherein R' has the same meaning as defined above), a group —CS—CS—N(R')— (wherein R' has the same meaning as defined above), a group —CO-$A^1$-N(R")— (wherein $A^1$ and R" have the same meanings as defined above), a group —CO-$A^2$-CO— (wherein $A^2$ has the same meaning as defined above), a group —CO-$A^3$-CO—NH— (wherein $A^3$ has the same meaning as defined above), or a group —CO-$A^3$-CO— (wherein $A^3$ has the same meaning as defined above).

Specifically the compound (1) of the present invention can be produced by subjecting a compound (49) to a dehydration reaction with an amine (50) in the presence of an acid catalyst such as p-toluenesulfonic acid to produce a compound (51), and then heating the resultant together with powdered sulfur in a solvent such as a liquid mixture of methanol/dichloromethane. For the conditions for producing the compound (51) from the compound (49) and the amine (50), those commonly used for the production of a Schiff base may be generally employed. Specifically, heating under reflux may be conducted in the presence of an acid catalyst in benzene or toluene, under conditions such that water is removed from the reaction system, by, for example, using a Dean-Stark water trap. Molecular sieve may also be used in removing water from the reaction system.

[Production Method 18]

A compound (1) in which $T^1$ is a group —CS—CO—N(R')— (wherein R' has the same meaning as defined above) can be produce by the following procedure.

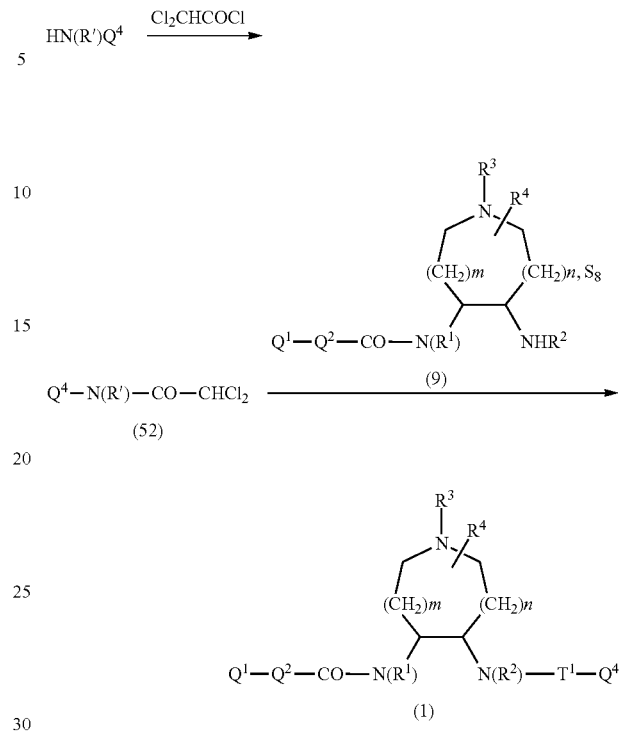

wherein $Q^1$, $Q^2$, $Q^4$, $R^1$, $R^2$, $R^3$, $R^4$, R', m and n have the same meanings as defined above; and $T^1$ represents a group —CS—CO—N(R')— (wherein R' has the same meaning as defined above).

A compound (52) can be produced by reacting an arylamine such as 4-chloroaniline or a heteroarylamine such as aminopyridine, which corresponds to HN(R')$Q^4$, with dichloroacetyl chloride in an inert solvent such as N,N-dimethylformamide or in a basic solvent such as pyridine, at −78° C. to 150° C. The compound (52) can also be produced by reacting dichloroacetic acid with an amine corresponding to HN(R')$Q^4$ using the reagents or conditions stated in the Production Method 1.

The compound (1) can be more efficiently produced by suspending the compound (52) and powdered sulfur in a solvent, adding a base such as diisopropylethylamine or triethylamine and the triamine (9), and allowing a reaction of the mixture at a reaction temperature of 0° C. to 200° C. The amount of the powdered sulfur used in the reaction is preferably 1 equivalent. The reaction temperature is preferably 60° C. to 160° C., and particularly preferably 90° C. to 140° C. The solvent used in this reaction may include an amide solvent such as N,N-dimethylformamide; a basic solvent such as N-methylmorpholine or pyridine; an alcohol such as ethanol or butanol; an ether solvent such as dioxane; acetonitrile, water, and the like.

[Production Method 19]

A compound (1) in which $T^1$ is a group —CS—CO—N (R')— (wherein R' has the same meaning as defined above) can be produced by the following procedure.

HN(R')Q⁴ $\xrightarrow{ClCH_2COCl}$

Q⁴—N(R')—CO—CH₂Cl
(53)

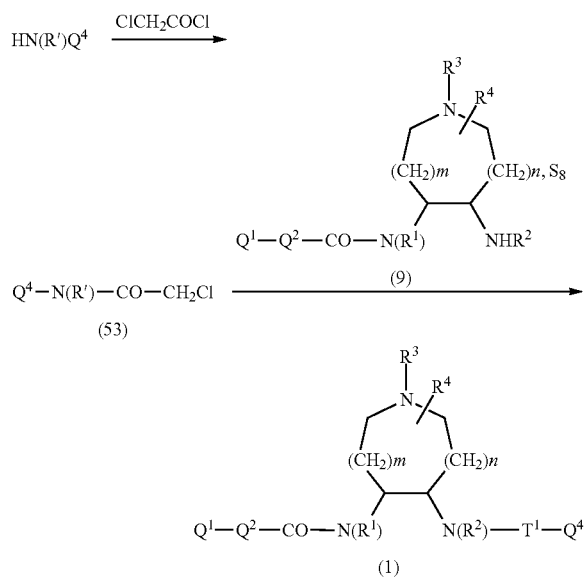

(9)

(1)

wherein Q¹, Q², Q⁴, R¹, R², R³, R⁴, R', m and n have the same meanings as defined above; T¹ represents a group —CS—CO—N(R')— (wherein R' has the same meaning as defined above).

A compound (53) can be produced by reacting an arylamine such as 4-chloroaniline or a heteroarylamine such as aminopyridine, which corresponds to HN(R')Q⁴, with dichloroacetyl chloride in an inert solvent such as N,N-dimethylformamide or in a basic solvent such as pyridine, at −78° C. to 150° C. The compound (53) can also be produced by reacting chloroacetic acid with an amine corresponding to HN(R')Q⁴ using the reagents or conditions stated in the Production Method 1.

The compound (1) can be produced by suspending the compound (53) and powdered sulfur in a solvent, adding a base such as diisopropylethylamine or triethylamine, stirring the mixture for 5 minutes to 8 hours, then adding the triamine (9) and a condensing agent to react the mixture. The amount of the powdered sulfur used in the reaction is preferably 2 equivalents or more, and the reaction temperature is preferably 0° C. to 80° C. The condensing agent may include 1-ethyl-3-(3-dimethylaminopropyl)carbodiimide-hydrochloride, N,N'-dicyclohexylcarbodiimide, and the like. The solvent used in this reaction include an amide solvent such as N,N-dimethylformamide; a basic solvent such as N-methylmorpholine or pyridine; a halogenated-alkyl solvent such as dichloromethane or chloroform; an ether solvent such as dioxane; acetonitrile, and the like. This reaction can also be performed without a condensing agent to produce the compound (1). In this case, an alcohol such as methanol or ethanol, water or the like can also be used, in addition to the above-described solvents.

[Production Method 20]

A compound (1) in which T¹ is a group —CS—CO—N(R')— (wherein R' has the same meaning as defined above) can be produced, involving a compound (54) in which T¹ is a group —CS—CO—N(R') (wherein R' has the same meaning as defined above).

Q⁴—N(R')—CO—CH₂—S—SO₃Na or
(46)

Q⁴—N(R')—CO—CHCl₂, S₈ or
(52)

Q⁴—N(R')—CO—CH₂Cl, S₈
(53)

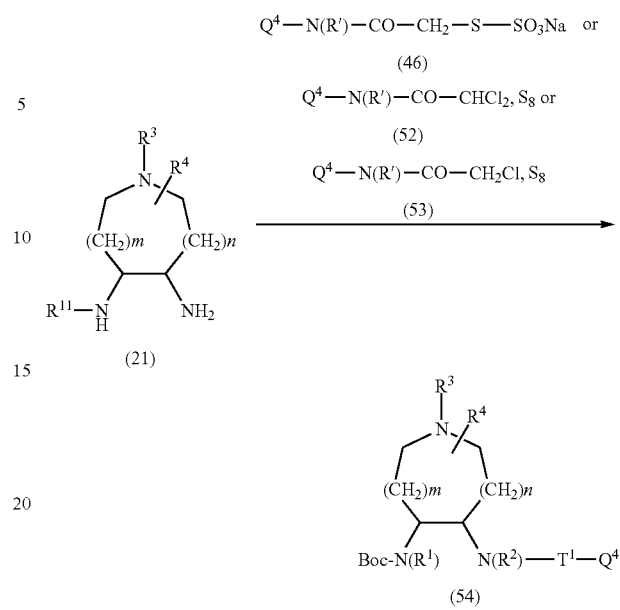

(21)

(54)

wherein Q¹, Q², Q⁴, R¹, R², R³, R⁴, R¹¹, R', m and n have the same meanings as defined above; and T¹ represents a group —CS—CO—N(R')— (wherein R' has the same meaning as defined above).

Specifically, the compound (1) of the present invention can be produced by reacting a dichloroacetamide derivative (52) or chloroacetamide derivative (53), powdered sulfur and the compound (21) in a solvent in the presence of a base, subsequently removing the protective group to produce a compound (4), and condensing the resulting compound (4) with a carboxylic acid (5). A compound (54) can be efficiently produced by suspending the compound (52) and powdered sulfur in a solvent, adding a base such as diisopropylethylamine or triethylamine and the compound (21), and allowing the mixture to react at a reaction temperature of 0° C. to 200° C. The amount of powdered sulfur used in the reaction is preferably 1 equivalent. The reaction temperature is preferably 60° C. to 160° C., and particularly preferably 90° C. to 140° C. The solvent that can be used in this reaction may include an amide solvent such as N,N-dimethylformamide; a basic solvent such as N-methylmorpholine or pyridine; an alcohol such as ethanol or butanol; an ether solvent such as dioxane; acetonitrile, water, and the like. Furthermore, the compound (54) can be produced by suspending the compound (53) and powdered sulfur in a solvent, adding a base such as diisopropylethylamine or triethylamine, stirring the mixture for 5 minutes to 5 hours, subsequently adding the compound (21) and a condensing agent, and allowing the mixture to react. The amount of powdered sulfur used in the reaction is preferably 2 equivalents or more, and the reaction temperature is preferably 0° C. to 80° C. The condensing agent may include 1-ethyl-3-(3-dimethylaminopropyl)carbodiimide.hydrochloride, N,N'-dicyclohexylcarbodiimide, and the like. The solvent that can be used in this reaction include an amide solvent such as N,N-dimethylformamide; a basic solvent such as N-methylmorpholine or pyridine; a halogenated-alkyl solvent such as dichloromethane or chloroform; an ether solvent such as dioxane; acetonitrile, and the like. Furthermore, this reaction can also be performed without any condensing agent to produce the compound (54). In this case, an alcohol such as methanol or ethanol, or water can also be used, in addition to the above-described solvents. Moreover, the compound (54) can also be produced by reacting sodium thiosulfate (46) with the compound (21) using the reaction conditions described in the Production Method 15.

The compound (4) can be produced by treating the compound (54) with trifluoroacetic acid or the like at −20° C. to 70° C.

The thus-produced compound (4) in which $T^1$ is a group —CS—CO—N(R')— (wherein R' has the same meaning as defined above) can be reacted with a carboxylic acid (5) according to the method described in the Production Method 1 to produce the compound (1) of the present invention.

For $R^{11}$ of the compound (21), a protective group therefore may be selected in accordance with the nature and the like of the compound, and upon cleaving the protective group, reagents or conditions may be selected depending on the protective group. A compound having a tert-butoxycarbonyl group for $R^{11}$ may be mentioned as a representative example.

[Production Method 21]

A compound (1) in which $T^1$ is a group —CO—N(H)—CO— can be produced by the following procedure.

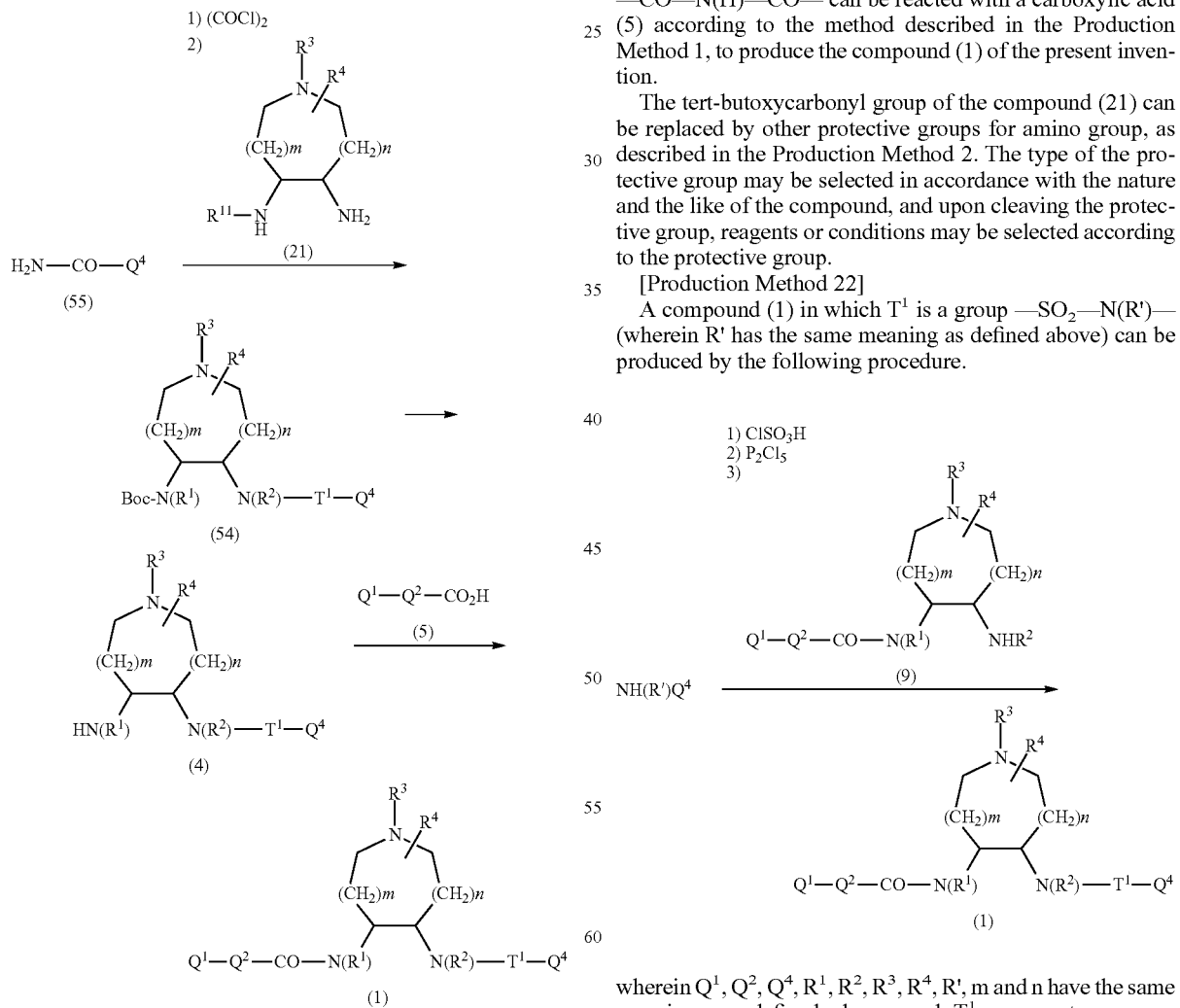

wherein $Q^1, Q^2, Q^4, R^1, R^2 R^3, R^4, R^{11}$, m and n have the same meanings as defined above; and $T^1$ represents a group —CO—N(H)—CO—.

Specifically, the compound (1) of the present invention can be produced by deprotecting a compound (54) produced by reacting an arylamide such as 4-chlorobenzamide or a heteroarylamide such as picolinamide, which corresponds to $H_2N$—CO-$Q^4$ (55), with the compound (21), via an acylisocyanate intermediate, and then condensing the resulting compound (4) with a carboxylic acid (5).

For example, an amide (55) is reacted with oxalyl chloride in an inert solvent at a reaction temperature of 20° C. to 100° C. to produce an acylisocyanate derivative, and this derivative is reacted with an amine (7) at a reaction temperature of 0° C. to 100° C., thus to produce the compound (54). The inert solvent that can be used in the present invention include a halogenated-alkyl solvent such as dichloromethane, chloroform or dichloroethane; an ether solvent such as tetrahydrofuran or dioxane; an aromatic solvent such as benzene or toluene; an amide solvent such as N,N-dimethylformamide or N,N-dimethylacetamide; acetonitrile, and the like.

The compound (4) can be produced by treating the compound (54) with trifluoroacetic acid or the like at −20° C. to 70° C.

The thus-produced compound (4) in which $T^1$ is a group —CO—N(H)—CO— can be reacted with a carboxylic acid (5) according to the method described in the Production Method 1, to produce the compound (1) of the present invention.

The tert-butoxycarbonyl group of the compound (21) can be replaced by other protective groups for amino group, as described in the Production Method 2. The type of the protective group may be selected in accordance with the nature and the like of the compound, and upon cleaving the protective group, reagents or conditions may be selected according to the protective group.

[Production Method 22]

A compound (1) in which $T^1$ is a group —$SO_2$—N(R')— (wherein R' has the same meaning as defined above) can be produced by the following procedure.

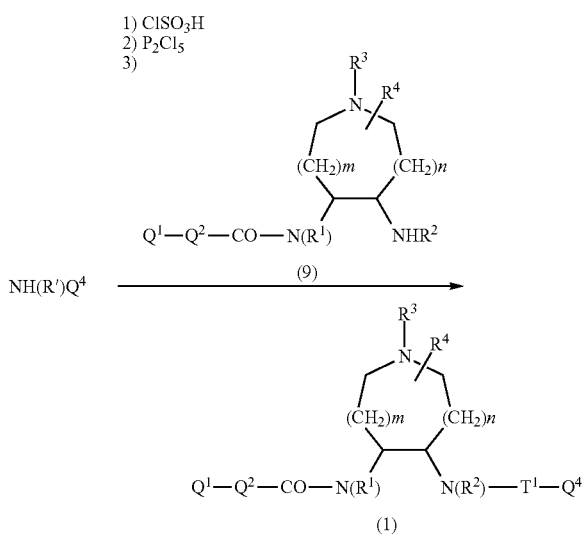

wherein $Q^1, Q^2, Q^4, R^1, R^2, R^3, R^4$, R', m and n have the same meanings as defined above; and $T^1$ represents a group —$SO_2$—N(R')— (wherein R' has the same meaning as defined above).

The compound (1) can be produced by producing an amidosulfuric acid derivative by reacting an amine such as 4-chloroaniline, which corresponds to $HN(R')Q^4$, with chlorosulfuric acid in an inert solvent at a reaction temperature of −78° C. to 30° C., subsequently activating the amidosulfuric acid derivative with a reagent such as phosphorus pentachloride, and then reacting the activated derivative with an amine (9). As the reagent for activating the amidosulfuric acid derivative, a halogenating reagent such as phosphorus pentachloride or phosphorus oxychloride, as well as a condensing agent such as, 1,1'-carbonyldiimidazole can be used. In the case of conducting activation using a halogenating reagent such as phosphorus pentachloride or phosphorus oxychloride in the present reaction, the reaction system is preferably heated at 50° C. to 120° C. The inert solvent that can be used in the present invention include a halogenated-alkyl solvent such as dichloromethane, chloroform or dichloroethane; an ether solvent such as tetrahydrofuran or dioxane; an aromatic solvent such as benzene or toluene; an amide solvent such as N,N-dimethylformamide or N,N-dimethylacetamide; acetonitrile, and the like.

The triamine derivative of the present invention exhibits a potent inhibitory effect on activated blood coagulation factor X, and thus is useful for mammals including humans, as a medicine, particularly as an activated blood coagulation factor X inhibitor, an anticoagulant, a prophylactic and/or therapeutic agent for thrombosis or embolism, a prophylactic and/or therapeutic agent for thrombotic diseases, as well as a prophylactic and/or therapeutic agent for cerebral infarction, cerebral embolism, myocardial infarction, angina pectoris, pulmonary infarction, pulmonary embolism, Buerger's disease, deep venous thrombosis, disseminated intravascular coagulation syndrome, thrombus formation after artificial valve or joint replacement, thrombus formation and reocclusion after angioplasty, systemic inflammatory response syndrome (SIRS), multiple organ dysfunction syndrome (MODS), thrombus formation during extracorporeal circulation, or blood clotting upon blood drawing.

Furthermore, the compound of the present invention exhibits excellent absorbability when orally administered, and exhibits potent anticoagulating effects and antithrombotic effects, thus being particularly useful as a medicine for oral administration.

When the compound of the present invention is used as a medicine for human body, the dose is in the range of 1 mg to 1 g, preferably 10 mg to 300 mg, per day for an adult. The dose for an animal may vary depending on the purpose of administration (therapy or prophylaxis), the type or size of the animal to be treated, the type of the infected pathogen, or the severity, but the daily dose is generally in the range of 0.1 mg to 200 mg, preferably 0.5 mg to 100 mg, per kg of the body weight of the animal. This daily dose may be administered once a day, or in 2 to 4 portions. Also, the daily dose may exceed the above-described amounts according to necessity.

A pharmaceutical composition containing the compound of the present invention can be prepared by selecting an appropriate formulation according to the mode of administration, using the method for preparing various formulations conventionally used. Dosage forms of the pharmaceutical composition containing the compound of the present invention as the main ingredient, include tablets, powders, granules, capsules, liquids, syrups, elixirs, oily or aqueous suspensions and the like, as exemplified preparations for oral administration.

An injectable preparation may employ a stabilizer, an antiseptic or a dissolution aid in the formulation, and a solution which may contain these auxiliaries may also be prepared into a prepared-upon-use formulation by filling the solution into a container and lyophilizing it to produce a solid formulation. Furthermore, a single dose may be filled in one container, or multiple doses may be filled in one container.

Also, as preparations for external use, liquids, suspensions, emulsions, ointments, gels, creams, lotions, sprays, patches and the like may be mentioned.

Solid preparations can contain pharmaceutically acceptable additives together with the compound of the present invention, and be prepared by, for example, selectively combining fillers, bulking agents, binding agents, disintegrants, dissolution promoting agents, wetting agents, lubricants or the like with the compound of the invention, as necessary.

Liquid preparation may include a solution, a suspension, an emulsion and the like, which may contain a suspending agent, an emulsifying agent and the like, as an additives.

EXAMPLES

Hereinafter, the present invention will be described in more detail by way of Reference Examples, Examples and Test Examples.

Reference Example 1

2-Amino-6,7-dihydrothiazolo[5,4-c]pyridine-5[4H]-carboxylic acid tert-butyl ester

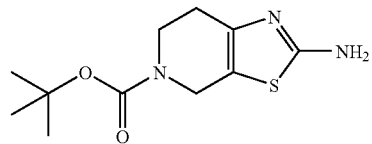

1-Tert-butoxycarbonyl-4-piperidone (40.0 g) was dissolved in cyclohexane (80 ml), and p-toluenesulfonic acid monohydrate (191 mg) and pyrrolidine (17.6 ml) were added thereto. The mixture was heated to reflux for 2 hours, while dehydrating by means of a Dean-Stark apparatus. The reaction mixture was concentrated under reduced pressure, subsequently the residue was dissolved in methanol (60 ml), and powdered sulfur (6.42 g) was added thereto. Under ice cooling, a methanol solution (10 ml) of cyanamide (8.44 g) was gradually added dropwise, and the mixture was stirred for 5 hours at room temperature. The precipitated solid was collected by filtration, thus to obtain the title compound (31.0 g).
$^1$H-NMR (DMSO-$d_6$) δ: 1.41 (9H, s), 2.44 (2H, t, J=5.6 Hz), 3.57 (2H, t, J=5.6 Hz), 4.29 (2H, s), 6.79 (2H, s).
MS(EI)m/z: 255 (M$^+$).

Reference Example 2

2-Bromo-6,7-dihydrothiazolo[5,4-c]pyridine-5[4H]-carboxylic acid tert-butyl ester

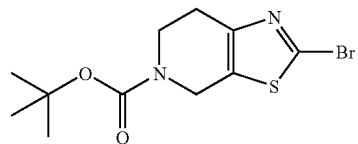

Cupric bromide (1.05 g) was suspended in N,N-dimethylformamide (20 ml), tert-butyl nitrite (0.696 ml) and the compound obtained in Reference Example 1 (1.00 g) were added thereto under ice cooling, and the reaction mixture was heated with stirring at 40° C. for 30 minutes. The reaction mixture was concentrated under reduced pressure, and the residue was purified by silica gel column chromatography (acetic acid ethyl ester:hexane=1:5), to obtain the title compound (568 mg).

$^1$H-NMR (CDCl$_3$) δ: 1.48 (9H, s), 2.85 (2H, br.s), 3.72 (2H, br.s) 4.56 (2H, br.s).

MS(FAB)m/z: 319 (M+H)$^+$.

Reference Example 3

2-Bromo-4,5,6,7-tetrahydrothiazolo[5,4-c]pyridine trifluoroacetate

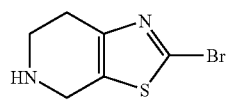

The compound obtained in Reference Example 2 (890 mg) was dissolved in methylene chloride (2 ml), trifluoroacetic acid 15 ml) was added thereto, and the mixture was stirred at room temperature for 30 seconds. The reaction mixture was concentrated under reduced pressure, and diethyl ether was added to the residue, and the precipitated solid was collected by filtration, to obtain the title compound (867 mg).

$^1$H-NMR (DMSO-d$_6$) δ: 2.98 (2H, t, J=6.1 Hz), 3.45 (2H, t, J=6.1 Hz), 4.35 (2H, s), 9.53 (2H, br.s).

MS(FAB)m/z: 219 (M+H)$^+$.

Reference Example 4

2-Bromo-5-methyl-4,5,6,7-tetrahydrothiazolo[5,4-c] pyridine

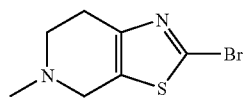

The compound obtained in Reference Example 3 (422 mg) was suspended in methylene chloride (10 ml), triethylamine (0.356 ml) was added and dissolved therein, subsequently acetic acid (0.216 ml), aqueous formaldehyde solution (35% solution, 0.202 ml), and sodium triacetoxyborohydride (428 mg) were added sequentially, and the mixture was stirred at room temperature for 1 hour. A saturated aqueous solution of sodium hydrogen carbonate (100 ml), methylene chloride (100 ml) and a 3 Normal aqueous solution of sodium hydroxide (3 ml) were added to the reaction mixture, and liquid separation was performed. The organic layer was dried over anhydrous sodium sulfate, and then the solvent was distilled off under reduced pressure. The residue was purified by silica gel column chromatography (methylene chloride:methanol=100:3), to obtain the title compound (286 mg).

$^1$H-NMR (CDCl$_3$) δ: 2.49 (3H, s), 2.79 (2H, t, J=5.7 Hz), 2.85-2.93 (2H, m), 3.58 (2H, t, J=1.8 Hz).

MS(FAB)m/z: 233 (M+H)$^+$.

Reference Example 5

5-Methyl-4,5,6,7-tetrahydrothiazolo[5,4-c]pyridine-2-carboxylic acid lithium salt

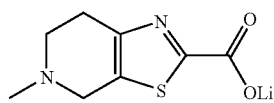

The compound obtained in Reference Example 4 (531 mg) was dissolved in anhydrous diethyl ether (20 ml), n-butyllithium N hexane solution, 1.63 ml) was added dropwise at −78° C., and the mixture was stirred for 30 minutes under ice cooling. Carbon dioxide gas was introduced into the reaction mixture over 10 minutes at −78° C., and then the mixture was heated to room temperature. The reaction mixture was concentrated under reduced pressure, to obtain the title compound (523 mg).

$^1$H-NMR (DMSO-d$_6$) δ: 2.37 (3H, s), 2.64-2.85 (4H, m), 3.54 (2H, s)

Reference Example 6

5-Methyl-4,5,6,7-tetrahydrothiazolo[5,4-c]pyridine-2-carboxylic acid hydrochloride

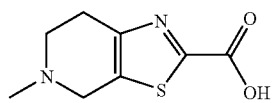

To the compound obtained in Reference Example 5 (3.00 g), a 1 N ethanol solution of hydrochloric acid (36 ml) was added, and the mixture was stirred at room temperature for 1 hour. The precipitating crystals were filtered and washed with ethanol (9 ml). The wet product was dried at room temperature under reduced pressure, to obtain the title compound (2.76 g).

$^1$H-NMR (D$_2$O) δ: 4.82-4.88 (1H, d, J=16.0 Hz), 4.51-4.57 (1H, d, J=16.0 Hz), 3.88-3.96 (1H, m), 3.60-3.70 (1H, m), 3.22-3.33 (2H, m), 3.15 (3H, s).

Reference Example 7

(4S)-4-[(E)-3-Ethoxy-3-oxo-1-propenyl]-2,2-dimethyl-1,3-oxazolidine-3-carboxylic acid tert-butyl ester

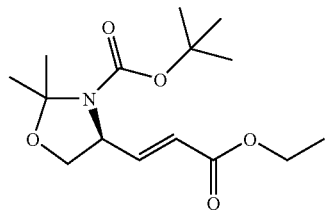

A mixed solution comprising (4R)-4-formyl-2,2-dimethyl-1,3-oxazolidine-3-carboxylic acid tert-butyl ester (11.7 g), (carboethoxymethylene)triphenylphosphorane (20.7 g) and toluene (100 ml) was heated with stirring at 100° C. for 18 hours. The reaction mixture was concentrated, and the resulting residue was purified by silica gel column chromatography (hexane:acetic acid ethyl ester=8:1), to obtain the title compound (17 g).

$^1$H-NMR (CDCl$_3$) δ: 1.29 (3H, t, J=6.6 Hz), 1.43-1.56 (15H, m), 3.80 (1H, dd, J=9.0, 2.4 Hz), 4.09 (1H, dd, J=9.0, 6.6 Hz), 4.11-4.23 (2H, m), 4.30-4.61 (1H, m), 5.83-6.02 (1H, m), 6.74-6.89 (1H, m).

Reference Example 8

(4S)-4-[1-(benzylamino)-3-ethoxy-3-oxopropyl]-2,2-dimethyl-1,3-oxazolidine-3-carboxylic acid tert-butyl ester

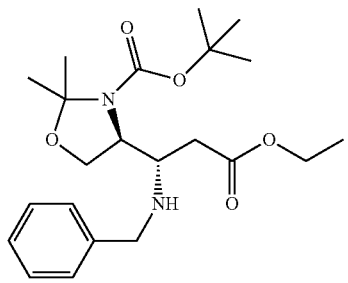

A mixed solution comprising the compound obtained in Reference Example 7 (22.2 g), benzylamine (16 g) and ethanol (100 ml) was heated to reflux for 2 days. The reaction mixture was concentrated, and the resulting residue was purified by silica gel column chromatography (hexane:acetic acid ethyl ester=8:1), to obtain the title compound (26 g).

$^1$H-NMR (CDCl$_3$) δ: 1.25 (3H, t, J=6.6 Hz), 1.42-1.63 (15H, m), 2.24-2.33 (0.5H, m), 2.40-2.50 (1H, m), 2.63-2.74 (0.5H, m), 3.41-3.52 (1H, m), 3.67-3.80 (1H, m), 3.83 (2H, s), 3.89-4.00 (1H, m), 4.03-4.22 (4H, m), 7.23-7.45 (5H, m).

Reference Example 9

(4S)-4-(1-amino-3-ethoxy-3-oxopropyl)-2,2-dimethyl-1,3-oxazolidine-3-carboxylic acid tert-butyl ester

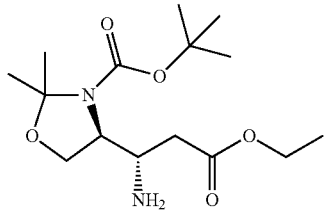

To a solution of the compound obtained in Reference Example 8 (13.6 g) in ethanol (200 ml), 10% palladium carbon (10 g) was added, and the mixture was stirred for 2 days in a hydrogen atmosphere. The insoluble matter was removed by filtration by passing the mixture through a Celite pad, and the filtrate was concentrated under reduced pressure, to obtain the title compound (10.5 g).

$^1$H-NMR (DMSO-d$_6$) δ: 1.19 (1.5H, t, J=6.6 Hz), 1.20 (1.5H, t, J=6.6 Hz), 1.32-1.50 (15H, m), 2.63-2.81 (2H, m), 3.22-3.34 (2H, m), 3.93 (1H, dd, J=10.0, 6.8 Hz), 4.08 (2H, q, J=6.6 Hz), 4.20-4.30 (1H, m).

Reference Example 10

(4S)-4-(1-{[(benzyloxy)carbonyl]amino}-3-ethoxy-3-oxopropyl)-2,2-dimethyl-1,3-oxazolidine-3-carboxylic acid tert-butyl ester

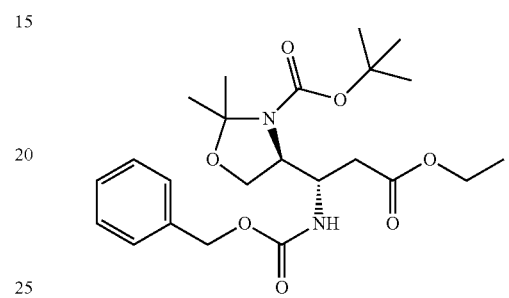

The compound obtained in Reference Example 9 (3.0 g) was suspended in a 9% aqueous solution of sodium hydrogen carbonate (56 ml), a solution of N-(benzyloxycarbonyloxy)succinimide (2.3 g) in dioxane (12 ml) was added dropwise under ice cooling, and the mixture was stirred for 3 hours while gradually returning to room temperature. The reaction mixture was diluted with acetic acid ethyl ester, the dilution was washed with water, a 10% aqueous solution of citric acid and saturated brine, and then dried over anhydrous sodium sulfate, and the solvent was distilled off under reduced pressure. The resulting residue was purified by silica gel column chromatography (chloroform), to obtain the title compound (3.8 g).

$^1$H-NMR (CDCl$_3$) δ: 1.23 (3H, t, J=6.6 Hz), 1.48 (9H, s), 1.56 (6H, s) 2.40-2.51 (2H, m), 2.63-2.70 (2H, m), 3.92-4.04 (1H, m) 4.06-4.10 (2H, m), 4.14-4.22 (1H, m), 5.09 (2H, s), 7.30-7.43 (5H, m).

Reference Example 11

(3S,4S)-3-{[(benzyloxy)carbonyl]amino}-4-[(tert-butoxycarbonyl)amino]-5-hydroxyvaleric acid ethyl ester (low polar compound) and (3R,4S)-3-{[(benzyloxy)carbonyl]amino}-4-[(tert-butoxycarbonyl)amino]-5-hydroxyvaleric acid ethyl ester (high polar compound)

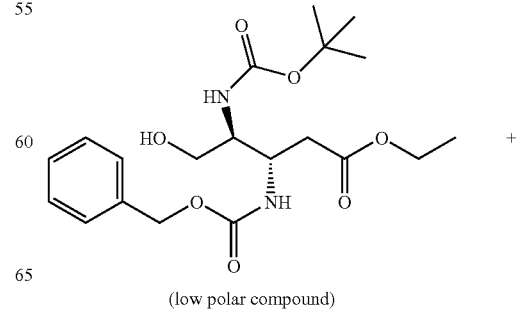

(low polar compound)

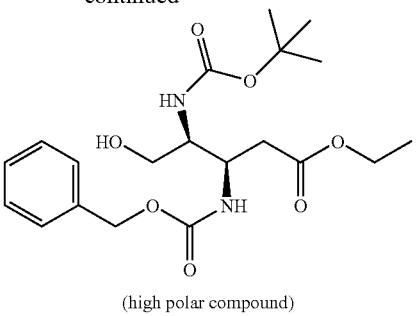

(high polar compound)

To a solution of the compound obtained in Reference Example 10 (30 g) in methylene chloride (100 ml), trifluoroacetic acid (100 ml) was added dropwise under ice cooling, and the mixture was stirred for 3 hours while gradually returning to room temperature. The reaction mixture was concentrated under reduced pressure, and the resulting residue was dissolved in methylene chloride (100 ml). To this solution, triethylamine (20 ml) and a solution of di-tert-butyl dicarbonate (19 g) in methylene chloride (100 ml) were sequentially added dropwise under ice cooling, and the mixture was stirred for 4 hours while gradually returning to room temperature. The reaction mixture was concentrated under reduced pressure, and the resulting residue was purified by silica gel column chromatography (hexane:acetic acid ethyl ester=2:1), to obtain the low polar title compound (7.6 g) and the high polar title compound (10 g).

Less polar compound:
$^1$H-NMR (CDCl$_3$) δ: 1.24 (3H, t, J=6.6 Hz), 1.42 (9H, s), 2.63 (2H, d, J=4.4 Hz), 3.30-3.41 (1H, m), 3.50 (1H, t, J=9.7 Hz), 3.65 (1H, t, J=9.7 Hz), 3.75 (1H, d, J=11.7 Hz), 3.90-4.00 (1H, m), 4.03-4.23 (2H, m), 5.12 (2H, s), 5.13-5.25 (1H, m), 5.79-6.02 (1H, m), 7.32-7.41 (5H, m).

More polar compound:
$^1$H-NMR (CDCl$_3$) δ: 1.22 (3H, t, J=6.6 Hz), 1.41 (9H, s), 2.50-2.70 (2H, m), 3.20-3.31 (1H, m), 3.43-3.51 (1H, m), 3.56-3.70 (1H, m), 3.74-3.78 (1H, m), 4.00-4.19 (2H, m), 4.23-4.30 (1H, m), 4.78-4.89 (1H, m), 5.10 (2H, s), 5.56-5.67 (1H, m), 7.31-7.40 (5H, m).

Reference Example 12

(3S,4R)-5-azide-3-{[(benzyloxy)carbonyl]amino}-4-[(tert-butoxycarbonyl)amino]valeric acid ethyl ester

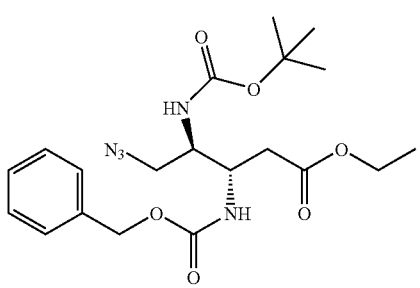

To a solution of the low polar compound obtained in Reference Example 11 (7.1 g) in methylene chloride (100 ml), triethylamine (4.80 ml) and methanesulfonyl chloride (1.55 ml) were sequentially added dropwise under ice cooling, and the mixture was stirred for 30 minutes under ice cooling. The reaction mixture was diluted with chloroform, and the dilution was washed with a 10% aqueous solution of citric acid, a saturated aqueous solution of sodium hydrogen carbonate and saturated brine. The organic layer was dried over anhydrous sodium sulfate, and then the solvent was distilled off under reduced pressure, to obtain a methanesulfonyl derivative (9.20 g). A mixed solution comprising the resulting methanesulfonyl derivative, sodium azide (5.64 g) and N,N-dimethylformamide (100 ml) was stirred at 80° C. for 20 hours. The reaction mixture was diluted with acetic acid ethyl ester, and the dilution was washed with water and saturated brine. The organic layer was dried over anhydrous sodium sulfate, subsequently the solvent was distilled off under reduced pressure, and the resulting residue was purified by silica gel column chromatography (chloroform), to obtain the title compound (5.42 g).

$^1$H-NMR (CDCl$_3$) δ: 1.24 (3H, t, J=7.1 Hz), 1.43 (9H, s), 2.56-2.68 (2H, m), 3.48-3.60 (2H, m), 3.88-3.97 (1H, m), 4.04-4.20 (3H, m), 4.88-4.97 (1H, br), 5.10 (2H, s), 5.60-5.75 (1H, br), 7.30-7.40 (5H, m).

MS(ESI)m/z: 436 (M+H)$^+$.

Reference Example 13

(4S,5R)-5-[(tert-butoxycarbonyl)amino]-2-oxopiperidine-4-carbamic acid benzyl ester

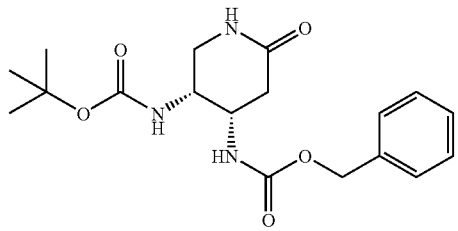

To a mixed solution of the compound obtained in Reference Example 12 (5.42 g) in ethanol (150 ml) and tetrahydrofuran ml), a Lindlar catalyst (2.71 g) was added, and the mixture was stirred for 3 hours in a hydrogen atmosphere, and then stirred for 14 hours under nitrogen conditions. The insoluble matter was removed by filtration by passing the mixture through a Celite pad, and the filtrate was concentrated under reduced pressure. Subsequently, the resulting residue was dissolved in tetrahydrofuran (30 ml), triethylamine (3.0 ml) was added thereto, and the mixture was stirred for 1.5 hours at room temperature. The reaction mixture was diluted with acetic acid ethyl ester, and the dilution was washed with a 10% aqueous solution of citric acid, a saturated aqueous solution of sodium hydrogen carbonate, and saturated brine. The organic layer was dried over anhydrous sodium sulfate, subsequently the solvent was distilled off under reduced pressure, and the resulting residue was purified by silica gel column chromatography (chloroform:methanol=25:1), to obtain the title compound (2.50 g).

$^1$H-NMR (CDCl$_3$) δ: 1.44 (9H, s), 2.30-2.50 (1H, br), 2.65-2.90 (1H, br), 3.15-3.30 (1H, br), 3.35-3.65 (1H, br), 4.00-4.25 (2H, br) 5.11 (2H, s), 5.55-5.60 (1H, br), 5.65-5.90 (1H, br), 6.25-6.55 (1H, br), 7.28-7.40 (5H, m).

MS(ESI)m/z: 364 (M+H)$^+$.

Reference Example 14

(3R,4S)-3-[(tert-butoxycarbonyl)amino]piperidine-4-carbamic acid benzyl ester

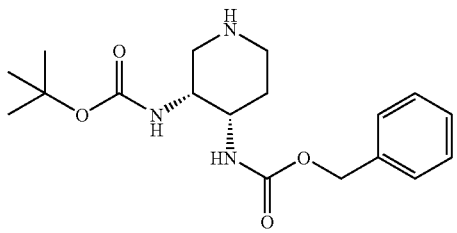

To a solution of the compound obtained in Reference Example 13 (2.49 g) in tetrahydrofuran (70 ml), 1 mole of borane-tetrahydrofuran complex (a tetrahydrofuran solution, 34.0 ml) was added dropwise under ice cooling, and the mixture was stirred for 20 hours while gradually returning to room temperature. Methanol (100 ml) was added to the reaction mixture, and the solvent was distilled off under reduced pressure. Ethanol (45 ml), water (5 ml) and triethylamine (10 ml) were added to the obtained residue, and the mixture was heated to reflux for 24 hours. The reaction mixture was concentrated, and the resulting residue was purified by silica gel column chromatography (chloroform:methanol:water=7:3:1, lower layer), to obtain the title compound (1.61 g).

$^1$H-NMR (CDCl$_3$) δ: 1.44 (9H, s), 1.65-1.72 (2H, m), 2.67 (1H, t, J=12.0 Hz), 2.82 (12H, d, J=12.0 Hz), 2.90-3.10 (1H, br), 3.60-3.80 (2H, m), 3.90-4.00 (1H, m), 5.00-5.20 (2H, m), 5.40-5.60 (2H, br), 7.25-7.74 (5H, m). MS(FAB)m/z: 350 (M+H)$^+$.

Reference Example 15

(3R,4S)-4-[(benzyloxycarbonyl)amino]-3-[(tert-butoxycarbonyl)amino]piperidine-1-carboxylic acid 2-trimethylsilanylethyl ester

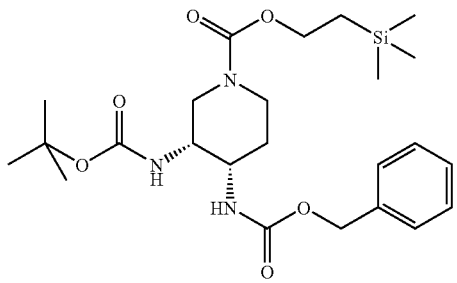

To a solution of the compound obtained in Reference Example 14 (5.98 g) in dioxane (50 ml), a 9% aqueous solution of sodium hydrogen carbonate (150 ml) was added, the mixture was cooled to 0° C., subsequently a dioxane solution (20 ml) of 1-[(2-trimethylsilyl)ethoxycarbonyloxy]pyrrolidine-2,5-dione (4.83 g) was added, and the mixture was stirred for 20 hours at room temperature. Acetic acid ethyl ester and water were added to the reaction mixture, the organic layer was washed with a saturated aqueous solution of sodium hydrogen carbonate, a 10% aqueous solution of citric acid, and a saturated aqueous solution of sodium chloride, subsequently the organic layer was dried over anhydrous sodium sulfate, and the solvent was distilled off under reduced pressure. The residue was purified by silica gel column chromatography (hexane:acetic acid ethyl ester=4:1→2:1), to obtain the title compound (6.75 g).

$^1$H-NMR (CDCl$_3$) δ: 0.00 (9H, s), 0.96 (2H, t, J=8.3 Hz), 1.36-1.53 (1H, m), 1.41 (9H, s), 1.82-2.00 (1H, m), 2.85 (1H, t, J=12.1 Hz), 3.01 (1H, d, J=13.4 Hz), 3.66-3.81 (1H, m), 3.87-4.25 (5H, m), 4.63-4.81 (1H, m), 5.06 (2H, br.s), 5.22-5.69 (1H, br), 7.23-7.40 (5H, m).

MS(ESI)m/z: 394 (M-Boc)$^+$.

Reference Example 16

(3R,4S)-4-({2-[(5-chloropyridin-2-yl)amino]-2-oxoacetyl}amino)-3-[(tert-butoxycarbonyl)amino]piperidine-1-carboxylic acid 2-trimethylsilanylethyl ester

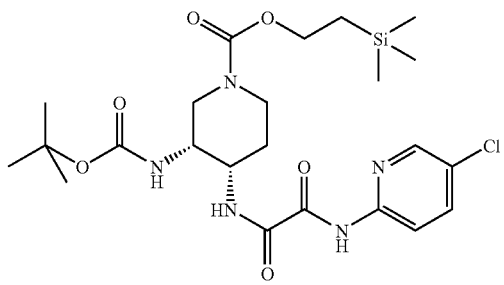

To a solution of the compound obtained in Reference Example 15 (7.13 g) in ethanol (70 ml), palladium carbon catalyst (700 mg) was added, and the mixture was stirred for 14 hours under hydrogen conditions. The catalyst was removed by filtration using Celite, and the filtrate was concentrated under reduced pressure and dried by means of a vacuum pump, to obtain (3R,4S)-4-amino-3-[(tert-butoxycarbonyl)amino]piperidine-1-carboxylic acid 2-trimethylsilanylethyl ester (5.22 g). This was dissolved in N,N-dimethylformamide (100 ml), then lithium 2-[(5-chloropyridin-2-yl)amino]-2-oxoacetate (4.50 g), 1-hydroxybenzotriazole (2.72 g) and 1-(3-dimethylaminopropyl)-3-ethylcarbodiimide hydrochloride (3.83 g) were added, and the mixture was stirred for 6 days at room temperature. The reaction mixture was concentrated under reduced pressure, and then dichloromethane and a saturated aqueous solution of sodium hydrogen carbonate were added to the residue. The organic layer was washed with a 10% aqueous solution of citric acid and a saturated aqueous solution of sodium chloride, and then dried over anhydrous sodium sulfate, and the solvent was distilled off under reduced pressure. The residue was purified by silica gel column chromatography (hexane:acetic acid ethyl ester=4:1→1:1 to chloroform:acetic acid ethyl ester=1:1), hexane was added to the acetic acid ethyl ester solution in a 5-fold amount, and the mixture was stirred at 0° C. for 30 minutes. The generated solid was collected by filtration, to obtain the title compound (6.81 g). Furthermore, the mother liquor was concentrated under reduced pressure, and then purified by silica gel column chromatography, to obtain the title compound (130 mg).

$^1$H-NMR (CDCl$_3$) δ: 0.05 (9H, s), 0.84-0.92 (2H, m), 1.47 (9H, s), 1.51-1.70 (1H, m), 1.98 (1H, d, J=11.2 Hz), 2.84-2.98

(1H, m), 3.07 (1H, d, J=13.9 Hz), 3.94-4.29 (6H, m), 4.81-4.95 (1H, br), 7.70 (1H, d, J=9.0 Hz), 8.09-8.34 (1H, br), 8.20 (1H, d, J=9.0 Hz) 8.31 (1H, s), 9.69 (1H, s).
MS(ESI)m/z: 442 (M-Boc)⁺, 486 (M-tBu)⁺.

Reference Example 17

(3R,4S)-4-({2-[(5-chloropyridin-2-yl)amino]-2-oxoacetyl}amino)piperidine-3-carbamic acid tert-butyl ester

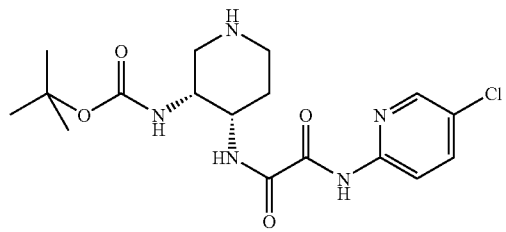

To a solution of the compound obtained in Reference Example 16 (6.92 g) in tetrahydrofuran (90 ml), a solution (40 ml) of 1.0 mmol/l tetrabutylammonium fluoride in tetrahydrofuran was added, and the mixture was stirred for 5 days at room temperature. Acetic acid ethyl ester and a saturated aqueous solution of sodium chloride were added to the reaction mixture. The aqueous layer was extracted with acetic acid ethyl ester and dichloroethane, and the combined organic layer was washed with a saturated aqueous solution of sodium hydrogen carbonate and a saturated aqueous solution of sodium chloride, and dried over anhydrous sodium sulfate. The solvent was distilled off under reduced pressure, and then the resulting residue was purified by silica gel column chromatography (dichloromethane:methanol=30:1→20:1→10:1), to obtain a crude product (7.96 g). Acetic acid ethyl ester was added to the crude product, and the insoluble matter was collected by filtration, to obtain the title compound (466 mg). Furthermore, water was added to the filtrate, the filtrate was extracted with acetic acid ethyl ester and dichloromethane, and the extracts were respectively washed with a saturated solution of sodium chloride, and then dried over anhydrous sodium sulfate. The solvent was distilled off under reduced pressure, to obtain a mixture of the title compound containing about 30% of tetrabutylammonium fluoride (4.86 g).
¹H-NMR (CD₃OD) δ: 1.43 (3H, s), 1.44 (6H, s), 1.95-2.22 (2H, m), 3.10-3.60 (4H, m), 4.04-4.24 (1H, m), 4.29-4.43 (1H, m), 7.83-7.92 (1H, m), 8.19 (1H, dd, J=9.0, 2.4 Hz), 8.35 (1H, d, J=2.7 Hz).
MS(ESI)m/z: 398 (M+H)⁺.

Reference Example 18

(3R,4S)-4-({2-[(5-chloropyridin-2-yl)amino]-2-oxoacetyl}amino)-1-methylpiperidine-3-carbamic acid tert-butyl ester

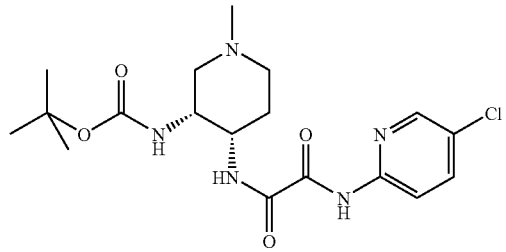

To a solution of the compound obtained in Reference Example 17 (487 mg) in dichloromethane (5.0 ml), a 37% aqueous solution of formaldehyde (58 μl), acetic acid (54 μl) and sodium triacetoxyborohydride (284 mg) were added, and the mixture was stirred for 23 hours at room temperature. Dichloromethane and a saturated aqueous solution of sodium hydrogen carbonate were added to the reaction mixture, the mixture was extracted with dichloromethane, and the combined organic layer was washed with a saturated aqueous solution of sodium chloride. The organic layer was dried over anhydrous sodium sulfate, and then the solvent was distilled off under reduced pressure. The residue was purified by silica gel column chromatography (dichloromethane:methanol=30:1→20:1), to obtain the title compound (333 mg).
¹H-NMR (CDCl₃) δ: 1.47 (9H, s), 1.60-1.80 (1H, m), 1.89-2.00 (1H, m) 2.01-2.13 (1H, m), 2.22-2.32 (1H, m), 2.24 (3H, s), 2.71-2.86 (2H, m), 3.77-3.89 (1H, m), 3.89-4.14 (1H, m), 5.46-5.60 (1H, m), 7.69 (1H, dd, J=8.8, 2.4 Hz), 8.10-8.19 (1H, m), 8.21 (1H, d, J=8.8 Hz), 8.30 (1H, d, J=2.4 Hz), 9.74 (1H, br.s).
MS(ESI)m/z: 412 (M+H)⁺.

Reference Example 19

(3R,4S)-3-[(tert-butoxycarbonyl)amino]-1-cyclopropylpiperidine-4-carbamic acid benzyl ester

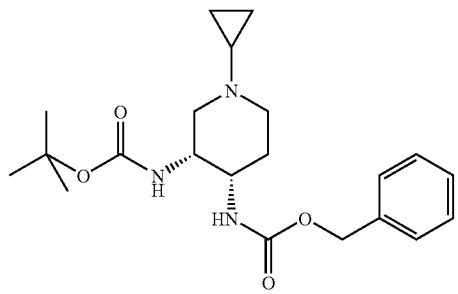

To a solution of the compound obtained in Reference Example 14 (375 mg) in methanol (10 ml), acetic acid (110 μl), molecular sieves 3A (about 1.0 g), [(1-ethoxycyclopropyl)oxy]trimethylsilane (1.60 ml), and sodium cyanoborohydride (98 mg) were added, and the mixture was stirred for 4 days at room temperature. After separating the molecular sieves by filtration, the solvent was distilled off under reduced pressure. Dichloromethane and 1 N aqueous solution of sodium hydroxide were added to the residue. After extracting the mixture with dichloromethane, the combined organic layer was washed with a saturated aqueous solution of sodium chloride. The organic layer was dried over anhydrous sodium sulfate, and then the solvent was distilled off under reduced pressure. The residue was purified by silica gel column chromatography (dichloromethane:methanol=50:1→30:1) and by silica gel column chromatography (dichloromethane:methanol=100:1), to obtain the title compound (147 mg).
¹H-NMR (CDCl₃) δ: 0.23-0.49 (4H, m), 1.19-1.32 (1H, m), 1.33-1.48 (0.5H, m), 1.44 (9H, s), 1.55-1.63 (1H, m), 1.86-1.99 (0.5H, m), 2.18-2.31 (1H, m), 2.44 (1H, d, J=9.5 Hz), 2.74-3.03 (2H, m), 3.52-3.66 (1H, m), 3.83-4.01 (1H, m), 4.93-5.24 (3H, m), 5.52 (1H, br.s), 7.24-7.41 (5H, m).
MS(ESI)m/z: 390 (M+H)⁺.

Reference Example 20

(3R,4S)-4-({2-[(5-chloropyridin-2-yl)amino]-2-oxoacetyl}amino)-1-cyclopropylpiperidine-3-carbamic acid tert-butyl ester

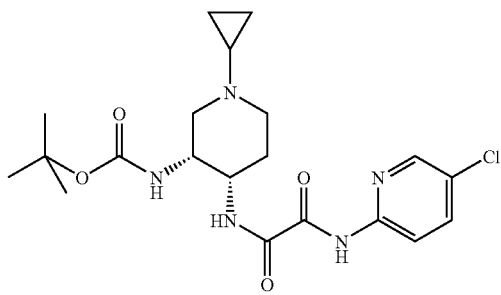

To a solution of the compound obtained in Reference Example 19 (313 mg) in ethanol (25 ml), a 10% palladium carbon catalyst (187 mg) was added, and the mixture was stirred for 6 days under hydrogen conditions. The catalyst was separated by filtration using Celite, and the solvent was distilled off under reduced pressure. The residue was purified by silica gel column chromatography (dichloromethane:methanol=10:1→7:1), and a mixture containing (3R,4S)-4-amino-1-cyclopropylpiperidine-3-carbamic acid tert-butyl ester (135 mg) was obtained as a colorless oil. To a solution of this compound (133 mg) in N,N-dimethylformamide (5 ml), lithium 2-[(5-chloropyridin-2-yl)amino]-2-oxoacetate (157 mg), 1-hydroxybenzotriazole (95 mg) and 1-(3-dimethylaminopropyl)-3-ethylcarbodiimide hydrochloride (134 mg) were added, and the mixture was stirred for 3 days at room temperature. The solvent was distilled off under reduced pressure, and then dichloromethane and a saturated aqueous solution of sodium hydrogen carbonate were added to the residue. The mixture was extracted with dichloromethane, and then the combined organic layer was washed with a saturated aqueous solution of sodium chloride. The organic layer was dried over anhydrous sodium sulfate, and the solvent was distilled off under reduced pressure. The residue was purified by flash column chromatography (dichloromethane:methanol=50:1) using silica gel as support, and by thin layer chromatography (dichloromethane:methanol=20:1), to obtain the title compound (58 mg).

$^1$H-NMR (CDCl$_3$) δ: 0.80-0.98 (2H, m), 1.21-1.48 (2H, m), 1.41 (9H, s) 1.50-1.69 (1H, m), 1.94-2.16 (1H, m), 2.39-2.68 (1.5H, m), 3.25-3.80 (3.5H, m), 4.20-4.63 (2H, m), 7.40-7.80 (2H, m), 7.99-8.35 (3H, m), 9.79 (1H, s).

MS(ESI)m/z: 438 (M+H)$^+$.

Reference Example 21

(3R,4S)-1-allyl-4-({2-[(5-chloropyridin-2-yl)amino]-2-oxoacetyl}amino)piperidine-3-carbamic acid tert-butyl ester

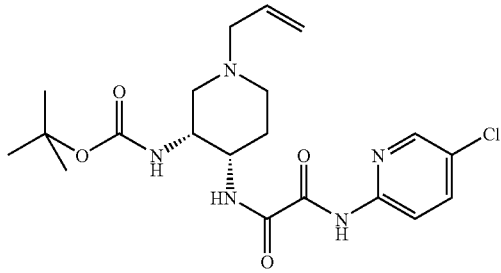

To a solution of the compound obtained in Reference Example 17 (258 mg) in N,N-dimethylformamide (5 ml), potassium carbonate (135 mg) and allyl bromide (71 µl) were added, and the mixture was stirred for 23 hours at room temperature. The solvent was distilled off under reduced pressure, and then acetic acid ethyl ester and water were added to the residue. After extracting the mixture with acetic acid ethyl ester, the combined organic layer was washed with a saturated aqueous solution of sodium chloride. The organic layer was dried over anhydrous sodium sulfate, and then the solvent was distilled off under reduced pressure. The residue was purified by flash column chromatography (dichloromethane:methanol=50:1) using silica gel as support, to obtain the title compound (216 mg).

$^1$H-NMR (CDCl$_3$) δ: 1.48 (9H, s), 1.56-1.76 (1H, m), 1.89-2.01 (1H, m), 2.02-2.12 (1H, m), 2.26 (1H, br.d, J=11.7 Hz), 2.79-3.05 (4H, m), 3.79-3.89 (1H, m),3.89-4.12 (1H, m), 5.12-5.22 (2H, m), 5.48 (1H, br.d, J=8.3 Hz), 5.73-5.87 (1H, m), 7.69 (1H, br.d, J=8.8 Hz), 8.10-8.24 (1H, m), 8.21 (1H, d, J=8.8 Hz), 8.30 (1H, d, J=2.2 Hz) 9.71 (1H, s).

MS(ESI)m/z: 438 (M+H)$^+$.

Reference Example 22

(3R,4S)-3-[(tert-butoxycarbonyl)amino]-1-(cyclopropylmethyl)piperidine-4-carbamic acid benzyl ester

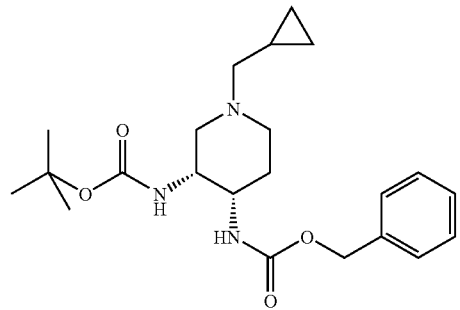

The title compound was obtained in the same manner as in the method described in Reference Example 18, by subjecting the compound obtained in Reference Example 14 to a reductive alkylation reaction using cyclopropanecarbaldehyde.

$^1$H-NMR (CDCl$_3$) δ: 0.00-0.12 (2H, m), 0.40-0.55 (2H, m), 0.71-0.86 (1H, m), 1.45 (9H, s), 1.48-1.64 (1H, m), 1.84-2.34 (5H, m), 2.79-3.01 (2H, m), 3.47-3.66 (1H, m), 3.83-4.03 (1H, m), 5.07 (1H, d, J=12.5 Hz), 5.11 (1H, d, J=12.5 Hz), 5.35-5.64 (2H, m) 7.24-7.40 (5H, m).

MS(ESI)m/z: 404 (M+H)$^+$.

Reference Example 23

(3R,4S)-4-({2-[(5-chloropyridin-2-yl)amino]-2-oxoacetyl}amino)-1-(cyclopropylmethyl)piperidine-3-carbamic acid tert-butyl ester

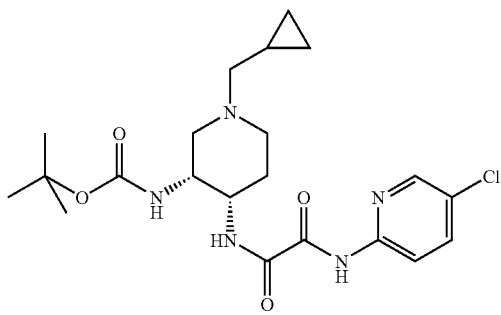

The title compound was obtained in the same manner as in the method described in Reference Example 20, by deprotecting the benzyloxycarbonyl group of the compound obtained in Reference Example 22, and then condensing the compound with lithium 2-[(5-chloropyridin-2-yl)amino]-2-oxoacetate.

$^1$H-NMR (CDCl$_3$) δ: 0.05-0.13 (2H, m), 0.46-0.58 (2H, m) 0.75-0.89 (1H, m), 1.48 (9H, s), 1.61-1.80 (1H, m), 1.96 (1H, br.d, J=11.7 Hz), 2.06-2.17 (1H, m), 2.18-2.35 (3H, m), 2.91-3.08 (2H, m), 3.78-3.89 (1H, m), 3.90-4.13 (1H, m), 5.28-5.64 (1H, m), 7.64-7.76 (1H, m), 8.14-8.23 (1H, m), 8.21 (1H, d, J=9.0 Hz), 8.30 (1H, d, J=2.2 Hz), 9.73 (1H, s).

MS(ESI)m/z: 452 (M+H)$^+$.

Reference Example 24

(3R,4S)-4-({2-[(5-chloropyridin-2-yl)amino]-2-oxoacetyl}amino)-1-methanesulfonylpiperidine-3-carbamic acid tert-butyl ester

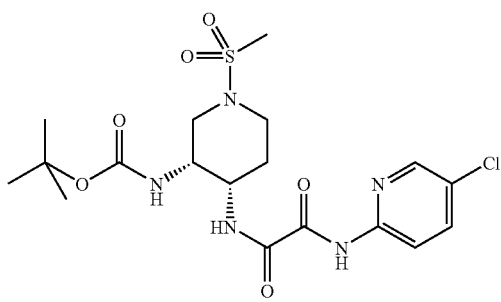

To a solution of the compound obtained in Reference Example 17 (251 mg) in tetrahydrofuran (3.0 ml), triethylamine 100 μl) was added, subsequently methanesulfonyl chloride (55 μl) was added at 0° C., and the mixture was stirred for 19 hours at room temperature. Ice was added thereto, the mixture was stirred at room temperature for 10 minutes, and then acetic acid ethyl ester and 1 N hydrochloric acid were added. The mixture was extracted with acetic acid ethyl ester, and subsequently the combined organic layer was washed with 1 N hydrochloric acid, a saturated aqueous solution of sodium hydrogen carbonate and a saturated aqueous solution of sodium chloride, and then dried over anhydrous sodium sulfate. The solvent was distilled off under reduced pressure, and then dried by means of a vacuum pump, to obtain the title compound (191 mg).

$^1$H-NMR (CDCl$_3$) δ: 1.47 (9H, s), 1.73-1.89 (1H, m), 2.03-2.18 (1H, m) 2.76-2.87 (1H, m), 2.83 (3H, s), 2.97 (1H, dd, J=12.3, 1.8 Hz), 3.78-4.01 (3H, m), 4.15-4.28 (1H, m), 5.22 (1H, br.d, J=7.8 Hz) 7.70 (1H, dd, J=8.8, 2.2 Hz), 8.16-8.27 (1H, br), 8.20 (1H, d, J=8.8 Hz), 8.31 (1H, d, J=2.2 Hz), 9.67 (1H, s).

MS(ESI)m/z: 420 (M-tBu)$^+$.

Reference Example 25

(3R,4S)-3-tert-butoxycarbonylamino-1-(trifluoromethanesulfonyl)piperidine-4-carbamic acid benzyl ester

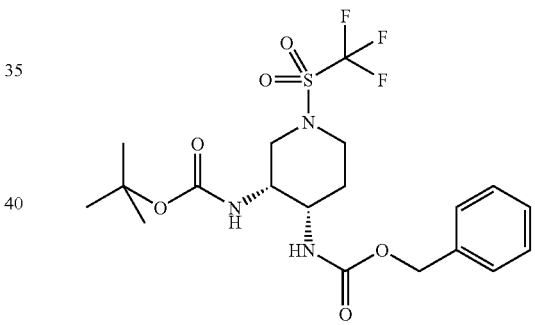

To a mixed solution of the compound obtained in Reference Example 14 (390 mg) in dichloromethane (10 ml) and triethylamine (1 ml), trifluoromethanesulfonic anhydride (220 μl) was added at 0° C., and the mixture was stirred for 14 hours from 0° C. to room temperature. Ice was added to the reaction mixture and stirred, and then dichloromethane and a 10% aqueous solution of citric acid were added. After extracting the mixture with dichloromethane, the combined organic layer was washed with a saturated aqueous solution of sodium hydrogen carbonate and a saturated aqueous solution of sodium chloride, and then dried over anhydrous sodium sulfate, and the solvent was distilled off under reduced pressure. The residue was purified by silica gel column chromatography (hexane:acetic acid ethyl ester=6:1→5:1), to obtain the title compound (252 mg).

$^1$H-NMR (CDCl$_3$) δ: 1.45 (9H, s), 1.57-1.74 (1H, m), 1.95-2.18 (1H, m) 3.05-3.38 (2H, m), 3.76-3.98 (3H, m), 4.00-4.15 (1H, m), 4.92 (1H, br.s), 5.03-5.16 (2H, m), 5.44 (1H, br.s), 7.28-7.41 (5H, m).

MS(ESI)m/z: 382 (M-Boc)$^+$, 504 (M+Na)$^+$.

Reference Example 26

(3R,4S)-4-({2-[(5-chloro-2-pyridinyl)amino]-2-oxoacetyl}amino)-1-(trifluoromethanesulfonyl)piperidine-3-carbamic acid tert-butyl ester

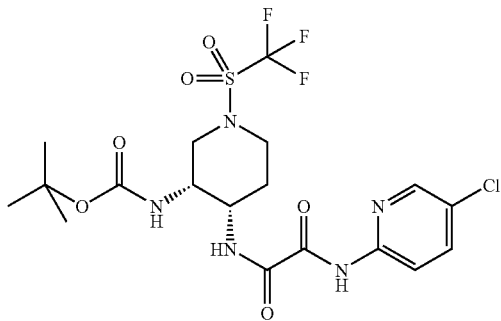

The title compound was obtained in the same manner as in the method described in Reference Example 20, by deprotecting the benzyloxycarbonyl group of the compound obtained in Reference Example 25, and then condensing the compound with lithium 2-[(5-chloropyridin-2-yl)amino]-2-oxoacetate.

$^1$H-NMR (CDCl$_3$) δ: 1.48 (9H, s), 1.71-1.89 (1H, m), 2.06-2.20 (1H, m) 3.12-3.26 (1H, m), 3.35 (1H, d, J=13.2 Hz), 3.88-4.28 (4H, m), 5.00 (1H, br.d, J=8.1 Hz), 7.71 (1H, dd, J=8.8, 2.4 Hz), 8.05-8.22 (1H, br), 8.19 (1H, d, J=9.0 Hz), 8.32 (1H, d, J=2.4 Hz) 9.67 (1H, s).

MS(ESI)m/z: 530 (M+H)$^+$, 474 (M-tBu)$^+$.

Reference Example 27

(3R,4S)-4-({2-[(5-chloropyridin-2-yl)amino]-2-oxoacetyl}amino)-1-phenylsulfonylpiperidine-3-carbamic acid tert-butyl ester

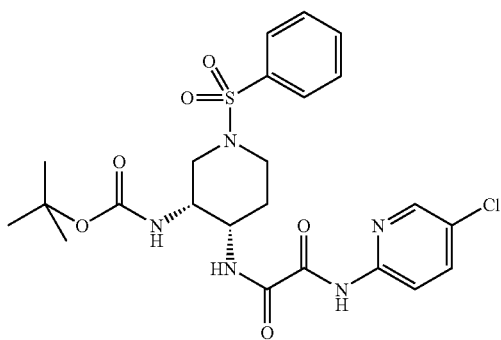

The title compound was obtained in the same manner as in the method described in Reference Example 24, by subjecting the compound obtained in Reference Example 17 to a reaction with benzenesulfonyl chloride.

$^1$H-NMR (CDCl$_3$) δ: 1.49 (9H, s), 1.75-1.89 (1H, m), 1.99-2.09 (1H, m) 2.30-2.40 (1H, m), 2.52 (1H, dd, J=12.1, 2.1 Hz), 3.71-3.92 (3H, m), 4.12-4.20 (1H, m), 5.28 (1H, br.d, J=7.8 Hz), 7.55-7.72 (4H, m), 7.73-7.78 (2H, m), 8.13-8.19 (1H, m), 8.18 (1H, d, J=9.0 Hz), 8.29 (1H, d, J=2.4 Hz), 9.63 (1H, s).

MS(ESI) m/z: 482 (M-tBu)$^+$.

Reference Example 28

(3R,4S)-4-({2-[(5-chloropyridin-2-yl)amino]-2-oxoacetyl}amino)-1-formylpiperidine-3-carbamic acid tert-butyl ester

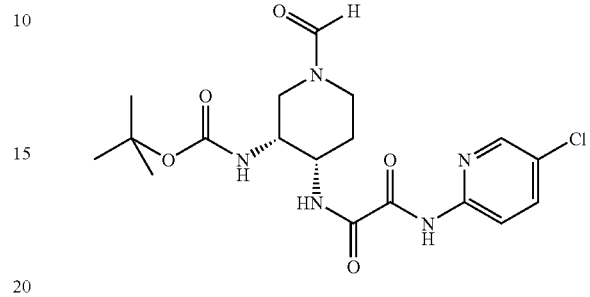

To a solution of the compound obtained in Reference Example 17 (252 mg) in dichloromethane (5.0 ml), formic acid (30 μl), 1-hydroxybenzotriazole (109 mg), 1-(3-dimethylaminopropyl)-3-ethylcarbodiimide hydrochloride (153 mg) and triethylamine (111 μl) were added, and the mixture was stirred for 22 hours at room temperature. Dichloromethane and 1 N hydrochloric acid were added to the reaction mixture, the mixture was extracted with dichloromethane, and the combined organic layer was washed with 1 N hydrochloric acid, a saturated aqueous solution of sodium hydrogen carbonate, and a saturated aqueous solution of sodium chloride. The organic layer was dried over anhydrous sodium sulfate, and the solvent was distilled off under reduced pressure, and then dried by means of a vacuum pump, to obtain the title compound (175 mg).

$^1$H-NMR (CDCl$_3$) δ: 1.44 (9H, br.s), 1.53-1.78 (1H, m), 1.86-2.20 (1H, m), 2.77-2.89 (0.5H, m), 2.97 (0.5H, br.d, J=13.9 Hz), 3.23 (0.5H, t, J=12.9 Hz), 3.39 (0.5H, br.d, J=12.9 Hz), 3.56-3.75 (1H, m), 4.05-4.24 (2H, m), 4.36-4.52 (1H, m), 4.78-5.11 (1H, m), 7.65-7.75 (1H, m), 7.83-7.94 (0.5H, m), 7.96-8.03 (0.5H, m), 8.11-8.23 (1.5H, m), 8.31 (1H, br.s), 8.30-8.49 (0.5H, br), 9.69 (1H, s).

MS(ESI)m/z: 370 (M-tBu)$^+$.

Reference Example 29

(3R,4S)-1-acetyl-4-({2-[(5-chloropyridin-2-yl)amino]-2-oxoacetyl}amino)piperidine-3-carbamic acid tert-butyl ester

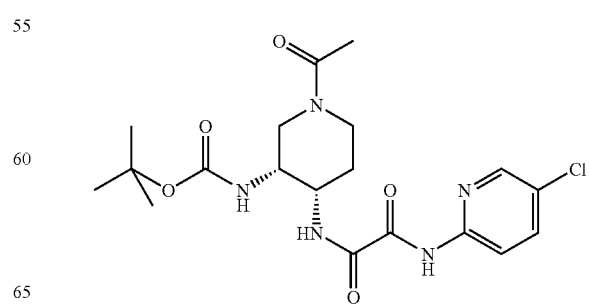

The title compound was obtained in the same manner as in the method described in Reference Example 24, by subjecting the compound obtained in Reference Example 17 to a reaction with acetyl chloride.

$^1$H-NMR (CDCl$_3$) δ: 1.47 (9H, s), 1.53-1.76 (1H, m), 1.91-2.25 (1H, m) 2.12, 2.18 (total 3H, each br.s), 2.72-2.84 (0.5H, m), 2.89 (0.5H, br.d, J=13.9 Hz), 3.15-3.29 (0.5H, m), 3.35 (0.5H, br.d, J=13.2 Hz), 3.81-3.96 (1H, m), 3.98-4.23 (2H, m), 4.56-4.79 (1H, m), 4.83-4.99 (1H, m), 7.66-7.83 (1.6H, m), 8.14-8.27 (1H, m), 8.33 (1H, br.s), 8.53-8.67 (0.4H, m), 9.70 (1H, br.s).

MS(ESI)m/z: 438 (M−H)$^−$.

Reference Example 30

(3R,4S)-4-({2-[(5-chloropyridin-2-yl)amino]-2-oxoacetyl}amino)-1-isobutyrylpiperidine-3-carbamic acid tert-butyl ester

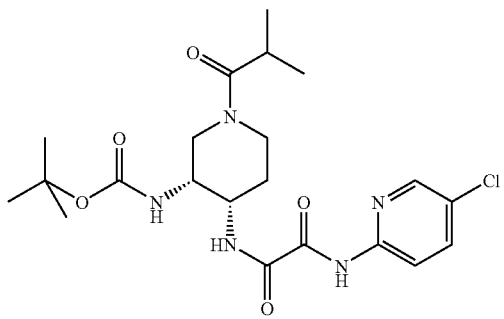

The title compound was obtained in the same manner as in the method described in Reference Example 24, by subjecting the compound obtained in Reference Example 17 to a reaction with isobutyryl chloride.

$^1$H-NMR (CDCl$_3$) δ: 1.02-1.21 (6H, m), 1.21-1.27 (1H, m), 1.45 (9H, s) 1.53-1.77 (1H, m), 1.85-2.22 (1H, m), 2.60-3.41 (2H, m), 3.86-4.29 (3H, m), 4.50-4.99 (2H, m), 7.63-7.86 (1.7H, m), 8.19 (1H, br.s), 8.31 (1H, s), 8.62 (0.3H, br.s), 9.70 (1H, s).

MS(ESI)m/z: 368 (M-Boc)$^+$.

Reference Example 31

(3R,4S)-1-benzoyl-4-({2-[(5-chloropyridin-2-yl)amino]-2-oxoacetyl}amino)piperidine-3-carbamic acid tert-butyl ester

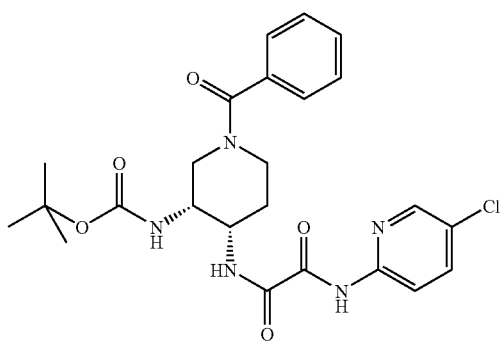

The title compound was obtained in the same manner as in the method described in Reference Example 24, by subjecting the compound obtained in Reference Example 17 to a reaction with benzoyl chloride.

$^1$H-NMR (CDCl$_3$) δ: 1.46 (9H, s), 1.62-1.76 (1H, m), 1.94-2.06 (1H, m), 2.97-3.36 (2H, m), 3.69-4.36 (3H, m), 4.48-5.40 (2H, m), 7.44 (5H, br.s), 7.50-7.58 (1H, m), 7.64-7.74 (1H, m), 8.13-8.23 (1H, m), 8.31 (1H, s), 9.69 (1H, s).

MS(ESI)m/z: 402 (M-Boc)$^+$.

Reference Example 32

(3R,4S)-3-(tert-butoxycarbonyl)amino-4-({2-[(5-chloropyridin-2-yl)amino]-2-oxoacetyl}amino)piperidine-1-carboxylic acid methyl ester

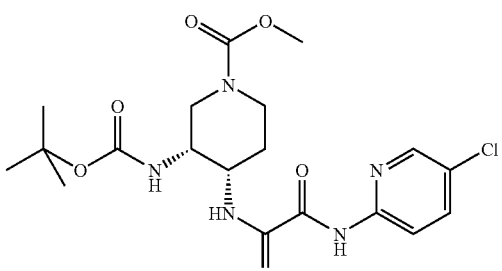

The title compound was obtained in the same manner as in the method described in Reference Example 24, by subjecting the compound obtained in Reference Example 17 to a reaction with methyl chloroformate ester.

$^1$H-NMR (CDCl$_3$) δ: 1.47 (9H, s), 1.52-1.75 (1H, m) 1.87-2.08 (1H, m) 2.86-2.99 (1H, m), 3.09 (1H, br.d, J=13.9 Hz) 3.73, 3.73 (total 3H, each s), 3.91-4.31 (5H, m), 4.75-4.99 (1H, m), 7.70 (1H, d, J=8.8 Hz), 8.19 (1H, dd, J=8.8, 1.8 Hz), 8.30, 8.31 (total 1H, each d, J=1.8 Hz), 9.70 (1H, s).

MS(ESI)m/z: 400 (M-tBu)$^+$.

Reference Example 33

(3R,4S)-3-(tert-butoxycarbonyl)amino-4-({2-[(5-chloropyridin-2-yl)amino]-2-oxoacetyl}amino)piperidine-1-carboxylic acid ethyl ester

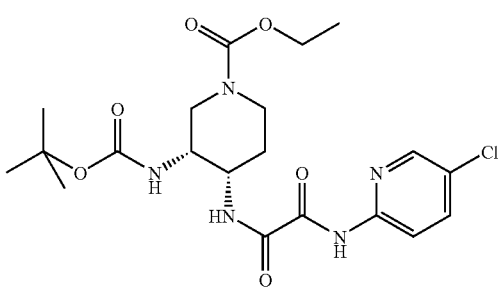

The title compound was obtained in the same manner as in the method described in Reference Example 24, by subjecting the compound obtained in Reference Example 17 to a reaction with ethyl chloroformate ester.

$^1$H-NMR (CDCl$_3$) δ: 1.28 (3H, t, J=7.3 Hz), 1.46 (9H, s), 1.58-1.74 (1H, m), 1.82-2.02 (1H, m), 2.85-2.99 (1H, m), 3.09 (1H, br.d, J=13.7 Hz), 3.96-4.27 (6H, m), 5.02 (1H, br.d, J=8.1 Hz), 7.70 (1H, dd, J=8.8, 1.7 Hz), 8.05-8.35 (1H, br), 8.19 (1H, d, J=8.8 Hz), 8.31 (1H, d, J=1.7 Hz), 9.74 (1H, s).

MS(ESI)m/z: 470 (M+H)$^+$.

Reference Example 34

(3R,4S)-3-(tert-butoxycarbonyl)amino-4-({2-[(5-chloropyridin-2-yl)amino]-2-oxoacetyl}amino)piperidine-1-carboxylic acid isopropyl ester

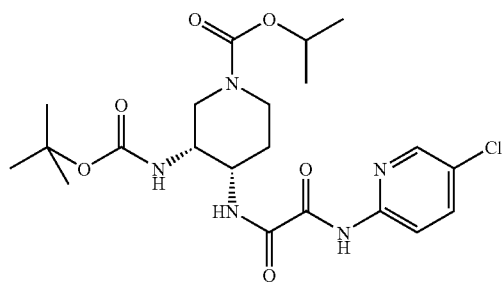

The title compound was obtained in the same manner as in the method described in Reference Example 24, by subjecting the compound obtained in Reference Example 17 to a reaction with isopropyl chloroformate ester.

¹H-NMR (CDCl₃) δ: 1.27 (6H, d, J=5.9 Hz), 1.47 (9H, s), 1.56-1.82 (1H, m), 1.90-2.02 (1H, m), 2.90 (1H, t, J=12.9 Hz), 3.06 (1H, d, J=13.9 Hz), 3.97-4.26 (3H, m), 4.85-5.02 (2H, m), 7.70 (1H, dd, J=8.8, 2.4 Hz), 8.04-8.33 (2H, br), 8.19 (1H, d, J=8.8 Hz), 8.31 (1H, d, J=2.4 Hz), 9.72 (1H, s).

MS(ESI)m/z: 384 (M-Boc)⁺, 428 (M-tBu)⁺.

Reference Example 35

(3R,4S)-4-({2-[(5-chloropyridin-2-yl)amino]-2-oxoacetyl}amino)-1-(dimethylcarbamoyl)piperidine-3-carbamic acid tert-butyl ester

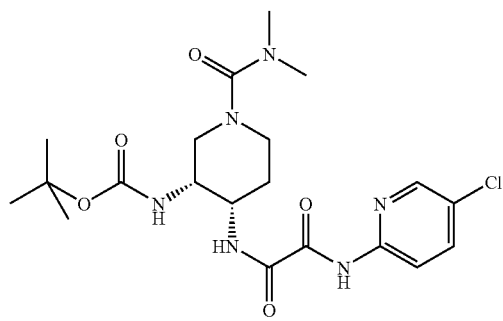

The title compound was obtained in the same manner as in the method described in Reference Example 24, by subjecting the compound obtained in Reference Example 17 to a reaction with N,N-dimethylcarbamoyl chloride.

¹H-NMR (CDCl₃) δ: 1.48 (9H, s), 1.60-1.79 (1H, m), 1.82-2.02 (1H, m) 2.86, 2.87 (total 6H, each s), 2.97-3.18 (2H, m), 3.59 (1H, br.d, J=13.2 Hz), 3.85 (1H, br.d, J=13.9 Hz), 3.95-4.05 (2H, m), 6.34-6.48 (1H, br), 7.69 (1H, d, J=8.8 Hz), 8.22 (1H, d, J=8.8 Hz) 8.30 (1H, s), 8.70 (1H, s), 9.73 (1H, s).

MS(ESI)m/z: 369 (M-Boc)⁺.

Reference Example 36

(3R,4S)-4-({2-[(5-chloropyridin-2-yl)amino]-2-oxoacetyl}amino)-1-(ethylcarbamoyl)piperidine-3-carbamic acid tert-butyl ester

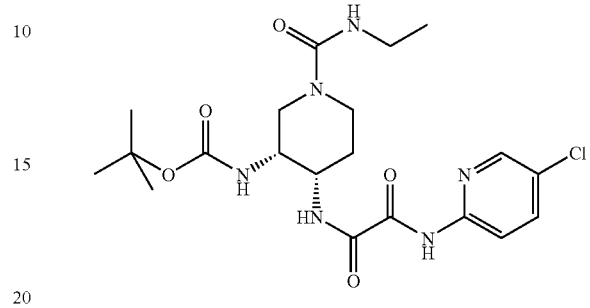

To a solution of the compound obtained in Reference Example 17 (250 mg) in tetrahydrofuran (5.0 ml), ethyl isocyanate (106 μl) was added, and the mixture stirred for 4 days at room temperature, and for 23 hours at 60° C. Acetic acid ethyl ester and a 10% aqueous solution of citric acid were added thereto. The mixture was extracted with acetic acid ethyl ester, and then the combined organic layer was washed with a saturated aqueous solution of sodium hydrogen carbonate and a saturated aqueous solution of sodium chloride. The organic layer was dried over anhydrous sodium sulfate, and the solvent was distilled off under reduced pressure, and then dried by means of a vacuum pump for 2 hours, to obtain the title compound (201 mg).

¹H-NMR (CDCl₃) δ: 1.16 (3H, t, J=7.1 Hz), 1.47 (9H, s), 1.61-1.74 (1H, m), 1.93-2.05 (1H, m), 2.91-3.07 (2H, m), 3.16-3.34 (2H, m), 3.89 (1H, br.d, J=13.7 Hz), 3.96-4.12 (3H, m), 4.48-4.55 (1H, m) 5.13-5.29 (1H, br), 7.70 (1H, dd, J=8.8, 2.4 Hz), 8.21 (1H, d, J=8.8 Hz), 8.27-8.39 (1H, br), 8.31 (1H, d, J=2.4 Hz), 9.69 (1H, br.s).

MS(ESI)m/z: 469 (M+H)⁺.

Reference Example 37

2-[(3R,4S)-4-benzyloxycarbonylamino-3-(tert-butoxycarbonylamino)piperidin-1-yl]-2-oxoacetic acid methyl ester

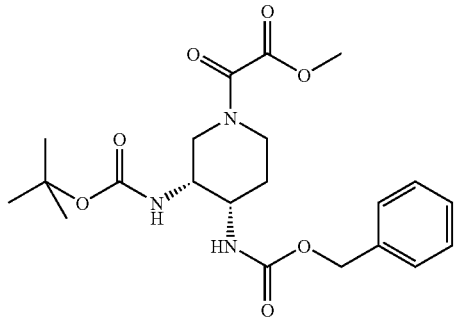

The title compound was obtained in the same manner as in the method described in Reference Example 24, by subjecting the compound obtained in Reference Example 14 to a reaction with methyl chlorooxoacetate ester.

¹H-NMR (CDCl₃) δ: 1.39-1.68 (1H, m), 1.44, 1.45 (total 9H, each s) 1.96-2.11 (1H, m), 2.79-2.91 (0.7H, m), 3.00-3.10 (0.3H, m), 3.13-3.23 (0.3H, m), 3.28-3.37 (0.7H, m), 3.64-3.72 (1H, m), 3.83-3.95 (1H, m), 3.87, 3.90 (total 3H, each s), 4.00-4.06 (0.5H, m), 4.08-4.16 (0.5H, m), 4.40-4.48 (1H, m), 4.66-4.74 (0.5H, m) 4.89-5.00 (0.5H, m), 5.10 (2H, br.s), 5.35-5.46 (0.5H, m), 5.58-5.71 (0.5H, m), 7.29-7.40 (5H, m).

MS(ESI)m/z: 336 (M-Boc)⁺.

Reference Example 38

(3R,4S)-3-(tert-butoxycarbonylamino)-1-(dimethylaminooxalyl)piperidine-4-carbamic acid benzyl ester

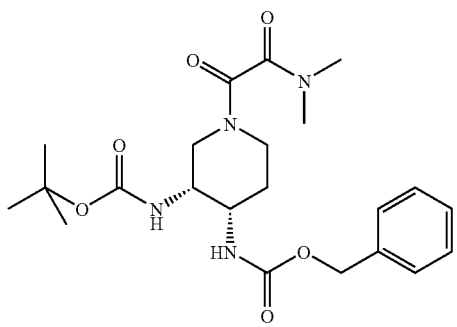

To a solution of the compound obtained in Reference Example 37 (572 mg) in tetrahydrofuran (10 ml), lithium hydroxide (40 mg) and water (2.0 ml) were added, and the mixture was stirred for 15 hours at room temperature. The reaction mixture was concentrated under reduced pressure, and then the resulting residue was dissolved in N,N-dimethylformamide (8 ml). 1-Hydroxybenzotriazole (243 mg), 1-(3-dimethylaminopropyl)-3-ethylcarbodiimide hydrochloride (347 mg) and dimethylamine hydrochloride (151 mg) were added, and the mixture was stirred for 4 days at room temperature. The solvent was distilled off under reduced pressure, and then dichloromethane and a 10% aqueous solution of citric acid were added to the residue. The mixture was extracted with dichloromethane, and the combined organic layer was washed with a saturated aqueous solution of sodium hydrogen carbonate and a saturated aqueous solution of sodium chloride. The organic layer was dried over anhydrous sodium sulfate, and then the solvent was distilled off under reduced pressure. The residue was purified by silica gel column chromatography (dichloromethane:methanol=50:1→30:1→20:1), to obtain the title compound (316 mg).

¹H-NMR (CDCl₃) δ: 1.44, 1.45 (total 9H, each s), 1.55-1.78 (1H, m) 1.87-2.09 (1H, m), 2.57-2.96 (1H, m), 2.96-3.01 (6H, m), 3.02-3.37 (1H, m), 3.56-3.76 (2H, m), 3.81-4.20 (1H, m), 4.29-4.50 (1H, m), 5.03-5.18 (2H, m), 5.49-6.43 (2H, m), 7.28-7.39 (5H, m).

MS(ESI)m/z: 349 (M-Boc)⁺.

Reference Example 39

(3R,4S)-4-({2-[(5-chloropyridin-2-yl)amino]-2-oxoacetyl}amino)-1-[(dimethylamino)oxalyl]piperidine-3-carbamic acid tert-butyl ester

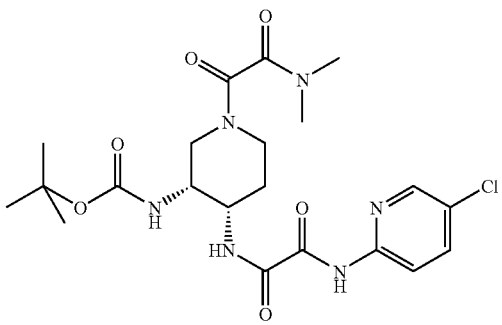

The title compound was obtained in the same manner as in the method described in Reference Example 16, by deprotecting the benzyloxycarbonyl group of the compound obtained in Reference Example 38, and then condensing the compound with lithium 2-[(5-chloropyridin-2-yl)amino]-2-oxoacetate.

Reference Example 40

(3R,4S)-4-({2-[(5-chloropyridin-2-yl)amino]-2-oxoacetyl}amino)-1-dimethylsulfamoylpiperidine-3-carbamic acid tert-butyl ester

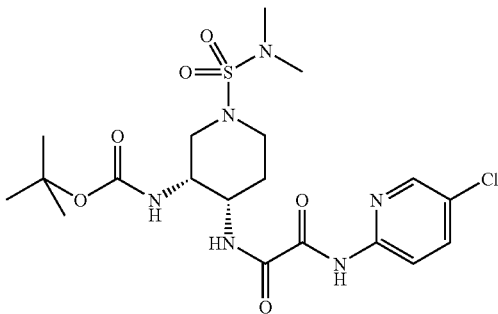

The title compound was obtained in the same manner as in the method described in Reference Example 24, by subjecting the compound obtained in Reference Example 17 to a reaction with N,N-dimethylsulfamoyl chloride.

¹H-NMR (CDCl₃) δ: 1.47 (9H, s), 1.69-1.83 (1H, m), 1.96-2.08 (1H, m), 2.86 (6H, s), 2.90-3.02 (1H, m), 3.11 (1H, br.d, J=12.9 Hz), 3.70-3.87 (2H, m), 3.93-4.03 (1H, m), 4.08-4.18 (1H, m), 5.29 (1H, br.d, J=6.6 Hz), 7.70 (1H, dd, J=8.8, 1.7 Hz), 8.13-8.20 (1H, m), 8.20 (1H, d, J=8.8 Hz), 8.31 (1H, d, J=1.7 Hz), 9.68 (1H, s).

MS(ESI)m/z: 405 (M-Boc)⁺, 449 (M-tBu)⁺.

Reference Example 41

(3R,4S)-4-({2-[(5-chloropyridin-2-yl)amino]-2-oxoacetyl}amino)-6-oxopiperidine-3-carbamic acid tert-butyl ester

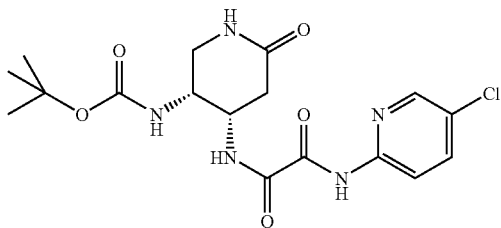

The title compound was obtained in the same manner as in the method described in Reference Example 16, by deprotecting the benzyloxycarbonyl group of the compound obtained in Reference Example 13, and condensing the compound with lithium 2-[(5-chloropyridin-2-yl)amino]-2-oxoacetate.

$^1$H-NMR (CDCl$_3$) δ: 1.46 (9H, s), 2.46-2.59 (1H, m), 2.72-2.98 (1H, m) 3.36 (1H, d, J=11.4 Hz), 3.66 (1H, d, J=11.4 Hz), 4.28 (1H, br.s), 4.42-4.48 (1H, m), 5.61 (1H, d, J=5.6 Hz), 6.62 (1H, s), 7.72 (1H, dd, J=8.8, 2.3 Hz), 8.19 (1H, d, J=8.8 Hz), 8.32 (1H, d, J=2.3 Hz) 8.40 (1H, d, J=7.6 Hz), 9.75 (1H, s).

Reference Example 42

(3R,4S)-4-({2-[(5-chloropyridin-2-yl)amino]-2-oxoacetyl}amino)-1-([1,2,3,4]-thiatriazol-5-yl)piperidine-3-carbamic acid tert-butyl ester

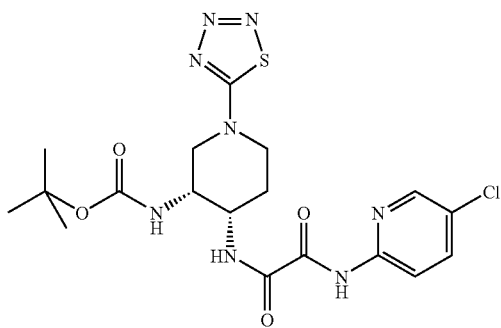

To a solution of the compound obtained in Reference Example 17 including tetrabutylammonium fluoride (666 mg) in acetonitrile (10 ml), thiocarbonyldiimidazole (302 mg) was added, and the mixture was stirred for 19 hours at room temperature. Methyl iodide (1042 μl) was added to the reaction mixture, and the mixture was further stirred for 2 days at room temperature. The solvent was distilled off under reduced pressure, acetonitrile (20 ml) and sodium azide (333 mg) were added, and the mixture was stirred for 7 days at room temperature. The solvent was distilled off under reduced pressure, and then dichloromethane and water were added to the residue. The mixture was extracted with dichloromethane, and the combined organic layer was washed with a saturated aqueous solution of sodium chloride. The organic layer was dried over anhydrous sodium sulfate, and then the solvent was distilled off under reduced pressure. The residue was purified by silica gel column chromatography (dichloromethane:methanol=100:1→50:1), and then by silica gel column chromatography (hexane:acetic acid ethyl ester=2:1→1:1), to obtain the title compound (318 mg).

$^1$H-NMR (CDCl$_3$) δ: 1.46 (9H, s), 1.86-2.24 (2H, m), 3.48-3.59 (1H, m) 3.66 (1H, dd, J=13.7, 2.4 Hz), 4.02 (1H, br.d, J=12.7 Hz), 4.09-4.33 (3H, m), 4.98-5.11 (1H, br), 7.72 (1H, dd, J=8.8, 2.7 Hz), 8.09-8.23 (1H, br), 8.18 (1H, d, J=8.8 Hz), 8.32 (1H, d, J=2.7 Hz) 9.69 (1H, br.s).

MS(ESI)m/z: 483 (M+H)$^+$.

Reference Example 43

(3R,4S)-3-[(tert-butoxycarbonyl)amino]-1-(hydrazinocarbonyl)piperidine-4-carbamic acid benzyl ester

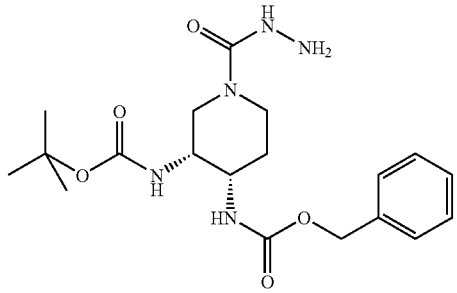

To a solution of the compound obtained in Reference Example 14 (687 mg) in tetrahydrofuran (15 ml), carbonyldiimidazole (342 mg) was added, and the mixture was stirred for 5 hours at room temperature. Hydrazine monohydrate (287 μl) was added to the reaction mixture, and the mixture was stirred for 24 hours at 50° C. A precipitated solid was collected by filtration, washed with acetic acid ethyl ester, and dried by means of a vacuum pump, to obtain the title compound (515 mg).

$^1$H-NMR (DMSO-d$_6$) δ: 1.37 (9H, s), 1.40-1.68 (2H, m), 2.95-3.98 (8H, m), 4.95-5.08 (2H, m), 6.23-6.31 (1H, m), 6.99-7.07 (1H, m), 7.27-7.39 (5H, m), 7.51 (1H, s).

MS(ESI)m/z: 408 (M+H)$^+$.

Reference Example 44

(3R,4S)-3-[(tert-butoxycarbonyl)amino]-1-[(N'-formylhydrazino)carbonyl]piperidine-4-carbamic acid benzyl ester

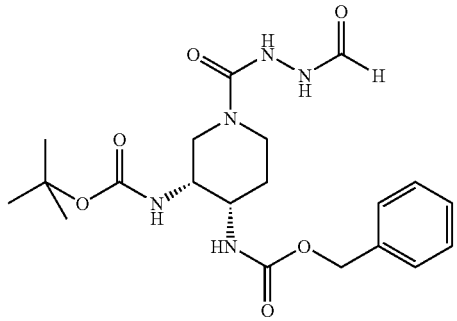

To a mixed suspension of the compound obtained in Reference Example 43 (330 mg) in N,N-dimethylformamide (10 ml) and dichloromethane (10 ml), formic acid (100 μl), 1-hydroxybenzotriazole (337 mg), 1-(3-dimethylaminopropyl)-

3-ethylcarbodiimide hydrochloride (480 mg), and triethylamine (350 µl) were added, and the mixture was stirred for 18 hours at room temperature. The solvent was distilled off under reduced pressure, and then dichloromethane and a saturated aqueous solution of sodium hydrogen carbonate were added to the residue. The mixture was extracted with dichloromethane, and then the combined organic layer was washed with a saturated aqueous solution of sodium chloride. The organic layer was dried over anhydrous sodium sulfate, and the solvent was distilled off under reduced pressure. The residue was purified by silica gel column chromatography (dichloromethane:methanol=20:1→10:1), to obtain the title compound (266 mg).

$^1$H-NMR (CDCl$_3$) δ: 1.41 (9H, s), 1.53-2.03 (2H, m), 2.66-3.31 (2H, m) 3.58-4.42 (4H, m), 4.98-5.19 (2H, m), 5.36-5.75 (1H, m), 6.20-6.39 (0.5H, m), 6.49-6.71 (0.5H, m), 7.15-7.43 (5H, m), 7.45-7.79 (1H, m), 7.94-8.16 (1H, m), 8.22-8.57 (0.25H, m), 8.70-8.92 (0.25H, m), 9.43-9.74 (0.5H, m).

MS(ESI)m/z: 336 (M-Boc)$^+$, 458 (M+Na)$^+$.

Reference Example 45

(3R,4S)-3-[(tert-butoxycarbonyl)amino]-1-([1,3,4]oxadiazol-2-yl)piperidine-4-carbamic acid benzyl ester

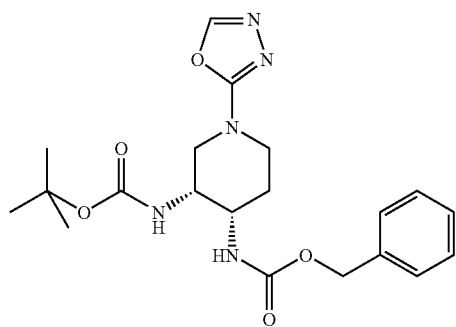

A dichloromethane (6.0 ml) solution containing the compound obtained in Reference Example 44 (257 mg), triphenylphosphine (189 mg), carbon tetrachloride (173 µl), and triethylamine (126 µl) were added, and the mixture was heated to reflux for 3 hours. After stirring the mixture for 44 hours at room temperature, triphenylphosphine (194 mg), carbon tetrachloride (173 µl) and triethylamine (126 µl) were added, and the mixture was heated to reflux for 3 days. After cooling, the solvent was distilled off under reduced pressure, and the residue was purified by silica gel column chromatography (dichloromethane:methanol=30:1→20:1), to obtain the title compound (190 mg).

$^1$H-NMR (CDCl$_3$) δ: 1.42 (9H, s), 1.65-2.10 (2H, m), 3.06-3.40 (2H, m) 3.75-4.16 (4H, m), 5.00-5.36 (3H, m), 5.58-5.82 (1H, m), 7.26-7.40 (5H, m), 7.91 (1H, s).

MS(ESI)m/z: 418 (M+H)$^+$.

Reference Example 46

(3R,4S)-4-({2-[(5-chloropyridin-2-yl)amino]-2-oxoacetyl}amino)-1-([1,3,4]oxadiazol-2-yl)piperidine-3-carbamic acid tert-butyl ester

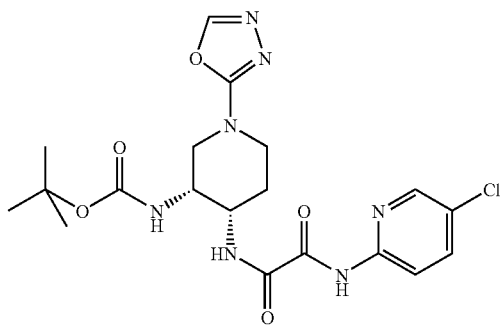

The title compound was obtained in the same manner as in the method described in Reference Example 20, by deprotecting the benzyloxycarbonyl group of the compound obtained in Reference Example 45, and then condensing the compound with lithium 2-[(5-chloropyridin-2-yl)amino]-2-oxoacetate.

$^1$H-NMR (CDCl$_3$) δ: 1.46 (9H, s), 1.71-2.20 (2H, m), 3.10-3.28 (1H, m) 3.28-3.44 (1H, m), 3.81-4.30 (4H, m), 5.01-5.64 (1H, m), 7.22-7.45 (1H, m), 7.71 (1H, dd, J=8.8, 2.4 Hz), 7.97 (1H, s), 8.19 (1H, d, J=8.8 Hz), 8.31 (1H, d, J=2.2 Hz), 9.73 (1H, s).

MS(ESI)m/z: 466 (M+H)$^+$.

Reference Example 47

(3R,4S)-1-(N'-acetylhydrazinocarbonyl)-3-[(tert-butoxycarbonyl)amino]piperidine-4-carbamic acid benzyl ester

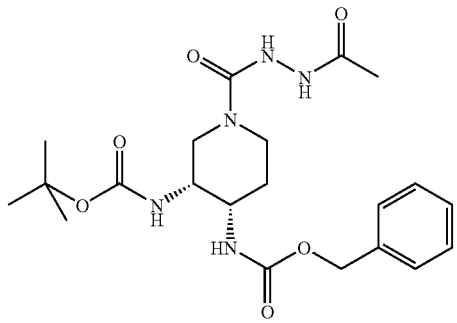

To a suspension of the compound obtained in Reference Example 43 (437 mg) in tetrahydrofuran (10 ml), triethylamine (420 µl), acetic anhydride (142 µl) and dichloromethane (5 ml) were added, and the mixture was stirred for 7 hours at room temperature. Ice was added to the reaction mixture, and the precipitated solid was collected by filtration, washed with water and acetic acid ethyl ester, and then dried, to obtain the title compound (435 mg).

¹H-NMR (CDCl₃) δ: 1.42 (9H, s), 1.53-1.99 (2H, m), 2.01 (3H, s), 2.72-3.27 (2H, m), 3.68-4.33 (4H, m), 4.95-5.69 (3.5H, m), 6.65-6.94 (0.5H, m), 6.97-7.22 (1H, m), 7.23-7.46 (5H, m), 7.70-7.98 (0.5H, m), 9.67-9.97 (0.5H, m).
MS(ESI)m/z: 350 (M-Boc)⁺.

Reference Example 48

(3R,4S)-3-[(tert-butoxycarbonyl)amino]-1-(5-methyl-[1,3,4]oxadiazol-2-yl)piperidine-4-carbamic acid benzyl ester

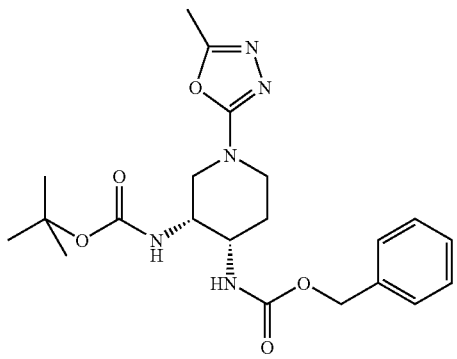

To a solution of triphenylphosphine (792 mg) in dichloromethane (9 ml), carbon tetrachloride (290 µl) was added, and the mixture was stirred for 15 minutes. Subsequently, a dichloromethane (12 ml) solution containing the compound obtained in Reference Example 47 (425 mg), and triethylamine (420 µl) were added, and the mixture was heated to reflux for hours. Carbon tetrachloride (290 µl) and triethylamine (420 µl) were added, and the mixture was heated to reflux for 19 hours. After cooling, the solvent was distilled off under reduced pressure, and the residue was purified by silica gel column chromatography (dichloromethane:methanol=50:1→40:1→30:1), to obtain the title compound (294 mg).
¹H-NMR (CDCl₃) δ: 1.44 (9H, s), 1.60-1.77 (1H, br), 1.88-2.15 (1H, br), 2.38 (3H, s), 3.04-3.17 (1H, m), 3.26 (1H, br.d, J=12.2 Hz) 3.76-3.96 (3H, m), 4.02-4.18 (1H, br), 4.96-5.22 (3H, m), 5.46-5.63 (1H, br), 7.26-7.41 (5H, m).
MS(ESI)m/z: 432 (M+H)⁺.

Reference Example 49

(3R,4S)-4-({2-[(5-chloropyridin-2-yl)amino]-2-oxoacetyl}amino)-1-(5-methyl-[1,3,4]oxadiazol-2-yl)piperidine-3-carbamic acid tert-butyl ester

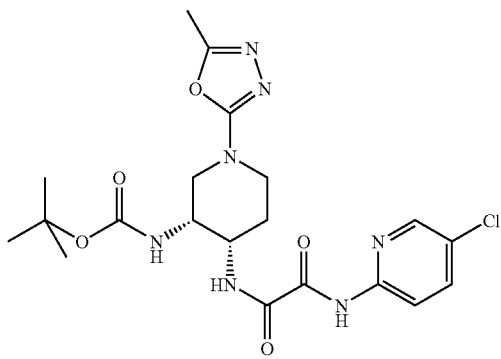

The title compound was obtained in the same manner as in the method described in Reference Example 20, by depro-tecting the benzyloxycarbonyl group of the compound obtained in Reference Example 48, and condensing the compound with lithium 2-[(5-chloropyridin-2-yl)amino]-2-oxoacetate.
¹H-NMR (CDCl₃) δ: 1.45 (9H, s), 1.82-2.18 (2H, m), 2.40 (3H, s), 3.07-3.22 (1H, m), 3.32 (1H, br.d, J=12.7 Hz) r 3.89-4.33 (4H, m) 5.56 (0.7H, br.d, J=7.1 Hz), 5.73-5.96 (0.3H, br), 7.71 (1H, dd, J=8.8, 2.4 Hz), 8.18 (1H, d, J=8.8 Hz), 8.24-8.34 (1H, m), 8.31 (1H, d, J=2.4 Hz), 9.82 (1H, s).
MS(ESI)m/z: 480 (M+H)⁺.

Reference Example 50

(3R,4S)-3-[(tert-butoxycarbonyl)amino]-1-formylpiperidine-4-carbamic acid benzyl ester

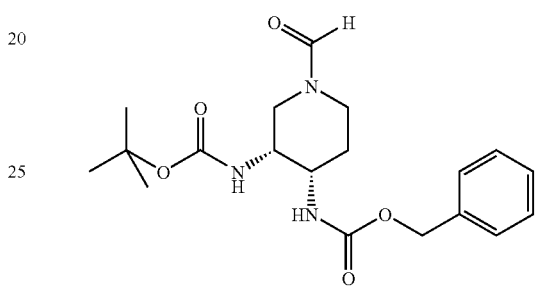

To a solution of the compound obtained in Reference Example 14 (5.17 g) in dichloromethane (100 ml), formic acid (1.13 ml), 1-hydroxybenzotriazole (4.06 g), 1-(3-dimethylaminopropyl)-3-ethylcarbodiimide hydrochloride (5.81 g) and triethylamine (4.20 ml) were added, and the mixture was stirred for 64 hours at room temperature. Dichloromethane and a 10% aqueous solution of citric acid were added to the reaction mixture. The organic layer was washed with a saturated aqueous solution of sodium hydrogen carbonate and a saturated aqueous solution of sodium chloride, and then dried over anhydrous sodium sulfate, and the solvent was distilled off under reduced pressure. The residue was purified by silica gel column chromatography (dichloromethane:methanol=40:1, 30:1), to obtain the title compound (3.76 g).
¹H-NMR (CDCl₃) δ: 1.43, 1.44 (total 9H, each s), 1.50-1.74 (1H, m), 1.83-2.17 (1H, m), 2.79-3.04 (1H, m), 3.17 (0.4H, t, J=11.2 Hz), 3.34 (0.6H, d, J=12.7 Hz), 3.45-3.68 (1H, m), 3.78-4.42 (3H, m), 4.64-4.98 (1H, m), 5.02-5.25 (3H, m), 7.27-7.42 (5H, m), 7.95, 8.11 (total 1H, each br.s).
MS(ESI)m/z: 378 (M+H)⁺.

Reference Example 51

(3R,4S)-4-amino-1-formylpiperidine-3-carbamic acid tert-butyl ester

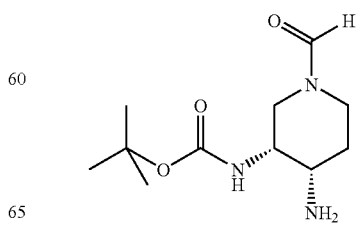

To a solution of the compound obtained in Reference Example 50 (3.64 g) in ethanol (100 ml), a palladium carbon catalyst (495 mg) was added, and the mixture was stirred for 18 hours in a hydrogen atmosphere. The catalyst was separated by filtration, the filtrate was concentrated under reduced pressure, and the solvent was distilled off under reduced pressure. The residue was purified by silica gel column chromatography (dichloromethane:methanol=20:1→10:1→an organic layer of chloroform:methanol:water=7:3:1), to obtain the title compound (2.09 g).

$^1$H-NMR (CDCl$_3$) δ: 1.41-1.64 (1H, m), 1.45 (9H, s), 1.65-1.84 (1H, m) 2.98-3.33 (3H, m), 3.38-4.24 (3H, m), 4.61-5.04 (1H, m), 7.97, 8.09 (total 1H, each br.s).

MS(ESI)m/z: 188 (M-tBu)$^+$.

Reference Example 52

(3R,4S)-4-({2-[(5-chlorothiophen-2-yl)amino]-2-oxoacetyl}amino)-1-formylpiperidine-3-carbamic acid tert-butyl ester

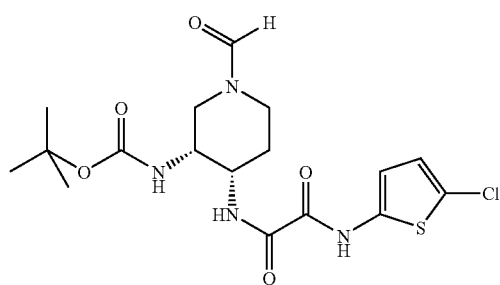

To a solution of 2-[(5-chloro-2-thienyl)amino]-2-oxoacetic acid methyl ester (331 mg) in tetrahydrofuran (4 ml), lithium hydroxide (39 mg) and water (1 ml) were added, and the mixture was stirred for 16 hours at room temperature. The reaction mixture was concentrated under reduced pressure, and then the resulting residue was dissolved in N,N-dimethylformamide (5 ml). The compound obtained in Reference Example 51 (223 mg), 1-hydroxybenzotriazole (202 mg) and 1-(3-dimethylaminopropyl)-3-ethylcarbodiimide hydrochloride (289 mg) were added, and the mixture was stirred for 4 days at room temperature. The solvent was distilled off under reduced pressure, and then acetic acid ethyl ester and a 10% aqueous solution of citric acid were added to the residue. The mixture was extracted with acetic acid ethyl ester, and then the combined organic layer was washed with a saturated aqueous solution of sodium hydrogen carbonate and a saturated aqueous solution of sodium chloride. Subsequently, the organic layer was dried over anhydrous sodium sulfate, and the solvent was distilled off under reduced pressure. The residue was purified by silica gel column chromatography (dichloromethane:methanol=50:1→30:1), to obtain the title compound (360 mg).

$^1$H-NMR (CDCl$_3$) δ: 1.43 (9H, s), 1.55-1.77 (1H, m), 1.85-2.10 (1H, m) 2.74-2.89 (0.6H, m), 2.96-3.04 (0.4H, m), 3.18-3.29 (0.4H, m), 3.34-3.44 (0.6H, m), 3.55-3.76 (1H, m), 4.07-4.27 (2H, m), 4.36-4.52 (1H, m), 4.79-4.94 (0.4H, m), 4.98-5.14 (0.6H, m), 6.56-6.78 (2H, m), 7.73-7.90 (0.4H, br), 8.01, 8.15 (total 1H, each s), 8.07-8.22 (0.6H, br), 9.86, 10.00 (total 1H, each br.s).

MS(ESI)m/z: 331 (M-Boc)$^+$.

Reference Example 53

5-Methyl-2-thienylcarbamic acid tert-butyl ester

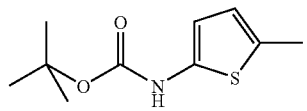

To a suspension of 5-methylthiophene-2-carboxylic acid (7.11 g) in toluene (100 ml), triethylamine (10.5 ml) and diphenylphosphoryl azide (12.9 ml) were added, and the mixture was stirred for 3 hours at 80° C. To this reaction mixture, tert-butanol (10 ml) was added, and the mixture was stirred overnight at 80° C. The reaction mixture was concentrated under reduced pressure, and acetic acid ethyl ester was added to the resulting residue. The mixture was washed sequentially with a 10% aqueous solution of citric acid, saturated brine, a saturated aqueous solution of sodium hydrogen carbonate, and saturated brine, and then was dried over anhydrous magnesium sulfate. The solvent was distilled off under reduced pressure, and the residue was subjected to silica gel column chromatography (hexane:acetic acid ethyl ester=4:1), to obtain the title compound (1.10 g).

$^1$H-NMR (CDCl$_3$) δ: 1.47 (9H, s), 2.34-2.36 (3H, m), 6.29 (1H, d, J=3.7 Hz), 6.38-6.41 (1H, m), 6.72 (1H, br.s).

MS(ESI)m/z: 236 (M+Na)$^+$, 158 (M-t-Bu)$^+$.

Reference Example 54

2-[(5-Methyl-2-thienyl)amino]-2-oxoacetic acid methyl ester

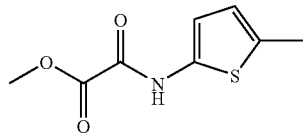

The compound obtained in Reference Example 53 (1.10 g) was dissolved in methylene chloride (5 ml), and to this solution, a 4 N hydrochloric acid-dioxane solution (5 ml) was added. After stirring the mixture for 1 hour at room temperature, the solvent was distilled off under reduced pressure. The residue was washed with diethyl ether, and the resulting powder was suspended in tetrahydrofuran (20 ml). Sodium hydrogen carbonate (1.07 g) and methyl chloroglyoxalate ester (0.618 ml) were added, and the mixture was stirred for 3 hours. The solvent was distilled off under reduced pressure, and acetic acid ethyl ester and a saturated aqueous solution of sodium hydrogen carbonate were added to the residue. After performing liquid separation, the organic layer was washed with a saturated aqueous solution of sodium chloride. The organic layer was dried over anhydrous magnesium sulfate, and then was concentrated under reduced pressure. A mixed solvent of diethyl ether-hexane (1:9) was added to the residue, solidified the residue, and collected by filtration, to obtain the title compound (614 mg).

$^1$H-NMR (CDCl$_3$) δ: 2.42 (3H, s), 3.94 (3H, s), 6.51-6.55 (1H, m) 6.66 (1H, d, J=3.7 Hz), 9.30 (1H, br.s).

MS(ESI)m/z: 200 (M+H)$^+$.

Reference Example 55

2-[(5-Methyl-2-thienyl)amino]-2-oxoacetic acid lithium salt

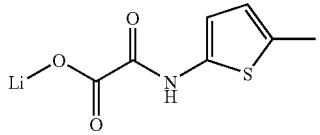

The compound obtained in Reference Example 54 (614 mg) was dissolved in tetrahydrofuran (12 ml), 1 N lithium hydroxide (3.08 ml) was added to this solution, and the mixture was stirred for 2 hours at room temperature. The reaction mixture was concentrated under reduced pressure, and the resulting solid was washed with acetonitrile, to obtain the title compound (551 mg).

$^1$H-NMR (DMSO-d$_6$) δ: 2.33-2.35 (3H, m), 6.50-6.54 (1H, m), 6.74 (1H, d, J=3.7 Hz), 11.29 (1H, br.s).

MS(ESI)m/z: 186 (M-Li+2H)$^+$.

Reference Example 56

(3R,4S)-1-formyl-4-({[(5-methylthiophen-2-yl)amino]-2-oxoacetyl}amino)piperidine-3-carbamic acid tert-butyl ester

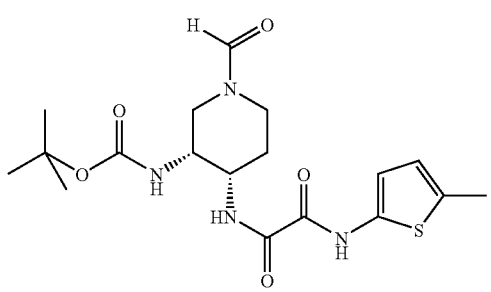

To a mixture of the compound obtained in Reference Example 51 (415 mg), the compound obtained in Reference Example 55 (326 mg) and N,N-dimethylformamide (10 ml), 1-(3-dimethylaminopropyl)-3-ethylcarbodiimide hydrochloride (492 mg) and 1-hydroxybenzotriazole (231 mg) were added, and the mixture was stirred overnight at room temperature. The solvent was distilled off under reduced pressure, a 10% aqueous solution of citric acid and dichloromethane were added to the residue. After performing liquid separation, the organic layer was washed sequentially with a saturated aqueous solution of sodium hydrogen carbonate and a saturated aqueous solution of sodium chloride. The organic layer was dried over anhydrous sodium sulfate, and then was concentrated under reduced pressure. A mixed solvent of acetic acid ethyl ester-hexane (about 1:9) was added to the residue, and a precipitated solid was collected by filtration, to obtain the title compound (470 mg).

$^1$H-NMR (CDCl$_3$) δ: 1.40 (9H, s), 1.60-2.05 (2H, m), 2.39-2.43 (3H, m) 2.77-3.02 (1H, m), 3.15-3.39 (1H, m), 3.57-3.71 (1H, m), 4.02-4.26 (2H, m), 4.32-4.45 (1H, m), 4.87-5.17 (1H, m), 6.49-6.54 (1H, m), 6.64-6.71 (1H, m), 7.79-8.15 (2H, m) 9.67-9.85 (1H, m).

MS(ESI)m/z: 433 (M+Na)$^+$, 311 (M-Boc)$^+$.

Reference Example 57

(3R,4S)-4-({2-[(5-fluoropyridin-2-yl)amino]-2-oxoacetyl}amino)-1-formylpiperidine-3-carbamic acid tert-butyl ester

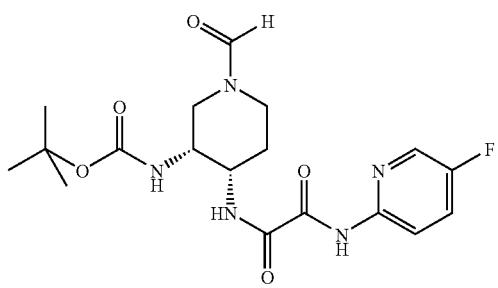

The title compound was obtained in the same manner as in the method described in Reference Example 52, by hydrolyzing a 2-[(5-fluoropyridin-2-yl)amino]-2-oxoacetic acid methyl ester, and then condensing the hydrolysis product with the compound obtained in Reference Example 51.

$^1$H-NMR (CDCl$_3$) δ: 1.45, 1.46 (total 9H, each s), 1.58-1.78 (1H, m) 1.90-2.19 (1H, m), 2.78-2.90 (0.6H, m), 2.99 (0.4H, dd, J=13.7, 2.4 Hz), 3.20-3.30 (0.4H, m), 3.40 (0.6H, dd, J=13.7, 2.0 Hz), 3.60-3.75 (1H, m), 4.08-4.27 (2H, m), 4.38-4.53 (1H, m), 4.94-5.04 (0.5H, m), 5.16-5.27 (0.5H, m), 7.44-7.53 (1H, m), 7.96 (0.6H, br.d, J=7.6 Hz), 8.00, 8.15 (total 1H, each s), 8.18-8.27 (2H, m), 8.36-8.47 (0.4H, br), 9.72, 9.74 (total 1H, each br.s).

MS(ESI)m/z: 354 (M-tBu)$^+$.

Reference Example 58

(3R,4S)-4-({2-[(5-bromopyridin-2-yl)amino]-2-oxoacetyl}amino)-1-formylpiperidine-3-carbamic acid tert-butyl ester

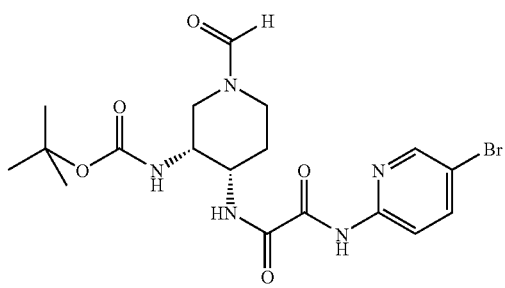

The title compound was obtained in the same manner as in the method described in Reference Example 56, by condensing the compound obtained in Reference Example 51 with 2-[(5-bromopyridin-2-yl)amino]-2-oxoacetic acid lithium ester.

$^1$H-NMR (CDCl$_3$) δ: 1.45, 1.46 (total 9H, each s), 1.52-1.76 (1H, m) 1.90-2.18 (1H, m), 2.75-2.90 (0.6H, m), 2.98 (0.4H, dd, J=14.3, 2.8 Hz), 3.17-3.30 (0.4H, m), 3.40 (0.6H, br.d, J=13.7 Hz), 3.52-3.75 (1H, m), 4.02-4.24 (2H, m), 4.34-4.53 (1H, m), 4.77-5.08 (1H, m), 7.77-7.93 (1.5H, m), 8.00 (0.5H, s), 8.08-8.19 (1.5H, m), 8.32-8.49 (1.5H, m), 9.70 (1H, br.s).
MS(ESI)m/z: 414 (M-tBu)+.

Reference Example 59

(3R,4S)-4-({2-[(4-chlorophenyl)amino]-2-oxoacetyl}amino)-1-formylpiperidine-3-carbamic acid tert-butyl ester

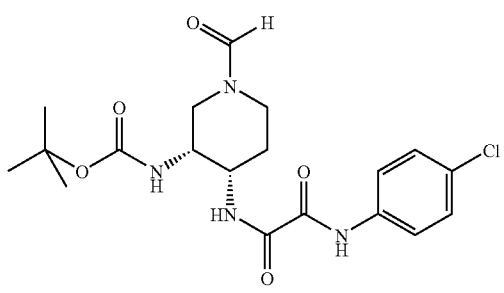

The title compound was obtained in the same manner as in the method described in Reference Example 56, by condensing the compound obtained in Reference Example 51 with 2-[(4-chlorophenyl)amino]-2-oxoacetic acid.
¹H-NMR (CDCl₃) δ: 1.44 (9H, s), 1.55-1.86 (1H, m), 1.87-2.15 (1H, m) 2.78-2.90 (0.6H, m), 3.00 (0.4H, dd, J=13.9, 2.7 Hz), 3.19-3.30 (0.4H, m), 3.40 (0.6H, dd, J=13.7, 2.0 Hz), 3.60-3.75 (1H, m), 4.08-4.25 (2H, m), 4.44 (1H, br.t, J=16.2 Hz) 4.90-5.00 (0.4H, m), 5.08-5.21 (0.6H, m), 7.30-7.36 (2H, m), 7.60, 7.61 (total 2H, each d, J=8.8 Hz), 7.89-7.98 (0.6H, m), 8.00, 8.15 (total 1H, each s), 8.25-8.34 (0.4H, m), 9.27, 9.29 (total 1H, each br.s).
MS(ESI)m/z: 325 (M-Boc)+.

Reference Example 60

(3R,4S)-4-({2-[(4-chloro-3-fluorophenyl)amino]-2-oxoacetyl}amino)-1-formylpiperidine-3-carbamic acid tert-butyl ester

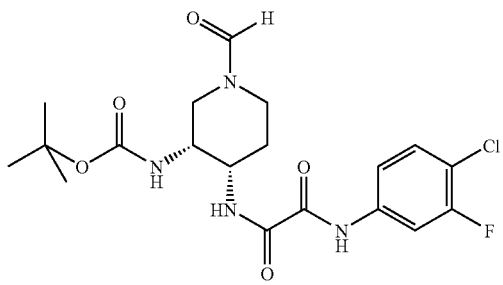

The title compound was obtained in the same manner as in the method described in Reference Example 56, by condensing the compound obtained in Reference Example 51 with 2-[(4-chloro-3-fluorophenyl)amino]-2-oxoacetic acid.
¹H-NMR (CDCl₃) δ: 1.44, 1.45 (total 9H, each s), 1.54-1.76 (1H, m) 1.90-2.13 (1H, m), 2.78-2.88 (0.6H, m), 2.99 (0.4H, dd, J=14.2, 2.7 Hz), 3.20-3.30 (0.4H, m), 3.40 (0.6H, dd, J=13.7, 2.0 Hz), 3.58-3.76 (1H, m), 4.06-4.25 (2H, m), 4.46 (1H, br.t, J=15.5 Hz) 4.81-5.05 (1H, m), 7.23-7.29 (1H, m), 7.33-7.40 (1H, m), 7.69-7.76 (1H, m), 7.84-7.96 (0.6H, m), 8.01, 8.16 (total 1H, each s), 8.28-8.40 (0.4H, m), 9.30, 9.32 (total 1H, each s).
MS(ESI)m/z: 343 (M-Boc)+.

Reference Example 61

(3R,4S)-4-({2-[(4-bromophenyl)amino]-2-oxoacetyl}amino)-1-formylpiperidine-3-carbamic acid tert-butyl ester

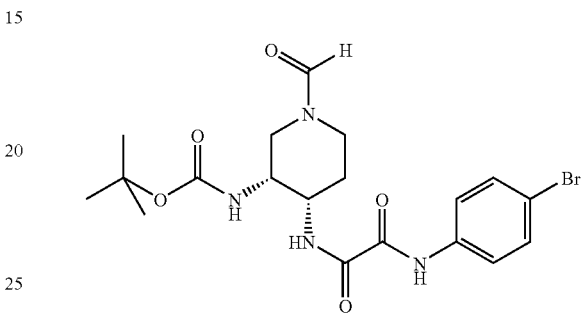

The title compound was obtained in the same manner as in the method described in Reference Example 52, by hydrolyzing 2-[(4-bromophenyl)amino]-2-oxoacetic acid methyl ester, and then condensing the hydrolysis product with the compound obtained in Reference Example 51.
¹H-NMR (CDCl₃) δ: 1.42 (9H, s), 1.67-2.07 (2H, m), 2.75-2.89 (0.5H, m), 2.94-3.06 (0.5H, m), 3.18-3.30 (0.5H, m), 3.37 (0.5H, dd, J=13.7, 2.2 Hz), 3.70 (1H, br.d, J=13.7 Hz), 4.05-4.30 (2H, m), 4.35-4.52 (1H, m), 5.37 (0.4H, d, J=7.1 Hz), 5.74 (0.6H, d, J=7.3 Hz), 7.47 (1H, d, J=8.5 Hz), 7.47 (1H, d, J=8.5 Hz), 7.58 (2H, d, J=8.5 Hz), 8.02, 8.12 (total 1H, each br.s), 8.15-8.33 (1H, m) 9.52, 9.52 (total 1H, each br.s).
MS(ESI)m/z: 369 (M-Boc)+.

Reference Example 62

(3R,4S)-4-({2-[(4-fluorophenyl)amino]-2-oxoacetyl}amino)-1-formylpiperidine-3-carbamic acid tert-butyl ester

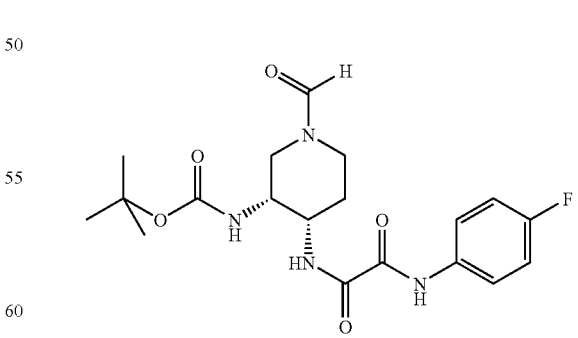

The title compound was obtained in the same manner as in the method described in Reference Example 52, by hydrolyzing 2-[(4-fluorophenyl)amino]-2-oxoacetic acid methyl ester, and then condensing the hydrolysis product with the compound obtained in Reference Example 51.

¹H-NMR (CDCl₃) δ: 1.41, 1.43 (total 9H, each s), 1.61-2.26 (2H, m), 2.74-3.05 (1H, m), 3.16-3.30 (0.4H, m), 3.31-3.42 (0.6H, m), 3.67 (1H, br.d, J=11.2 Hz), 4.02-4.28 (2H, m), 4.33-4.49 (1H, m), 5.00-5.77 (1H, m), 6.97-7.10 (2H, m), 7.57-7.66 (2H, m), 7.92-8.34 (2H, m), 9.25-9.48 (1H, m).

MS(ESI)m/z: 309 (M-Boc)⁺.

Reference Example 63

(3R,4S)-4-({2-[(5-chloropyridin-2-yl)amino]-2-oxoethanethioyl}amino)-1-formylpiperidine-3-carbamic acid tert-butyl ester

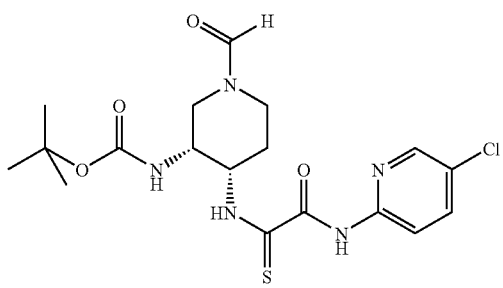

To a solution of the compound obtained in Reference Example 51 (270 mg) in N,N-dimethyl formamide (4 ml), 2,2-dichloro-N-(5-chloropyridin-2-yl)acetamide (266 mg), diisopropylethylamine (580 μl) and powdered sulfur (35 mg) were added, and the mixture was stirred for 20 minutes at 130 to 140° C. After cooling, the mixture was diluted with acetic acid ethyl ester, and the insoluble matter was separated by filtration. A saturated aqueous solution of sodium hydrogen carbonate was added to the filtrate, the mixture was extracted with acetic acid ethyl ester, and then the combined organic layer was washed with a 10% aqueous solution of citric acid and a saturated aqueous solution of sodium chloride. The organic layer was dried over anhydrous sodium sulfate, and then the solvent was distilled off under reduced pressure. The residue was purified by silica gel column chromatography (dichloromethane only→dichloromethane:methanol=50:1), and by flash column chromatography (dichloromethane:methanol=40:1) using silica gel as support, to obtain the title compound (321 mg).

¹H-NMR (CDCl₃) δ: 1.46, 1.48 (total 9H, each s), 1.56-1.83 (1H, m) 2.14-2.49 (1H, m), 2.82 (0.5H, br.t, J=11.7 Hz), 3.01 (0.5H, br.d, J=13.9 Hz), 3.28 (0.5H, br.t, J=11.6 Hz), 3.43 (0.5H, br.d, J=13.4 Hz), 3.61-3.82 (1H, m), 4.23-4.40 (1H, m), 4.45-4.69 (2H, m), 4.92-5.20 (1H, m), 7.67-7.76 (1H, m), 8.02 (0.5H, s), 8.15-8.25 (1.5H, m), 8.29-8.37 (1H, m), 9.80 (0.5H, br.s), 10.38 (0.5H, br.s), 10.50, 10.51 (total 1H, each s).

MS(ESI)m/z: 442 (M+H)⁺.

Reference Example 64

(3R,4S)-4-({2-[(5-fluoropyridin-2-yl)amino]-2-oxoethanethioyl}amino)-1-formylpiperidine-3-carbamic acid tert-butyl ester

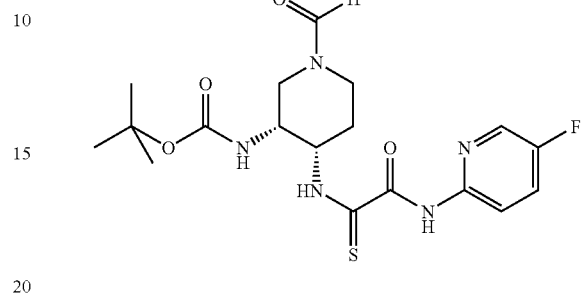

The title compound was obtained in the same manner as in the method described in Reference Example 63, by reacting 2,2-dichloro-N-(5-fluoropyridin-2-yl)acetamide with the compound obtained in Reference Example 51 in the presence of diisopropylethylamine and powdered sulfur.

¹H-NMR (CDCl₃) δ: 1.43-1.59 (0.5H, m), 1.46, 1.47 (total 9H, each s), 1.64-1.83 (0.5H, m), 2.10-2.26 (0.5H, m), 2.31-2.46 (0.5H, m) 2.73-3.09 (1H, m), 3.21-3.35 (0.5H, m), 3.42 (0.5H, d, J=13.4 Hz) 3.64-3.82 (1H, m), 4.22-4.37 (1H, m), 4.44-4.70 (2H, m), 5.10-5.26 (0.5H, br), 5.41-5.60 (0.5H, br), 7.44-7.54 (1H, m), 8.02 (0.5H, s), 8.16 (0.5H, s), 8.18-8.32 (2H, m), 9.88, 10.34 (total 1H, each br.s), 10.51 (1H, s).

MS(ESI)m/z: 370 (M-tBu)⁺, 426 (M+H)⁺.

Reference Example 65

(3R,4S)-4-{[(7-chloroisoquinolin-3-yl)carbonyl]amino}-1-formylpiperidine-3-carbamic acid tert-butyl ester

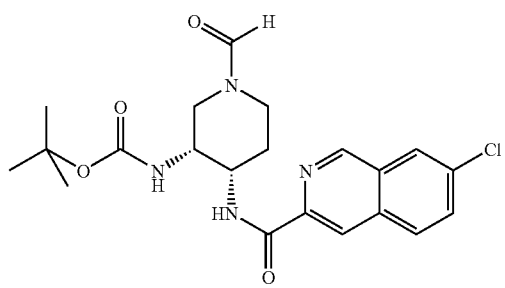

The title compound was obtained in the same manner as in the method described in Reference Example 56, by condensing the compound obtained in Reference Example 51 with 7-chloroisoquinoline-3-carboxylic acid.

¹H-NMR (CDCl₃) δ: 1.43 (9H, s), 1.66-1.87 (1H, m), 1.96-2.27 (1H, m) 2.84-3.20 (1H, m), 3.24-3.39 (0.5H, m), 3.41-3.77 (1.5H, m), 4.08-4.56 (3H, m), 5.17-5.30, 5.43-5.76 (total 1H, m), 7.65-7.76 (1H, m), 7.88-7.97 (1H, m), 7.98-8.02 (1H, m), 8.03, 8.16 (total 1H, each s), 8.48-8.63, 8.68-8.79 (total 2H, m), 9.03, 9.04 (total 1H, each s).

MS(ESI)m/z: 377 (M-tBu)⁺, 433 (M+H)⁺.

Reference Example 66

(3R,4S)-4-{[(5-fluoro-1H-indol-2-yl)carbonyl]amino}-1-formylpiperidine-3-carbamic acid tert-butyl ester

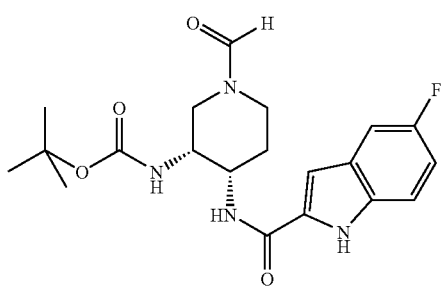

The title compound was obtained in the same manner as in the method described in Reference Example 56, by condensing the compound obtained in Reference Example 51 with 5-fluoroindole-2-carboxylic acid.

$^1$H-NMR (CDCl$_3$) δ: 1.51 (9H, br.s), 1.62-1.94 (1H, m), 2.11-2.27, 2.29-2.46 (total 1H, each m), 2.68-2.88 (0.5H, m), 2.99 (0.5H, br.d, J=13.7 Hz), 3.18-3.32 (0.5H, m), 3.44 (0.5H, br.d, J=12.9 Hz), 3.55-3.74 (1H, m), 4.07-4.60 (3H, m), 4.92-5.30 (1H, m), 6.81-6.90 (1H, m), 6.99-7.07 (1H, m), 7.21-7.30 (1H, m), 7.32-7.40 (1H, m) 7.49 (0.4H, br.s), 8.01, 8.02, 8.15, 8.16 (total 1H, each s), 8.39 (0.6H, br.s), 9.43-9.86 (1H, m).

MS(ESI)m/z: 305 (M-Boc)$^+$.

Reference Example 67

(3R,4S)-4-{[(Z)-3-(4-chlorophenyl)-2-fluoro-2-propenoyl]amino}-1-formylpiperidine-3-carbamic acid tert-butyl ester

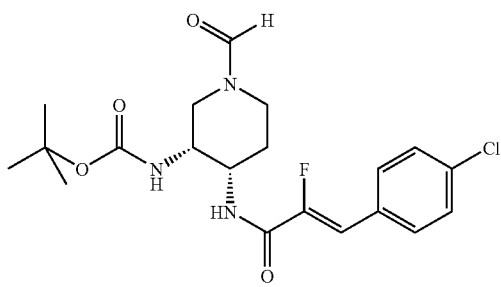

The title compound was obtained in the same manner as in the method described in Reference Example 56, by condensing the compound obtained in Reference Example 51 with (Z)-3-(4-chlorophenyl)-2-fluoro-2-propenoic acid.

$^1$H-NMR (CDCl$_3$) δ: 1.43-1.64 (10H, m), 2.07-2.25 (1H, m), 2.79-2.98 (1H, m), 3.23-3.72 (2H, m), 4.10-4.54 (3H, m), 4.86-5.01 (1H, m), 6.81-6.94 (1H, m), 7.11, 7.98 (total 1H, each s), 7.35 (2H, dd, J=8.6, 2.6 Hz), 7.54 (2H, dd, J=8.6, 2.6 Hz), 8.00, 8.16 (total 1H, each s).

MS(FAB)m/z: 426 (M+H)$^+$.

Reference Example 68

(3R,4S)-1-acetyl-4-aminopiperidine-3-carbamic acid tert-butyl ester

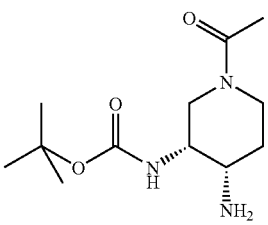

The title compound was obtained from (3R,4S)-1-acetyl-3-[(tert-butoxycarbonyl)amino]piperidine-4-carbamic acid benzyl ester, in the same manner as in the method described in Reference Example 51.

$^1$H-NMR (CDCl$_3$) δ: 1.46 (9H, s), 1.59-1.97 (2H, m), 2.07 (1H, br.s) 2.15 (2H, br.s), 2.61-4.82 (8H, m), 5.08-6.40 (1H, m).

MS(ESI)m/z: 258 (M+H)$^+$, 158 (M-Boc)$^+$.

Reference Example 69

(3R,4S)-1-acetyl-4-({2-[(5-bromopyridin-2-yl)amino]-2-oxoacetyl}amino)piperidine-3-carbamic acid tert-butyl ester

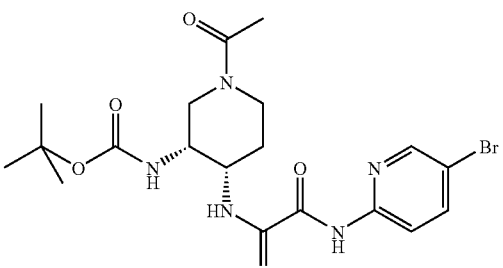

The title compound was obtained in the same manner as in the method described in Reference Example 56, by condensing the compound obtained in Reference Example 68 with 2-[(5-bromo-2-pyridinyl)amino]-2-oxoacetic acid lithium salt.

$^1$H-NMR (CDCl$_3$) δ: 1.45, 1.46 (total 9H, each s), 1.58-1.76 (1H, m) 1.84-1.87 (0.5H, m), 2.04-2.19 (0.5H, m), 2.10, 2.17 (total 3H, each s), 2.69-2.81 (0.5H, m), 2.89 (0.5H, br.d, J=12.0 Hz), 3.15-3.27 (0.5H, m), 3.32 (0.5H, br.d, J=12.5 Hz), 3.82-4.23 (3H, m), 4.58-4.76 (1H, m), 4.92-5.02 (0.5H, m), 5.24 (0.5H, br.d, J=8.5 Hz), 7.79-7.93 (1.6H, m), 8.09-8.19 (1H, m), 8.38-8.44 (1H, m), 8.51-8.63 (0.4H, br), 9.69, 9.71 (total 1H, each br.s).

MS(ESI)m/z: 484 (M+H)$^+$.

Reference Example 70

(3R,4S)-1-acetyl-4-({2-[(4-bromophenyl)amino]-2-oxoacetyl}amino)piperidine-3-carbamic acid tert-butyl ester

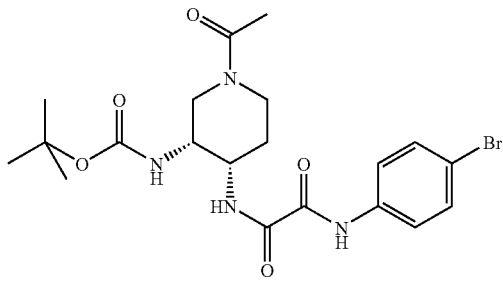

The title compound was obtained in the same manner as in the method described in Reference Example 52, by hydrolyzing 2-[(4-bromophenyl)amino]-2-oxoacetic acid methyl ester, and then condensing the hydrolysis product with the compound obtained in Reference Example 68.

$^1$H-NMR (CDCl$_3$) δ: 1.44 (9H, s), 1.52-1.76 (1H, m), 1.83-2.20 (1H, m) 2.11, 2.17 (total 3H, each s), 2.69-2.82 (0.5H, m), 2.90 (0.5H, br.d, J=13.9 Hz), 3.16-3.27 (0.5H, m), 3.33 (0.5H, br.d, J=13.4 Hz), 3.80-4.23 (3H, m), 4.56-4.77 (1H, m), 4.87-4.99 (0.5H, br), 5.05-5.17 (0.5H, br), 7.43-7.58 (4H, m), 7.80-7.90 (0.5H, br), 8.37-8.48 (0.5H, br), 9.21 (0.5H, br.s), 9.26 (0.5H, br.s)

MS(ESI)m/z: 383 (M-Boc)$^+$.

Reference Example 71

(3R,4S)-1-acetyl-4-({2-[(4-chloro-3-fluorophenyl)amino]-2-oxoacetyl}amino)piperidine-3-carbamic acid tert-butyl ester

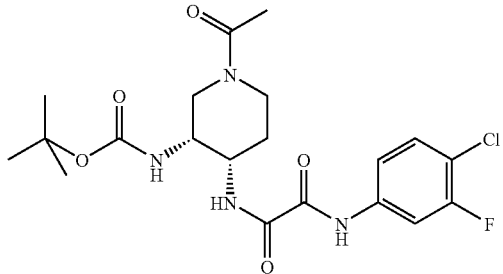

The title compound was obtained in the same manner as in the method described in Reference Example 56, by condensing the compound obtained in Reference Example 68 with 2-[(4-chloro-3-fluorophenyl)amino]-2-oxoacetic acid.

$^1$H-NMR (CDCl$_3$) δ: 1.44 (9H, s), 1.54-1.77 (1H, m), 1.84-2.16 (1H, m) 2.11, 2.17 (total 3H, each s), 2.67-2.95 (1H, m), 3.10-3.38 (1H, m), 3.72-4.24 (3H, m), 4.36-5.26 (2H, m), 7.19-7.41 (2H, m), 7.73 (1H, d, J=10.5 Hz), 7.87, 8.45 (total 1H, each br.s), 9.29, 9.36 (total 1H, each br.s).

MS(ESI)m/z: 357 (M-Boc)$^+$.

Reference Example 72

(3R,4S)-1-acetyl-4-({2-[(5-chlorothiophen-2-yl)amino]-2-oxoacetyl}amino)piperidine-3-carbamic acid tert-butyl ester

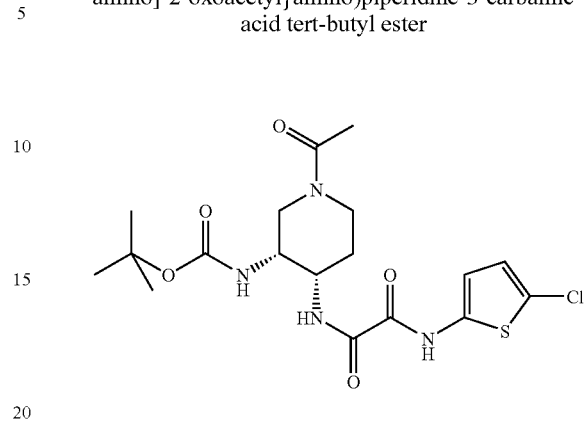

The title compound was obtained in the same manner as in the method described in Reference Example 56, by condensing the compound obtained in Reference Example 68 with 2-[(5-chlorothiophen-2-yl)amino]-2-oxoacetic acid lithium salt.

$^1$H-NMR (CDCl$_3$) δ: 1.43 (9H, s), 1.64-1.90 (1.5H, m), 1.96-2.08 (0.5H, m), 2.17 (3H, s), 2.62-2.77 (0.7H, m) 2.90 (0.3H, br.d, J=13.2 Hz) 3.14-3.40 (1H, m), 3.81-4.29 (3H, m), 4.71 (1H, br.d, J=12.2 Hz), 4.98 (0.4H, br.d, J=6.8 Hz), 5.56-5.70 (0.6H, br), 6.63 (0.4H, d, J=3.9 Hz), 6.70-6.82 (1H, m) 6.74 (0.6H, d, J=4.2 Hz), 8.07 (0.6H, br.s), 8.26 (0.4H, br.s), 9.85 (0.4H, br.s), 10.46 (0.6H, br.s)

MS(ESI)m/z: 445 (M+H)$^+$.

Reference Example 73

(3R,4S)-1-acetyl-4-({2-[(5-chloropyridin-2-yl)amino]-2-oxoethanethioyl}amino)piperidine-3-carbamic acid tert-butyl ester

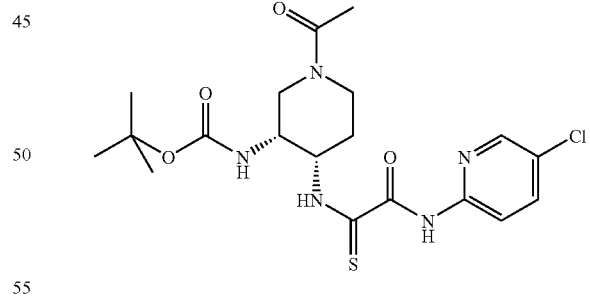

The title compound was obtained in the same manner as in the method described in Reference Example 63, reacting 2,2-dichloro-N-(5-chloropyridin-2-yl)acetamide with the compound obtained in Reference Example 68 in the presence of diisopropylethylamine and powdered sulfur.

$^1$H-NMR (CDCl$_3$) δ: 1.45 (9H, s), 1.59-1.99 (1H, m), 2.02-2.21 (0.6H, m), 2.12, 2.18 (total 3H, each s), 2.32-2.47 (0.4H, m), 2.63-2.79 (0.6H, m), 2.93 (0.4H, br.d, J=13.7 Hz), 3.18-3.40 (1H, m), 3.92 (0.5H, d, J=13.5 Hz), 4.04 (0.5H, d, J=13.5 Hz), 4.24 (1H, br.s), 4.39-4.53 (0.4H, br), 4.58-4.84 (1.6H, m), 5.17 (0.4H, d, J=7.6 Hz), 5.73 (0.6H, d, J=7.6 Hz), 7.66-7.77 (1H, m), 8.16, 8.21 (total 1H, each d, J=8.8 Hz), 8.29-8.35 (1H, m), 9.71-9.96 (0.6H, br), 10.40-10.52 (0.4H, m), 10.53 (1H, s).

MS(ESI)m/z: 456 (M+H)+.

Reference Example 74

(3R,4S)-1-acetyl-4-({2-[(5-fluoropyridin-2-yl)amino]-2-oxoethanethioyl}amino)piperidine-3-carbamic acid tert-butyl ester

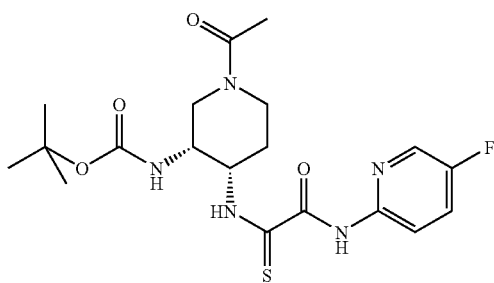

The title compound was obtained in the same manner as in the method described in Reference Example 63, reacting 2,2-dichloro-N-(5-fluoropyridin-2-yl)acetamide with the compound obtained in Reference Example 68 in the presence of diisopropylethylamine and powdered sulfur.

¹H-NMR (CDCl₃) δ: 1.45 (9H, s), 1.60-1.90 (1H, m), 2.01-2.22 (0.5H, m), 2.12, 2.18 (total 3H, each s), 2.32-2.46 (0.5H, m), 2.64-2.79 (0.6H, t, J=12.2 Hz), 2.93 (0.4H, br.d, J=13.9 Hz), 3.20-3.39 (1H, m), 3.92 (0.5H, br.d, J=13.7 Hz), 4.04 (0.5H, br.d, J=13.7 Hz), 4.15-4.32 (1H, br), 4.41-4.54 (0.5H, br), 4.57-4.69 (0.5H, br), 4.70-4.85 (1H, m), 5.18 (0.4H, d, J=7.3 Hz) 5.73 (0.6H, d, J=8.3 Hz), 7.43-7.53 (1H, m), 8.17-8.29 (2H, m), 9.86 (0.5H, br.s), 10.47 (0.5H, br.s), 10.53 (1H, s).

MS(ESI)m/z: 340 (M-Boc)+, 440 (M+H)+.

Reference Example 75

(3R,4S)-4-(benzyloxycarbonyl)amino-3-(tert-butoxycarbonyl)amino piperidine-1-carboxylic acid methyl ester

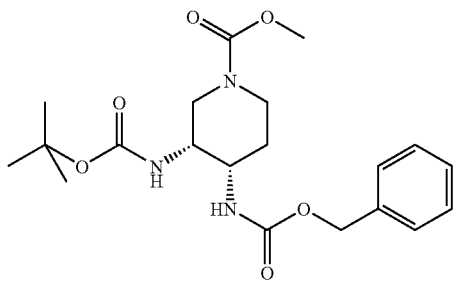

To a mixed solution of the compound obtained in Reference Example 14 (1.20 g) in dichloromethane (10 ml) and triethylamine (1.0 ml), methyl chloroformate ester (330 μl) was added at 0° C., and the mixture was stirred for 150 minutes at 0° C. After adding ice to the reaction mixture and stirring, dichloromethane and a 10% aqueous solution of citric acid were added. The mixture was extracted with dichloromethane, and then the combined organic layer was washed with a saturated aqueous solution of sodium hydrogen carbonate and a saturated aqueous solution of sodium chloride. Subsequently, the organic layer was dried over anhydrous sodium sulfate, and the solvent was distilled off under reduced pressure. The residue was purified by silica gel column chromatography (dichloromethane:methanol=50:1→30:1), to obtain the title compound (1.17 g).

¹H-NMR (CDCl₃) δ: 1.39-1.56 (1H, m), 1.44 (9H, s), 1.82-2.07 (1H, m) 2.86-2.97 (1H, m), 3.07 (1H, br.d, J=13.2 Hz), 3.70 (3H, s), 3.73-3.85 (1H, m), 3.88-4.24 (3H, m), 4.72-4.83 (1H, m), 5.04-5.15 (2H, m), 5.23-5.79 (1H, br), 7.28-7.39 (5H, m).

MS(ESI)m/z: 352 (M-tBu)+, 408 (M+H)+.

Reference Example 76

(3R,4S)-4-amino-3-(tert-butoxycarbonyl)aminopiperidine-1-carboxylic acid methyl ester

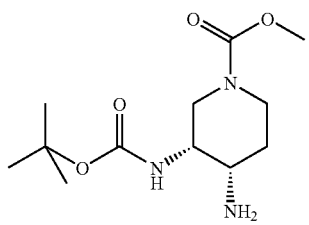

To a solution of the compound obtained in Reference Example 75 (1.16 g) in ethanol (20 ml), a 10% palladium carbon catalyst (237 mg) was added, and the mixture was stirred for 2 days under hydrogen conditions. The catalyst was removed by filtration, and the filtrate was concentrated under reduced pressure, and dried by means of a vacuum pump, to obtain the title compound (904 mg).

MS(ESI)m/z: 174 (M-Boc)+, 274 (M+H)+.

Reference Example 77

(3R,4S)-3-(tert-butoxycarbonyl)amino-4-({2-[(5-chloropyridin-2-yl)amino]-2-oxoethanethioyl}amino)piperidine-1-carboxylic acid methyl ester

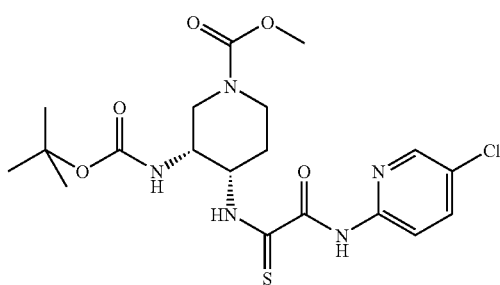

The title compound was obtained in the same manner as in the method described in Reference Example 63, by reacting 2,2-dichloro-N-(5-chloropyridin-2-yl)acetamide with the compound obtained in Reference Example 76 in the presence of diisopropylethylamine and powdered sulfur.

¹H-NMR (CDCl₃) δ: 1.48 (9H, s), 1.60-1.75 (1H, m), 2.16-2.31 (1H, m) 2.87-3.03 (1H, m), 3.13 (1H, br.d, J=13.2 Hz), 3.74 (3H, s), 4.16-4.32 (3H, m), 4.39-4.50 (1H, m), 5.12 (1H, br.d, J=7.8 Hz), 7.71 (1H, dd, J=8.8, 2.4 Hz), 8.20 (1H, d, J=8.8 Hz), 8.31 (1H, d, J=2.4 Hz), 9.43-10.39 (1H, m), 10.53 (1H, s).

MS(ESI) m/z: 472 (M+H)⁺.

Reference Example 78

(3R,4S)-3-(tert-butoxycarbonyl)amino-4-({2-[(5-fluoropyridin-2-yl)amino]-2-oxoethanethioyl}amino)piperidine-1-carboxylic acid methyl ester

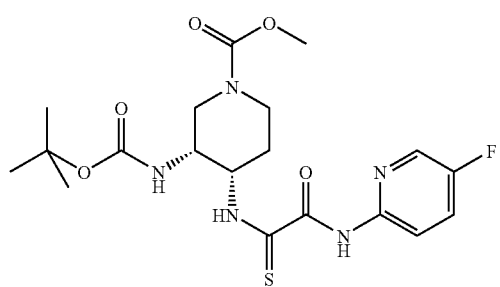

The title compound was obtained in the same manner as in the method described in Reference Example 63, by reacting 2,2-dichloro-N-(5-fluoropyridin-2-yl)acetamide with the compound obtained in Reference Example 76 in the presence of diisopropylethylamine and powdered sulfur.

¹H-NMR (CDCl₃) δ: 1.49 (9H, s), 1.55-1.71 (1H, m), 2.18-2.33 (1H, m) 2.90-3.02 (1H, m), 3.13 (1H, br.d, J=12.7 Hz), 3.75 (3H, s), 4.16-4.31 (3H, m), 4.39-4.49 (1H, m), 4.88-5.04 (1H, br), 7.43-7.52 (1H, m), 8.22 (1H, d, J=2.9 Hz), 8.25 (1H, dd, J=9.1, 4.2 Hz), 9.94-10.37 (1H, br), 10.53 (1H, s).

MS(ESI)m/z: 400 (M-tBu)⁺, 456 (M+H)⁺.

Reference Example 79

(3R,4S)-3-[(tert-butoxycarbonyl)amino]-1-methylpiperidine-4-carbamic acid benzyl ester

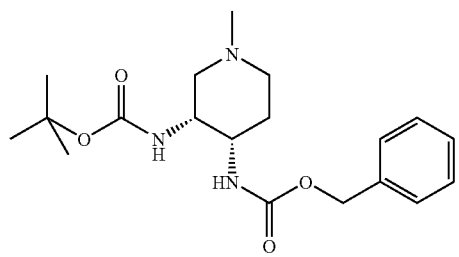

The title compound was obtained from the compound obtained in Reference Example 14, in the same manner as in the method described in Reference Example 18.

¹H-NMR (CDCl₃) δ: 1.44 (9H, s), 1.49-1.63 (1H, m), 1.85-2.08 (2H, m) 2.12-2.26 (1H, br), 2.21 (3H, s), 2.61-2.79 (2H, m), 3.46-3.63 (1H, m), 3.86-4.01 (1H, m), 5.06 (1H, d, J=12.7 Hz), 5.11 (1H, d, J=12.7 Hz), 5.25-5.61 (2H, br), 7.26-7.38 (5H, m).

MS(ESI)m/z: 364 (M+H)⁺.

Reference Example 80

(3S)-3-{[(benzyloxy)carbonyl]amino}-4-[(tert-butoxycarbonyl)amino]-5-oxovaleric acid ethyl ester

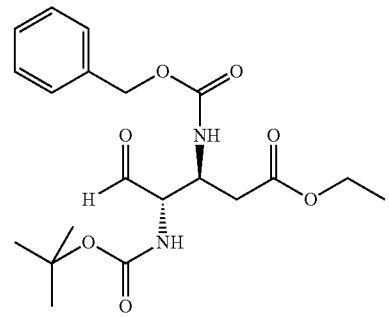

The (3S,4S)-compound obtained in Reference Example 11 (500 mg) was dissolved in a mixed solvent of dimethylsulfoxide (6.8 μl) and triethylamine (2.6 ml), sulfur trioxide-pyridine complex (1.50 g) was added, and the mixture was stirred for 30 minutes at room temperature. Water and acetic acid ethyl ester were added to the reaction mixture, and liquid separation was performed. The organic layer was washed with a saturated aqueous solution of ammonium chloride, a saturated aqueous solution of sodium hydrogen carbonate, and saturated brine, the organic layer was dried over anhydrous sodium sulfate, and the solvent was distilled off under reduced pressure. The residue was purified by column chromatography (hexane:acetic acid ethyl ester=3:1) using silica gel as support, to obtain the title compound (285 mg) as a diastereomer mixture.

¹H-NMR (CDCl₃) δ: 1.20-1.26 (3H, m), 1.43-1.44 (9H, m), 2.51-2.70 (2H, m), 4.07-4.18 (2H, m), 4.34-5.16 (4H, m), 5.33-6.36 (2H, m), 7.28-7.37 (5H, m), 9.62-9.66 (1H, m).

MS(ESI)m/z: 409 (M+H)⁺.

Reference Example 81

(4S)-5-[(tert-butoxycarbonyl)amino]-1-methyl-2-oxopiperidine-4-carbamic acid benzyl ester

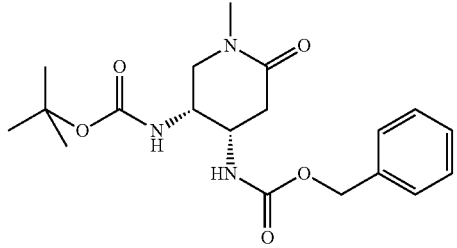

The compound obtained in Reference Example 80 (280 mg) was dissolved in ethanol (5 ml), acetic acid (157 μl), methylamine (583 μl) and sodium cyanoborohydride (86 mg) were added thereto, and the mixture was stirred for 16 hours at room temperature. Dichloromethane and a saturated aqueous solution of sodium hydrogen carbonate were added to the reaction mixture, liquid separation was performed, and the organic layer was washed with a saturated aqueous solution of sodium hydrogen carbonate. This was dried over anhydrous sodium sulfate, the solvent was distilled off under reduced pressure, and the resulting residue was purified by column chromatography (dichloromethane→dichloromethane:methanol=98:2) using silica gel as support, to obtain the title compound (123 mg) as a mixture of stereoisomers.

$^1$H-NMR (CDCl$_3$) δ: 1.40-1.45 (9H, m), 2.26-2.44 (1H, m) 2.78-2.91 (4H, m), 3.06-3.23 (1H, m), 3.47-3.62 (1H, m), 3.79-3.97 (1H, m), 4.15 (1H, s), 5.06-5.18 (3H, m), 5.55 (1H, br.s) 7.31-7.37 (5H, m).

MS(ESI)m/z: 378 (M+H)$^+$.

Reference Example 82

(4S)-4-({2-[(5-chloropyridin-2-yl)amino]-2-oxoacetyl}amino)-1-methyl-6-oxopiperidine-3-carbamic acid tert-butyl ester

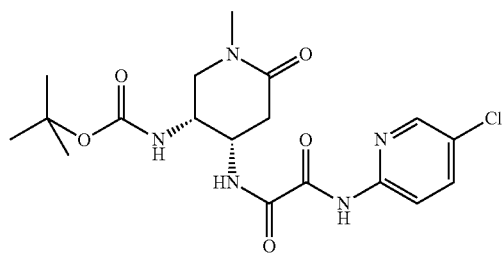

The title compound was obtained as a mixture of stereoisomers in the same manner as in the method described in Reference Example 20, by deprotecting the benzyloxycarbonyl group of the compound obtained in Reference Example 81, and condensing the compound with 2-[(5-chloropyridin-2-yl)amino]-2-oxoacetic acid lithium salt.

$^1$H-NMR (CDCl$_3$) δ: 1.37-1.47 (9H, m), 2.48-2.57 (1H, m), 2.88-2.97 (4H, m), 3.16-3.34 (1H, m), 3.53-3.71 (1H, m), 4.01-4.54 (2H, m), 5.11 (1H, d, J=8.3 Hz), 7.69-7.74 (1H, m), 7.89-8.02 (1H, m), 8.18 (1H, dd, J=8.8, 1.5 Hz), 8.32-8.33 (1H, m), 9.74-9.79 (1H, m).

MS(ESI)m/z: 426 (M+H)$^+$.

Example 1

N$^1$-(5-chloropyridin-2-yl)-N$^2$-((3R,4S)-1-methyl-3-{[(5-methyl-4,5,6,7-tetrahydrothiazolo[5,4-c]pyridin-2-yl)carbonyl]amino}piperidin-4-yl)ethanediamide hydrochloride

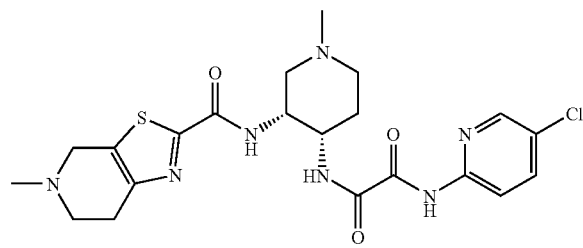

To a solution of the compound obtained in Reference Example 18 (184 mg) in dioxane (5.0 ml), a 4 N hydrochloric acid-dioxane solution (4.0 ml) was added, and the mixture was stirred for 4 hours at room temperature. The solvent was distilled off under reduced pressure, and then dried by means of a vacuum pump. The resulting powder was dissolved in N,N-dimethylformamide (5.0 ml), then the compound obtained in Reference Example 5 (137 mg), 1-hydroxybenzotriazole (90 mg), 1-(3-dimethylaminopropyl)-3-ethylcarbodiimide hydrochloride (134 mg) and triethylamine (200 µl) were added, and the mixture was stirred for 3 days at room temperature. The solvent was distilled off under reduced pressure, and then dichloromethane and a saturated aqueous solution of sodium hydrogen carbonate were added to the residue. The mixture was extracted with dichloromethane, and then the combined organic layer was washed with a saturated aqueous solution of sodium chloride. The organic layer was dried over anhydrous sodium sulfate, subsequently the solvent was distilled off under reduced pressure, the residue was purified by flash column chromatography (dichloromethane:methanol=20:1) using silica gel as support, to obtain a free form of the title compound (127 mg). To a solution of the free form (124 mg) in ethanol (4.0 ml), an ethanol solution (1.0 ml) of 1 N hydrochloric acid was added, and the solvent was distilled off under reduced pressure. The residue was dried by means of a vacuum pump, and the title compound (151 mg) was obtained.

$^1$H-NMR (DMSO-d$_6$) δ: 1.73-1.91 (1H, m), 1.98-2.12 (0.5H, m), 2.13-2.26 (0.5H, m), 2.33-2.53 (1H, m), 2.74-2.83 (3H, m), 2.90 (3H, br.s), 3.02-3.83 (7H, m), 4.15-4.78 (4H, m), 7.97-8.08 (2H, m), 8.45 (1H, s), 8.94-9.17 (1H, m), 9.23-9.33 (0.4H, m), 9.37-9.51 (0.6H, m), 10.00-10.42 (1.5H, m) 11.00-11.24 (0.5H, m), 11.54-11.77 (0.5H, m), 11.88-12.12 (0.5H, m).

MS(ESI)m/z: 492 (M+H)$^+$.

Example 2

N$^1$-(5-chloropyridin-2-yl)-N$^2$-((3R,4S)-1-cyclopropyl-3-{[(5-methyl-4,5,6,7-tetrahydrothiazolo[5,4-c]pyridin-2-yl)carbonyl]amino}piperidin-4-yl)ethanediamide hydrochloride

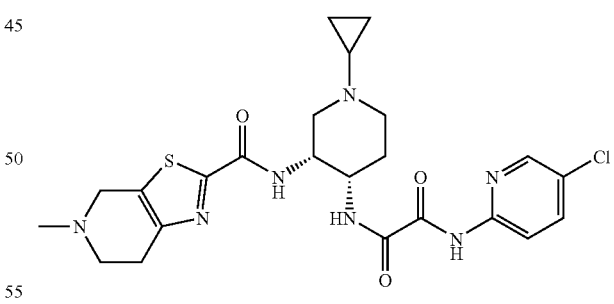

The title compound was obtained in the same manner as in the method described in Example 1, deprotecting the compound obtained in Reference Example 20 by a hydrochloric acid treatment, and condensing the treated product with the compound obtained in Reference Example 6.

$^1$H-NMR (DMSO-d$_6$) δ: 0.71-0.89 (1.5H, m), 0.94-1.29 (2.5H, m) 1.73-2.48 (2H, m), 2.88 (3H, s), 3.01-3.83 (9H, m), 3.87-4.90 (4H, m), 8.02 (2H, d, J=14.6 Hz), 8.45 (1H, s), 8.93-9.61 (1.8H, m), 10.01-10.55 (1.2H, m), 11.24 (0.2H, br.s), 11.59-12.23 (0.8H, m).

MS(ESI)m/z: 518 [(M+H)$^+$, $^{35}$Cl], 520 [(M+H)$^+$, $^{37}$Cl]

Example 3

N[1]-((3R,4S)-1-aryl-3-{[(5-methyl-4,5,6,7-tetrahydrothiazolo[5,4-c]pyridin-2-yl)carbonyl]amino}piperidin-4-yl)-N[2]-(5-chloropyridin-2-yl)ethanediamide hydrochloride

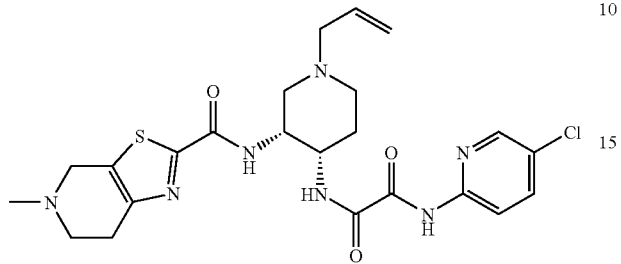

The title compound was obtained in the same manner as in the method described in Example 1, by deprotecting the compound obtained in Reference Example 21 by a hydrochloric acid treatment, and condensing the deprotection product with the compound obtained in Reference Example 6.

$^1$H-NMR (DMSO-d$_6$) δ: 1.77-1.92 (0.5H, m), 2.02-2.14 (0.5H, m) 2.17-2.33 (0.5H, m), 2.36-2.55 (0.5H, m), 2.89 (3H, s), 3.01-3.38 (3.5H, m), 3.39-3.85 (6.5H, m), 4.17-4.80 (4H, m), 5.45-5.58 (2H, m), 5.87-6.10 (1H, m), 7.96-8.08 (2H, m), 8.45 (1H, s), 8.99-9.29 (1.4H, m), 9.44 (0.3H, d, J=7.8 Hz), 9.49 (0.3H, d, J=8.1 Hz), 10.17 (0.25H, s), 10.27 (0.25H, s), 10.36 (0.5H, br.d, J=4.6 Hz), 10.41 (0.3H, br.s), 10.66 (0.3H, br.s), 11.61-12.24 (1.4H, m).

MS(ESI)m/z: 518 [(M+H)$^+$, $^{35}$Cl], 520 [(M+H)$^+$, $^{37}$Cl]

Example 4

N[1]-(5-chloropyridin-2-yl)-N[2]-((3R,4S)-1-cyclopropylmethyl-3-{[(5-methyl-4,5,6,7-tetrahydrothiazolo[5,4-c]pyridin-2-yl)carbonyl]amino}piperidin-4-yl)ethanediamide hydrochloride

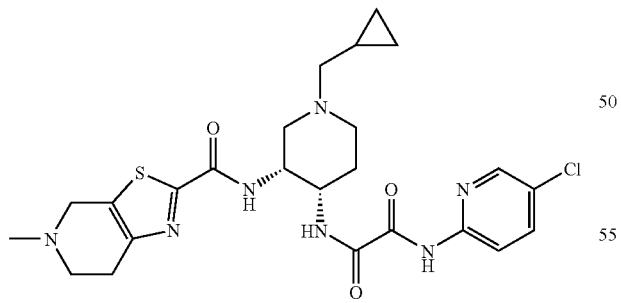

The title compound was obtained in the same manner as in the method described in Example 1, by deprotecting the compound obtained in Reference Example 23 by a hydrochloric acid treatment, and condensing the deprotection product with the compound obtained in Reference Example 6.

$^1$H-NMR (DMSO-d$_6$) δ: 0.32-0.47 (2H, m), 0.57-0.69 (2H, m) 1.01-1.23 (1H, m), 1.75-1.93 (0.5H, m), 2.02-2.15 (0.5H, m), 2.22-2.37 (0.5H, m), 2.39-2.54 (0.5H, m), 2.89 (3H, s), 2.92-3.78 (9H, m), 3.91-4.51 (3H, m), 4.59-4.83 (2H, m), 7.96-8.08 (1H, m), 8.00 (1H, s), 8.45 (1H, s), 9.07-9.29 (1.4H, m) 9.41 (0.3H, d, J=8.3 Hz), 9.49 (0.3H, d, J=8.3 Hz), 10.13-10.53 (1.6H, m), 11.36-11.58 (0.4H, m), 11.84-12.31 (1H, m).

MS(ESI)m/z: 532 [(M+H)$^+$, $^{35}$Cl], 534 [(M+H)$^+$, $^{37}$Cl].

Example 5

N[1]-(5-chloropyridin-2-yl)-N[2]-((3R,4S)-1-methanesulfonyl-3-{[(5-methyl-4,5,6,7-tetrahydrothiazolo[5,4-c]pyridin-2-yl)carbonyl]amino}piperidin-4-yl)ethane diamide hydrochloride

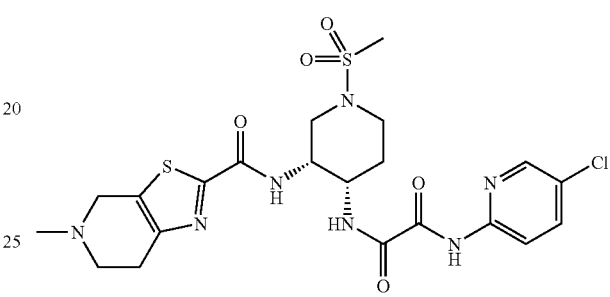

The title compound was obtained in the same manner as in the method described in Example 1, by deprotecting the compound obtained in Reference Example 24 by a hydrochloric acid treatment, and condensing the deprotection product with the compound obtained in Reference Example 5.

$^1$H-NMR (DMSO-d$_6$) δ: 1.69-1.81 (1H, m), 2.12-2.29 (1H, m) 2.87-3.04 (4H, m), 2.89 (3H, s), 3.09-3.30 (3H, m), 3.39-3.60 (2H, m), 3.64-3.77 (2H, m), 4.11-4.24 (1H, m), 4.26-4.36 (1H, m), 4.37-4.50 (1H, m), 4.63-4.78 (1H, m), 8.01 (2H, br.s), 8.33-8.47 (1H, m), 8.45 (1H, br.s), 9.30 (0.5H, d, J=8.8 Hz), 9.37 (0.5H, d, J=8.1 Hz), 10.28 (1H, d, J=13.2 Hz), 11.14, 11.48 (total 1H, each br.s).

MS(ESI)m/z: 556 [(M+H)$^+$, $^{35}$Cl], 558 [(M+H)$^+$, $^{37}$Cl]

Example 6

N[1]-(5-chloropyridin-2-yl)-N[2]-((3R,4S)-3-{[(5-methyl-4,5,6,7-tetrahydrothiazolo[5,4-c]pyridin-2-yl)carbonyl]amino-1-trifluoromethanesulfonyl}piperidin-4-yl)ethanediamide hydrochloride

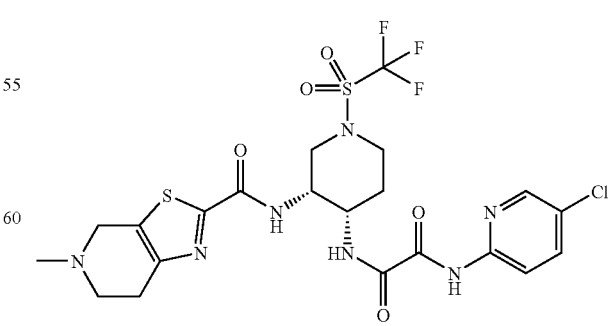

The title compound was obtained in the same manner as in the method described in Example 1, by deprotecting the compound obtained in Reference Example 26 by a hydrochloric acid treatment, and condensing the deprotection product with the compound obtained in Reference Example 5.

$^1$H-NMR (DMSO-d$_6$) δ: 1.71-1.86 (1H, m), 2.22-2.39 (1H, m), 2.91 (3H, s), 3.04-3.90 (7H, m), 4.03 (1H, br.d, J=12.5 Hz), 4.17 (1H, br.s), 4.32-4.54 (2H, m), 4.60-4.81 (1H, br), 7.97-8.08 (2H, m), 8.44 (1H, s), 8.76-8.97 (1H, m), 9.47 (1H, br.s), 10.29 (1H, br.s), 11.42, 11.70 (total 1H, each br.s).

MS(ESI)m/z: 610 [(M+H)$^+$, $^{35}$Cl], 612 [(M+H)$^+$, $^{37}$Cl].

Example 7

N$^1$-(5-chloropyridin-2-yl)-N$^2$-((3R,4S)-3-{[(5-methyl-4,5,6,7-tetrahydrothiazolo[5,4-c]pyridin-2-yl)carbonyl]amino}-1-phenylsulfonylpiperidin-4-yl)ethanediamide hydrochloride

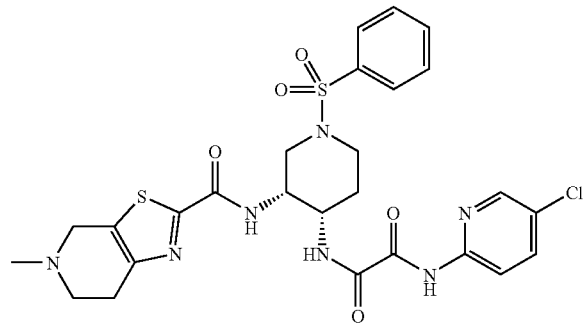

The title compound was obtained in the same manner as in the method described in Example 1, by deprotecting the compound obtained in Reference Example 27 by a hydrochloric acid treatment, and condensing the deprotection product with the compound obtained in Reference Example 5.

$^1$H-NMR (DMSO-d$_6$) δ: 1.66-1.76 (1H, m), 2.16-2.30 (1H, m) 2.54-2.86 (2H, m), 2.93 (3H, br.s), 3.10-3.33 (2H, m), 3.37-3.62 (2H, m), 3.67-3.79 (2H, m), 4.02-4.15 (1H, m), 4.19-4.30 (1H, m), 4.39-4.50 (1H, m), 4.66-4.80 (1H, m), 7.57-7.66 (2H, m), 7.68-7.76 (3H, m), 7.99 (2H, s), 8.40-8.49 (2H, m), 9.22-9.35 (1H, m), 10.23, 10.26 (total 1H, each s), 11.23 (0.5H, br.s), 11.46 (0.5H, br.s).

MS(ESI)m/z: 618 [(M+H)$^+$, $^{35}$Cl], 620 [(M+H)$^+$, $^{37}$Cl].

Example 8

N$^1$-(5-chloropyridin-2-yl)-N$^2$-((3R,4S)-1-formyl-3-{[(5-methyl-4,5,6,7-tetrahydrothiazolo[5,4-c]pyridin-2-yl)carbonyl]amino}piperidin-4-yl)ethanediamide hydrochloride

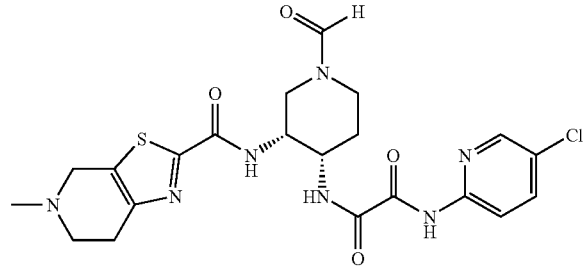

The title compound was obtained in the same manner as in the method described in Example 1, by deprotecting the compound obtained in Reference Example 28 by a hydrochloric acid treatment, and condensing the deprotection product with the compound obtained in Reference Example 5.

$^1$H-NMR (DMSO-d$_6$) δ: 1.58-1.74 (1H, m), 1.95-2.18 (1H, m), 2.91 (3H, s), 2.94-3.05 (0.5H, m), 3.06-3.31 (3H, m), 3.39-3.51 (1.5H, m), 3.62-3.75 (1.5H, m), 3.76-3.84 (0.5H, m), 3.92-4.08 (0.5H, m), 4.12-4.50 (3.5H, m), 4.62-4.77 (1H, m), 7.85 (0.5H, br.d, J=10.3 Hz), 7.96-8.07 (2.5H, m), 8.45 (1H, s), 8.47-8.63 (1H, m) 9.26-9.42 (1H, m), 10.28, 10.32 (total 1H, each br.s), 11.22-11.61 (1H, m).

MS(ESI)m/z: 506 [(M+H)$^+$, $^{35}$Cl], 508 [(M+H)$^+$, $^{37}$Cl].

Example 9

N$^1$-((3R,4S)-1-acetyl-3-{[(5-methyl-4,5,6,7-tetrahydrothiazolo[5,4-c]pyridin-2-yl)carbonyl]amino}piperidin-4-yl)-N$^2$-(5-chloropyridin-2-yl)ethanediamide hydrochloride

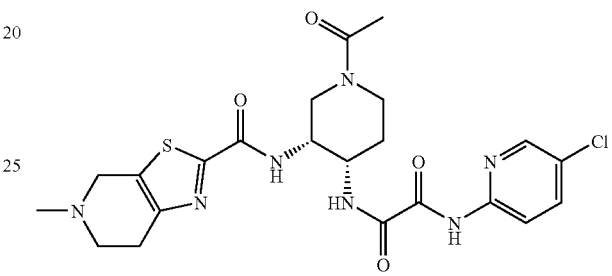

The title compound was obtained in the same manner as in the method described in Example 1, by deprotecting the compound obtained in Reference Example 29 by a hydrochloric acid treatment, and condensing the deprotection product with the compound obtained in Reference Example 5.

$^1$H-NMR (DMSO-d$_6$) δ: 1.54-1.76 (1H, m), 1.80, 2.01 (total 3H, each s), 2.02-2.17 (1H, m), 2.75-2.99 (0.5H, m), 2.91 (3H, s), 3.06-3.59 (4.5H, m), 3.62-3.79 (1.5H, m), 4.00-4.52 (4.5H, m), 4.63-4.79 (1H, m), 8.01 (2H, br.s), 8.44 (1H, s), 8.49-8.74 (1H, m), 9.17-9.47 (1H, m), 10.28, 10.31 (total 1H, each br.s), 11.15-11.33 (0.5H, br), 11.38-11.57 (0.5H, br).

MS(ESI)m/z: 520 [(M+H)$^+$, $^{35}$Cl], 522 [(M+H)$^+$, $^{37}$Cl].

Example 10

N$^1$-(5-chloropyridin-2-yl)-N$^2$-((3R,4S)-1-isobutyryl-3-{[(5-methyl-4,5,6,7-tetrahydrothiazolo[5,4-c]pyridin-2-yl)carbonyl]amino}piperidin-4-yl)ethanediamide hydrochloride

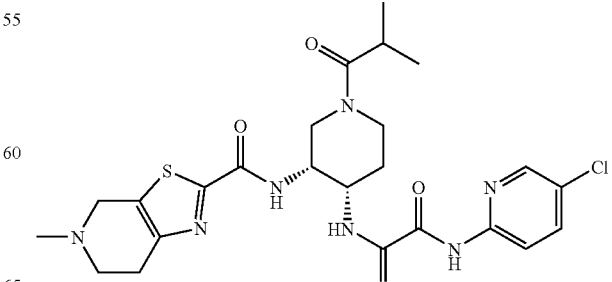

The title compound was obtained in the same manner as in the method described in Example 1, by deprotecting the compound obtained in Reference Example 30 by a hydrochloric acid treatment, and condensing the deprotection product with the compound obtained in Reference Example 5.

$^1$H-NMR (DMSO-$d_6$) δ: 0.70-0.85 (2H, m), 0.86-1.08 (5H, m) 1.56-1.77 (1H, m), 1.94-2.20 (1H, m), 2.58-2.74 (0.5H, m), 2.79-2.98 (1H, m), 2.90 (3H, s), 3.02-3.92 (4.5H, m), 4.09-4.50 (5H, m), 4.63-4.78 (1H, m), 8.01 (2H, br.s), 8.28-8.70 (1H, m), 8.44 (1H, s), 9.17-9.48 (1H, m), 10.29 (1H, br.d, J=16.6 Hz), 11.34 (0.5H, br.s), 11.62 (0.5H, br.s).

MS(ESI)m/z: 548 [(M+H)$^+$, $^{35}$Cl], 550 [(M+H)$^+$, $^{37}$Cl]

Example 11

N$^1$-((3R,4S)-1-benzoyl-3-{[(5-methyl-4,5,6,7-tetrahydrothiazolo[5,4-c]pyridin-2-yl)carbonyl]amino}piperidin-4-yl)-N$^2$-(5-chloropyridin-2-yl)ethanediamide hydrochloride

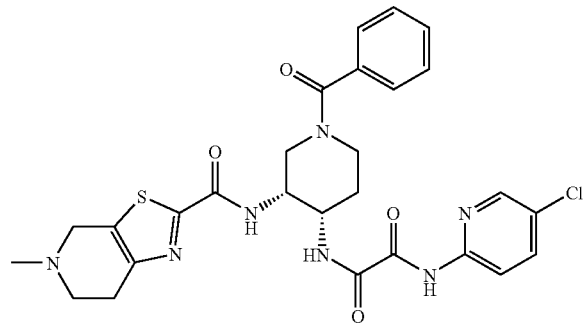

The title compound was obtained in the same manner as in the method described in Example 1, by deprotecting the compound obtained in Reference Example 31 by a hydrochloric acid treatment, and condensing the deprotection product with the compound obtained in Reference Example 5.

$^1$H-NMR (DMSO-$d_6$) δ: 1.60-1.75 (1H, m), 2.07-2.32 (1H, m), 2.91, 2.92 (total 3H, each s), 2.97-4.07 (6H, m), 4.17-4.82 (6H, m), 6.85-7.58 (5H, m), 7.92-8.06 (2H, m), 8.43 (1H, s), 8.47-8.89 (1H, br), 9.12-9.54 (1H, br), 10.28 (1H, s), 11.21-11.84 (1H, br).

MS(ESI)m/z: 582 [(M+H)$^+$, $^{35}$Cl], 584 [(M+H)$^+$, $^{37}$Cl]

Example 12

(3R,4S)-4-({2-[(5-chloropyridin-2-yl)amino]-2-oxoacetyl}amino)-3-[(5-methyl-4,5,6,7-tetrahydrothiazolo[5,4-c]pyridin-2-yl) carbonylamino]piperidine-1-carboxylic acid methyl ester hydrochloride

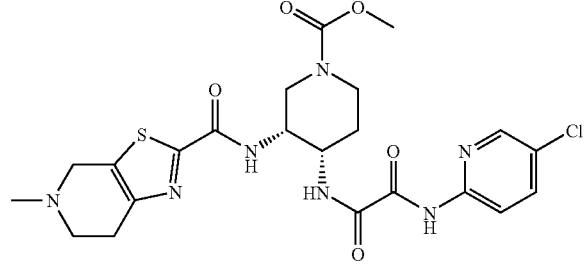

The title compound was obtained in the same manner as in the method described in Example 1, by deprotecting the compound obtained in Reference Example 32 by a hydrochloric acid treatment, and condensing the deprotection product with the compound obtained in Reference Example 5.

$^1$H-NMR (DMSO-$d_6$) δ: 1.57-1.69 (1H, m), 2.03-2.17 (1H, m), 2.91 (3H, s), 3.01-3.31 (3.5H, m), 3.34-3.94 (6.5H, m), 4.03-4.30 (3H, m), 4.37-4.51 (1H, m), 4.64-4.80 (1H, m), 8.01 (2H, br.s), 8.44 (1H, br.s), 8.49-8.64 (0.5H, m), 9.23-9.40 (0.5H, m), 10.27, 10.31 (total 1H, each br.s), 11.36 (1H, br.s), 11.54 (1H, br.s)

MS(ESI)m/z: 536 [(M+H)$^+$, $^{35}$Cl], 538 [(M+H)$^+$, $^{37}$Cl].

Example 13

(3R,4S)-4-({2-[(5-chloropyridin-2-yl)amino]-2-oxoacetyl}amino)-3-[(5-methyl-4,5,6,7-tetrahydrothiazolo[5,4-c]pyridin-2-yl) carbonylamino]piperidine-1-carboxylic acid ethyl ester hydrochloride

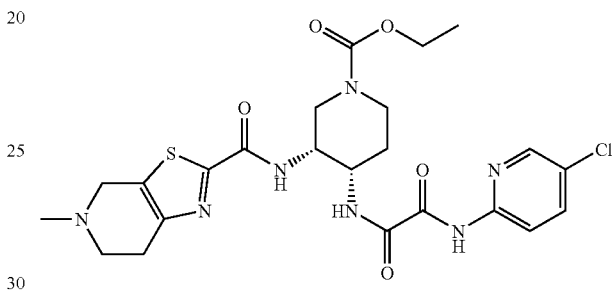

The title compound was obtained in the same manner as in the method described in Example 1, by deprotecting the compound obtained in Reference Example 33 by a hydrochloric acid treatment, and condensing the deprotection product with the compound obtained in Reference Example 5.

—H-NMR (DMSO-$d_6$) δ: 0.79-1.27 (3H, m), 1.56-1.67 (1H, m), 2.03-2.17 (1H, m), 2.90 (3H, br.s), 2.98-3.33 (3.5H, m), 3.40-3.53 (1H, m), 3.64-4.29 (5.5H, m), 4.37-4.49 (1H, m), 4.52-4.77 (3H, m), 8.01 (2H, br.s), 8.44 (1H, s), 8.48 (0.5H, d, J=6.8 Hz), 8.57 (0.5H, d, J=6.1 Hz), 9.21-9.48 (1H, m), 10.26, 10.31 (total 1H, each s), 11.54-11.71 (0.5H, br), 11.73-11.86 (0.5H, br).

MS(ESI)m/z: 550 [(M+H)$^+$, $^{35}$Cl], 552 [(M+H)$^+$, $^{37}$Cl].

Example 14

(3R,4S)-4-({2-[(5-chloropyridin-2-yl)amino]-2-oxoacetyl}amino)-3-(5-methyl-4,5,6,7-tetrahydrothiazolo[5,4-c]pyridin-2-yl)carbonylamino]piperidine-1-carboxylic acid isopropyl ester hydrochloride

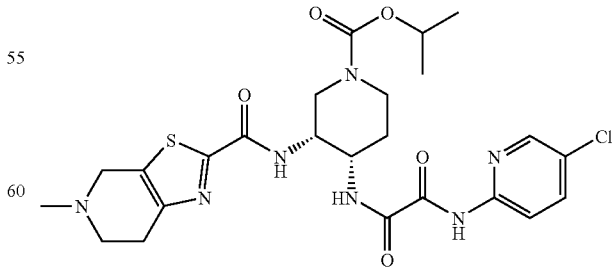

The title compound was obtained in the same manner as in the method described in Example 1, by deprotecting the compound obtained in Reference Example 34 by a hydrochloric acid treatment, and condensing the deprotection product with the compound obtained in Reference Example 5.

¹H-NMR (DMSO-d₆) δ: 0.83 (1H, s), 1.00-1.25 (5H, m), 1.55-1.66 (1H, m), 2.02-2.16 (1H, m), 2.90 (3H, br.s), 2.96-3.32 (3.5H, m), 3.40-3.54 (1H, m), 3.64-3.75 (3H, m), 4.02-4.29 (2.5H, m), 4.37-4.49 (1H, m), 4.57-4.78 (2H, m), 8.01 (2H, br.s), 8.40-8.56 (1H, m), 8.44 (1H, s), 9.26-9.46 (1H, m), 10.26, 10.30 (total 1H, each s), 11.41-11.74 (1H, m).

MS(ESI)m/z: 564 [(M+H)⁺, ³⁵Cl], 566 [(M+H)⁺, ³⁷Cl].

Example 15

N¹-(5-chloropyridin-2-yl)-N²-((3R,4S)-1-dimethyl-carbamoyl-3-{[(5-methyl-4,5,6,7-tetrahydrothiazolo[5,4-c]pyridin-2-yl)carbonyl]amino}piperidin-4-yl)ethanediamide hydrochloride

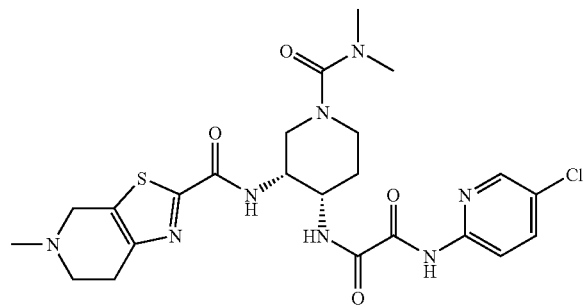

The title compound was obtained in the same manner as in the method described in Example 1, by deprotecting the compound obtained in Reference Example 35 by a hydrochloric acid treatment, and condensing the deprotection product with the compound obtained in Reference Example 5.

¹H-NMR (DMSO-d₆) δ: 1.57-1.69 (1H, m), 2.04-2.19 (1H, m), 2.67 (6H, s), 2.82-3.01 (1H, m), 2.91 (3H, s), 3.04-3.54 (5.5H, m), 3.61-3.78 (1.5H, m), 4.10-4.25 (2H, m), 4.33-4.53 (1H, m), 4.58-4.79 (1H, m), 8.00 (1H, dd, J=8.8, 2.2 Hz), 8.03 (1H, d, J=8.8 Hz), 8.44 (1H, d, J=2.2, 1.0 Hz), 8.50-8.70 (1H, m), 9.25 (1H, br.s), 10.26 (1H, s), 11.34, 11.53 (total 1H, each br.s).

MS(ESI)m/z: 549 [(M+H)⁺, ³⁵Cl], 551 [(M+H)⁺, ³⁷Cl].

Example 16

N¹-(5-chloropyridin-2-yl)-N²-((3R,4S)-1-ethylcarbamoyl-3-{[(5-methyl-4,5,6,7-tetrahydrothiazolo[5,4-c]pyridin-2-yl)carbonyl]amino}piperidin-4-yl)ethanediamide hydrochloride

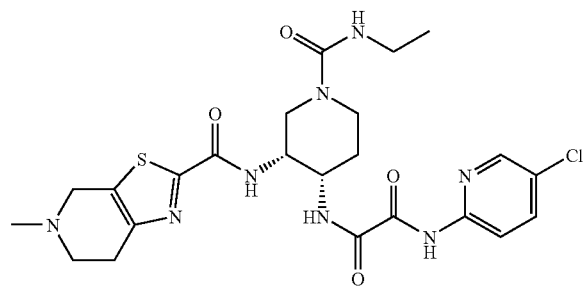

The title compound was obtained in the same manner as in the method described in Example 1, by deprotecting the compound obtained in Reference Example 36 by a hydrochloric acid treatment, and condensing the deprotection product with the compound obtained in Reference Example 5.

¹H-NMR (DMSO-d₆) δ: 0.94 (3H, t, J=7.1 Hz), 1.53-1.64 (1H, m) 1.93-2.08 (1H, m), 2.90 (3H, br.s), 2.98 (2H, q, J=7.1 Hz), 3.00-3.30 (4H, m), 3.39-3.52 (1H, m), 3.65-3.82 (2H, m), 3.90-4.05 (1H, m), 4.10-4.29 (2H, m), 4.36-4.47 (1H, m), 4.64-4.76 (1H, m), 6.44-6.70 (1H, br), 8.01 (2H, br.s)₁ 8.23 (0.6H, d, J=8.3 Hz), 8.33 (0.4H, d, J=8.1 Hz), 8.45 (1H, s), 9.19 (0.4H, d, J=7.3 Hz), 9.27 (0.6H, d, J=7.3 Hz), 10.25, 10.29 (total 1H, each s), 11.34-11.50 (0.5H, br), 11.58-11.74 (0.5H, br).

MS(ESI)m/z: 549 [(M+H)⁺, ³⁵Cl], 551 [(M+H)⁺, ³⁷Cl]

Example 17

N¹-(5-chloropyridin-2-yl)-N²-((3R,4S)-1-dimethylaminooxalyl-3-{[(5-methyl-4,5,6,7-tetrahydrothiazolo[5,4-c]pyridin-2-yl)carbonyl]amino}piperidin-4-yl)ethanediamide hydrochloride

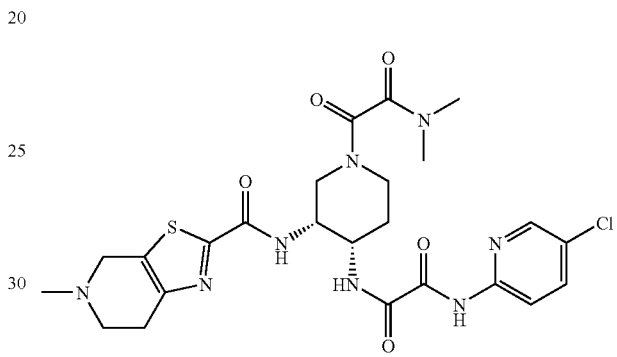

The title compound was obtained in the same manner as in the method described in Example 1, by deprotecting the compound obtained in Reference Example 39 by a hydrochloric acid treatment, and condensing the deprotection product with the compound obtained in Reference Example 5.

¹H-NMR (DMSO-d₆) δ: 1.65-1.77 (1H, m), 2.04-2.29 (1H, m) 2.64-2.75 (3H, m), 2.82-3.01 (7H, m), 3.01-3.36 (3.5H, m), 3.41-3.55 (2H, m), 3.59-3.88 (1.5H, m), 4.06-4.23 (1H, m), 4.30-4.50 (2H, m), 4.66-4.79 (1H, m), 8.01 (2H, s), 8.45 (1H, s) 8.60-8.80 (1H, m), 9.32-9.44 (1H, m), 10.26-10.34 (1H, m), 10.92-11.33 (1H, m).

MS(ESI)m/z: 577 [(M+H)⁺, ³⁵Cl], 579 [(M+H)⁺, ³⁷Cl].

Example 18

N¹-(5-chloropyridin-2-yl)-N²-((3R,4S)-1-dimethylsulfamoyl-3-{[(5-methyl-4,5,6,7-tetrahydrothiazolo[5,4-c]pyridin-2-yl)carbonyl]amino}piperidin-4-yl)ethanediamide hydrochloride

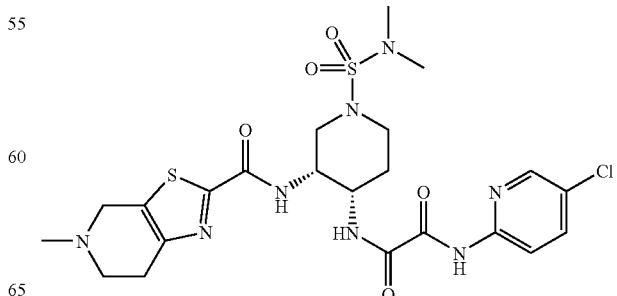

The title compound was obtained in the same manner as in the method described in Example 1, by deprotecting the compound obtained in Reference Example 40 by a hydrochloric acid treatment, and condensing the deprotection product with the compound obtained in Reference Example 5.

$^1$H-NMR (DMSO-$d_6$) δ: 1.65-1.75 (1H, m), 2.10-2.23 (1H, m), 2.73 (6H, s), 2.92 (3H, s), 3.04-3.40 (4H, m), 3.42-3.80 (4H, m), 4.14-4.29 (2H, m), 4.36-4.52 (1H, m), 4.62-4.78 (1H, m), 8.01 (2H, br.s), 8.36-8.52 (1H, m), 8.45 (1H, s), 9.22-9.41 (1H, br), 10.28 (1H, br.s), 11.03-11.24 (0.5H, br), 11.31-11.52 (0.5H, br).

MS(ESI)m/z: 585 [(M+H)$^+$, $^{35}$Cl], 587 [(M+H)$^+$, $^{37}$Cl].

Example 19

N$^1$-(5-chloropyridin-2-yl)-N$^2$-((4S,5R)-5-{[(5-methyl-4,5,6,7-tetrahydrothiazolo[5,4-c]pyridin-2-yl)carbonyl]amino}-2-oxopiperidin-4-yl)ethanediamide hydrochloride

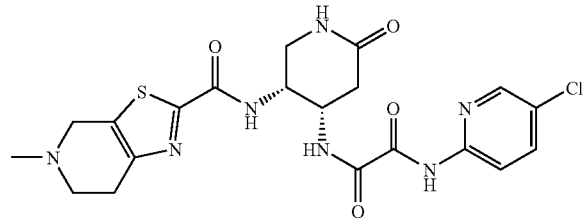

The title compound was obtained in the same manner as in the method described in Example 1, by deprotecting the compound obtained in Reference Example 41 by a hydrochloric acid treatment, and condensing the deprotection product with the compound obtained in Reference Example 6.

$^1$H-NMR (DMSO-$d_6$) d: 2.47-2.59 (1H, m), 2.65-2.77 (1H, m), 2.91 (3H, s), 3.07-3.32 (2H, m), 3.35-3.77 (4H, m), 4.39-4.49 (3H, m), 4.69-4.73 (1H, m), 7.62 (1H, s), 8.00-8.07 (2H, m), 8.46 (1H, s) 8.75-8.82 (1H, m), 9.25-9.32 (1H, m), 10.32 (1H, d, J=10.3 Hz), 11.60-11.73 (1H, m).

MS(FAB)m/z: 492 [(M+H)$^+$, $^{35}$Cl], 494 [(M+H)$^+$, $^{37}$Cl].

Example 20

N$^1$-(5-chloropyridin-2-yl)-N$^2$-((3R,4S)-3-{[(5-methyl-4,5,6,7-tetrahydrothiazolo[5,4-c]pyridin-2-yl)carbonyl]amino}-1-([1,2,3,4]thiatriazol-5-yl)piperidin-4-yl)ethanediamide hydrochloride

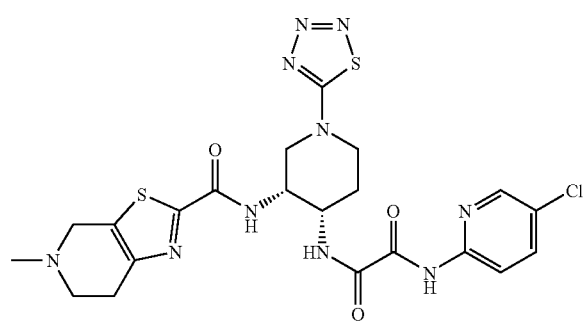

The title compound was obtained in the same manner as in the method described in Example 1, by deprotecting the compound obtained in Reference Example 42 by a hydrochloric acid treatment, and condensing the deprotection product with the compound obtained in Reference Example 6.

$^1$H-NMR (DMSO-$d_6$) δ: 1.71-1.97 (1H, m), 2.22-2.47 (1H, m) 2.76-4.05 (7H, m), 2.89 (3H, s), 4.09-4.26 (1H, m), 4.28-4.56 (3H, m), 4.59-4.85 (1H, m), 7.90-8.17 (1H, m), 8.02 (1H, s), 8.45 (1H, s), 8.78-9.06 (1H, m), 9.23-9.54 (1H, m), 10.20-10.44 (1H, m), 11.19-11.39 (0.5H, m), 11.47-11.73 (0.5H, m).

MS(ESI)m/z: 563 [(M+H)$^+$, $^{35}$Cl], 565 [(M+H)$^+$, $^{37}$Cl].

Example 21

N$^1$-(5-chloropyridin-2-yl)-N$^2$-((3R,4S)-3-{[(5-methyl-4,5,6,7-tetrahydrothiazolo[5,4-c]pyridin-2-yl)carbonyl]amino}-1-([1,3,4]oxadiazol-2-yl)piperidin-4-yl)ethanediamide

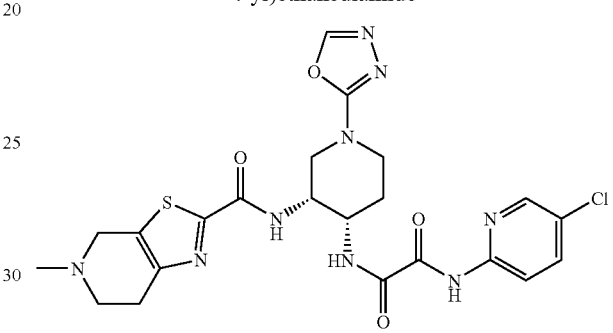

The title compound was obtained in the same manner as in the method described in Example 1, by deprotecting the compound obtained in Reference Example 46 by a hydrochloric acid treatment, and condensing the deprotection product with the compound obtained in Reference Example 6.

$^1$H-NMR (CDCl$_3$) δ: 1.81-2.07 (1H, m), 2.10-2.25 (1H, m), 2.60 (3H, s) 2.90-3.06 (4H, m), 3.06-3.16 (1H, m), 3.23-3.34 (1H, m), 3.43-3.53 (1H, m), 3.86 (2H, br.s), 3.97-4.30 (2H, m), 4.67-4.75 (1H, m), 7.66 (1H, br.d, J=8.5 Hz), 7.70 (1H, dd, J=8.8, 2.4 Hz), 7.99 (1H, s), 8.19 (1H, d, J=8.8 Hz), 8.23 (1H, br.d, J=7.1 Hz), 8.31 (1H, d, J=2.4 Hz), 9.69 (1H, s).

MS(ESI)m/z: 546 [(M+H)$^+$, $^{35}$Cl], 548 [(M+H)$^+$, $^{37}$Cl].

Example 22

N$^1$-(5-chloropyridin-2-yl)-N$^2$-((3R,4S)-1-(5-methyl-[1,3,4]oxadiazol-2-yl)-3-{[(5-methyl-4,5,6,7-tetrahydrothiazolo[5,4-c]pyridin-2-yl)carbonyl]amino}piperidin-4-yl)ethanediamide hydrochloride

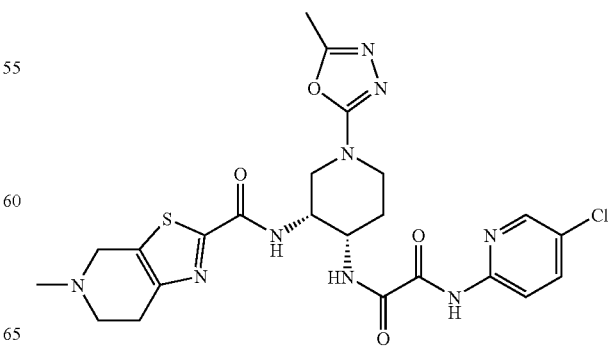

The title compound was obtained in the same manner as in the method described in Example 1, by deprotecting the compound obtained in Reference Example 49 by a hydrochloric acid treatment, and condensing the deprotection product with the compound obtained in Reference Example 6.

$^1$H-NMR (DMSO-d$_6$) δ: 1.65-1.78 (1H, m), 2.13, 2.17 (total 3H, each br.s), 2.20-2.36 (1H, m), 2.90 (3H, s), 3.01-3.15 (1H, m), 3.16-3.33 (2H, m), 3.34-3.56 (2H, m), 3.61-3.86 (2H, m), 3.90-4.03 (1H, m), 4.18-4.35 (2H, m), 4.36-4.50 (1H, m), 4.59-4.78 (1H, m), 7.94-8.08 (2H, m), 8.44 (1H, s), 8.59 (0.5H, br.d, J=6.6 Hz), 8.68 (0.5H, br.d, J=5.9 Hz), 9.30 (0.5H, br.d, J=7.8 Hz), 9.36 (0.5H, br.d, J=6.8 Hz), 10.27, 10.31 (total 1H, each br.s), 11.56-11.85 (1H, m).

MS(ESI)m/z: 560 [(M+H)$^+$, $^{35}$Cl], 562 [(M+H)$^+$, $^{37}$Cl].

Example 23

N$^1$-(5-chlorothiophen-2-yl)-N$^2$-((3R,4S)-1-formyl-3-{[(5-methyl-4,5,6,7-tetrahydrothiazolo[5,4-c]pyridin-2-yl)carbonyl]amino}piperidin-4-yl)ethanediamide hydrochloride

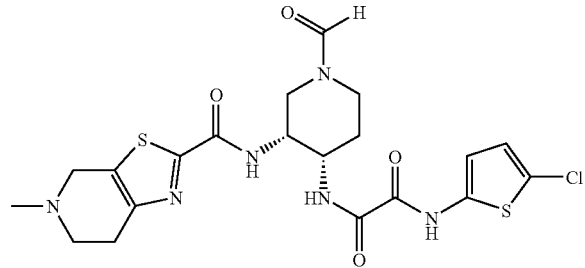

The title compound was obtained in the same manner as in the method described in Example 1, by deprotecting the compound obtained in Reference Example 52 by a hydrochloric acid treatment, and condensing the deprotection product with the compound obtained in Reference Example 5.

$^1$H-NMR (DMSO-d$_6$) δ: 1.58-1.75 (1H, m), 1.93-2.16 (1H, m), 2.85-3.05 (0.5H, m), 2.91 (3H, s), 3.06-3.31 (3H, m), 3.32-3.53 (1.5H, m), 3.60-3.86 (2H, m), 3.90-4.05 (0.5H, m), 4.13-4.24 (1.5H, m), 4.27-4.49 (2H, m), 4.64-4.78 (1H, m), 6.89 (1H, d, J=4.2 Hz), 6.93 (1H, d, J=4.2 Hz), 7.83, 7.86 (total 0.5H, each br.s), 8.05 (0.5H, s), 8.48-8.67 (1H, m) 9.23-9.41 (1H, m), 11.16-11.53 (1H, m), 12.34 (1H, s).

MS(ESI)m/z: 511 [(M+H)$^+$, $^{35}$Cl], 513 [(M+H)$^+$, $^{37}$Cl].

Example 24

N$^1$-((3R,4S)-1-formyl-3-{[(5-methyl-4,5,6,7-tetrahydrothiazolo[5,4-c]pyridin-2-yl)carbonyl]amino}piperidin-4-yl)-N$^2$-(5-methylthiophen-2-yl)ethanediamide hydrochloride

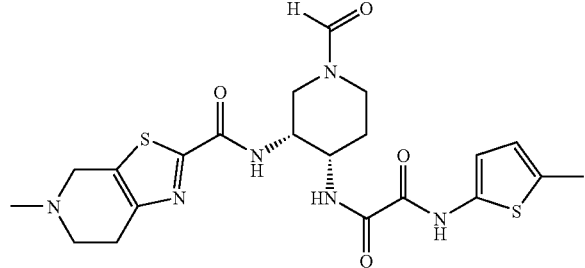

The title compound was obtained in the same manner as in the method described in Example 1, by deprotecting the compound obtained in Reference Example 56 by a hydrochloric acid treatment, and condensing the deprotection product with the compound obtained in Reference Example 6.

$^1$H-NMR (DMSO-d$_6$) δ: 1.59-1.76 (1H, m), 1.95-2.20 (1H, m), 2.35 (3H, s), 2.92 (3H, s), 2.96-3.04 (1H, m), 3.17-3.48 (4.5H, m), 3.60-3.76 (1H, m), 3.77-3.86 (0.5H, m), 3.91-4.06 (0.5H, m), 4.14-4.26 (1.5H, m), 4.27-4.38 (1H, m), 4.39-4.53 (0.5H, m), 4.69 (0.5H, br.s), 6.57 (1H, dd, J=3.8, 1.1 Hz), 6.86 (1H, d, J=3.8 Hz), 7.86 (0.5H, br.s), 8.07 (0.5H, s), 8.51-8.71 (1H, m), 9.27 (1H, br.s), 11.44 (1H, br.s), 11.92 (1H, s).

MS(ESI) m/z: 491 (M+H)$^+$.

Example 25

N$^1$-(5-fluoropyridin-2-yl)-N$^2$-((3R,4S)-1-formyl-3-{[(5-methyl-4,5,6,7-tetrahydrothiazolo[5,4-c]pyridin-2-yl)carbonyl]amino}piperidin-4-yl)ethanediamide hydrochloride

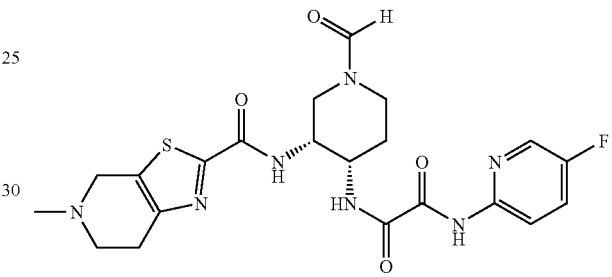

The title compound was obtained in the same manner as in the method described in Example 1, by deprotecting the compound obtained in Reference Example 57 by a hydrochloric acid treatment, and condensing the deprotection product with the compound obtained in Reference Example 5.

$^1$H-NMR (DMSO-d$_6$) δ: 1.57-1.75 (1H, m), 1.94-2.19 (1H, m), 2.91 (3H, s), 2.91-3.04 (0.5H, m), 3.05-3.31 (3H, m), 3.34-3.59 (1.5H, m), 3.60-3.87 (2H, m), 3.91-4.09 (0.5H, m), 4.10-4.51 (3.5H, m), 4.61-4.79 (1H, m), 7.79-7.89 (1.5H, m), 7.98-8.09 (1.5H, m), 8.41 (1H d, J=2.9 Hz) 8.48-8.67 (1H, m), 9.26-9.44 (1H, m), 10.27, 10.30 (total 1H, each br.s), 11.14-11.58 (1H, m).

MS(ESI)m/z: 490 (M+H)$^+$.

Example 26

N$^1$-(5-bromopyridin-2-yl)-N$^2$-((3R,4S)-1-formyl-3-{[(5-methyl-4,5,6,7-tetrahydrothiazolo[5,4-c]pyridin-2-yl)carbonyl]amino}piperidin-4-yl)ethanediamide hydrochloride

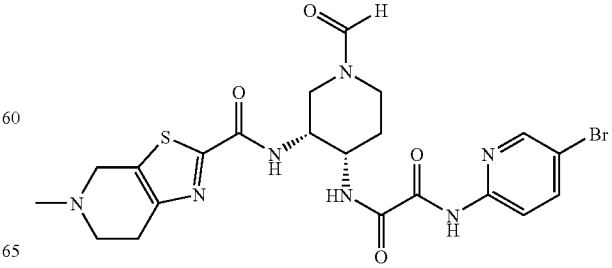

The title compound was obtained in the same manner as in the method described in Example 1, by deprotecting the compound obtained in Reference Example 58 by a hydrochloric acid treatment, and condensing the deprotection product with the compound obtained in Reference Example 5.

$^1$H-NMR (DMSO-d$_6$) δ: 1.58-1.74 (1H, m), 1.94-2.18 (1H, m) 2.90 (3H, s), 2.91-3.04 (0.5H, m), 3.05-3.34 (3H, m), 3.39-3.52 (1.5H, m) 3.60-3.85 (2H, m), 3.88-4.11 (0.5H, m), 4.14-4.48 (3.5H, m), 4.63-4.76 (1H, m),7.85 (0.5H, d, J=12.0 Hz), 7.97 (1H, d, J=8.8 Hz) 8.03-8.07 (0.5H, m), 8.11 (1H, d, J=8.8 Hz), 8.46-8.64 (1H, m), 8.51 (1H, br.s), 9.26-9.44 (1H, m), 10.25, 10.30 (total 1H, each br.s), 11.40-12.00 (1H, m).

MS(ESI)m/z: 550 [(M+H)$^+$, $^{79}$Br], 552 [(M+H)$^+$, $^{81}$Br].

Example 27

N$^1$-(4-chlorophenyl)-N$^2$-((3R,4S)-1-formyl-3-{[(5-methyl-4,5,6,7-tetrahydrothiazolo[5,4-c]pyridin-2-yl)carbonyl]amino}piperidin-4-yl)ethanediamide hydrochloride

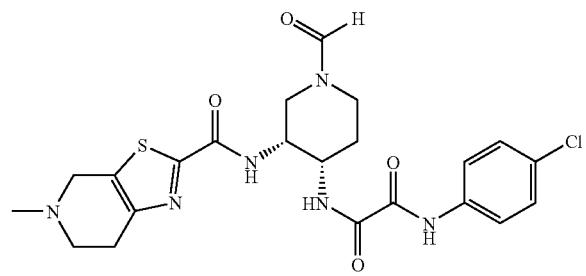

The title compound was obtained in the same manner as in the method described in Example 1, by deprotecting the compound obtained in Reference Example 59 by a hydrochloric acid treatment, and condensing the deprotection product with the compound obtained in Reference Example 5.

$^1$H-NMR (DMSO-d$_6$) δ: 1.57-1.75 (1H, m), 1.95-2.20 (1H, m), 2.89-3.04 (0.5H, m), 2.91 (3H, s), 3.05-3.35 (3H, m), 3.37-3.54 (1.5H, m), 3.59-4.08 (2.5H, m), 4.10-4.48 (3.5H, m), 4.61-4.78 (1H, m), 7.40 (2H, d, J=8.8 Hz), 7.83 (2H, d, J=8.8 Hz), 7.86, 8.06 (total 1H, each s), 8.49-8.69 (1H, m), 9.16-9.34 (1H, m), 10.83, 10.84 (total 1H, each br.s), 11.32-11.92 (1H, m).

MS(ESI)m/z: 505 [(M+H)$^+$, $^{35}$Cl], 507 [(M+H)$^+$, $^{37}$Cl].

Example 28

N$^1$-(4-chloro-3-fluorophenyl)-N$^2$-((3R,4S)-1-formyl-3-{[(5-methyl-4,5,6,7-tetrahydrothiazolo[5,4-c]pyridin-2-yl)carbonyl]amino}piperidin-4-yl)ethanediamide hydrochloride

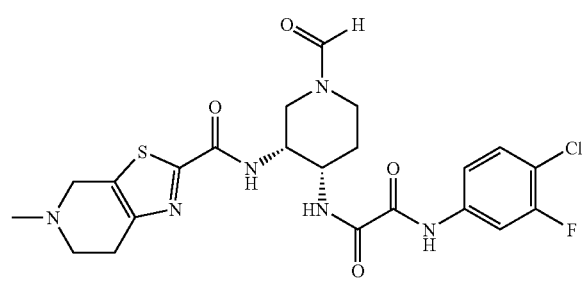

The title compound was obtained in the same manner as in the method described in Example 1, by deprotecting the compound obtained in Reference Example 60 by a hydrochloric acid treatment, and condensing the deprotection product with the compound obtained in Reference Example 5.

$^1$H-NMR (DMSO-d$_6$) δ: 1.57-1.75 (1H, m), 1.94-2.29 (1H, m), 2.90-3.04 (0.5H, m), 2.90 (3H, s), 3.04-3.36 (3H, m), 3.39-3.85 (3.5H, m), 3.92-4.08 (0.5H, m), 4.12-4.49 (3.5H, m), 4.63-4.76 (1H, m), 7.56 (1H, t, J=8.7 Hz), 7.70 (1H, br.d, J=8.3 Hz) 7.81-7.96 (1.5H, m), 8.06 (0.5H, s), 8.49-8.68 (1H, m), 9.17-9.45 (1H, m), 11.02, 11.03 (total 1H, each br.s), 11.32-11.94 (1H, m).

MS(ESI)m/z: 523 [(M+H)$^+$, $^{35}$Cl], 525 [(M+H)$^+$, $^{37}$Cl].

Example 29

N$^1$-(4-bromophenyl)-N$^2$-((3R,4S)-1-formyl-3-{[(5-methyl-4,5,6,7-tetrahydrothiazolo[5,4-c]pyridin-2-yl)carbonyl]amino}piperidin-4-yl)ethanediamide hydrochloride

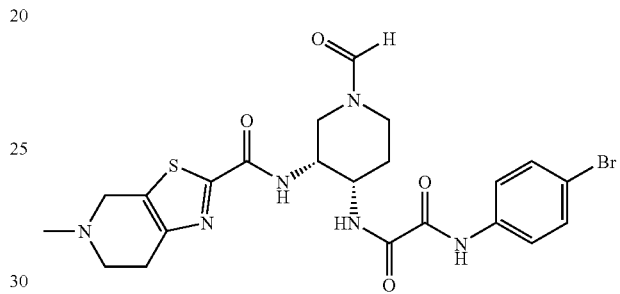

The title compound was obtained in the same manner as in the method described in Example 1, by deprotecting the compound obtained in Reference Example 61 by a hydrochloric acid treatment, and condensing the deprotection product with the compound obtained in Reference Example 5.

$^1$H-NMR (DMSO-d$_6$) δ: 1.57-1.74 (1H, m), 1.96-2.19 (1H, m), 2.87-3.03 (0.5H, m), 2.91 (3H, s), 3.04-3.55 (4.5H, m), 3.60-3.86 (2H, m), 3.92-4.08 (0.5H, m), 4.11-4.52 (3.5H, m), 4.61-4.79 (1H, m), 7.52 (2H, d, J=8.8 Hz), 7.77 (2H, d, J=8.5 Hz), 7.81-7.88 (0.5H, m), 8.05 (0.5H, s), 8.51-8.71 (1H, m), 9.15-9.35 (1H, m), 10.83 (1H, s), 11.20-11.60 (1H, m).

MS(ESI)m/z: 549 [(M+H)$^+$, $^{79}$Br], 551 [(M+H)$^+$, $^{81}$Br].

Example 30

N$^1$-(4-fluorophenyl)-N$^2$-((3R,4S)-1-formyl-3-{[(5-methyl-4,5,6,7-tetrahydrothiazolo[5,4-c]pyridin-2-yl)carbonyl]amino}piperidin-4-yl)ethanediamide hydrochloride

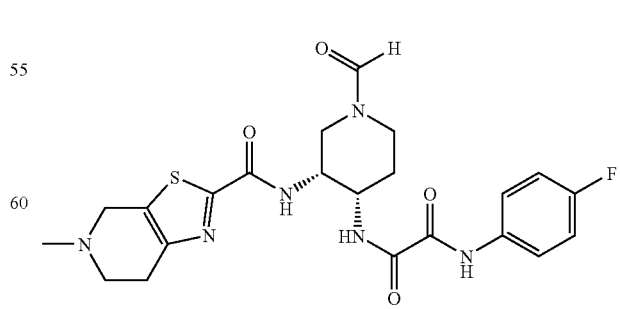

The title compound was obtained in the same manner as in the method described in Example 1, by deprotecting the compound obtained in Reference Example 62 by a hydrochloric acid treatment, and condensing the deprotection product with the compound obtained in Reference Example 5.

$^1$H-NMR (DMSO-d$_6$) δ: 1.58-1.74 (1H, m), 1.96-2.20 (1H, m), 2.91 (3H, s), 2.91-3.01 (0.5H, m), 3.05-3.54 (4.5H, m), 3.60-3.86 (2H, m) 3.92-4.08 (0.5H, m), 4.12-4.52 (3.5H, m), 4.61-4.79 (1H, m), 7.18 (2H, t, J=8.8 Hz), 7.82 (2H, dd, J=8.8, 5.1 Hz), 7.83, 8.06 (total 1H, each, s), 8.52-8.73 (1H, m), 9.16-9.34 (1H, m), 10.78 (1H, s), 11.19-11.66 (1H, m).

MS(ESI)m/z: 489 (M+H)$^+$.

Example 31

N-[(3R,4S)-4-({2-[(5-chloropyridin-2-yl)amino]-2-oxoethanethioyl}amino)-1-formylpiperidin-3-yl]-5-methyl-4,5,6,7-tetrahydrothiazolo[5,4-c]pyridin-2-carboxamide hydrochloride

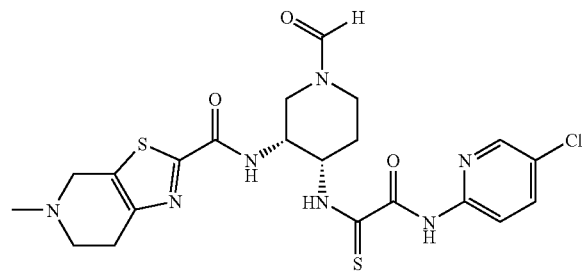

To a mixed solution of the compound obtained in Reference Example 63 (307 mg) in 1,4-dioxane (5 ml) and dichloromethane (1 ml), a 4 N hydrochloric acid-dioxane solution (3 ml) was added, and the mixture was stirred for 2 hours at room temperature. The solvent was distilled off under reduced pressure, and then dried for 2 hours by means of a vacuum pump. The resulting powder was dissolved in N,N-dimethylformamide (6 ml), and the compound obtained in Reference Example 5 (205 mg), 1-hydroxybenzotriazole (134 mg), and 1-(3-dimethylaminopropyl)-3-ethylcarbodiimide hydrochloride (193 mg) were added and stirred for 17 hours at room temperature. The solvent was distilled off under reduced pressure, and then ethyl acetate and a saturated aqueous solution of sodium hydrogen carbonate were added to the residue. After extracting the mixture with ethyl acetate, the combined organic layer was washed with a saturated aqueous solution of sodium chloride. The organic layer was dried over anhydrous sodium sulfate, the solvent was distilled off under reduced pressure, and the residue was purified by flash column chromatography (dichloromethane:methanol=15:1) using silica gel as support, to obtain a free form of the title compound (291 mg). To a solution of the free form (291 mg) in ethanol (10 ml), a 1 N hydrochloric acid ethanol solution (0.80 ml) was added, and the solvent was distilled off under reduced pressure. The residue was dried by means of a vacuum pump, to obtain the title compound (305 mg).

$^1$H-NMR (DMSO-d$_6$) δ: 1.70-1.88 (1H, m), 2.15-2.41 (1H, m), 2.90 (3H, s), 2.90-3.34 (3.5H, m), 3.39-3.52 (1.5H, m), 3.55-3.89 (2H, m) 4.02-4.19 (0.5H, m), 4.25-4.54 (2.5H, m), 4.62-4.76 (1H, m), 4.77-4.90 (1H, m), 7.88 (0.5H, d, J=10.7 Hz), 7.99-8.11 (2.5H, m) 8.45 (1H, d, J=2.2 Hz), 8.48-8.68 (1H, m), 10.50-10.61 (1H, m), 11.09-11.23 (1H, m), 11.46-11.86 (1H, m).

MS(ESI)m/z: 522 [(M+H)$^+$, $^{35}$Cl], 524 [(M+H)$^+$, $^{37}$Cl].

Example 32

N-[(3R,4S)-4-({2-[(5-fluoro-2-pyridinyl)amino]-2-oxoethanethioyl}amino)-1-formylpiperidin-3-yl]-5-methyl-4,5,6,7-tetrahydrothiazolo[5,4-c]pyridin-2-carboxamide hydrochloride

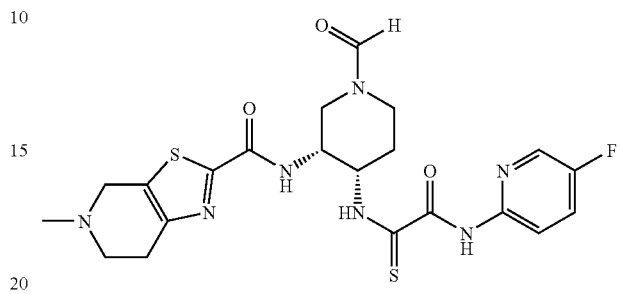

The title compound was obtained in the same manner as in the method described in Example 31, by deprotecting the compound obtained in Reference Example 64 by a hydrochloric acid treatment, and condensing the deprotection product with the compound obtained in Reference Example 5.

$^1$H-NMR (DMSO-d) δ: 1.70-1.87 (1H, m), 2.16-2.42 (1H, m), 2.90 (3H, s), 2.90-3.34 (3.5H, m), 3.39-3.52 (1.5H, m), 3.62-3.91 (2H, m) 4.03-4.19 (0.5H, m), 4.28-4.54 (2.5H, m), 4.61-4.76 (1H, m), 4.76-4.90 (1H, m), 7.81-7.92 (1.5H, m), 8.03-8.15 (1.5H, m), 8.41 (1H, d, J=2.7 Hz), 8.49-8.70 (1H, m), 10.48-10.58 (1H, m), 11.09-11.25 (1H, m), 11.51-11.95 (1H, m).

MS(ESI)m/z: 506 (M+H)$^+$.

Example 33

7-Chloro-N-((3R,4S)-1-formyl-3-{[(5-methyl-4,5,6,7-tetrahydrothiazolo[5,4-c]pyridin-2-yl)carbonyl]amino}piperidin-4-yl)-3-isoquinoline carboxamide hydrochloride

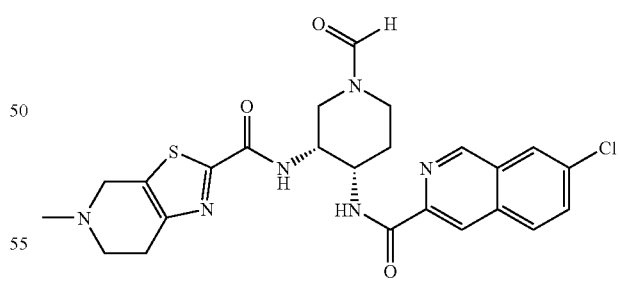

The title compound was obtained in the same manner as in the method described in Example 1, by deprotecting the compound obtained in Reference Example 65 by a hydrochloric acid treatment, and condensing the deprotection product with the compound obtained in Reference Example 5.

$^1$H-NMR (DMSO-d$_6$) δ: 1.62-1.80 (1H, m), 2.11-2.34 (1H, m), 2.90 (3H, br.s), 2.92-3.03 (1H, m), 3.05-3.34 (3H, m), 3.39-3.51 (1H, m), 3.62-4.16 (2.5H, m), 4.21-4.47 (2.5H, m), 4.49-4.76 (2H, m), 7.81-7.93 (1.6H, m), 8.08 (0.4H, br.s), 8.26 (1H, d, J=8.8 Hz), 8.37 (1H, br.s), 8.62 (1H, s), 8.69-8.88 (1H, m), 9.11-9.30 (1H m), 9.36 (1H, s), 11.32-11.76 (1H, m).
MS(ESI)m/z: 513 [(M+H)$^+$, $^{35}$Cl], 515 [(M+H)$^+$, $^{37}$Cl].

Example 34

5-Fluoro-N-((3R,4S)-1-formyl-3-{[(5-methyl-4,5,6,7-tetrahydrothiazolo[5,4-c]pyridin-2-yl)carbonyl]amino}piperidin-4-yl)-2-indolecarboxamide hydrochloride

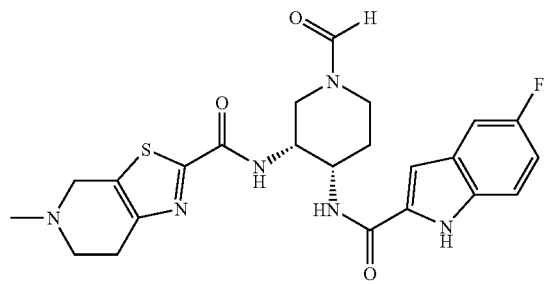

The title compound was obtained in the same manner as in the method described in Example 1, by deprotecting the compound obtained in Reference Example 66 by a hydrochloric acid treatment, and condensing the deprotection product with the compound obtained in Reference Example 5.

$^1$H-NMR (DMSO-d$_6$) δ: 1.66-1.82 (1H, m), 1.82-2.06 (1H, m), 2.90 (3H, s), 3.00-3.59 (5.5H, m), 3.63-3.83 (1.5H, m), 3.87-4.14 (1H, m) 4.23-4.54 (3H, m), 4.59-4.78 (1H, m), 6.97-7.17 (2H, m), 7.34-7.47 (2H, m), 7.92 (0.5H, br.d, J=8.1 Hz) 8.09 (0.5H, br.d, J=3.7 Hz), 8.18-8.37 (1H, m), 8.38-8.49 (1H, m), 11.20-11.61 (1H, m), 11.76 (1H, br.s).
MS(ESI)m/z: 485 (M+H)$^+$.

Example 35

N-((3R,4S)-4-{[(Z)-3-(4-chlorophenyl)-2-fluoro-2-propenoyl]amino}-1-formylpiperidin-3-yl)-5-methyl-4,5,6,7-tetrahydrothiazolo[5,4-c]pyridine-2-carboxamide hydrochloride

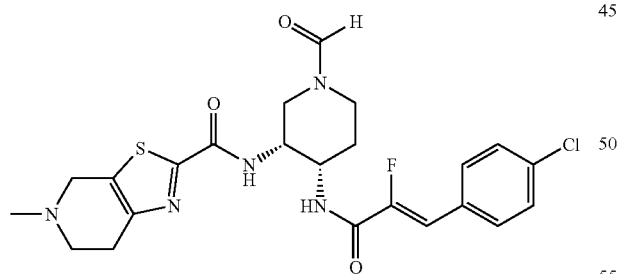

The title compound was obtained in the same manner as in the method described in Example 1, by deprotecting the compound obtained in Reference Example 67 by a hydrochloric acid treatment, and condensing the deprotection product with the compound obtained in Reference Example 6.

$^1$H-NMR (DMSO-d$_6$) d: 1.68 (1H, br.s), 1.93-2.06 (1H, m), 2.91 (3H, s) 3.18-3.81 (7H, m), 4.05-4.68 (5H, m), 6.93 (1H, d, J=39.0 Hz), 7.50-7.52 (2H, m), 7.67-7.69 (2H, m), 7.89, 8.09 (total 1H, each s), 8.37 (1H, br.s), 8.70 (1H, s), 11.79 (1H, br.s).
MS(ESI)m/z: 506 [(M+H)$^+$, $^{35}$Cl], 508 [(M+H)$^+$, $^{37}$Cl].

Example 36

N$^1$-(5-chloropyridin-2-yl)-N$^2$-((3R,4S)-1-formyl-3-{[(6-methyl-5,6,7,8-tetrahydro-[1,6]naphthyridin-2-yl)carbonyl]amino}piperidin-4-yl)ethanediamide hydrochloride

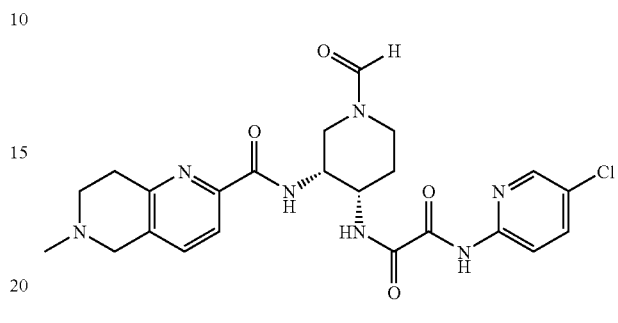

The title compound was obtained in the same manner as in the method described in Example 1, by deprotecting the compound obtained in Reference Example 28 by a hydrochloric acid treatment, and condensing the deprotection product with 6-methyl-5,6,7,8-tetrahydro-[1,6]naphthyridine-2-carboxylic acid.

$^1$H-NMR (DMSO-d$_6$) δ: 1.61-1.83 (1H, m), 1.83-2.09 (1H, m), 2.90 (3H, s), 2.94-3.59 (5H, m), 3.63-3.84 (2H, m), 3.94-4.66 (5H, m), 7.75-8.06 (4.6H, m), 8.13 (0.4H, d, J=6.1 Hz), 8.30-8.49 (2H, m) 9.21-9.43 (1H, m), 10.28, 10.33 (total 1H, each s), 11.50-12.01 (1H, m).
MS(ESI)m/z: 500 [(M+H)$^+$, $^{35}$Cl], 502 [(M+H)$^+$, $^{37}$Cl].

Example 37

N$^1$-(5-chloropyridin-2-yl)-N$^2$-((3R,4S)-1-formyl-3-{[(2-methyl-2,3-dihydro-1H-pyrrolo[3,4-c]pyridin-6-yl)carbonyl]amino}piperidin-4-yl)ethanediamide hydrochloride

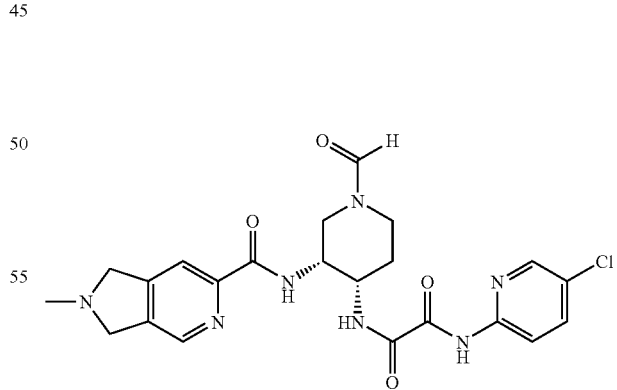

The title compound was obtained in the same manner as in the method described in Example 1, by deprotecting the compound obtained in Reference Example 28 by a hydrochloric acid treatment, and condensing the deprotection product with 2-methyl-2,3-dihydro-1H-pyrrolo[3,4-c]pyridine-6-carboxylic acid.

¹H-NMR (DMSO-d₆) δ: 1.60-1.79 (1H, m), 1.87-2.13 (1H, m) 2.92-3.05 (0.5H, m), 3.00 (3H, s), 3.11-3.34 (1H, m), 3.39-3.53 (0.5H, m), 3.62-3.97 (1H, m), 3.97-4.11 (0.5H, m), 4.12-4.23 (0.5H, m), 4.24-4.40 (2H, m), 4.45-4.63 (2H, m), 4.78-4.99 (2H, m), 7.87 (0.55H, s), 8.00 (2H, s), 8.09 (0.45H, s), 8.11 (1H, s), 8.44 (1H, s), 8.45-8.61 (1H, m), 8.71 (1H, d, J=10.5 Hz), 9.29-9.41 (1H, m), 10.27, 10.31 (total 1H, each br.s), 11.79-12.29 (1H, m).

HRMS(FAB)m/z: 485.1573 (Calcd C₂₂H₂₄³⁵ClN₇O₄: 485.1578)

Example 38

N¹-(5-chloropyridin-2-yl)-N²-((3R,4S)-3-{[(6,7-dihydro-4H-pyrano[4,3-d]thiazol-2-yl)carbonyl]amino}-1-formylpiperidin-4-yl)ethanediamide

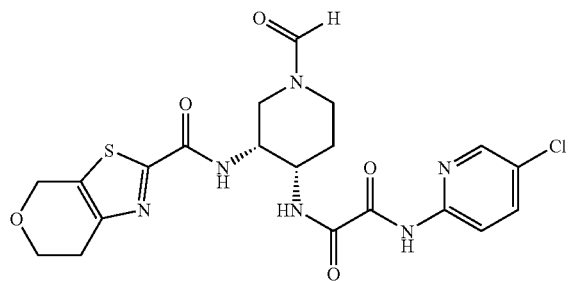

To a solution of N¹-(5-chloropyridin-2-yl)-N²-((3R,4S)-1-formyl-3-aminopiperidin-4-yl)ethanediamide hydrochloride (97 mg), which had been obtained by treating the compound obtained in Reference Example 28 with hydrochloric acid, in N,N-dimethylformamide (4 ml), 6,7-dihydro-4H-pyrano[4,3-d]thiazole-2-carboxylic acid lithium salt (93 mg), 1-hydroxybenzotriazole (51 mg), 1-(3-dimethylaminopropyl)-3-ethylcarbodiimide hydrochloride (71 mg) and triethylamine (38 μl) were added, and the mixture was stirred for 3 days at room temperature. The solvent was distilled off under reduced pressure, and a saturated aqueous solution of sodium hydrogen carbonate was added to the residue. The mixture was extracted with dichloromethane, and then the organic layer was washed with a 10% aqueous solution of citric acid and a saturated aqueous solution of sodium chloride. The organic layer was dried over anhydrous sodium sulfate, subsequently the solvent was distilled off under reduced pressure, and the residue was purified twice by silica gel column chromatography (dichloromethane:methanol=50:1→30:1→20:1), to obtain the title compound (117 mg).

¹H-NMR (CDCl₃) δ: 1.70-1.91 (1H, m), 2.00-2.21 (1H, m) 2.86-2.99 (3H, m), 3.08-3.15 (0.4H, m), 3.28-3.38 (0.4H, m), 3.47-3.56 (0.6H, m), 3.69-3.85 (0.6H, m), 3.96-4.10 (2H, m), 4.23-4.39 (1H, m), 4.48-4.67 (2H, m), 4.87 (2H, s), 7.45 (1H, br.d, J=8.5 Hz), 7.70 (1H, dd, J=8.8, 2.6 Hz), 7.94 (0.6H, br.d, J=7.8 Hz) 8.04 (0.6H, s), 8.15 (0.6H, d, J=8.8 Hz), 8.20 (0.4H, d, J=8.8 Hz), 8.25 (0.4H, s), 8.31 (0.4H, d, J=2.6 Hz), 8.32 (0.6H, d, J=2.6 Hz), 8.45 (0.4H, br.d, J=7.3 Hz), 9.70 (1H, br.s).

MS(ESI)m/z: 493 [(M+H)⁺, ³⁵Cl], 495 [(M+H)⁺, ³⁷Cl].

Example 39

N¹-(5-chloropyridin-2-yl)-N²-((3R,4S)-1-formyl-3-{[4-(3-oxomorpholin-4-yl)benzoyl]amino}piperidin-4-yl)ethanediamide

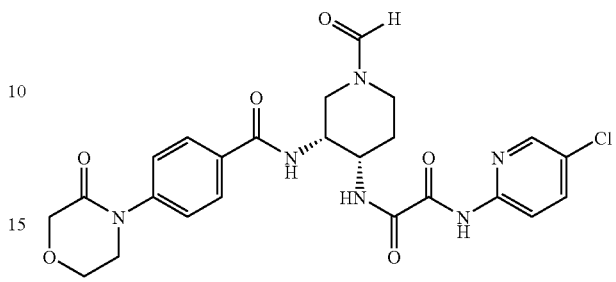

The title compound was obtained in the same manner as in the method described in Example 38 by deprotecting the compound obtained in Reference Example 28 by a hydrochloric acid treatment, and condensing the deprotection product with 4-(3-oxo-4-morpholinyl)benzoic acid.

¹H-NMR (CDCl₃) δ: 1.70 (1H, t, J=14.9 Hz), 1.92-2.18 (1H, m), 2.90-3.10 (1H, m), 3.22-3.46 (1H, m), 3.69-3.82 (3H, m), 3.99 (2H, t, J=4.4 Hz), 4.09-4.26 (4H, m), 4.34 (1H, br.s), 7.51-7.56 (2H, m), 7.76-7.81 (2H, m), 7.84-8.11 (4H, m), 8.45 (1H, s), 9.00 (1H, d, J=7.1 Hz), 10.32 (1H, s).

MS(FAB)m/z: 529 [(M+H)⁺, ³⁵Cl], 531 [(M+H)⁺, ³⁷Cl].

Example 40

N¹-((3R,4S)-1-acetyl-3-{[(5-methyl-4,5,6,7-tetrahydrothiazolo[5,4-c]pyridin-2-yl)carbonyl]amino}piperidin-4-yl)-N²-(5-bromopyridin-2-yl)ethanediamide hydrochloride

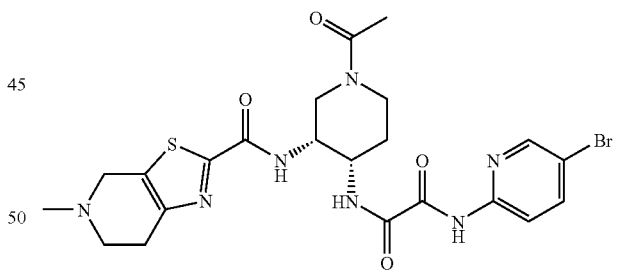

The title compound was obtained in the same manner as in the method described in Example 1, by deprotecting the compound obtained in Reference Example 69 by a hydrochloric acid treatment, and condensing the deprotection product with the compound obtained in Reference Example 6.

¹H-NMR (DMSO-d₆) δ: 1.54-1.76 (1H, m), 1.80, 2.02 (total 3H, each s), 1.96-2.18 (1H, m), 2.77-3.01 (0.5H, m), 2.91 (3H, s), 3.04-3.53 (5H, m), 3.61-3.78 (1H, m), 4.01-4.50 (4.5H, m), 4.62-4.78 (1H, m), 7.97 (1H, d, J=8.6 Hz), 8.1 (1H, dd, J=8.8, 2.5 Hz), 8.47-8.74 (1H, m), 8.51 (1H, d, J=2.5 Hz), 9.18-9.47 (1H, m), 10.23-10.34 (1H, m), 11.33, 11.55 (total 1H, each br.s).

MS(ESI)m/z: 564 [(M+H)⁺, ⁷⁹Br], 566 [(M+H)⁺, ⁸¹Br].

Example 41

N$^1$-((3R,4S)-1-acetyl-3-{[(5-methyl-4,5,6,7-tetrahydrothiazolo[5,4-c]pyridin-2-yl)carbonyl]amino}piperidin-4-yl)-N$^2$-(4-bromophenyl)ethanediamide hydrochloride

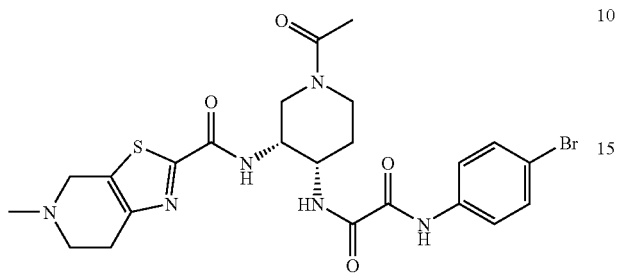

The title compound was obtained in the same manner as in the method described in Example 1, by deprotecting the compound obtained in Reference Example 70 by a hydrochloric acid treatment, and condensing the deprotection product with the compound obtained in Reference Example 6.

$^1$H-NMR (DMSO-d$_6$) δ: 1.52-1.75 (1H, m), 1.79, 2.01 (total 3H, each s), 1.93-2.20 (1H, m), 2.76-2.96 (0.5H, m), 2.90 (3H, s), 3.04-3.36 (3H, m), 3.36-3.54 (2H, m), 3.60-3.78 (1H, m), 4.01-4.50 (4.5H, m), 4.61-4.78 (1H, m), 7.52 (2H, d, J=8.8 Hz), 7.77 (2H, d, J=8.8 Hz), 8.53-8.79 (1H, m), 9.07-9.39 (1H, m), 10.83 (1H, br.s), 11.53, 11.70 (total 1H, each br.s).

MS(ESI)m/z: 563 [(M+H)$^+$, $^{79}$Br], 565 [(M+H)$^+$, $^{81}$Br].

Example 42

N$^1$-((3R,4S)-1-acetyl-3-{[(5-methyl-4,5,6,7-tetrahydrothiazolo[5,4-c]pyridin-2-yl)carbonyl]amino}piperidin-4-yl)-N$^2$-(4-chloro-3-fluorophenyl)ethanediamide hydrochloride

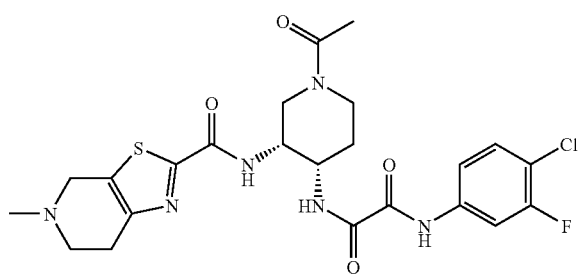

The title compound was obtained in the same manner as in the method described in Example 1, by deprotecting the compound obtained in Reference Example 71 by a hydrochloric acid treatment, and condensing the deprotection product with the compound obtained in Reference Example 6.

$^1$H-NMR (DMSO-d$_6$) δ: 1.55-1.88 (1H, m), 1.80, 2.01 (total 3H, each s), 1.96-2.19 (1H, m), 2.77-2.96 (0.5H, m), 2.90 (3H, s), 3.03-3.36 (3H, m), 3.36-3.78 (3H, m), 4.00-4.35 (3.5H, m), 4.35-4.50 (1H, m), 4.61-4.77 (1H, m), 7.56 (1H, t, J=8.7 Hz), 7.70 (1H, br.d, J=9.3 Hz), 7.91 (1H, dd, J=11.8, 2.1 Hz), 8.51-8.77 (1H, m), 9.09-9.41 (1H, m), 11.01, 11.03 (total 1H, each s), 11.62, 11.79 (total 1H, each br.s).

MS(ESI)m/z: 537 [(M+H)$^+$, $^5$Cl], 539 [(M+H)$^+$, $^{37}$Cl]

Example 43

N$^1$-((3R,4S)-1-acetyl-3-{[(5-methyl-4,5,6,7-tetrahydrothiazolo[5,4-c]pyridin-2-yl)carbonyl]amino}piperidin-4-yl)-N$^2$-(5-chlorothiophen-2-yl)ethanediamide hydrochloride

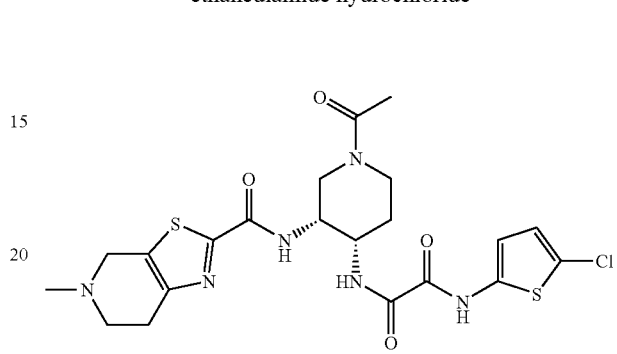

The title compound was obtained in the same manner as in the method described in Example 1, by deprotecting the compound obtained in Reference Example 72 by a hydrochloric acid treatment, and condensing the deprotection product with the compound obtained in Reference Example 6.

$^1$H-NMR (DMSO-d$_6$) δ: 1.54-1.75 (1H, m), 1.80, 2.01 (total 3H, each s), 1.94-2.15 (1H, m), 2.77-2.95 (0.5H, m), 2.82 (3H, s), 3.07-3.54 (5.5H, m), 3.63-3.74 (0.5H, m), 4.00-4.55 (5.5H, m), 6.90 (1H, d, J=4.2 Hz), 6.93 (1H, d, J=4.2 Hz), 8.57 (0.4H, d, J=7.1 Hz), 8.64 (0.6H, d, J=6.1 Hz), 9.21 (0.4H, d, J=7.6 Hz), 9.36 (0.6H, d, J=8.5 Hz), 11.25-11.78 (1H, br), 12.33 (1H, s).

MS(ESI)m/z: 525 [(M+H)$^+$, $^{35}$Cl], 527 [(M+H)$^+$, $^{37}$Cl].

Example 44

N-[(3R,4S)-1-acetyl-4-({2-[(5-chloropyridin-2-yl)amino]-2-oxoethanethioyl}amino)piperidin-3-yl]-5-methyl-4,5,6,7-tetrahydrothiazolo[5,4-c]pyridine-2-carboxamide hydrochloride

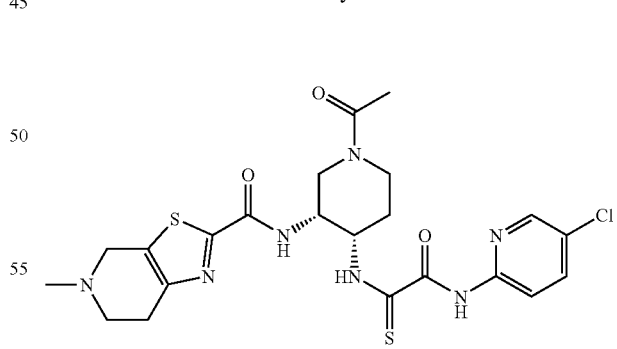

The title compound was obtained in the same manner as in the method described in Example 31, by deprotecting the compound obtained in Reference Example 73 by a hydrochloric acid treatment, and condensing the deprotection product with the compound obtained in Reference Example 5.

$^1$H-NMR (DMSO-d$_6$) δ: 1.69-1.84 (1H, m), 1.81, 2.03 (total 3H, each s), 2.19-2.38 (1H, m), 2.80-2.91 (0.5H, m), 2.91 (3H, s), 3.06-3.89 (6H, m), 4.12 (0.5H, br.d, J=14.9 Hz), 4.25-4.50 (3H, m) 4.65-4.86 (2H, m), 8.02 (1H, d, J=9.0 Hz), 8.08 (1H, d, J=9.0 Hz) 8.45 (1H, d, J=2.0 Hz), 8.51-8.78 (1H, m), 10.54-10.61 (1H, m), 11.02-11.24 (1H, m).
MS(ESI)m/z: 536 [(M+H)$^+$, $^{35}$Cl], 538 [(M+H)$^+$, $^{37}$Cl].

Example 45

N-[(3R,4S)-1-acetyl-4-({2-[(5-fluoropyridin-2-yl)amino]-2-oxoethanethioyl}amino)piperidin-3-yl]-5-methyl-4,5,6,7-tetrahydrothiazolo[5,4-c]pyridine-2-carboxamide hydrochloride

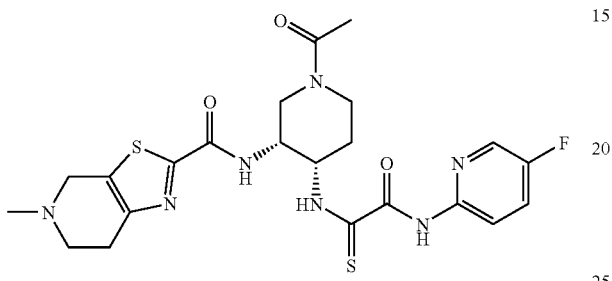

The title compound was obtained in the same manner as in the method described in Example 31, by deprotecting the compound obtained in Reference Example 74 by a hydrochloric acid treatment, and condensing the deprotection product with the compound obtained in Reference Example 5.

$^1$H-NMR (DMSO-d$_6$) δ: 1.69-1.80 (1H, m), 1.81, 2.03 (total 3H, each s), 2.18-2.40 (1H, m), 2.78-2.88 (0.5H, m), 2.92 (3H, br.s), 3.06-3.53 (4H, m), 3.65-4.16 (2.5H, m), 4.25-4.49 (3H, m), 4.65-4.87 (2H, m), 7.82-7.90 (1H, m), 8.07-8.14 (1H, m), 8.42 (1H, d, J=2.7 Hz), 8.52-8.80 (1H, m), 10.49-10.57 (1H, m), 11.02-11.25 (1H, m), 11.28 (0.5H, br.s), 11.53 (0.5H, br.s).
MS(ESI)m/z: 520 (M+H)$^+$.

Example 46

(3R,4S)-4-{2-[(5-chloropyridin-2-yl)amino]-2-oxoethanethioyl}amino-3-{[(5-methyl-4,5,6,7-tetrahydrothiazolo[5,4-c]pyridin-2-yl)carbonyl]amino}piperidine-1-carboxylic acid methyl ester hydrochloride

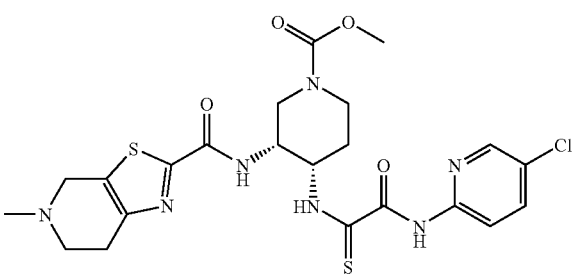

The title compound was obtained in the same manner as in the method described in Example 31, by deprotecting the compound obtained in Reference Example 77 by a hydrochloric acid treatment, and condensing the deprotection product with the compound obtained in Reference Example 5.

$^1$H-NMR (DMSO-d$_6$) δ: 1.69-1.79 (1H, m), 2.25-2.38 (1H, m), 2.92 (3H, s), 3.03-3.29 (3.5H, m), 3.34-3.79 (5.5H, m), 3.86-4.00 (1H, m), 4.17 (1H, br.d, J=11.7 Hz), 4.34-4.50 (2H, m), 4.65-4.80 (2H, m), 8.02 (1H, d, J=9.0 Hz), 8.08 (1H, d, J=9.0 Hz), 8.45 (1H, d, J=2.2 Hz), 8.53-8.67 (1H, m), 10.56, 10.58 (total 1H, each s), 11.08-11.20 (1H, m).
MS(ESI)m/z: 552 [(M+H)$^+$, $^{35}$Cl], 554 [(M+H)$^+$, $^{37}$Cl].

Example 47

(3R,4S)-4-{2-[(5-fluoropyridin-2-yl)amino]-2-oxoethanethioyl}amino-3-{[(5-methyl-4,5,6,7-tetrahydrothiazolo[5,4-c]pyridin-2-yl)carbonyl]amino}piperidine-1-carboxylic acid methyl ester hydrochloride

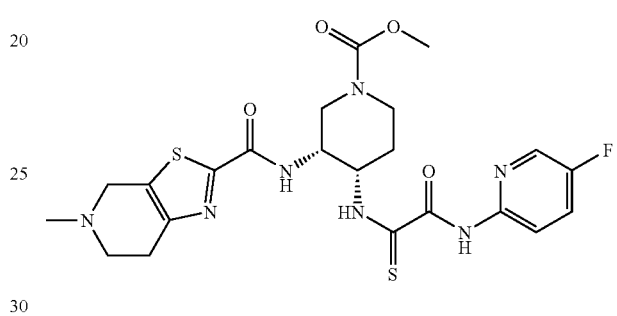

The title compound was obtained in the same manner as in the method described in Example 31, by deprotecting the compound obtained in Reference Example 78 by a hydrochloric acid treatment, and condensing the deprotection product with the compound obtained in Reference Example 5.

$^1$H-NMR (DMSO-d$_6$) δ: 1.69-1.81 (1H, m), 2.26-2.39 (1H, m), 2.93 (3H, br.s), 3.01-3.30 (3.5H, m), 3.32-4.04 (6.5H, m) 4.19 (1H, br.d, J=13.9 Hz), 4.35-4.49 (2H, m), 4.67-4.80 (2H, m), 7.82-7.90 (1H, m), 8.06-8.13 (1H, m), 8.42 (1H, d, J=2.9 Hz), 8.59 (0.5H, d, J=6.6 Hz), 8.65 (0.5H, d, J=6.6 Hz), 10.53, 10.54 (total 1H, each s), 11.06-11.21 (1H, m), 11.26-11.38 (1H, m).
MS(ESI)m/z: 536 (M+H)$^+$.

Example 48

N$^1$-(5-chloropyridin-2-yl)-N$^2$-((3R,4S)-1-methyl-3-{[(6,7-dihydro-4H-pyrano[4,3-d]thiazol-2-yl)carbonyl]amino}piperidin-4-yl)ethanediamide hydrochloride

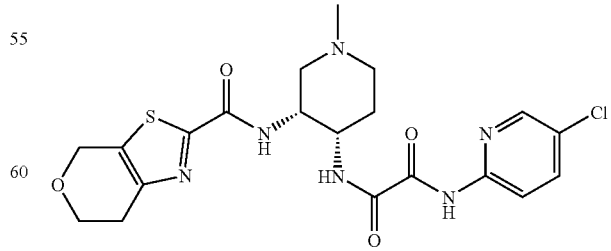

The title compound was obtained in the same manner as in the method described in Example 1, by deprotecting the compound obtained in Reference Example 18 by a hydrochloric acid treatment, and condensing the deprotection product with 6,7-dihydro-4H-pyrano[4,3-d]thiazole-2-carboxylic acid lithium salt.

$^1$H-NMR (DMSO-$d_6$): 1.78-1.90 (1H, m), 2.01-2.22 (1H, m) 2.29-2.48 (1H, m), 2.76-2.95 (5H, m), 3.11-3.69 (3H, m), 3.91-4.01 (2H, m), 4.20-4.37 (1H, m), 4.53-4.66 (1H, m), 4.84 (2H, br.s), 8.00 (1H, d, J=1.7 Hz), 8.01-8.08 (1H, m), 8.44-8.47 (1H, m), 8.88 (0.6H, d, J=8.1 Hz), 9.13 (0.4H, d, J=7.6 Hz), 9.20 (0.4H, d, J=8.1 Hz), 9.44 (0.6H, d, J=8.1 Hz), 9.75-9.96 (0.6H, br), 10.25 (0.6H, s), 10.37 (0.4H, s), 10.59-10.79 (0.4H, m).

MS(ESI)m/z: 479 [(M+H)$^+$, $^{35}$Cl], 481 [(M+H)$^+$, $^{37}$Cl].

Example 49

2-[N-((3R,4S)-4-({2-[(5-chloropyridin-2-yl)amino]-2-oxoacetyl}amino)-1-methylpiperidin-3-yl)carbamoyl]-6,7-dihydro-4H-thiazolo[5,4-c]pyridine-5-carboxylic acid tert-butyl ester

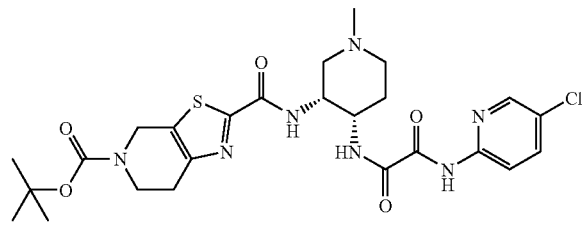

The title compound was obtained in the same manner as in the method described in Example 38, by deprotecting the compound obtained in Reference Example 18 by a hydrochloric acid treatment, and condensing the deprotection product with 5-(tert-butoxycarbonyl)-6,7-dihydro-4H-thiazolo[5,4-c]pyridine-2-carboxylic acid lithium salt.

$^1$H-NMR (CDCl$_3$) δ: 1.50 (9H, s), 1.79-1.93 (1H, m), 1.95-2.06 (1H, m) 2.11-2.25 (1H, m), 2.29-2.47 (1H, m), 2.33 (3H, br.s), 2.83-3.03 (4H, m), 3.70-3.86 (2H, m), 3.92-4.06 (1H, m), 4.48-4.60 (1H, m), 4.65-4.80 (2H, m), 7.66-7.75 (1H, m), 7.96-8.10 (1H, m), 8.16-8.37 (3H, m), 9.81 (1H, s).

MS(ESI)m/z: 578 [(M+H)$^+$, $^{35}$Cl], 580 [(M+H)$^+$, $^{37}$Cl].

Example 50

N$^1$-(5-chloropyridin-2-yl)-N$^2$-{(3R,4S)-3-[(5-formyl-4,5,6,7-tetrahydrothiazolo[5,4-c]pyridin-2-yl)carbonylamino]-1-methylpiperidin-4-yl}ethanediamide hydrochloride

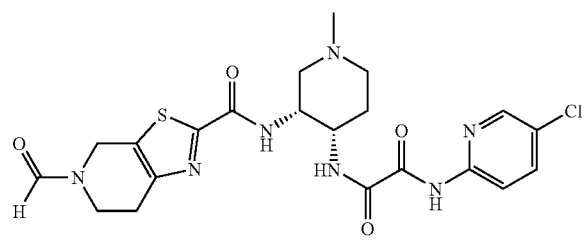

To a solution of the compound obtained in Example 49 (197 mg) in dioxane (5 ml), a 4 N hydrochloric acid-dioxane solution (6 ml) and methanol (3 ml) were added, and the mixture was stirred for 5 hours at room temperature. The solvent was distilled off under reduced pressure, and the residue was dried overnight at room temperature by means of a vacuum pump. The residue was dissolved in N,N-dimethylformamide (12 ml), and formic acid (75 μl), 1-hydroxybenzotriazole (95 mg), 1-(3-dimethylaminopropyl)-3-ethylcarbodiimide hydrochloride (273 mg), and triethylamine (240 μl) were added and stirred for 3 days at room temperature. The solvent was distilled off under reduced pressure, and then dichloromethane and a saturated aqueous solution of sodium hydrogen carbonate were added to the residue. The organic layer was dried over anhydrous sodium sulfate, and the solvent was distilled off under reduced pressure. The residue was purified by silica gel column chromatography (dichloromethane:methanol=20:1, 10:1), to obtain a free form of the title compound (86 mg). To a solution of the free form (86 mg) in ethanol (10 ml), a 1 N hydrochloric acid-ethanol solution (180 μl) was added, and the solvent was distilled off under reduced pressure. The residue was dissolved in ethanol (about 2 ml), subsequently ether was added, and the insoluble matter was collected by filtration. The resulting solid was dissolved in ethanol, and then the solvent was distilled off under reduced pressure, to obtain the title compound (64 mg).

$^1$H-NMR (DMSO-$d_6$) δ: 1.84 (0.5H, br.d, J=13.4 Hz), 2.00-2.25 (1H, m) 2.31-2.49 (0.5H, m), 2.79 (3H, br.s), 2.85-2.99 (2H, m), 3.11-3.56 (3H, m), 3.57-3.67 (1H, m), 3.69-3.83 (2H, m), 4.19-4.29 (0.5H, m), 4.31-4.39 (0.5H, m), 4.52-4.68 (1H, m), 4.71, 4.77 (total 2H, each br.s), 7.98-8.08 (1H, m), 8.00 (1H, s), 8.15-8.24 (1H, m), 8.45 (1H, br.s), 8.85-8.96 (0.6H, m), 9.12 (0.4H, br.d, J=7.6 Hz), 9.14-9.23 (0.4H, m), 9.41 (0.6H, br.d, J=7.6 Hz), 9.81-10.03 (0.5H, m), 10.24, 10.33, 10.35 (total 1H, each s), 10.61-10.79 (0.5H, m).

MS(ESI)m/z: 506 [(M+H)$^+$, $^{35}$Cl], 508 [(M+H)$^+$, $^{37}$Cl].

Example 51

N$^1$-{(3R,4S)-3-[(5-acetyl-4,5,6,7-tetrahydrothiazolo[5,4-c]pyridin-2-yl)carbonylamino]-1-methylpiperidin-4-yl}-N$^2$-(5-chloropyridin-2-yl)ethanediamide hydrochloride

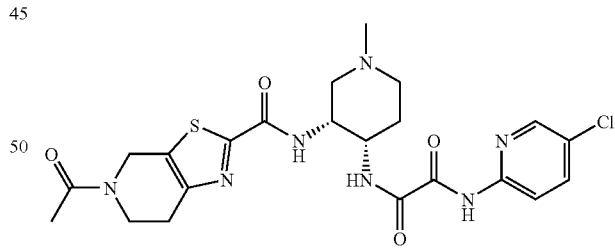

The title compound was obtained in the same manner as in the method described in Example 50, by deprotecting the compound obtained in Example 49 by a hydrochloric acid treatment, and reacting the deprotection product with acetyl chloride.

$^1$H-NMR (DMSO-$d_6$) δ: 1.79-1.94 (0.5H, m), 2.01-2.26 (4H, m), 2.33-2.48 (0.5H, m), 2.78 (3H, s), 2.79-2.99 (2H, m), 3.10-3.91 (6H, m), 4.18-4.29 (0.5H, m), 4.31-4.40 (0.5H, m), 4.53-4.89 (3H, m), 8.00 (1H, s), 8.01-8.08 (1H, m), 8.44 (1H, s), 8.86-8.96 (0.5H, m), 9.04-9.22 (1H, m), 9.33-9.45 (0.5H, m), 10.05-10.39 (1.5H, m), 11.06-11.31 (0.5H, m).

MS(ESI)m/z: 520 [(M+H)$^+$, $^{35}$Cl], 522 [(M+H)$^+$, $^{37}$Cl].

Example 52

N$^1$-(5-chloropyridin-2-yl)-N$^2$-((4S)-1-methyl-5-{[(5-methyl-4,5,6,7-tetrahydrothiazolo[5,4-c]pyridin-2-yl)carbonyl]amino}-2-oxopiperidin-4-yl)ethanediamide

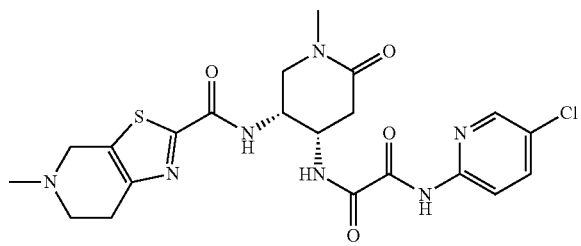

The title compound was obtained as a mixture of stereoisomers at the 5-position (about 1:1.7) in the same manner as in the method described in Example 38, by deprotecting the compound obtained in Reference Example 82 by a hydrochloric acid treatment, and condensing the deprotection product with the compound obtained in Reference Example 6.

$^1$H-NMR (CDCl$_3$) δ: 2.54-2.69 (2H, m), 2.81 (3H, s), 2.91 (3H, s) 3.06-3.55 (5H, m), 3.68 (1H, br.s), 4.33-4.57 (3H, m), 4.64-4.76 (1H, m), 7.97-8.05 (2H, m), 8.42-8.48 (1H, m), 8.87-9.39 (2H, m), 10.26-10.29 (1H, m), 11.33-11.56 (1H, m).

MS(ESI)m/z: 506 [(M+H)$^+$, $^{35}$Cl], 508 [(M+H)$^+$, $^{37}$Cl].

Example 53

N$^1$-(5-chloropyridin-2-yl)-N$^2$-((4S,5S)-1-methyl-5-{[(5-methyl-4,5,6,7-tetrahydrothiazolo[5,4-c]pyridin-2-yl)carbonyl]amino}-2-oxopiperidin-4-yl)ethanediamide and N$^1$-(5-chloropyridin-2-yl)-N$^2$-((4S,5R)-1-methyl-5-{[(5-methyl-4,5,6,7-tetrahydrothiazolo[5,4-c]pyridin-2-yl)carbonyl]amino}-2-oxopiperidin-4-yl)ethanediamide

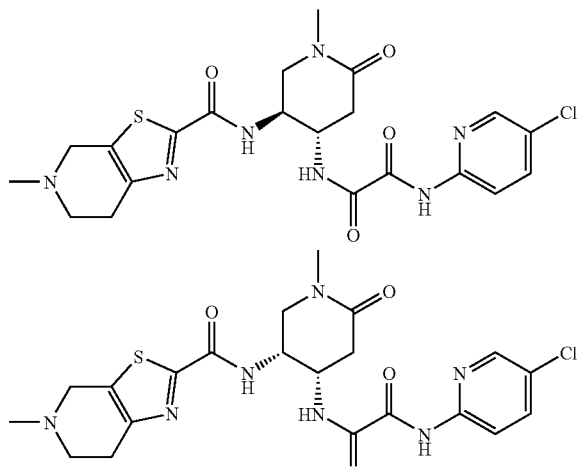

The compound obtained in Example 52 (422 mg) was purified by CHIRALPAK-AS (diameter: 2 cm, length: 25 cm, eluent: a mixed solvent of hexane:ethanol:diethylamine=100:100:1), and the two diastereomers were separated. The component to be eluted first (isomer A, 143 mg) was obtained as a pale yellow solid, and the component to be eluted later (isomer B, 120 mg) was obtained as a pale yellow solid. The components were respectively purified by preparative thin layer chromatography (thickness: 1 mm, dichloromethane:methanol=92:8), to obtain the isomer A (60 mg) and the isomer B (35 mg).

Isomer A:
$^1$H-NMR (CDCl$_3$) δ: 2.48 (3H, s), 2.63 (1H, dd, J=17.2, 10.8 Hz), 2.74-3.03 (8H, m), 3.38 (1H, dd, J=12.0, 10.0 Hz), 3.57-3.74 (3H, m), 4.37-4.48 (1H, m), 4.51-4.61 (1H, m), 7.55 (1H, d, J=8.6 Hz), 7.68 (1H, dd, J=8.8, 2.7 Hz), 7.90 (1H, d, J=8.6 Hz), 8.11 (1H, dd, J=8.8, 0.6 Hz), 8.28 (1H, dd, J=2.6, 0.6 Hz), 9.64 (1H, s).

HR-MS(EI): 505.1301 (Calcd. for C$_{21}$H$_{24}$$^{35}$ClN$_7$O$_4$S: 505.1299).

Isomer B:
$^1$H-NMR (CDCl$_3$) δ: 2.52 (3H, s), 2.59-2.67 (1H, m), 2.77-3.04 (8H, m) 3.39-3.44 (1H, m), 3.62-3.83 (3H, m), 4.50-4.57 (1H, m), 4.73-4.79 (1H, m), 7.71 (1H, dd, J=8.9, 2.7 Hz), 7.78 (1H, d, J=7.6 Hz), 8.17 (1H, dd, J=8.9 Hz), 8.27 (1H, d, J=7.4 Hz), 8.31 (1H, d, J=2.7 Hz), 9.73 (1H, s).

HR-MS(EI): 505.1313 (Calcd. for C$_{21}$H$_{24}$$^{35}$ClN$_7$O$_4$S: 505.1299).

Test Example 1

Determination of Human FXa Inhibitory Effect (IC$_{50}$ Value)

To each well of a 96-well microplate, 10 μl of 5% DMSO solutions of each test compound, the concentrations of which were appropriately prepared stepwise, 40 μl of Tris buffer (100 mM Tris, 200 mM potassium chloride, 0.2% BSA, pH 7.4) and 10 μl of 0.0625 U/ml human FXa (Enzyme Research Laboratories, Inc. dissolved and diluted with Tris buffer) were added, and 40 μl of a 750 μM aqueous solution of S-2222 (Chromogenix Co.) was added. Absorbance at 405 nm was measured for 10 minutes at room temperature to determine an increase in absorbance (ΔOD/min). As a control, Tris buffer was used in place of the test compound.

The rate of inhibition (%) at the final concentration of the test compound calculated using the following equation and the final concentration of the test compound were plotted as ordinate and as abscissa, respectively on a logarithmic normal probability paper, to determine the 50% inhibition dose (IC$^{50}$ value).

Rate of inhibition (%)=(1−(ΔOD/min) of test compound÷(ΔOD/min) of control)×100

(Results) In Table 1, it is demonstrated that the compounds according to the present invention have a potent FXa-inhibiting effect.

Test Example 2

Determination of Prothrombin Time (PT)

Human blood plasma (50 μl) was added to 50 μl of each test compound dissolved in 4% DMSO/physiological saline, and the mixture was pre-incubated at 37° C. for 1 minute. Subsequently, 100 μl of 0.5 U/ml Thromboplastin C Plus (Dade Behring) was added to initiate the reaction. The coagulation time was measured using Amelung KC-10A micro coagulometer (MC Medical). As a control, 4% DMSO/physiological saline was used in place of the test compound. The concentration at which PT is doubled (PTCT2) was calculated by linear regression. The results are presented in Table 1.

Test Example 3

Test for Oral Administration

To a monkey which had been fasted for over 15 hours, each test compound was orally administered in a free form at a dose of 1 mg/2 mL/kg. The test compound was dissolved or suspended in a 0.5% methyl cellulose solution. Before and 0.5, 1, 2, 4, 8 and 24 hours after the administration, the blood was collected at a ratio of 9 volumes to 1 volume of 3.13 trisodium citrate dihydrate (total 1 ml). The blood was centrifuged (3000 rpm, 10 minutes, 4° C.), and the plasma was collected by separation. The separated plasma was pretreated, and was subjected to measurement with HPLC/MS/MS, to calculate the plasma concentration from the areas under peak of the internal standard material and the test compound given by SRM chromatography using a calibration curve. The results are presented in Table 1.

In addition, for the Test Examples 1 to 3, $N^1$-(5-chloropyridin-2-yl)-$N^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide hydrochloride (compound A) (Example 259 described in WO 2004/058715) was used as a positive control.

TABLE 1

| Test compound | FXaIC$_{50}$ (nM) | PTCT2 (μM) | AUC (ng · h/ml) |
|---|---|---|---|
| Example 8 | 2.2 | 0.26 | 826 |
| Example 9 | 1.6 | 0.25 | 482 |
| Example 23 | 0.9 | 0.14 | 899 |
| Example 38 | 3.0 | 0.50 | 880 |
| Compound A | 2.3 | 0.37 | 157 |

As is obvious from Table 1, the compound of the present invention has excellent FXa inhibitory effects and potent anticoagulant effects, and exhibited excellent oral absorbability.

The invention claimed is:
1. A compound represented by general formula (1):

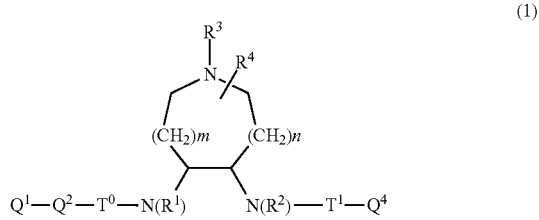

a salt thereof or an N-oxide of the compound or the salt,
wherein $R^1$ and $R^2$ each independently represent a hydrogen atom, a hydroxy group, an alkyl group or an alkoxy group;
$Q^1$ represents a 6,7-dihydro-4H-pyrano[4,3-d]thiazol-2-yl group;
$Q^2$ represents a single bond;
$R^3$ and $R^4$ are substituted at the carbon atom or nitrogen atom on the ring, and each independently represent a hydrogen atom, a hydroxy group, an alkyl group, an alkenyl group, an alkynyl group, a halogen atom, a halogenoalkyl group, a cyano group, a cyanoalkyl group, an amino group, an aminoalkyl group, an N-alkylaminoalkyl group, an N,N-dialkylaminoalkyl group, an acyl group, an acylalkyl group, an acylamino group, an alkoxyimino group, a hydroxyimino group, an acylaminoalkyl group, an alkoxy group, an alkoxyalkyl group, a hydroxyalkyl group, a carboxy group, a carboxyalkyl group, an alkoxycarbonyl group, an alkoxycarbonylalkyl group, an alkoxycarbonylalkylamino group, a carboxyalkylamino group, an alkoxycarbonylamino group, an alkoxycarbonylaminoalkyl group, a carbamoyl group, an N-alkylcarbamoyl group, an N,N-dialkylcarbamoyl group, an N-alkenylcarbamoyl group, an N-alkenylcarbamoylalkyl group, an N-alkenyl-N-alkylcarbamoyl group, an N-alkenyl-N-alkylcarbamoylalkyl group, an N-alkoxycarbamoyl group, an N-alkyl-N-alkoxycarbamoyl group, an N-alkoxycarbamoylalkyl group, an N-alkyl-N-alkoxycarbamoylalkyl group, a carbazoyl group which may be substituted with 1 to 3 alkyl groups, an alkylsulfonyl group which may be substituted with a halogen atom, an alkylsulfonylalkyl group, a carbamoylalkyl group, an N-alkylcarbamoylalkyl group, an N,N-dialkylcarbamoylalkyl group, a carbamoyloxyalkyl group, an N-alkylcarbamoyloxyalkyl group, an N,N-dialkylcarbamoyloxyalkyl group, an aryl group, an aralkyl group, an alkylsulfonylamino group, an arylsulfonylamino group, an alkylsulfonylaminoalkyl group, an arylsulfonylaminoalkyl group, an alkylsulfonylaminocarbonyl group, an arylsulfonylaminocarbonyl group, an alkylsulfonylaminocarbonylalkyl group, an arylsulfonylaminocarbonylalkyl group, an oxo group, a carbamoyloxy group, an aralkyloxy group, a carboxyalkyloxy group, an alkoxycarbonylalkyloxy group, an acyloxy group, an acyloxyalkyl group, an arylsulfonyl group, an alkoxycarbonylalkylsulfonyl group, a carboxyalkylsulfonyl group, an alkoxycarbonylacyl group, an alkoxyalkyloxycarbonyl group, a hydroxyacyl group, an alkoxyacyl group, a halogenoacyl group, a carboxyacyl group, an aminoacyl group, an acyloxyacyl group, an acyloxyalkylsulfonyl group, a hydroxyalkylsulfonyl group, an alkoxyalkylsulfonyl group, an N-alkylaminosulfonyl group, an N,N-dialkylaminosulfonyl group, an N,N-dialkylaminoacyl group, an N,N-dialkylcarbamoylacyl group, an N,N-dialkylcarbamoylalkylsulfonyl group, an alkylsulfonylacyl group, an N-arylcarbamoyl group, an N-alkyl-N-arylcarbamoyl group, an N-arylcarbamoylalkyl group, an N-alkyl-N-arylcarbamoylalkyl group, an N-alkylaminooxalyl group, an N,N-dialkylaminooxalyl group, an aminocarbothioyl group, an N-alkylaminocarbothioyl group, an N,N-dialkylaminocarbothioyl group, an alkoxyalkyl(thiocarbonyl) group, an alkylthioalkyl group, an N-acyl-N-alkylaminoalkyl group or an oxo group, or $R^3$ and $R^4$ are joined together to represent an alkylene group having 1 to 5 carbon atoms, or an alkenylene group having 2 to 5 carbon atoms;
m and n each independently represent an integer from 0 to 2, and (CH$_2$)m and (CH$_2$)n form a piperidinyl ring with the ring nitrogen;
$Q^4$ represents a pyridyl group;
$T^0$ represents a carbonyl group; and
$T^1$ represents a carbonyl group, a sulfonyl group, a —C(=O)—C(=O)—N(R')— group, a —C(=S)—C(=O)—N(R')— group, a —C(=O)—C(=S)—N(R')— group, a —C(=S)—C(=S)—N(R')— group (wherein R' represents a hydrogen atom, a hydroxy group, an alkyl group or an alkoxy group), a —C(=O)-A$^1$-N(R")- group (wherein A$^1$ represents a C$_{1-5}$ alkylene group; and R" represents a hydrogen atom, a hydroxy group, an alkyl group or an alkoxy group), a —C(=O)—NH— group, a —C(=S)—NH— group, a —C(=O)—NH—NH— group, a —C(=O)-A$^2$-C(=O)— group (wherein A$^2$ represents a single bond or an alkylene group having 1 to 5 carbon atoms), a —C(=O)-A$^3$-C(=O)—NH— group (wherein A$^3$ represents an alkylene group having 1 to 5 carbon atoms), a —C(=O)—C(=NOR$^a$)—N(R$^b$)— group, a —C(=S)—C(=NOR$^a$)—N(R$^b$)— group (wherein R$^a$ represents a hydrogen atom, an alkyl group or an alkanoyl group; and R$^b$ represents a hydrogen atom, a hydroxy group, an alkyl group or an alkoxy group), a —C(=O)—N=N— group, a —C(=S)—N=N— group, a —C(=NOR$^c$)—C(=O)—N(R$^d$)— group (wherein R$^c$ represents a hydrogen atom, an alkyl group, an alkanoyl group, an aryl group or an aralkyl group; and R$^d$ represents a hydrogen atom, a hydroxy group, an alkyl group or an alkoxy group), a —C(=N—N(R$^e$))(R$^f$)—C(=O)—N(R$^g$)— group (wherein R$^e$ and R$^f$ each independently represent a hydrogen atom, an alkyl group, an alkanoyl group or an alkyl(thiocarbonyl) group; and R$^g$ represents a hydrogen atom, a hydroxy group, an alkyl group or an alkoxy group), a —C(=O)—NH—C(=O)— group, a —C(=S)—NH—C(=O)— group, a —C(=O)—NH—C(=S)— group, a —C(=S)—NH—C(=S)— group, a —C(=O)—NH—SO$_2$— group, a —SO$_2$—NH— group, a —C(=NCN)—NH—C(=O)— group, a —C(=S)—C(=O)— group or a thiocarbonyl group.

2. The compound according to claim 1, a salt thereof, or an N-oxide of the compound or the salt, wherein the group Q$^4$ has one to three substituents selected from a hydroxy group, a halogen atom, a halogenoalkyl group, an amino group, a cyano group, an aminoalkyl group, a nitro group, a hydroxyalkyl group, an alkoxyalkyl group, a carboxy group, a carboxyalkyl group, an alkoxycarbonylalkyl group, an acyl group, an amidino group, a hydroxyamidino group, a straight-chained, branched or cyclic alkyl group having 1 to 6 carbon atoms, a straight-chained, branched or cyclic alkoxy group having 1 to 6 carbon atoms, an amidino group substituted with a straight-chained, branched or cyclic alkyl group having 1 to 6 carbon atoms, an amidino group substituted with a straight-chained, branched or cyclic alkoxy group having 1 to 6 carbon atoms, an amidino group substituted with a straight-chained, branched or cyclic alkoxycarbonyl group having 2 to 7 carbon atoms, a straight-chained, branched or cyclic alkenyl group having 2 to 6 carbon atoms, a straight-chained or branched alkynyl group having 2 to 6 carbon atoms, a straight-chained, branched or cyclic alkoxycarbonyl group having 2 to 6 carbon atoms, a carbamoyl group, a mono- or dialkylcarbamoyl group substituted on the nitrogen atom with a straight-chained, branched or cyclic alkyl group having 1 to 6 carbon atoms, and a mono- or dialkylamino group substituted with a straight-chained, branched or cyclic alkyl group having 1 to 6 carbon atoms.

3. The compound according to claim 1, a salt thereof, or an N-oxide of the compound or the salt, wherein in the formula (1), the group Q$^4$ represents

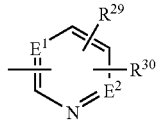

(j)

wherein E$^1$ and E$^2$ each independently represent CH; and R$^{29}$ and R$^{30}$ each independently represent a hydrogen atom, a hydroxy group, a nitro group, an amino group, a cyano group, a halogen atom, an alkyl group, an alkenyl group, an alkynyl group, a halogenoalkyl group, a hydroxyalkyl group, an alkoxy group, an alkoxyalkyl group, a carboxy group, a carboxyalkyl group, an acyl group, a carbamoyl group, an N-alkylcarbamoyl group, an N,N-dialkylcarbamoyl group, an alkoxycarbonyl group, an amidino group or an alkoxycarbonylalkyl group.

4. The compound according to claim 1, a salt thereof, or an N-oxide of the compound or the salt, wherein in the formula (1), the group Q$^4$ represents

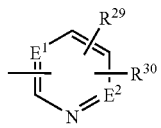

(j)

wherein E$^1$ and E$^2$ each independently represent or CH; R$^{29}$ represents a hydrogen atom or a halogen atom; and R$^{30}$ represents a hydrogen atom, a halogen atom, an alkyl group or an alkynyl group.

5. The compound according to claim 1 or 2, a salt thereof, or an N-oxide of the compound or the salt, wherein the group Q$^4$ is a 2-pyridyl group, a 3-pyridyl group, a 4-pyridyl group, a 4-chloro-2-pyridyl group, a 4-fluoro-2-pyridyl group, a 4-bromo-2-pyridyl group, a 4-methyl-2-pyridyl group, a 4-ethynyl-2-pyridyl group, a 4-chloro-3-pyridyl group, a 4-fluoro-3-pyridyl group, a 4-bromo-3-pyridyl group, a 4-methyl-3-pyridyl group, a 4-ethynyl-3-pyridyl group, a 5-chloro-2-pyridyl group, a 5-fluoro-2-pyridyl group, a 5-bromo-2-pyridyl group, a 5-methyl-2-pyridyl group, a 5-ethynyl-2-pyridyl group, a 4-chloro-5-fluoro-2-pyridyl group, a 5-chloro-4-fluoro-2-pyridyl group, a 5-chloro-3-pyridyl group, a 5-fluoro-3-pyridyl group, a 5-bromo-3-pyridyl group, a 5-methyl-3-pyridyl group, or a 5-ethynyl-3-pyridyl group.

6. The compound according to any one of claims 1 and 2-5, a salt thereof, or an N-oxide of the compound or the salt, wherein in the formula (1), the group T$^1$ is a carbonyl group, a group —C(=O)—C(=O)—N(R')—, a group —C(=S)—C(=O)—N(R')—, a group —C(=O)—C(=S)—N(R')— or a group —C(=S)—C(=S)—N(R')— (wherein R' represents a hydrogen atom, a hydroxy group, an alkyl group or an alkoxy group).

7. The compound according to any one of claims 2 and 5-6, a salt thereof, or an N-oxide of the compound or the salt, wherein in the formula (1), the group T$^1$ is a group —C(=O)—C(=O)—N(R')—, a group —C(=S)—C(=O)—N(R')—, a group —C(=O)—C(=S)—N(R')— or a group —C(=S)—C(=S)—N(R')— (wherein R' represents a hydrogen atom, a hydroxy group, an alkyl group or an alkoxy group).

8. The compound according to any one of claims 1, 2-5, and 6-7, a salt thereof, or an N-oxide of the compound or the salt, wherein m and n are each an integer of 1.

9. The compound according to any one of claims 1, 2-5, 6-7, and 8, a salt thereof, or an N-oxide of the compound or the salt, wherein $R^3$ is a hydrogen atom, an alkyl group, an alkenyl group, an acyl group, an alkoxycarbonyl group, an N-alkylcarbamoyl group, an N,N-dialkylcarbamoyl group, an alkylsulfonyl group which may be substituted with a halogen atom, an N-alkylaminosulfonyl group, an N,N-dialkylaminosulfonyl group, an N-alkylaminooxalyl group, or an N,N-dialkylaminooxalyl group.

10. The compound according to any one of claims 1, 2-5, 6-7, and 8-9, a salt thereof, or an N-oxide of the compound or the salt, wherein $R^4$ is a hydrogen atom or an oxo group.

11. The compound according to any one of claims 1, 2-5, 6-7, and 8-10, a salt thereof, or an N-oxide of the compound or the salt, wherein $R^3$ is an alkanoyl group having 1 to 6 carbon atoms, and $R^4$ is a hydrogen atom.

12. The compound according to any one of claims 1, 2-5, 6-7, and 8-11, a salt thereof, or an N-oxide of the compound or the salt, wherein $R^3$ is a formyl group, and $R^4$ is a hydrogen atom.

13. A pharmaceutical composition comprising the compound according to any one of claims 1, 2-5, 6-7, and 8-12, a salt thereof, or an N-oxide of the compound or the salt, and a pharmaceutically acceptable carrier.

14. The compound: $N^1$-(5-chloropyridin-2-yl)-$N^2$-((3R,4S)-3-{[6,7-dihydro-4H-pyrano[4,3-d]thiazol-2-yl)carbonyl]amino}-1-formylpiperidin-4-yl)ethanediamide, a salt of the compound, an N-oxide of the compound, or an N-oxide of a salt of the compound.

15. A pharmaceutical composition comprising the compound of claim 14, a salt of the compound, an N-oxide of the compound, or an N-oxide of a salt of the compound; and a pharmaceutically acceptable carrier.

16. The compound: $N^1$-(5-chloropyridin-2-yl)-$N^2$-((3R,4S)-3-{[6,7-dihydro-4H-pyrano[4,3-d]thiazol-2-yl)carbonyl]amino}-1-formylpiperidin-4-yl)ethanediamide or a salt thereof.

17. A pharmaceutical composition comprising the compound of claim 16 or a salt thereof; and a pharmaceutically acceptable carrier.

18. The compound according to claim 1, a salt thereof, or an N-oxide of the compound or a salt thereof, wherein $Q^4$ represents a 2-pyridyl group.

19. A pharmaceutical composition comprising the compound of claim 18 or a salt thereof, or an N-oxide of the compound or a salt thereof; and a pharmaceutically acceptable carrier.

* * * * *

UNITED STATES PATENT AND TRADEMARK OFFICE
CERTIFICATE OF CORRECTION

PATENT NO. : 8,088,796 B2  
APPLICATION NO. : 11/909802  
DATED : January 3, 2012  
INVENTOR(S) : Akiyoshi Mochizuki et al.

Page 1 of 1

It is certified that error appears in the above-identified patent and that said Letters Patent is hereby corrected as shown below:

Column 155, line 23, "...a -C(=N-N($R^e$)" should read --...a -C(=N-N($R^e$)--

Column 156, line 60, "...claims 2 and 5-6," should read --...claims 1 and 2-5,--

Signed and Sealed this  
Third Day of July, 2012

David J. Kappos  
*Director of the United States Patent and Trademark Office*